US012600749B2

(12) United States Patent
Shelton et al.

(10) Patent No.: US 12,600,749 B2
(45) Date of Patent: *Apr. 14, 2026

(54) COMPSTATIN ANALOGUES AND THEIR MEDICAL USES

(71) Applicant: ZP SPV 3 K/S, Søborg (DK)

(72) Inventors: Anne Pernille Tofteng Shelton, Søborg (DK); Jacob Ulrik Fog, Søborg (DK); Jens Kvist Madsen, Søborg (DK)

(73) Assignee: ZP SPV 3 K/S, Søborg (DK)

( * ) Notice: Subject to any disclaimer, the term of this patent is extended or adjusted under 35 U.S.C. 154(b) by 0 days.

This patent is subject to a terminal disclaimer.

(21) Appl. No.: 18/601,031

(22) Filed: Mar. 11, 2024

(65) Prior Publication Data

US 2024/0309046 A1 Sep. 19, 2024

Related U.S. Application Data

(63) Continuation of application No. 16/976,439, filed as application No. PCT/EP2019/054685 on Feb. 26, 2019, now Pat. No. 11,965,039.

(30) Foreign Application Priority Data

Feb. 27, 2018 (EP) .................................... 18158834
Dec. 20, 2018 (EP) .................................... 18214949

(51) Int. Cl.

*C07K 7/08* (2006.01)
*A61K 38/00* (2006.01)
*A61K 47/54* (2017.01)
*A61K 47/65* (2017.01)

(52) U.S. Cl.

CPC .............. *C07K 7/08* (2013.01); *A61K 47/542* (2017.08); *A61K 47/545* (2017.08); *A61K 47/65* (2017.08); *A61K 38/00* (2013.01)

(58) Field of Classification Search

CPC ......... C07K 7/08; A61K 47/542; A61K 38/00
See application file for complete search history.

(56) References Cited

U.S. PATENT DOCUMENTS

| | | | |
|---|---|---|---|
| 11,965,039 B2 * | 4/2024 | Shelton ................ C07K 14/472 | |
| 2014/0113874 A1 | 4/2014 | Lambris et al. | |
| 2015/0158915 A1 | 6/2015 | Lambris et al. | |
| 2015/0329594 A1 | 11/2015 | Morikis et al. | |
| 2018/0057538 A1 | 3/2018 | Morikis et al. | |
| 2022/0306695 A1 * | 9/2022 | Shelton .................. A61P 25/00 | |
| 2023/0192770 A1 | 6/2023 | Shelton et al. | |

FOREIGN PATENT DOCUMENTS

| | | | |
|---|---|---|---|
| CN | 101400692 | A | 4/2009 |
| CN | 102458438 | A | 5/2012 |
| CN | 103987725 | A | 8/2014 |
| CN | 114630836 | A | 6/2022 |
| EP | 2424557 | A1 | 3/2012 |
| WO | WO-99/13899 | A1 | 3/1999 |
| WO | WO-2004/026328 | A1 | 4/2004 |
| WO | WO-2007/044668 | A2 | 4/2007 |
| WO | WO-2007/062249 | A2 | 5/2007 |
| WO | WO-2008/153963 | A1 | 12/2008 |
| WO | WO-2010/039690 | A1 | 4/2010 |
| WO | WO-2010/127336 | A1 | 11/2010 |
| WO | WO-2011/119484 | A1 | 9/2011 |
| WO | WO-2012/040259 | A2 | 3/2012 |
| WO | WO-2013/036778 | A2 | 3/2013 |
| WO | WO-2013/040142 | A2 | 3/2013 |
| WO | WO-2013/142362 | A1 | 9/2013 |
| WO | WO-2014/078734 | A2 | 5/2014 |
| WO | WO-2014/100407 | A1 | 6/2014 |
| WO | WO-2015/128403 | A2 | 9/2015 |
| WO | WO-2015/142701 | A1 | 9/2015 |
| WO | WO-2016/049385 | A1 | 3/2016 |
| WO | WO-2019/166411 | A1 | 9/2019 |
| WO | WO-2021/037942 | A1 | 3/2021 |
| WO | WO-2022/013374 | A1 | 1/2022 |

OTHER PUBLICATIONS

Bellows et al., "New compstatin variants through two de novo protein design frameworks," Biophys J. 98(10):2337-46 (2010).
International Search Report for International Application No. PCT/EP2019/054685, mailed Apr. 18, 2019 (5 pages).
Tamamis et al., "Molecular dynamics in drug design: new generations of compstatin analogs," Chem Biol Drug Des. 79(5):703-18 (May 2012).
Third Party Observation for International Patent Application No. PCT/EP2019/054685, submitted Oct. 28, 2019 (13 pages).
Written Opinion for International Application No. PCT/EP2019/054685, mailed Apr. 18, 2019 (5 pages).
Zhang et al., "Compstatin analog Cp40 inhibits complement dysregulation in vitro in C3 glomerulopathy," Immunobiology. 220(8):993-8 (Aug. 2015).
Berger et al., "New Analogs of the Complement C3 Inhibitor Compstatin with Increased Solubility and Improved Pharmacokinetic Profile," J Med Chem. 61(14):6153-6162 (Jul. 2018).

(Continued)

*Primary Examiner* — Amber D Steele
(74) *Attorney, Agent, or Firm* — Clark & Elbing LLP

(57) ABSTRACT

Compstatin analogues having improved binding and complement-inhibiting activity as compared to the 13 amino acid compstatin peptide (ICVVQDWGHHRCT (cyclic C2-C12)) (SEQ ID NO: 1) are described, in particular compstatin analogues that additionally possess useful physicochemical properties, such as increased solubility. These analogues include variants with an isoleucine residue at position 3 in place of the wild type valine residue, which provides compstatin peptides with improved binding and complement-inhibiting activity and also enables the introduction of other modifications, for example modifications that are capable of increasing solubility, such as the introduction of charged or polar amino acids at position 9 and/or the introduction of N- and/or C-terminal sequences.

19 Claims, 3 Drawing Sheets

Specification includes a Sequence Listing.

(56) References Cited

OTHER PUBLICATIONS

De Araujo et al., "Selenoether oxytocin analogues have analgesic properties in a mouse model of chronic abdominal pain," Nat Commun. 5:3165 (2014) (12 pages).

Knerr et al., "Synthesis and activity of thioether-containing analogues of the complement inhibitor compstatin," ACS Chem Biol. 6(7):753-60 (Jul. 2011).

Morikis et al., "The structural basis of compstatin activity examined by structure-function-based design of peptide analogs and NMR," J Biol Chem. 277(17):14942-53 (Apr. 2002) (1 page).

Muttenthaler et al., "Modulating oxytocin activity and plasma stability by disulfide bond engineering," J Med Chem. 53(24):8585-96 (2010).

Yu et al., "A simple and efficient method for the syntheses of thioether cyclic peptides," Tetrahedron Lett. 39(37):6633-36 (Sep. 1998).

Fang et al., "Discovery, structure, and chemical synthesis of disulfide-rich peptide toxins and their analogs," Chinese Chemical Letters 29(7):1033-42 (Jul. 2018).

Qu et al., "New analogs of the clinical complement inhibitor compstatin with subnanomolar affinity and enhanced pharmacokinetic properties," Immunobiology. 218(4):496-505 (2013).

Kourra et al., "Converting disulfide bridges in native peptides to stable methylene thioacetals," Chem Sci. 7(12):7007-12 (Jul. 2016).

* cited by examiner

Complement Alternative Pathway Activity ex vivo

Complement Alternative Pathway Activity ex vivo

COMPSTATIN ANALOGUES AND THEIR MEDICAL USES

SEQUENCE LISTING

The instant application contains a Sequence Listing which has been submitted electronically in XML format and is hereby incorporated by reference in its entirety. Said XML copy, created on Mar. 20, 2024, is named 51574-002004_Sequence_Listing_3_20_24 and is 836,536 bytes in size.

FIELD OF THE INVENTION

The present invention relates to inhibiting activation of the complement cascade in the body, and more particularly to compstatin analogues that are capable of binding to C3 protein and inhibiting complement activation. The present invention also relates to the medical uses of the compstatin analogues, in particular for the treatment of conditions characterized by unwanted activation of the complement cascade, such as autoimmune and inflammatory diseases.

BACKGROUND OF THE INVENTION

The human complement system is a powerful player in the defense against pathogenic organisms and the mediation of immune responses. Complement can be activated through three different pathways: the classical, lectin and alternative pathways. The major activation event that is shared by all three pathways is the proteolytic cleavage of the central protein of the complement system, C3, into its activation products C3a and C3b by C3 convertases. Generation of these fragments leads to the opsonization of pathogenic cells by C3b and iC3b, a process that renders them susceptible to phagocytosis or clearance, and to the activation of immune cells through an interaction with complement receptors (Markiewski & Lambris, 2007, Am. J. Pathol., 171: 715-727). Deposition of C3b on target cells also induces the formation of new convertase complexes and thereby initiates a self-amplification loop. An ensemble of plasma and cell surface-bound proteins carefully regulates complement activation to prevent host cells from self-attack by the complement cascade. However, excessive activation or inappropriate regulation of complement can lead to a number of pathologic conditions, ranging from autoimmune to inflammatory diseases (Holers, 2003, Clin. Immunol., 107: 140-51; Markiewski & Lambris, 2007, supra; Ricklin & Lambris, 2007, Nat. Biotechnol., 25: 1265-75; Sahu et al., 2000, J. Immunol., 165: 2491-9). The development of therapeutic complement inhibitors is therefore highly desirable. In this context, C3 and C3b have emerged as promising targets because their central role in the cascade allows for the simultaneous inhibition of the initiation, amplification, and downstream activation of complement (Ricklin & Lambris, 2007, supra).

Compstatin was first identified as a 27 amino acid peptide and was the first non-host-derived complement inhibitor that was shown to be capable of blocking all three activation pathways (Sahu et al., 1996, J. Immunol., 157: 884-91; U.S. Pat. No. 6,319,897). It has been shown that it is possible to truncate compstatin without loss of activity to a 13 amino acid peptide. However, attempts to further truncate this peptide led to loss of activity. The sequence of the 13 amino acid truncated (or "core") compstatin peptide is $Ile^1$-$Cys^2$-$Val^3$-$Val^4$-$Gln^5$-$Asp^6$-$Trp^7$-$Gly^8$-$His^9$-$His^{10}$-$Arg^{11}$-$Cys^{12}$-$Thr^{13}$-$NH_2$ (SEQ ID NO: 1), where $Cys^2$ and $Cys^{12}$ are disulfide bonded. This cyclic tridecapeptide binds to C3 (and fragments of C3), thereby inhibiting the activation of the downstream complement cascade and preventing the cleavage of native C3 by the C3 convertases. Its inhibitory efficacy was confirmed by a series of studies using experimental models that pointed to its potential as a therapeutic agent (Fiane et al, 1999a, Xenotransplantation, 6: 52-65; Fiane et al, 1999b, Transplant Proc., 31:934-935; Nilsson et al., 1998, Blood, 92: 1661-1667; Ricklin & Lambris, 2008, Adv. Exp. Med. Biol., 632: 273-292; Schmidt et al., 2003, J. Biomed. Mater. Res., A66: 491-499; Soulika et al., 2000, Clin. Immunol., 96: 212-221).

Progressive optimization of the 13 amino acid compstatin peptide has led to analogues with improved biological activity (Ricklin & Lambris, 2008, supra; WO 2004/026328; WO 2007/062249, WO 2013/036778, WO 2014/100407).

Earlier structure-activity studies have identified the cyclic nature of the compstatin peptide and the presence of both a β-turn and hydrophobic cluster as key features of the molecule (Morikis et al., 1998, Protein Sci., 7: 619-627; WO 99/13899; Morikis et al., 2002, J. Biol. Chem., 277:14942-14953; Ricklin & Lambris, 2008, supra). Hydrophobic residues at positions 4 and 7 were found to be of particular importance, and their modification with unnatural amino acids generated an analogue with 264-fold improved activity over the original compstatin peptide (Katragadda et al., 2006, J. Med. Chem., 49: 4616-4622; WO 2007/062249). Further attempts to optimize compstatin for use in the treatment of eye disorders are described in WO 2007/044668.

While previous optimization steps have been based on combinatorial screening studies, solution structures, and computational models (Chiu et al., 2008, Chem. Biol. Drug Des., 72: 249-256; Mulakala et al., 2007, Bioorg. Med. Chem., 15: 1638-1644; Ricklin & Lambris, 2008, supra), the publication of a co-crystal structure of compstatin complexed with the complement fragment C3c (Janssen et al., 2007, J. Biol. Chem., 282: 29241-29247; WO 2008/153963) provided a basis for initiating rational optimization. The crystal structure revealed a shallow binding site at the interface of macroglobulin (MG) domains 4 and 5 of C3c and showed that 9 of the 13 amino acids were directly involved in the binding, either through hydrogen bonds or hydrophobic interactions. As compared to the structure of the compstatin peptide in solution (Morikis et al., 1998, supra), the bound form of compstatin experienced a conformational change, with a shift in the location of the β-turn from residues 5-8 to 8-11 (Janssen et al., 2007, supra; WO 2008/153963).

In view of its therapeutic potential in AMD, C3G, PNH and other diseases, it remains a problem in the art to further optimize compstatin analogues, for example to achieve an even greater activity and/or to modulate pharmacokinetic properties, such as increased half-life in vivo and/or physicochemical properties such as increased solubility.

SUMMARY OF THE INVENTION

Broadly, the present invention is based on work to develop a new family of compstatin analogues having improved binding and complement-inhibiting activity as compared to the 13 amino acid compstatin peptide (ICVVQDWGHHRCT (cyclic C2-C12)) (SEQ ID NO: 1). In some cases, these compstatin analogues additionally possess useful physicochemical properties, such as increased solubility. In particular, the present inventors found that introducing an isoleucine residue at position 3 in place of the wild type valine residue led to compstatin peptides with improved binding and complement-inhibiting activity. The present inventors further discovered that the introduction of isoleucine at position 3 enables the introduction of other modifications, for example modifications that are capable of increasing solubility, such as the introduction of glutamic acid at position 6, particular charged or polar amino acids at position 9, and/or the introduction of N- and/or C-terminal sequences. Example of such additional modifications include the replacement of Ile at position 1 with Tyr, Phe or Sar, replacement of Val at position 4 with Trp, a Trp analogue (as described herein); replacement of Asp in position 6 with Glu; replacement of His at position 9 with Ala, Glu, Asp, Lys, Ser or Arg; replacement of Arg at position 11 with Ser; replacement of Thr at position 13 with Ser, Glu, Sar or Ile. Preferred compstatin peptides including one or more of these modifications have improved solubility, for example as compared to the 13 amino acid compstatin peptide (ICVVQDWGHHRCT (cyclic C2-C12)) (SEQ ID NO: 1). Further examples of these compstatin peptides combine modification at position 9 with extensions to the N-terminal and/or C-terminus of the peptide.

Accordingly, the present invention provides a compstatin analogue represented by the formula:

```
(Formula I)
                                        (SEQ ID NO: 2)
Y1-R1-X1-C-I-X4-Q-X6-W-X8-X9-H-X11-C-X13-R2-Y2
```

wherein:
- Y1 is hydrogen, acetyl or a lipophilic group ϕ;
- X1 is I, Y, F or Sar;
- X4 is W, F, V, Y, 1-Me-Trp, D-Trp, N-Me-Trp, 1-For-Trp, 1-Nal, 2-Nal, 5-Me-Trp, Bpa or 2-Igl;
- X6 is E, K or D;
- X8 is G or Sar;
- X9 is H, A, E, D, K, R or S;
- X11 is R, S or K;
- X13 is T, S, E, F, H, K, Sar, G, I, D, N-Me-Ile or N-Me-Thr;
- Y2 is $NH_2$, OH or a lipophilic group ϕ;
- R1 is absent or is a sequence of 1 to 6 amino acid residues selected from A, E, G, L, K, F, P, S, T, W, Y, R, V, Sar, εLys, γGlu, βAsp, or βAla, or a corresponding D form thereof; or Peg3, Peg4, or 8-aminooctanoyl, or derivatives thereof; and
- R2 is absent or is a sequence of 1 to 8 amino acid residues selected from A, E, G, L, K, F, P, S, T, W, Y, R, V, Sar, εLys, γGlu, βAsp, or βAla, or a corresponding D form thereof; or Peg3, Peg4, or 8-aminooctanoyl, or derivatives thereof;
- wherein the compstatin analogue has a disulphide bond between the cysteine residues at positions 2 and 12;
- and wherein the compstatin analogue optionally has a lipophilic group ϕ covalently linked to the side chain of one or more amino acid residues;
- or a pharmaceutically acceptable salt and/or solvate thereof.

In some embodiments, X11 is R or S.

In some embodiments, if a lipophilic group ϕ is linked to the side chain of an amino acid residue, that residue is the residue at position X1, X11 or X13, or is a residue in R1 or R2. It may be a lysine residue. For example, it may be a lysine residue at position X11 or X13, or a lysine residue in R1 or R2.

In some embodiments, Y1 is hydrogen or acetyl.

In some embodiments, Y2 is $NH_2$ or OH.

In some embodiments, the compstatin analogue comprises at least one lipophilic group ϕ, e.g. exactly one lipophilic group ϕ.

In some embodiments, the compstatin analogue does not comprise a lipophilic group ϕ.

The present invention further provides a compstatin analogue represented by the formula:

```
(Formula II)
                                        (SEQ ID NO: 3)
Y1-R1-X1-C-I-X4-Q-X6-W-X8-X9-H-X11-C-X13-R2-Y2
```

wherein:
- Y1 is hydrogen, acetyl, or a lipophilic group ϕ;
- X1 is I, Y, F or Sar;
- X4 is W, V, Y, 2-Nal, 1-Nal or 1-Me-Trp;
- X6 is E or D;
- X8 is G or Sar;
- X9 is A, E, D, K or S;
- X11 is R, S or K;
- X13 is T, S, E, I, Sar, K, G or N-Me-Ile;
- Y2 is $NH_2$, OH or a lipophilic group ϕ;
- R1 is absent or is a sequence of 1 to 6 amino acid residues selected from A, E, G, L, K, F, P, S, T, W, Y, R, V, Sar, εLys, γGlu, βAsp, or βAla, or a corresponding D form thereof, or Peg3, Peg4, or 8-aminooctanoyl, or derivatives thereof; and
- R2 is absent or is a sequence of 1 to 8 amino acid residues selected from A, E, G, L, K, F, P, S, T, W, Y, R, V, Sar, εLys, γGlu, βAsp, or βAla, or a corresponding D form thereof; or Peg3 or Peg4, or 8-aminooctanoyl, or derivatives thereof;
- wherein the compstatin analogue has a disulphide bond between the cysteine residues at positions 2 and 12;
- and wherein the compstatin analogue optionally has a lipophilic group ϕ covalently linked to the side chain of one or more amino acids;
- or a pharmaceutically acceptable salt and/or solvate thereof.

In some embodiments, X11 is R or S.

In some embodiments, if a lipophilic group ϕ is linked to the side chain of an amino acid residue, that residue is the residue at position X1, X11 or X13, or is a residue in R1 or R2. It may be a lysine residue. For example, it may be a lysine residue at position X13, or a lysine residue in R1 or R2.

In some embodiments, Y1 is hydrogen or acetyl.

In some embodiments, Y2 is $NH_2$ or OH.

In some embodiments, the compstatin analogue comprises at least one lipophilic group ϕ, e.g. exactly one lipophilic group ϕ.

In some embodiments of this formula, the compstatin analogue does not comprise a lipophilic group ϕ.

The present invention further provides a compstatin analogue represented by the formula:

```
(Formula III)
                                        (SEQ ID NO: 4)
Y1-R1-X1-C-I-X4-Q-X6-W-G-X9-H-X11-C-X13-R2-Y2
```

wherein:
- Y1 is hydrogen, acetyl or a lipophilic group ϕ;
- X1 is I, Y, F or Sar;
- X4 is W, V, Y, 1-Nal, 2-Nal or 1-Me-Trp;
- X6 is E or D;
- X9 is A, E, D, K or S;
- X11 is R, S or K;

X13 is T, I, S, E, K or Sar;

Y2 is $NH_2$, OH or a lipophilic group ϕ;

R1 is absent or is a sequence of 1 to 6 amino acid residues selected from A, E, G, L, K, F, P, S, T, W, Y, R, V, Sar, εLys, γGlu, βAsp, or βAla, or a corresponding D form thereof, or Peg3, Peg4, or 8-aminooctanoyl, or derivatives thereof; and R2 is absent or is a sequence of 1 to 8 amino acid residues selected from A, E, G, L, K, F, P, S, T, W, Y, R, V, Sar, εLys, γGlu, βAsp, or βAla, or a corresponding D form thereof; or Peg3 or Peg4, or 8-aminooctanoyl, or derivatives thereof;

wherein the compstatin analogue has a disulphide bond between the cysteine residues at positions 2 and 12;

and wherein the compstatin analogue optionally has a lipophilic group ϕ covalently linked to the side chain of one or more amino acids;

or a pharmaceutically acceptable salt and/or solvate thereof.

In some embodiments, X11 is R or S.

In some embodiments, if a lipophilic group ϕ is linked to the side chain of an amino acid residue, that residue is the residue at position X1, X11 or X13, or is a residue in R1 or R2. It may be a lysine residue. For example, it may be a lysine residue at position X11 or X13, or a lysine residue in R1 or R2.

In some embodiments, Y1 is hydrogen or acetyl.

In some embodiments, Y2 is $NH_2$ or OH.

In some embodiments, the compstatin analogue comprises at least one lipophilic group ϕ, e.g. exactly one lipophilic group ϕ.

In some embodiments of this formula, the compstatin analogue does not comprise a lipophilic group ϕ.

The compstatin analogue may be represented by the formula:

```
(Formula IV)
                                        (SEQ ID NO: 5)
Y1-R1-X1-C-I-X4-Q-X6-W-G-X9-H-R-C-X13-R2-Y2
```

wherein:

Y1 is hydrogen, acetyl or a lipophilic group ϕ;

X1 is I, Y, F or Sar;

X4 is W, V, Y, 1-Nal, 2-Nal or 1-Me-Trp;

X6 is E or D;

X9 is A, E, D, K or S;

X13 is T, S, E or Sar;

Y2 is $NH_2$, OH or a lipophilic group ϕ;

R1 is absent or is a sequence of 1 to 6 amino acid residues selected from A, E, G, L, K, F, P, S, T, W, Y, R, V, Sar, εLys, γGlu, βAsp, or βAla, or a corresponding D form thereof, or Peg3, Peg4, or 8-aminooctanoyl, or derivatives thereof; and R2 is absent or is a sequence of 1 to 8 amino acid residues selected from A, E, G, L, K, F, P, S, T, W, Y, R, V, Sar, εLys, γGlu, βAsp, or βAla, or a corresponding D form thereof; or Peg3 or Peg4, or 8-aminooctanoyl, or derivatives thereof;

wherein the compstatin analogue has a disulphide bond between the cysteine residues at positions 2 and 12;

and wherein the compstatin analogue optionally has a lipophilic group ϕ covalently linked to the side chain of one or more amino acids;

or a pharmaceutically acceptable salt and/or solvate thereof.

In some embodiments, if a lipophilic group ϕ is linked to the side chain of an amino acid residue, that residue is the residue at position X1, X11 or X13, or is a residue in R1 or R2. It may be a lysine residue. For example, it may be a lysine residue at position X13, or a lysine residue in R1 or R2.

In some embodiments, Y1 is hydrogen or acetyl.

In some embodiments, Y2 is $NH_2$ or OH.

In some embodiments, the compstatin analogue comprises at least one lipophilic group ϕ, e.g. exactly one lipophilic group ϕ.

In some embodiments of this formula, the compstatin analogue does not comprise a lipophilic group ϕ.

In some embodiments of the formulae above, X6 is D.

In one aspect, compstatin analogues which do not possess a lipophilic group ϕ may be represented by the formula:

```
(Formula V)
                                        (SEQ ID NO: 6)
Y1-R1-X1-C-I-X4-Q-X6-W-G-X9-H-R-C-X13-R2-Y2
```

wherein:

Y1 is hydrogen or acetyl;

X1 is Y or F;

X4 is W, Y, 1-Me-Trp;

X6 is E or D;

X9 is A, E or K;

X13 is T, E or Sar;

Y2 is $NH_2$ or OH;

R1 is absent or is a sequence of 1 to 6 amino acid residues selected from A, E, G, L, K, F, P, S, T, W, Y, R, V, Sar, εLys, γGlu, βAsp, or βAla, or a corresponding D form thereof, or Peg3, Peg4, or 8-aminooctanoyl, or derivatives thereof; and R2 is absent or is a sequence of 1 to 6 amino acid residues selected from A, E, G, L, K, F, P, S, T, W, Y, R, V, Sar, εLys, γGlu, βAsp, or βAla, or a corresponding D form thereof; or Peg3 or Peg4, or 8-aminooctanoyl, or derivatives thereof;

wherein the compstatin analogue has a disulphide bond between the cysteine residues at positions 2 and 12;

or a pharmaceutically acceptable salt and/or solvate thereof.

The compstatin analogue may be represented by the formula:

```
(Formula VI)
                                        (SEQ ID NO: 7)
Y1-R1-X1-C-I-[1-Me-Trp]-Q-X6-W-G-E-H-R-C-X13-R2-Y2
```

wherein:

Y1 is hydrogen or acetyl;

X1 is Y or F;

X6 is E or D;

X13 is T, E or Sar;

Y2 is $NH_2$ or OH;

R1 is absent or is a sequence of 1 to 6 amino acid residues selected from A, E, G, L, K, F, P, S, T, W, Y, R, V, Sar, εLys, γGlu, βAsp, or βAla, or a corresponding D form thereof, or Peg3, Peg4, or 8-aminooctanoyl, or derivatives thereof; and R2 is absent or is a sequence of 1 to 6 amino acid residues selected from A, E, G, L, K, F, P, S, T, W, Y, R, V, Sar, εLys, γGlu, βAsp, or βAla, or a corresponding D form thereof; or Peg3 or Peg4, or 8-aminooctanoyl, or derivatives thereof;

wherein the compstatin analogue has a disulphide bond between the cysteine residues at positions 2 and 12;

or a pharmaceutically acceptable salt and/or solvate thereof.

In the formulae above X6 may be D. Alternatively it may be E.

In some embodiments, the compstatin analogue has the formula:

```
(Formula VII)
                                        (SEQ ID NO: 8)
Y1-R1-X1-C-I-X4-Q-X6-W-X8-X9-H-X11-C-X13-R2-Y2
```

wherein:
- Y1 is hydrogen, acetyl or a lipophilic group φ;
- X1 is I, Y, F or Sar;
- X4 is W, V, 1-Me-Trp, 1-Nal or 2-Nal;
- X6 is E, K or D;
- X8 is G or Sar;
- X9 is H, A, E, D, K, R or S;
- X11 is R, S, K or K*;
- X13 is T, S, E, Sar or N-Me-Ile;
- Y2 is $NH_2$ or OH;
- R1 and R2 may be as defined in any of the formulae above, or elsewhere in this specification. In some embodiments, R1 is absent or is a sequence of 1 to 6 amino acid residues selected from A, E, G, K, K*, S, Y, or a corresponding D form thereof; and/or R2 is absent or is a sequence of 1 to 8 amino acid residues selected from A, E, G, K, K*, P, S, Peg3, γGlu, 8-aminooctanoyl, or a corresponding D form thereof;
- wherein * indicates that the amino acid residue bears a lipophilic group φ covalently linked to its side chain.

It may be desirable that the compstatin analogue comprises at least one lipophilic group φ, e.g. exactly one lipophilic group φ. Alternatively, it may comprise no lipophilic group φ.

In an alternative aspect, compstatin analogues which comprise a lipophilic group φ may be represented by the formula:

```
(Formula VIII)
                                        (SEQ ID NO: 9)
Y1-R1-X1-C-I-X4-Q-X6-W-X8-X9-H-X11-C-X13-R2-Y2
```

wherein:
- Y1 is hydrogen, acetyl or a lipophilic group φ;
- X1 is I, Y, F or Sar;
- X4 is W, V, Y, 2-Nal, 1-Nal or 1-Me-Trp;
- X6 is E or D;
- X8 is G or Sar;
- X9 is A, E, D, K or S;
- X11 is R, S or K*;
- X13 is T, S, E, I, Sar, K, G or N-Me-Ile;
- Y2 is $NH_2$, OH or a lipophilic group φ;
- R1 is absent or is a sequence of 1 to 6 amino acid residues selected from A, E, G, L, K, K*, F, P, S, T, W, Y, R, V or Sar, or a corresponding D form thereof;
- R2 is absent or is a sequence of 1 to 8 amino acid residues selected from A, E, G, L, K, K*, F, P, S, T, W, Y, R, V Sar, εLys, γGlu, βAsp, or βAla, or a corresponding D form thereof; or Peg 3 or Peg4, or 8-aminooctanoyl, or derivatives thereof;
- wherein * indicates that the amino acid residue bears a lipophilic group φ covalently linked to its side chain;
- wherein the compstatin analogue has a disulphide bond between the cysteine residues at positions 2 and 12;
- and wherein the compstatin analogue comprises at least one lipophilic group φ, e.g. exactly one lipophilic group φ;
- or a pharmaceutically acceptable salt and/or solvate thereof.

In some embodiments, Y2 is $NH_2$ or OH.

The compstatin analogue may be represented by the formula:

```
(Formula IX)
                                        (SEQ ID NO: 10)
Y1-R1-X1-C-I-X4-Q-X6-W-G-X9-H-X11-C-X13-R2-Y2
```

wherein:
- Y1 is hydrogen, acetyl, or a lipophilic group φ;
- X1 is I, Y, F or Sar;
- X4 is W, V, Y, 1-Nal, 2-Nal or 1-Me-Trp;
- X6 is E or D;
- X9 is A, E, D, K or S;
- X11 is R, S or K*;
- X13 is T, I, S, E, Kor Sar;
- Y2 is $NH_2$, OH or a lipophilic group φ;
- R1 is absent or is a sequence of 1 to 6 amino acid residues selected from A, E, G, L, K, K*, F, P, S, T, W, Y, R, V or Sar, or a corresponding D form thereof;
- R2 is absent or is a sequence of 1 to 8 amino acid residues selected from A, E, G, L, K, K* F, P, S, T, W, Y, R, V, Sar, εLys, γGlu, βAsp, or βAla, or a corresponding D form thereof; or Peg3 or Peg4, or 8-aminooctanoyl, or derivatives thereof;
- wherein * indicates that the amino acid residue bears a lipophilic group φ covalently attached to its side chain;
- wherein the compstatin analogue has a disulphide bond between the cysteine residues at positions 2 and 12;
- and wherein the compstatin analogue comprises at least one lipophilic group φ, e.g. exactly one lipophilic group φ;
- or a pharmaceutically acceptable salt and/or solvate thereof.

In some embodiments, Y2 is $NH_2$ or OH.

The compstatin analogue may be represented by the formula:

```
(Formula X)
                                        (SEQ ID NO: 11)
Y1-R1-X1-C-I-X4-Q-X6-W-G-X9-H-R-C-X13-R2-Y2
```

wherein:
- Y1 is hydrogen, acetyl or a lipophilic group φ;
- X1 is I, Y, F or Sar;
- X4 is W, V, 1-Nal, 2-Nal or 1-Me-Trp;
- X6 is E or D;
- X9 is A, E, D, K or S;
- X13 is T, S, E or Sar;
- Y2 is $NH_2$, OH or a lipophilic group φ;
- R1 is absent or is a sequence of 1 to 6 amino acid residues selected from A, E, G, L, K, K*, F, P, S, T, W, Y, R, V or Sar, or a corresponding D form thereof;
- R2 is absent or is a sequence of 1 to 8 amino acid residues selected from A, E, G, L, K, K*, F, P, S, T, W, Y, R, V, Sar, εLys, γGlu, βAsp, or βAla, or a corresponding D form thereof; or Peg3 or Peg4, or 8-aminooctanoyl, or derivatives thereof;
- wherein * indicates that the amino acid residue bears a lipophilic group φ covalently attached to its amino acid side chain;

wherein the compstatin analogue has a disulphide bond between the cysteine residues at positions 2 and 12;

and wherein the compstatin analogue comprises at least one lipophilic group ϕ, e.g. exactly one lipophilic group ϕ;

or a pharmaceutically acceptable salt and/or solvate thereof.

In some embodiments, Y2 is $NH_2$ or OH.

In any of the formulae above, X6 may be D. Alternatively X6 may be E.

In any of the formulae above, X1 may be Y. Alternatively X1 may be F.

In any of the formulae above, X13 may be Sar. Alternatively X13 may be T.

Additionally or alternatively, any of the frmulae above may comprise one of the following combinations of residues:

X4 is 1-Me-Trp and X9 is E.

X1 is F, X4 is 1-Me-Trp and X9 is E.

X4 is 1-Me-Trp, X9 is E and X13 is Sar.

X4 is 1-Me-Trp, X9 is E and X13 is T.

X4 is 1-Me-Trp, X6 is D, X9 is E and X13 is Sar.

X4 is 1-Me-Trp, X6 is E, X9 is E and X13 is Sar.

X4 is 1-Me-Trp, X6 is D, X9 is E and X13 is T.

X4 is 1-Me-Trp, X6 is E, X9 is E and X13 is T.

The compstatin analogue may be represented by the formula:

```
(Formula XI)
                                                (SEQ ID NO: 12)
Y1-R1-X1-C-I-[1-Me-Trp]-Q-X6-W-G-E-H-R-C-X13-R2-Y2
```

wherein:

Y1 is hydrogen or acetyl;

X1 is Y or F;

X6 is E or D;

X13 is T, E or Sar;

Y2 is $NH_2$ or OH;

R1 is absent or is a sequence of 1 to 6 amino acid residues selected from A, E, G, L, K, K*, F, P, S, T, W, Y, R, V or Sar, or a corresponding D form thereof;

R2 is absent or is a sequence of 1 to 8 amino acid residues selected from A, E, G, L, K, K* F, P, S, T, W, Y, R, V, Sar, εLys, γGlu, βAsp, or βAla, or a corresponding D form thereof; or Peg3 or Peg4, or 8-aminooctanoyl, or derivatives thereof;

wherein * indicates that the amino acid residue bears a lipophilic group ϕ covalently attached to its side chain;

wherein the compstatin analogue has a disulphide bond between the cysteine residues at positions 2 and 12;

and wherein the compstatin analogue comprises at least one lipophilic group ϕ, e.g. exactly one lipophilic group ϕ;

or a pharmaceutically acceptable salt and/or solvate thereof.

In some embodiments, the 13-mer peptide portion (X1-X13) of the compstatin analogue has a sequence selected from:

```
                                                (SEQ ID NO: 13)
[Sar]C(1)|[1-Me-Trp]QDWGEHRC(1)[Sar];

                                                (SEQ ID NO: 14)
[Sar]C(1)|[1-Me-Trp]QDWGEHRC(1)T;

                                                (SEQ ID NO: 15)
[Sar]C(1)|[1-Me-Trp]QEW[Sar]EHRC(1)T;

                                                (SEQ ID NO: 16)
[Sar]C(1)|[1-Me-Trp]QEWGEHRC(1)[Sar];

                                                (SEQ ID NO: 17)
[Sar]C(1)IWQDWGEHRC(1)T;

                                                (SEQ ID NO: 18)
FC(1)|[1-Me-Trp]QDW[Sar]EHRC(1)[Sar];

                                                (SEQ ID NO: 19)
FC(1)|[1-Me-Trp]QDW[Sar]EHRC(1)T;

                                                (SEQ ID NO: 20)
FC(1)|[1-Me-Trp]QDWGEHKC(1)[Sar];
```

-continued (SEQ ID NO: 21)
FC(1)||[1-Me-Trp]QDWGEHRC(1)[Sar];

(SEQ ID NO: 22)
FC(1)||[1-Me-Trp]QDWGEHRC(1)E;

(SEQ ID NO: 23)
FC(1)||[1-Me-Trp]QDWGEHRC(1)S;

(SEQ ID NO: 24)
FC(1)||[1-Me-Trp]QDWGEHRC(1)T;

(SEQ ID NO: 25)
FC(1)||[1-Me-Trp]QEWGEHRC(1)[Sar];

(SEQ ID NO: 26)
FC(1)||[1-Nal]QDWGEHRC(1)T;

(SEQ ID NO: 27)
FC(1)||[2-Nal]QDWGEHRC(1)T;

(SEQ ID NO: 28)
FC(1)IWQDWGEHRC(1)[Sar];

(SEQ ID NO: 29)
FC(1)IWQDWGEHRC(1)T;

(SEQ ID NO: 30)
IC(1)||[1-Me-Trp]QDW[Sar]AHRC(1)[N-Me-Ile];

(SEQ ID NO: 31)
IC(1)||[1-Me-Trp]QDWGEHRC(1)[Sar];

(SEQ ID NO: 32)
IC(1)||[1-Me-Trp]QDWGEHRC(1)T;

(SEQ ID NO: 33)
IC(1)||[2-Nal]QDWGEHRC(1)[Sar];

(SEQ ID NO: 34)
IC(1)IWQDWGAHRC(1)E;

(SEQ ID NO: 35)
IC(1)IWQDWGAHRC(1)T;

(SEQ ID NO: 36)
IC(1)IWQDWGAHSC(1)T;

(SEQ ID NO: 37)
IC(1)IWQDWGDHRC(1)T;

(SEQ ID NO: 38)
IC(1)IWQDWGEHRC(1)[Sar];

(SEQ ID NO: 39)
IC(1)IWQDWGEHRC(1)E;

(SEQ ID NO: 40)
IC(1)IWQDWGEHRC(1)S;

(SEQ ID NO: 41)
IC(1)IWQDWGEHRC(1)T;

(SEQ ID NO: 42)
IC(1)IWQDWGEHSC(1)T;

(SEQ ID NO: 43)
IC(1)IWQDWGKHRC(1)T;

(SEQ ID NO: 44)
IC(1)IWQDWGRHRC(1)T;

(SEQ ID NO: 45)
IC(1)IWQDWGSHRC(1)T;

(SEQ ID NO: 46)
IC(1)IWQEWGEHRC(1)T;

(SEQ ID NO: 47)
IC(1)IWQKWGAHRC(1)T;

-continued

```
                                                (SEQ ID NO: 48)
IC(1)IWQKWGEHRC(1)T;

                                                (SEQ ID NO: 49)
YC(1)|[1-Me-Trp]QDWGEHRC(1)[Sar];

                                                (SEQ ID NO: 50)
YC(1)|[1-Me-Trp]QDWGEHRC(1)T;

                                                (SEQ ID NO: 51)
YC(1)|[1-Me-Trp]QEWGEHRC(1)[Sar];

                                                (SEQ ID NO: 52)
YC(1)|[2-Nal]QDWGEHRC(1)T;

                                                (SEQ ID NO: 53)
YC(1)IWQDWGEHRC(1)T;

                                                (SEQ ID NO: 54)
YC(1)|[1-Me-Trp]QDWGEH[K*]C(1)[Sar];
and

                                                (SEQ ID NO: 55)
YC(1)|[1-Me-Trp]QEW[Sar]EHRC(1)[Sar];
wherein * indicates that the amino acid residue
bears a lipophilic group ϕ covalently attached
to its side chain.
```

In some embodiments, R1 is absent or is a sequence of 1 to 6 amino acid residues selected from A, E, G, L, K, F, P, S, T, W, R, V or Sar, or a corresponding D form thereof, and/or R2 may be a sequence of 1 to 6 amino acid residues selected from A, E, G, L, K, F, P, S, T, W, R, V or Sar, or a corresponding D form thereof.

For example, R1 is selected from ESSA (SEQ ID NO: 56), AKGE (SEQ ID NO: 57), ASSE (SEQ ID NO: 58), ASES (SEQ ID NO: 59), GSAE (SEQ ID NO: 60), ESSE (SEQ ID NO: 61), ESGA (SEQ ID NO: 62), SEG, GES, ESS, EGSA (SEQ ID NO: 63), ESE, EGE, ESA, SAE, SGA, YLEA (SEQ ID NO: 64), GSA, KEK, EKG, ES, AS, SE, SA or E, and/or R2 is selected from GAES (SEQ ID NO: 65), EYGS (SEQ ID NO: 66), EGYA (SEQ ID NO: 67), EAGS (SEQ ID NO: 68), EAKS (SEQ ID NO: 69), EKSA (SEQ ID NO: 70), EGGS (SEQ ID NO: 71), EGGA (SEQ ID NO: 72), ESSG (SEQ ID NO: 73), ESAG (SEQ ID NO: 74), GEES (SEQ ID NO: 75), AEES (SEQ ID NO: 76), ESEG (SEQ ID NO: 77), AEGS (SEQ ID NO: 78), ESGS (SEQ ID NO: 79), SEGA (SEQ ID NO: 80), SEG, ESG, EAG, GAE, EGEA (SEQ ID NO: 81), EGE, EA, E, GE, EG, EKE or EKP.

In alternative embodiments, R1 is absent or is a sequence of 1 to 6 amino acid residues selected from A, E, G, L, K, F, P, S, T, W, Y, R, V, Sar, εLys, γGlu, βAsp, or βAla, or a corresponding D form thereof, or Peg3, Peg4, or 8-aminooctanoyl, or derivatives thereof.

In some embodiments, R1 is absent or is a sequence of 1 to 6 amino acid residue selected from A, E, G, L, K, F, P, S, T, W, Y, R, V or Sar, or a corresponding D form thereof.

For example, R1 may be absent or a sequence of 1 to 6 amino acid residues selected from A, E, G, K, S and Y, or a corresponding D-form thereof.

A lipophilic group ϕ may be covalently linked to the side chain of one or more of the residues in Y1, especially to the side chain of a lysine residue (which may be designated K*). It may be desirable that the residue bearing ϕ is at the N-terminus of Y1.

Examples of sequences for the group R1 include:

{d}Y, EGSE (SEQ ID NO: 82), AGSE (SEQ ID NO: 83), SASE (SEQ ID NO: 84), EYSE (SEQ ID NO: 85), GSE, ASE, ESSA (SEQ ID NO: 56), KGSA (SEQ ID NO: 86), AKGE (SEQ ID NO: 57), ASGE (SEQ ID NO: 87), ASSE (SEQ ID NO: 58), ASES (SEQ ID NO: 59), GSAE (SEQ ID NO: 60), ESSE (SEQ ID NO: 61), ESGA (SEQ ID NO: 62), SEG, GES, ESS, EGSA (SEQ ID NO: 63), ESE, EGE, ESA, SAE, SGA, YLEA (SEQ ID NO: 64), GSA, KEK, EKG, ES, RS, SR, AE, TE, KE, GE, FE, YE, AS, SE, RS, SR, SA, GE, S, Y and E.

In some embodiments, R1 is two amino acid residues in length, for example, AE, TE, KE, GE, FE, YE, AS, SE, SA, or GE; preferably AE, TE, KE, GE, FE, YE, SE, or GE.

In some embodiments, R1 is one amino acids in length, for example, E.

As mentioned above, a lipophilic group ϕ may be covalently linked to the side chain of one or more of the residues in Y1, especially to the side chain of a lysine residue (which may be designated K*), e.g. to yield a sequence K*GSA (SEQ ID NO: 325).

R2 may be absent or is a sequence of 1 to 8 amino acid residues selected from A, E, G, L, K, F, P, S, T, W, Y, R, V, Sar, εLys, γGlu, βAsp, or βAla, or a corresponding D form thereof; or Peg3, Peg4, or 8-aminooctanoyl, or derivatives thereof.

For example, R2 may be absent or a sequence of 1 to 8 amino acid residues selected from A, E, G, K, S, γGlu, Peg3 or 8-aminooctanoyl or selected from A, E, G, K and S.

When K is present in R2, it may be desirable that K is present at the C-terminus of R2.

A lipophilic group ϕ may be covalently linked to the side chain of one or more of the residues in Y2, especially to the side chain of a lysine residue. It may be desirable that the residue bearing is at the C-terminus of Y2.

Examples of sequences for the group R2 include:

EGASGSG (SEQ ID NO: 88), EGAGSG (SEQ ID NO: 89), EGASAG (SEQ ID NO: 90), EGAGAG (SEQ ID NO: 91), EGESGSG (SEQ ID NO: 92), EGEGSG (SEQ ID NO: 93), EGESAG (SEQ ID NO: 94), EGEGAG (SEQ ID NO: 95), EK[γGlu]AK (SEQ ID NO: 96), EGEGG (SEQ ID NO: 97), EGAGG (SEQ ID NO: 98), EGESS (SEQ ID NO: 99), GAESK (SEQ ID NO: 100), EGAK (SEQ ID NO: 101), EGEK (SEQ ID NO: 102), EGG, EGK, EGKK (SEQ ID NO: 103), EGS, EK, EGA, EGAK (SEQ ID NO: 101), EK[γGlu], EK[γGlu]-K (SEQ ID NO: 104), EGE-[Peg3, EGE

[Peg3]-K (SEQ ID NO: 105), EGE[Peg3][Peg3], EGE [Peg3][Peg3]-K (SEQ ID NO: 106), EGE[Peg3][Peg3] [Peg3], GESESE (SEQ ID NO: 107), GAESES (SEQ ID NO: 108), EGESES (SEQ ID NO: 109), EGESESK (SEQ ID NO: 110), EGE[Peg3]-ES (SEQ ID NO: 111), EGE[Peg3]-ESK (SEQ ID NO: 112), GESESE (SEQ ID NO: 107), EGE-[8-aminooctanoyl], EGE-[8-aminooctanoyl]-K (SEQ ID NO: 113), EGE-[8-aminooctanoyl]-EK (SEQ ID NO: 114), EGEGGG (SEQ ID NO: 115), EGEGGGK (SEQ ID NO: 116), EK[γGlu] GGG (SEQ ID NO: 117), EK[γGlu]GGGK (SEQ ID NO: 118), EGE-[8-aminooctanoyl]-E (SEQ ID NO: 119), GAES (SEQ ID NO: 65), EYGS (SEQ ID NO: 66), EGYA (SEQ ID NO: 67), EAGS (SEQ ID NO: 68), EAKS (SEQ ID NO: 69), EKSA (SEQ ID NO: 70), ESGA (SEQ ID NO: 62), EGGS (SEQ ID NO: 71), EGGA (SEQ ID NO: 72), ESSG (SEQ ID NO: 73), ESAG (SEQ ID NO: 74), GEES (SEQ ID NO: 75), AEES (SEQ ID NO: 76), ESEG (SEQ ID NO: 77), AEGS (SEQ ID NO: 78), ESGS (SEQ ID NO: 79), SEGA (SEQ ID NO: 80), SEG, EGK, ESG, EAG, GAE, EGEA (SEQ ID NO: 81), EGE, EA, E, S, GE, GEK, EG, EA, EKE and EKP.

Examples of sequences for the group R2 include:

EGASGSG (SEQ ID NO: 88), EGAGSG (SEQ ID NO: 89), EGASAG (SEQ ID NO: 90), EGAGAG (SEQ ID NO: 91), EGESGSG (SEQ ID NO: 92), EGEGSG (SEQ ID NO: 93), EGESAG (SEQ ID NO: 94), EGEGAG (SEQ ID NO: 95), EK[γGlu]AK (SEQ ID NO: 96), EK[γGlu]A (SEQ ID NO: 266), EGEGG (SEQ ID NO: 97), EGAGG (SEQ ID NO: 98), EGESS (SEQ ID NO: 99), GAESK (SEQ ID NO: 100), EGAK (SEQ ID NO: 101), EGEK (SEQ ID NO: 102), EGG, EGK, EGKK (SEQ ID NO: 103), EGS, EK, EGA, EGAK (SEQ ID NO: 101), EK[γGlu], EK[γGlu]-K (SEQ ID NO: 104), EGE[Peg3], EGE[Peg3]-K (SEQ ID NO: 105), EGE[Peg3][Peg3], EGE[Peg3][Peg3]-K (SEQ ID NO: 106), EGE[Peg3][Peg3][Peg3], EGE [Peg3][Peg3][Peg3]-K (SEQ ID NO: 120), GESESE (SEQ ID NO: 107), GAESES (SEQ ID NO: 108), EGESES (SEQ ID NO: 109), EGESESK (SEQ ID NO: 110), EGE[Peg3]-ES (SEQ ID NO: 111), EGE[Peg3]-ESK (SEQ ID NO: 112), GESESE (SEQ ID NO: 107), EGE-[8-aminooctanoyl], EGE-[8-aminooctanoyl]-K (SEQ ID NO: 113), EGE-[8-aminooctanoyl]-EK (SEQ ID NO: 114), EGEGGG (SEQ ID NO: 115), EGEGGGK (SEQ ID NO: 116), EK[γGlu]GGG (SEQ ID NO: 117), EK[γGlu]GGGK (SEQ ID NO: 118), EGE-[8-aminooctanoyl]-E (SEQ ID NO: 119), E[Peg3] [Peg3], E[Peg3][Peg3]-K, EA[Peg3][Peg3], EA[Peg3] [Peg3]-K, GAES (SEQ ID NO: 65), EYGS (SEQ ID NO: 66), EGYA (SEQ ID NO: 67), EAGS (SEQ ID NO: 68), EAKS (SEQ ID NO: 69), EKSA (SEQ ID NO: 70), ESGA (SEQ ID NO: 62), EGGS (SEQ ID NO: 71), EGGA (SEQ ID NO: 72), ESSG (SEQ ID NO: 73), ESAG (SEQ ID NO: 74), GEES (SEQ ID NO: 75), AEES (SEQ ID NO: 76), ESEG (SEQ ID NO: 77), AEGS (SEQ ID NO: 78), ESGS (SEQ ID NO: 79), SEGA (SEQ ID NO: 80), SEG, EGK, ESG, EAG, GAE, EGEA (SEQ ID NO: 81), EGE, EA, E, S, GE, GEK, EG, EA, EKE and EKP.

As mentioned above, a lipophilic group ϕ may be covalently linked to the side chain of one or more of the residues in Y2, especially the side chain of a lysine residue, e.g. to yield a sequence EK[γGlu]AK* (SEQ ID NO: 121), EGKK* (SEQ ID NO: 122), EK[γGlu]K* (SEQ ID NO: 123), EGE[Peg3]-K* (SEQ ID NO: 124), EGESESK* (SEQ ID NO: 125), EGE[Peg3]-ESK* (SEQ ID NO: 126), EGE-[8-aminooctanoyl]-K* (SEQ ID NO: 127), EGE-[8-aminooctanoyl]-EK* (SEQ ID NO: 128), EGEGGGK* (SEQ ID NO: 129), EK[γGlu]GGGK* (SEQ ID NO: 130), EGE [Peg3][Peg3]-K* (SEQ ID NO: 131), GAESK* (SEQ ID NO: 132), EGAK* (SEQ ID NO: 133), EGEK* (SEQ ID NO: 134), EGK* EGE[Peg3]-ESK* (SEQ ID NO: 135), GESESEK* (SEQ ID NO: 136), GEK* or EK*.

As mentioned above, a lipophilic group ϕ may be covalently linked to the side chain of one or more of the residues in Y2, especially the side chain of a lysine residue, e.g. to yield a sequence EK[γGlu]AK* (SEQ ID NO: 121), EGKK* (SEQ ID NO: 122), EK[γGlu]K* (SEQ ID NO: 123), EGE[Peg3]-K* (SEQ ID NO: 124), EGESESK* (SEQ ID NO: 125), EGE[Peg3]-ESK* (SEQ ID NO: 126), EGE-[8-aminooctanoyl]-K* (SEQ ID NO: 127), EGE-[8-aminooctanoyl]-EK* (SEQ ID NO: 128), EGEGGGK* (SEQ ID NO: 129), EK[γGlu]GGGK* (SEQ ID NO: 130), EGE [Peg3][Peg3]-K* (SEQ ID NO: 131), EGE[Peg3][Peg3] [Peg3]-K* (SEQ ID NO: 137), E[Peg3][Peg3]-K*, EA[Peg3][Peg3]-K*, GAESK* (SEQ ID NO: 132), EGAK* (SEQ ID NO: 133), EGEK* (SEQ ID NO: 134), EGK* EGE[Peg3]-ESK* (SEQ ID NO: 135), GESESEK* (SEQ ID NO: 136), GEK* or EK*.

Where R1 or R2 is one amino acid in length, it may be a D amino acid, e.g. {d}Y.

R1 and R2 may independently be present or absent. It may be desirable that R2 is present. Without wishing to be bound by any particular theory, it is believed that the presence of R1 and/or R2 may improve the stability of the compounds.

Preferred classes of compstatin analogues and exemplified compounds are discussed further below.

In a further aspect, the present invention provides a composition comprising a compstatin analogue of the present invention, or a pharmaceutically acceptable salt or solvate thereof, in admixture with a carrier. In some instances, the composition is a pharmaceutical composition and the carrier is a pharmaceutically acceptable carrier.

In a further aspect, the present invention provides a pharmaceutical composition comprising a compstatin analogue of the present invention, or a pharmaceutically acceptable salt or solvate thereof, in admixture with a pharmaceutically acceptable carrier, excipient or vehicle.

In a further aspect, the present invention provides a compstatin analogue of the present invention for use in therapy.

In a further aspect, the present invention provides a compstatin analogue of the present invention for use in a method of inhibiting complement activation. By way of example, inhibiting complement activation includes one or more biological activities selected from (1) binding to C3 protein, (2) binding to C3b protein and/or (3) inhibiting the cleavage of native C3 by C3 convertases. Examples of disease or condition that may be treated using the compstatin analogues of the present invention are discussed below.

In a further aspect, the present invention provides a compstatin analogue of the present invention for use in a method of inhibiting complement activation that occurs during cell or organ transplantation.

In a further aspect, the present invention provides a method of inhibiting complement activation for treating a subject in need thereof, the method comprising administering to the subject a compstatin analogue of the present invention thereby to inhibit complement activation in the subject. Examples of disease or condition that may be treated using the compstatin analogues of the present invention are discussed below.

In a further aspect, the present invention provides an ex vivo method of inhibiting complement activation during extracorporeal shunting of a physiological fluid, the method comprising contacting the physiological fluid with a compstatin of the present invention, thereby to inhibiting complement activation.

In a further aspect, the present invention provides the use of a compstatin analogue of the present invention in the preparation of a medicament for inhibiting complement activation. Examples of disease or condition that may be treated using the compstatin analogues of the present invention are discussed below.

Embodiments of the present invention will now be described by way of example and not limitation.

DETAILED DESCRIPTION

Figure 1A:
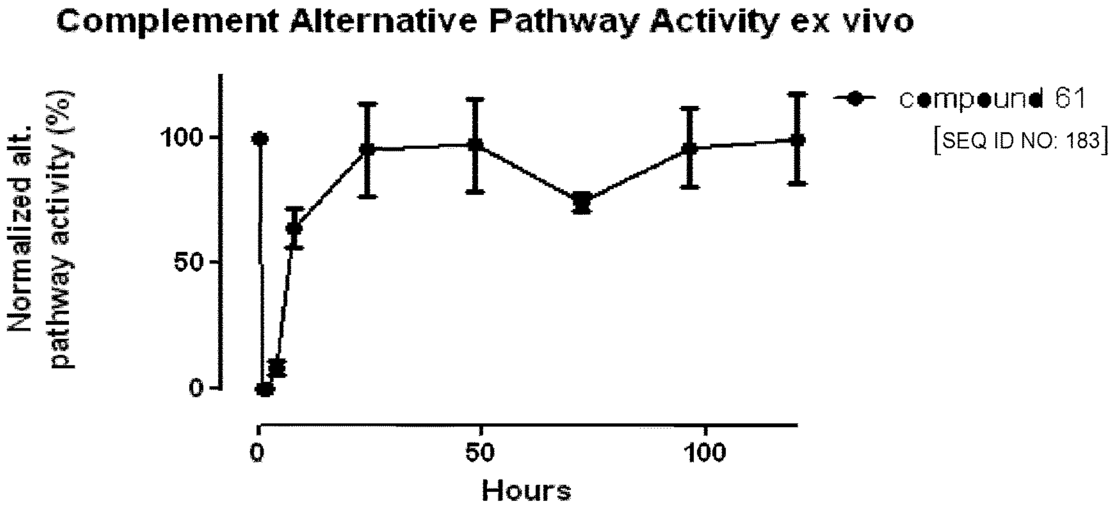
FIG. 1 (*a-f*): Normalized "ex vivo" activity of the alternative complement pathway over time after administration of a test compound at time 0 to one or two non-human primates. Compounds were given subcutaneously at a dose of 1840 nmol/kg. Complement activity (alternative pathway) was measured using the Wieslab kit. Activity was normalized using the predose (0) sample (set to 100%) and the negative control included in the kit. Normalized activity or average normalized activity for both animals and standard deviation is shown. (a) compound 61 (2 animals), (b) compound 123, compound 126 & comp 128, all with one animal per compound and Cp40 (2 animals), (c) compound 107, compound 111, compound 118 & compound 119 all with 2 animals per compound, (d) compound 104 & compound 106 with 2 animals per compound, (e) compound 54 (2 animals), and compound 122, compound 124, compound 139, and compound 140 all with 1 animal per compound, and (f) compound 141, compound 142, compound 127 and compound 130, all with one animal per compound.
Figure 1B:
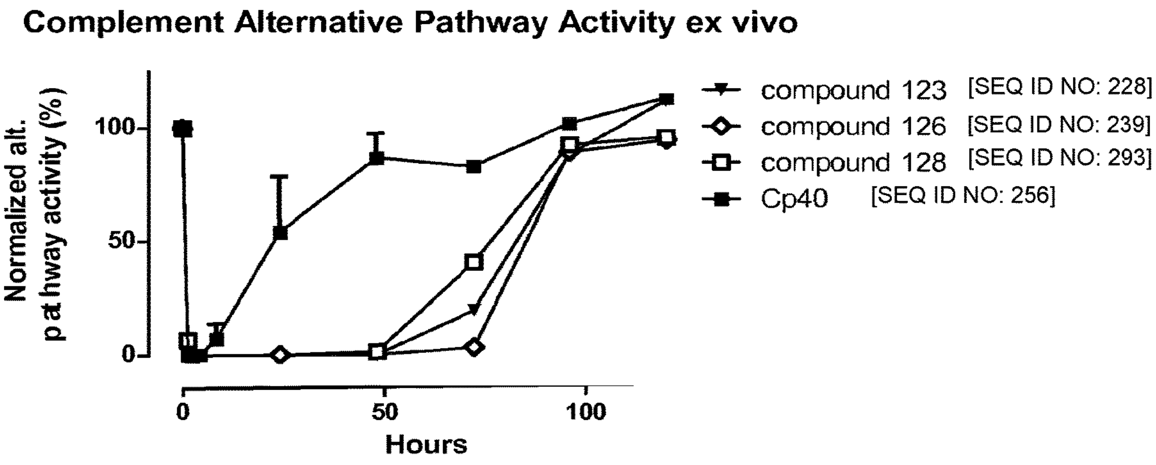
Figure 1C:
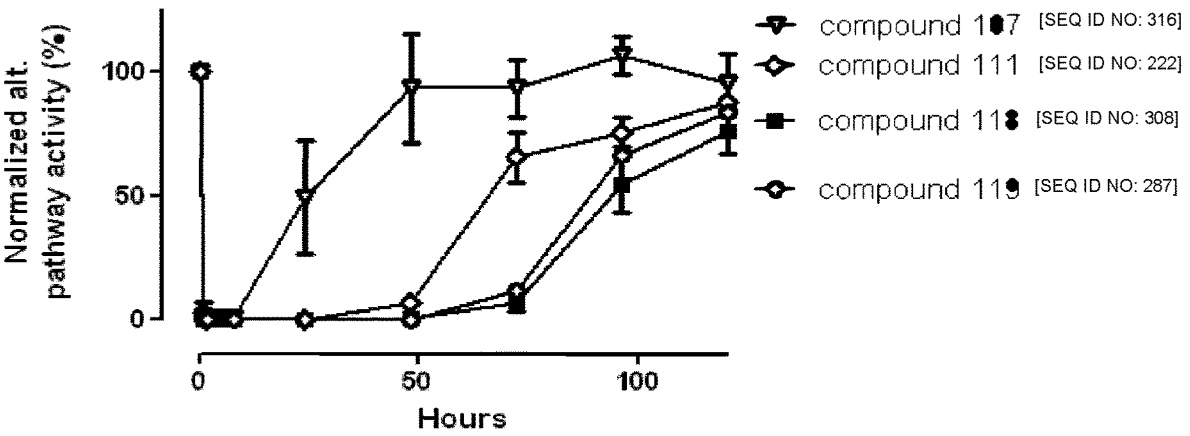
Figure 1D:
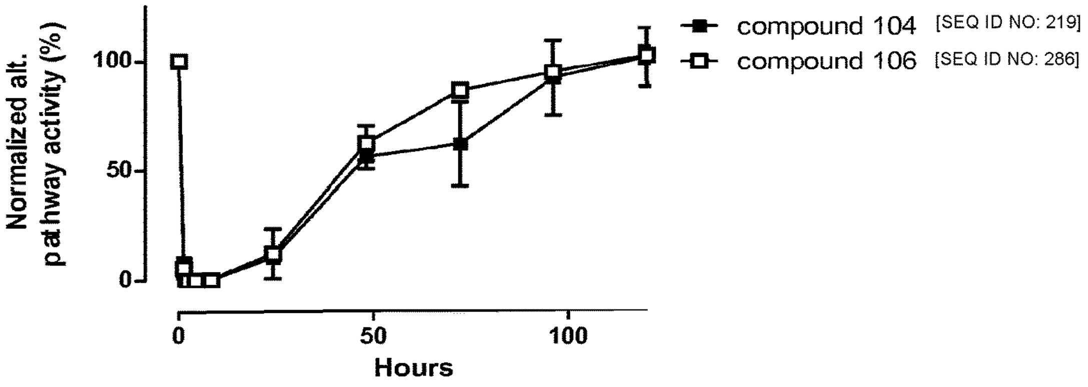

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Various publications, including patents, published applications, technical articles and scholarly articles are cited throughout the specification. Each of these cited publications is incorporated by reference herein, in its entirety.

Unless otherwise defined herein, scientific and technical terms used in this application shall have the meanings that are commonly understood by those of ordinary skill in the art. Generally, nomenclature used in connection with, and techniques of, chemistry, molecular biology, cell and cancer biology, immunology, microbiology, pharmacology, and protein and nucleic acid chemistry, described herein, are those well known and commonly used in the art.

Each embodiment of the invention described herein may be taken alone or in combination with one or more other embodiments of the invention.

Unless specified otherwise, the following definitions are provided for specific terms which are used in the present written description.

Definitions

Throughout this specification, the word "comprise", and grammatical variants thereof, such as "comprises" or "comprising", will be understood to imply the inclusion of a stated integer or component, or group of integers or components, but not the exclusion of any other integer or component, or group of integers or components.

The singular forms "a," "an," and "the" include the plurals unless the context clearly dictates otherwise.

The term "including" is used to mean "including but not limited to". "Including" and "including but not limited to" may be used interchangeably.

The terms "patient", "subject" and "individual" may be used interchangeably. A subject may be a mammal, including a human or a non-human mammal, such as a non-human primate (e.g. ape, Old World monkey or New World monkey), livestock animal (e.g. bovine or porcine), companion animal (e.g. canine or feline) or laboratory animal such as a rodent (e.g. mouse or rat).

Throughout the present description and claims the conventional three-letter and one-letter codes for naturally occurring amino acids are used, i.e. A (Ala), G (Gly), L (Leu), I (Ile), V (Val), F (Phe), W (Trp), S (Ser), T (Thr), Y (Tyr), N (Asn), Q (Gln), D (Asp), E (Glu), K (Lys), R (Arg), H (His), M (Met), C (Cys) and P (Pro); as well as generally accepted three-letter codes for other α-amino acids, such as norleucine (Nle), sarcosine (Sar), α-aminoisobutyric acid (Aib), 2,3-diaminopropanoic acid (Dap), 2,4-diaminobutanoic acid (Dab) and 2,5-diaminopentanoic acid (ornithine; Orn), 1-methyl-tryptophan(1-Me-Trp, 1Me-Trp or 1MeTrp), 1-formyl-tryptophan (1-For-Trp or 1For-Trp or 1ForTrp), 1-naphathalin (1-Nal or 1Nal), 2-naphathalin (2-Nal or 2Nal), 5-methyl-tryptophan (5-Me-Trp or 5Me-Trp or 5MeTrp), p-Benzoyl-phenylalanine (Bpa) 2-indanylglycine (2Igl or 2-Igl). Other α-amino acids may be shown in square brackets "[ ]" (e.g. "[Nle]") when used in a general formula or sequence in the present specification, especially when the rest of the formula or sequence is shown using the single letter code. The 20 "naturally occurring" amino acids listed above are those which are encoded by the standard genetic code, and may also be referred to as "proteinogenic" amino acids.

Gamma-Glu and beta-Asp, also referred to as γGlu (γ-Glu) and βAsp (β-Asp) (or isoGlu and isoAsp), refers to glutamate or aspartate participating in peptide bonds via the γ- or β-carboxylic acid respectively (normally regarded as the side chain carboxyl groups), rather than the conventional configuration. Similarly, εLys or isoLys refers to lysine participating in a peptide bond via the epsilon amino group (normally regarded as the side chain amino group) rather than the alpha amino group.

Beta-Ala, also referred to as β-Ala or βAla, refers to 3-aminopropanoic acid.

Peg3 refers to a residue of 8-amino-3,6-dioxaoctanoic acid (also known as {2-[2-aminoethoxy]ethoxy}acetic acid) and Peg4 refers to a residue of 11-amino-3,6,9-trioxaundecanoic acid. The residue may also be denoted [8-Amino-3,6-dioxaoctanoyl].

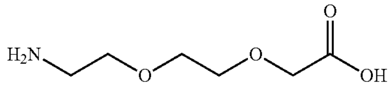 [SMILES: NCCOCCOCC(=O)O]

8-amino-3,6-dioxaoctanoic acid (Peg3)

Unless otherwise specified, amino acid residues in peptides of the invention are of the L-configuration. However, in some instances, D-configuration amino acids may be incorporated.

In the present context, an amino acid code written with a small letter represents the D-configuration of said amino acid, e.g. "k" represents the D-configuration of lysine (K), or a D-configuration amino acid may be written as (d)X or {d}X, where X is the amino acid, e.g. (d)Y or {d}Y represents the D-configuration of tyrosine (Y).

Cysteine residues shown as "C(1)" indicate that their sid-chains participate in a disulphide bond. Thus there will typically be two such residues in any given molecule.

The terminal groups present at the N- and C-termini of the peptide backbone are designated Y1 and Y2 respectively. Thus Y1 is bonded to the nitrogen atom of the N-terminal amino group and Y2 is bonded to the C-terminal carbonyl carbon atom.

Y1=hydrogen (also indicated as "H—" or "Hy-") indicates a hydrogen atom, corresponding to the presence of a free primary or secondary amino group at the N-terminus. Y1=acetyl ("Ac") indicates the presence of an N-terminal secondary acetyl amide group.

Y2="OH" or "$NH_2$" indicates the presence of a carboxy (COOH) group or an amido ($CONH_2$) group at the C-terminus of the molecule.

Either or both of Y1 and Y2 may alternatively be a lipophilic group ϕ. Typicaly, only one of Y1 or Y2 will be a lipophilic group ϕ.

In some embodiments, whether or not the molecule comprises a lipophilic group elsewhere, Y2 is $NH_2$ or OH. In some embodiments, Y1 is hydrogen or acetyl, and Y2 is OH or $NH_2$.

In some embodiments, whether or not the molecule comprises a lipophilic group elsewhere, Y2 is $NH_2$. In some embodiments, Y1 is hydrogen or acetyl, and Y2 is $NH_2$.

In some embodiments, whether or not the molecule comprises a lipophilic group elsewhere, Y2 is $NH_2$ amd Y1 is acetyl.

Various terms relating to the methods and other aspects of the present invention are used throughout the specification and claims. Such terms are to be given their ordinary meaning in the art unless otherwise indicated. Other specifically defined terms are to be construed in a manner consistent with the definition provided herein. The term "about" as used herein when referring to a measurable value such as an amount, a temporal duration, and the like, is meant to encompass variations of ±20% or ±10%, in some embodiments ±5%, in some embodiments ±1%, and in some embodiments ±0.1% from the specified value, as such variations are appropriate to make and used the disclosed compounds and compositions.

The term "full length compstatin" as used herein refers to a 27 amino acid peptide having the sequence IC(1)VVQDWGHHRC(1)TAGHMANLTSHASAI (SEQ ID NO: 138), wherein C(1) denotes the cysteine residue linked by a disulphide bond. As described above, a truncated form of full length compstatin, the tridecapeptide $Ile^1$-$Cys^2$-$Val^3$-$Val^4$-$Gln^5$-$Asp^6$-$Trp^7$-$Gly^8$-$His^9$-$His^{10}$-$Arg^{11}$-$Cys^{12}$-$Thr^{13}$-$NH_2$ (SEQ ID NO: 1) linked by a disulphide bond between the cysteine residues at positions 2 and 12 retains the activity of the full length peptide. An N-terminally acetylated version of this tridecapeptide peptide is referred to herein as "Ac-compstatin".

The term "compstatin analogue" refers to a modified Ac-compstatin comprising one or more substitutions of natural and unnatural amino acids, or amino acid analogs, as well as modifications within or between various amino acids, as described in greater detail herein. A compstatin analogue may comprise about 1, 2, 3, 4 or 5 amino acid modifications relative to Ac-compstatin. A compstatin analogue may comprise 5, 6, 7, 8 or more amino acid modifications relative to Ac-compstatin. A compstatin analogue may comprise about 5, 6, 7 or 8 amino acid modifications relative to Ac-compstatin.

The term "analogue" is frequently used for a protein or peptide in question before it undergoes further chemical modification (derivatisation), and in particular acylation. The product resulting from such a chemical modification (derivatisation) is sometimes referred to as a "derivative" or "acylated analogue". However, in the context of this application, the term "analogue" designates analogues of Ac-compstatin as well as (the acylated) derivatives of such Ac-compstatin analogues.

When referring to the position of amino acids or analogs within Ac-compstatin or compstatin analogs, the positions are numbered from 1 (Ile in compstatin) to 13 (Thr in compstatin). For example, the Gly residue occupies "position 8." As used to describe the compstatin analogue peptides of the present invention "C(1)" denotes a disulphide bond between the respective cysteine residues in the compstatin analogue.

The terms "pharmaceutically active" and "biologically active" refer to the ability of the compounds of the invention to bind C3 or fragments thereof and inhibit complement activation. The biological activities of compstatin analogs may be measured by one or more of several art-recognized assays, as described in greater detail herein.

As used herein, "L-amino acid" refers to any of the naturally occurring levorotatory alpha-amino acids normally present in proteins or the alkyl esters of those alpha-amino acids. The term "D-amino acid" refers to dextrorotatory alpha-amino acids. Unless specified otherwise, all amino acids referred to herein are L-amino acids.

"Hydrophobic" or "non-polar" are used synonymously herein, and refer to any inter- or intra-molecular interaction not characterized by a dipole.

As used herein, "pharmaceutically-acceptable salts" refers to derivatives of the disclosed compounds wherein the parent compound is modified by making acid or base salts thereof. Examples of pharmaceutically-acceptable salts include, but are not limited to, mineral or organic acid salts of basic residues such as amines; alkali or organic salts of acidic residues such as carboxylic acids; and the like. Thus, the term "acid addition salt" refers to the corresponding salt derivative of a parent compound that has been prepared by the addition of an acid. The pharmaceutically-acceptable salts include the conventional salts or the quaternary ammonium salts of the parent compound formed, for example, from inorganic or organic acids. For example, such conventional salts include, but are not limited to, those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Certain acidic or basic compounds of the present invention may exist as zwitterions. All forms of the compounds, including free acid, free base, and zwitterions, are contemplated to be within the scope of the present invention.

Compstatin Analogues

Ac-Compstatin, an N-terminally acetylated 13 amino acid peptide, is known to bind to C3 and prevent C3 convertase-mediated cleavage. Since its discovery by phage display, modification to the 13 amino acid Ac-Compstatin sequence has been carried out in an effort to find analogues with increased biological activity. However, in the core sequence between the two cysteines residues at positions 2 and 12, alanine scanning experiments have previously produced analogues showing only modest improvements in biological activity, with few modifications being tolerated. The modifications include changing the valine at position 4 to tryptophan, or a tryptophan analogue, that leads to an increase in biological activity and changing the histidine at position 9 to alanine or analogs thereof.

In particular, previous attempts to introduce modifications to the valine residue at position 3, replacing it with glycine, alanine, D-valine or leucine have been shown to lead to a decrease in biological activity. In contrast to these prior art findings, the present inventors surprisingly found that a change of valine to isoleucine is well tolerated and provides improvements in biological activity, as shown in the Examples below.

Without wishing to be bound by any specific theory, the present inventors reasoned that this modification might be combined with introduction of one or more polar or charged amino acids in the core sequence and may be used as an approach to increase the ability of the compstatin peptides to solubilize. Initially, glutamic acid or serine at position 9 were combined with valine 3 and led to a decrease in activity compared to the reference sequence 4W9A. However, when these changes were combined with the introduction of isoleucine at position 3, a surprising increase in biological activity was observed, in particular for the combination of isoleucine at position 3 and glutamic acid at position 9. This observation correlates with improved binding to C3 as measured by surface plasmon resonance (SPR), see Table 7.

In a further series of experiments to validate these findings, compstatin peptides with glutamic acid at position 9 are combined with different substitutions in position 3 which would normally be considered "conservative" replacements for isoleucine, again showing that the peptides with isoleucine at position 3 are most active.

Taken together, these experiments show that replacing the valine residue at position 3 with isoleucine surprisingly provides compstatin peptides having increased biological activity and improved binding to C3. Furthermore, the experiments surprisingly demonstrate that these changes can be readily combined with other modifications in the core sequence of the compstatin analogues and with addition of N and C-terminal sequences, for example for improving the solubility of the compstatin peptides, e.g. at higher concentrations.

Introduction of isoleucine instead of valine at position 3 of a further prior art compound designated "Cp40" (Qu et al., Immunobiology 2013, 281(4): 496-505; also referred to in that paper as "peptide 14) also increased the binding affinity to C3 as measured by SPR.

In any embodiment X1 may be Y, I or F. In any embodiment, X4 may be W, V, 1-Nal, 2-Nal or 1-Me-Trp. In any embodiment, X6 may be E or D. In any embodiment, X9 may be A, E, D, K or S. In any embodiment, X13 may be T, S, E, I, Sar, K, or G. In any embodiment, X13 may be T, I, S, E, K or Sar. In any embodiment, X13 may be T, S, E or Sar.

Lipophilic Substituents

The compstatin analogues may bear a lipophilic group, designated $\phi$.

The lipophilic group may be covalently linked to the N-terminus and/or the C terminus of the molecule, i.e. Y1 may be $\phi$ (in place of H or Ac) and/or Y2 may be $\phi$ (in place of OH or NH2).

Additionally or alternatively, the lipophilic group may be covalently linked to the side chain of an amino acid residue within the analogue. The residue may be part of R1, R2 or the compstatin analogue portion X1-X13 of the molecule.

The lipophilic group $\phi$ is typically attached via an acyl group. The modification may therefore be termed acylation but can also be refered to as lipidation.

The lipophilic group includes a long chain alkylene group derived from a fatty acid, termed $Z^1$ herein and referred to as the lipophilic substituent. Without wishing to be bound by theory, it is believed that a lipophilic substituent binds plasma proteins (e.g. albumin) in the blood stream, thus shielding the compounds employed in the context of the invention from enzymatic degradation, and thereby enhancing the half-life of the compounds. The lipophilic substituent may also modulate the potency of the compound.

$Z^1$ may be attached directly to the amino acid sequence (including the R1 and R2 extensions, or as Y1) or via a spacer $Z^2$ as defined herein.

In other words, $\phi$ may be $Z^1$— or $Z^1$—$Z^2$—.

Where Y1 is $\phi$, $\phi$ is preferably $Z^1$—.

Where the lipophilic group $\phi$ is linked to an amino acid side chain (i.e. where Y1 is hydrogen or Ac) $\phi$ may preferably be $Z^1$—$Z^2$—.

In certain embodiments, only one amino acid side chain is conjugated to a lipophilic substituent. In other embodiments, two amino acid side chains are each conjugated to a lipophilic substituent. In yet further embodiments, three or even more amino acid side chains are each conjugated to a lipophilic substituent. When a compound contains two or more lipophilic substituents, they may be the same or different substituents.

In certain embodiments, only one lipophilic group $\phi$ is present in the molecule.

The term "conjugated" is used here to describe the covalent attachment of one identifiable chemical moiety to another, and the structural relationship between such moieties. It should not be taken to imply any particular method of synthesis. The one or more spacers $Z^2$, when present, are used to provide a spacing between the compound and the lipophilic substituent $Z^1$.

A lipophilic substituent may be attached to an N-terminal nitrogen, or to an amino acid side chain or to a spacer via an ester, a sulphonyl ester, a thioester, an amide or a sulphonamide. Accordingly, it will be understood that a lipophilic substituent may include an acyl group, a sulphonyl group, an N atom, an O atom or an S atom which forms part of the ester, sulphonyl ester, thioester, amide or sulphonamide.

Suitably, an acyl group in the lipophilic substituent forms part of an amide or ester with the N-terminal nitrogen, or amino acid side chain, or the spacer. The lipophilic substituent may include a hydrocarbon chain having 10 to 24 carbon (C) atoms, e.g. 10 to 22 C atoms, e.g. 10 to 20 C atoms. Preferably, it has at least 11 C atoms, and preferably it has 18 C atoms or fewer. For example, the hydrocarbon chain may contain 12, 13, 14, 15, 16, 17 or 18 carbon atoms. The hydrocarbon chain may be linear or branched and may be saturated or unsaturated.

The hydrocarbon chain may incorporate a phenylene or piperazinylene moiety in its length as, for example, shown below (wherein --- represents the points of attachment within the chain). These groups should be "counted" as 4 carbon atoms in the chain length.

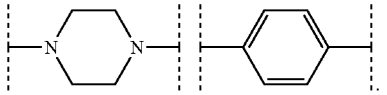

From the discussion above, it will be understood that the hydrocarbon chain may be substituted with a moiety which forms part of the attachment to the amino acid side chain or the spacer, for example an acyl group, a sulphonyl group, an N atom, an O atom or an S atom. Most preferably, the hydrocarbon chain is substituted with an acyl group, and accordingly the hydrocarbon chain may be part of an alkanoyl group, for example a dodecanoyl, 2-butyloctanoyl, tetradecanoyl, hexadecanoyl, heptadecanoyl, octadecanoyl or eicosanoyl group. Alternatively, $Z^1$ groups are derived from long-chain saturated α,ω-dicarboxylic acids of formula HOOC—$(CH_2)_{12-22}$—COOH, preferably from long-chain saturated α,ω-dicarboxylic acids having an even number of carbon atoms in the aliphatic chain.

In other words, $Z^1$ may be A-$C_{12-22}$alkylene-(CO)—, where A is H or —COOH, and wherein the akylene may be linear or branched and may be saturated or unsaturated, and may optionally incorporate a phenylene or piperazinylene moiety in its length.

For example, $Z^1$ may be:

Dodecanoyl i.e. H—$(CH_2)_{11}$—(CO)—;

Tetradecanoyl i.e. H—$(CH_2)_{13}$—(CO)—;

Hexadecanoyl, i.e. H—$(CH_2)_{15}$—(CO)—;

13-carboxytridecanoyl, i.e. HOOC—$(CH_2)_{12}$—(CO)—;

15-carboxypentadecanoyl, i.e. HOOC—$(CH_2)_{14}$—(CO)—;

17-carboxyheptadecanoyl, i.e. HOOC—$(CH_2)_{16}$—(CO)—;

19-carboxynonadecanoyl, i.e. HOOC—$(CH_2)_{18}$—(CO)—; or 21-carboxyheneicosanoyl, i.e. HOOC—$(CH_2)_{20}$—(CO)—

The carboxylic acid, if present, may be replaced by a bioisotere, phosphate or sulfonate. Suitable bioisoteres for carboxylic acids are known in the art and include tetrazole, acylsulfomides, acylhydroxylamine, and squaric acid derivatives.

As mentioned above, the lipophilic substituent $Z^1$ may be conjugated to the amino acid side chain or N-terminal nitrogen by one or more spacers $Z^2$.

When present, the spacer is attached to the lipophilic substituent and to the amino acid side chain or N-terminal nitrogen. The spacer may be attached to the lipophilic substituent and to the amino acid side chain independently by an ester, a sulphonyl ester, a thioester, an amide or a sulphonamide. Accordingly, it may include two moieties independently selected from acyl, sulphonyl, an N atom, an O atom or an S atom. The spacer may consist of a linear $C_{1-10}$hydrocarbon chain or more preferably a linear $C_{1-5}$ hydrocarbon chain. Furthermore the spacer can be substituted with one or more substituents selected from $C_{1-6}$ alkyl, $C_{1-6}$ alkyl amine, $C_{1-6}$ alkyl hydroxy and $C_{1-6}$ alkyl carboxy.

The spacer may be, for example, a residue of any naturally occurring or unnatural amino acid. For example, the spacer may be a residue of Gly, Pro, Ala, Val, Leu, Ile, Met, Cys, Phe, Tyr, Trp, His, Lys, Arg, Gln, Asn, Glu, Asp, γ-Glu, β-Asp, ε-Lys, Asp, Ser, Thr, Dapa, Gaba, Aib, β-Ala (i.e., 3-aminopropanoyl), 4-aminobutanoyl, 5-aminopentanoyl, 6-aminohexanoyl, 7-aminoheptanoyl, 8-aminooctanoyl, 9-aminononanoyl, 10-aminodecanoyl, 8-amino-3,6-dioxaoctanoyl. In certain embodiments, the spacer is a residue of Glu, γ-Glu, ε-Lys, β-Ala (i.e., 3-aminopropanoyl), 4-aminobutanoyl, 8-aminooctanoyl or 8-amino-3,6-dioxaoctanoyl (Peg3), 11-amino-3,6,9-trioxaundecanoic acid (Peg4) or (piperazine-1-yl)-carboxylic acid. In the present invention, γGlu and isoGlu are used interchangeably.

$Z^2$ is suitably a sequence of 1 to 6 residues of compounds selected from γGlu, βAsp, D, E, K, Orn, S, T, A, βAla, G, P, V, L, I, Y, Q, N, Dapa, Gaba, or Aib, or a corresponding D form thereof, 5-aminopentanoyl, 6-aminohexanoyl, 7-aminoheptanoyl, 8-aminooctanoyl, 9-aminononanoyl, and 10-aminodecanoyl. 8-amino-3,6-dioxaoctanoic acid (Peg3), 11-amino-3,6,9-trioxaundecanoic acid (Peg4) or (piperazine-1-yl)-carboxylic acid.

For example, $Z^2$ may be, or may comprise:

[yGlu];

[yGlu][Peg3][Peg3]-;

[(Piperazine-1-yl)-acetyl][Peg3][Peg3];

[yGlu]-G-[yGlu];

[yGlu]-K-[yGlu];

(SEQ ID NO: 139)
[YGlu]-KG-[yGlu];
or

[yGlu]-G-[Peg3][yGlu][Peg3].

$Z^2$ is suitably bound at each side by amide linkage. Other suitable linkages may be used, with the commensurate atom replacement; for example sulfinamide, sulfonamide, or ester linkages or amino, ether, or thioether linkages are envisaged.

In other words, in some aspects the lipophilic group ϕ is $Z^1$— or $Z^1$—$Z^2$—; wherein $Z^1$ is A-$C_{12-22}$alkylene-(CO)—;

where A is H or —COOH, and wherein the akylene may be linear or branched and may be saturated or unsaturated, and may optionally incorporate a phenylene or piperazinylene moiety in its length; and $Z^2$ is a sequence of 1 to 6 of residues of compounds selected from γ-Glu, βAsp, D, E, K, Orn, S, T, A, β-Ala, G, P, V, L, I, Y, Q, N, Dapa, Gaba, or Aib, or a correspdoning D form thereof, 5-aminopentanoyl, 6-aminohexanoyl, 7-aminoheptanoyl, 8-aminooctanoyl, 9-aminononanoyl, and 10-aminodecanoyl. 8-amino-3,6-dioxaoctanoic acid (Peg3), 11-amino-3,6,9-trioxaundecanoic acid (Peg4) or (piperazine-1-yl)-carboxylic acid, e.g. a linker selected from

[Glu],

[yGlu][Peg3][Peg3] -;

[(Piperazine-1-yl)-acetyl][Peg3][Peg3];

[YGlu]-G-[yGlu];

[YGlu)-K-[yGlu];

-continued (SEQ ID NO: 139)

[YGlu]-KG-[yGlu];
and

[YGlu]-G-[Peg3][yGlu][Peg3].

The amino acid side chain to which the lipophilic substituent is conjugated typically includes a carboxy, hydroxyl, thiol, amide or amine group, for forming an ester, a sulphonyl ester, a thioester, an amide, or a sulphonamide with the spacer or lipophilic substituent. An amide linkage may be particularly preferred, and thus the amino acid may be any amino acid having an amine group in its side chain, although it will be clear that side chains having other functional groups are contemplated. Thus, the amino acid side chain may be a side chain of a Glu, Lys, Ser, Cys, Dbu, Dpr or Orn residue. For example, it may be a side chain of a Lys, Glu or Cys residue. Where two or more side chains carry a lipophilic substituent, they may be independently selected from those residues.

Typically, the amino acid side chain is a side chain of a Lys residue.

An example of a lipophilic substituent comprising a lipophilic moiety $Z^1$ and spacer $Z^2$ is shown in the formula below:

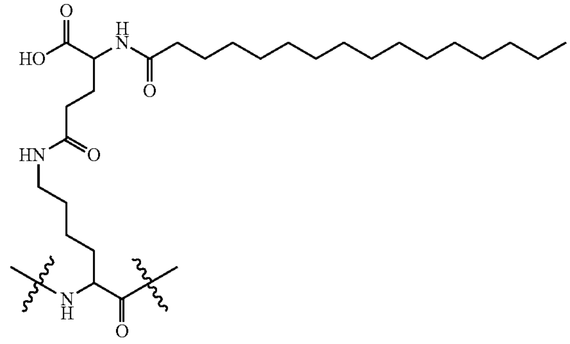 [SMILES: *NC(CCCCNC(=O)CCC(NC(=O)CCCCCCCCCCCCCCC)C(=O)O)C(*)=O]

Here, the side chain of a Lys residue is covalently attached to a γGlu spacer ($Z^2$) via an amide linkage. A hexadecanoyl group ($Z^1$) is covalently attached to the γGlu spacer via an amide linkage. This combination of lipophilic moiety and spacer, conjugated to a Lys residue, may be referred to by the short-hand notation K(Hexadecanoyl-γGlu), e.g., when shown in formulae of specific compounds. γGlu can also be referred to as isoGlu, and a hexadecanoyl group as a palmitoyl group. Thus it will be apparent that the notation (Hexadecanoyl-γGlu) is equivalent to the notations (isoGlu (Palm)) or (isoGlu(Palmitoyl)) as used for example in PCT/GB2008/004121.

Alternative $Z^1$ groups are derived from long-chain saturated α,ω-dicarboxylic acids of formula HOOC—$(CH_2)_{12-22}$—COOH as exemplified below

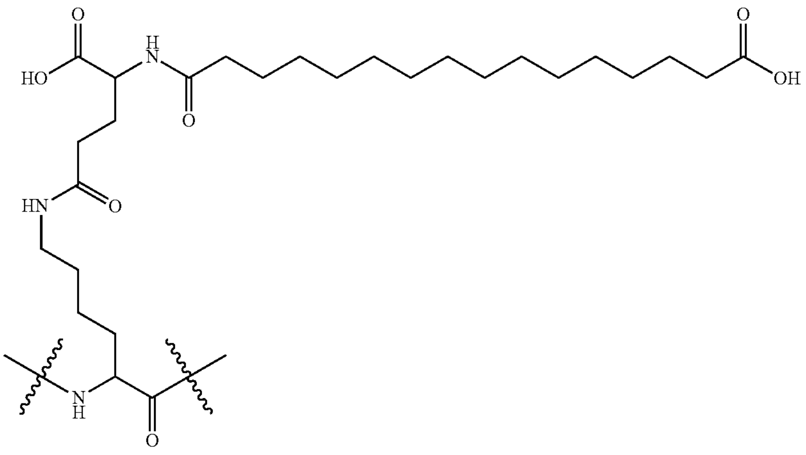 [SMILES: *NC(CCCCNC(=O)CCC(NC(=O)CCCCCCCCCCCCCCC(=O)O)C(=O)O)C(*)=O]

Here, the side chain of a Lys residue is covalently attached to a γGlu spacer ($Z^2$) via an amide linkage. A 15-carboxy-pentadecanoyl group ($Z^1$) is covalently attached to the γGlu spacer via an amide linkage. This combination of lipophilic moiety and spacer, conjugated to a Lys residue, may be referred to by the short-hand notation K(15-carboxypentadecanoyl-γ-Glu), e.g., when shown in formulae of specific compounds. γGlu can also be referred to as isoGlu.

Certain preferred ϕ groups ($Z^1$— and $Z^1$—$Z^2$—) include:

[15-Carboxy-pentadecanoyl];
[15-carboxy-pentadecanoyl][γGlu],
[15-carboxy-pentadecanoyl][γGlu][Peg3][Peg3];
[19-carboxy-nonadecanoyl][γGlu][Peg3][Peg3];
[15-carboxy-pentadecanoyl][(Piperazine-1-yl)-acetyl][Peg3][Peg3];
[17-carboxy-heptadecanoyl][γGlu]G[γGlu];
[17-carboxy-heptadecanoyl][γGlu]K[γGlu];
[17-carboxy-heptadecanoyl][γGlu]KG[γGlu] (SEQ ID NO: 267);
[17-carboxy-heptadecanoyl][γGlu]G[Peg3][γGlu][Peg3];
[15-carboxy-pentadecanoyl][γGlu]G[γGlu];
[17-carboxy-heptadecanoyl];
[17-carboxy-heptadecanoyl][γGlu]
[19-carboxy-nonadecanoyl][γGlu]G[γGlu]; and
[17-carboxy-heptadecanoyl][γGlu][Peg3][Peg3].

Illustrative structures of ϕ groups ($Z^1$— and $Z^1$—$Z^2$—) are shown below, where the wavy line indicates the linkage to the peptide (to an amino acid side chain, N-terminal nitrogen, or C-terminal carbon):

[19-carboxy-nonadecanoyl][γGlu]G[γGlu]:
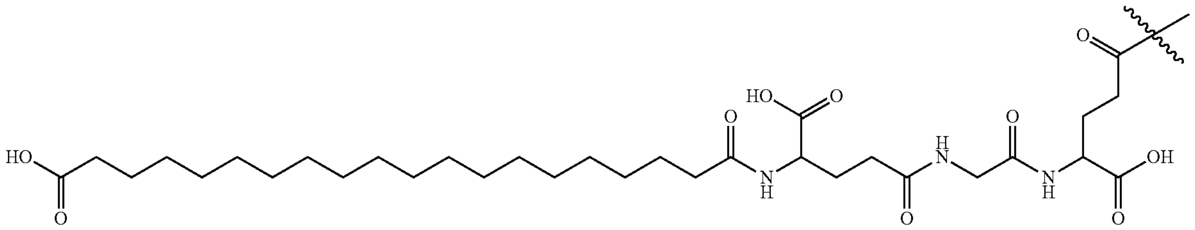
[17-carboxy-heptadecanoyl][γGlu]G[γGlu]:
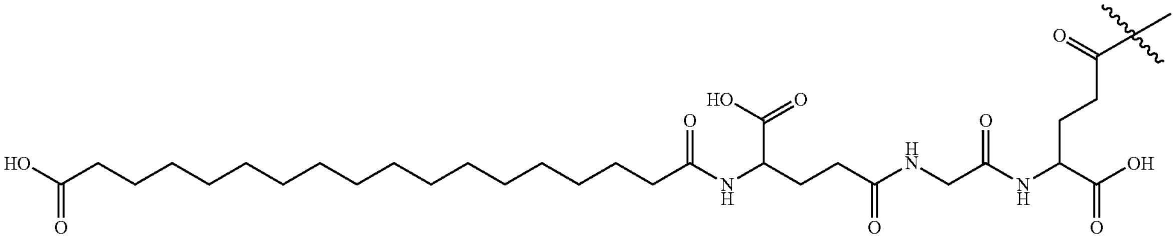
[15-carboxy-pentadecanoyl]-:
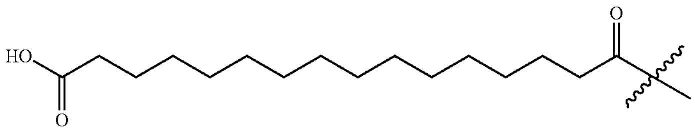
[17-carboxy-heptadecanoyl]-:
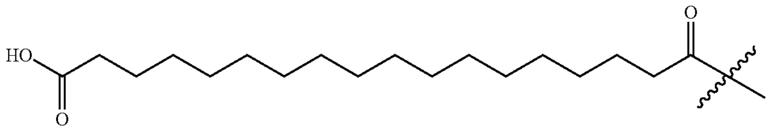
[(15-carboxy-pentadecanoyl)-[(Piperazine-1-yl)-acetyl][Peg3][Peg3]:
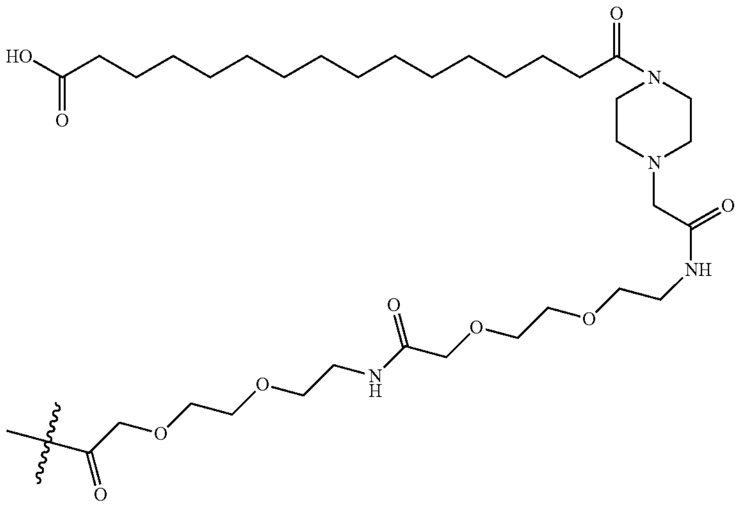
[17-carboxy-heptadecanoyl][γGlu]:
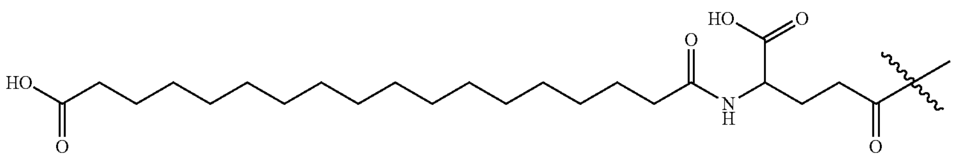

-continued

[17-carboxy-heptadecanoyl][γGlu]G[Peg3][γGlu][Peg3]:

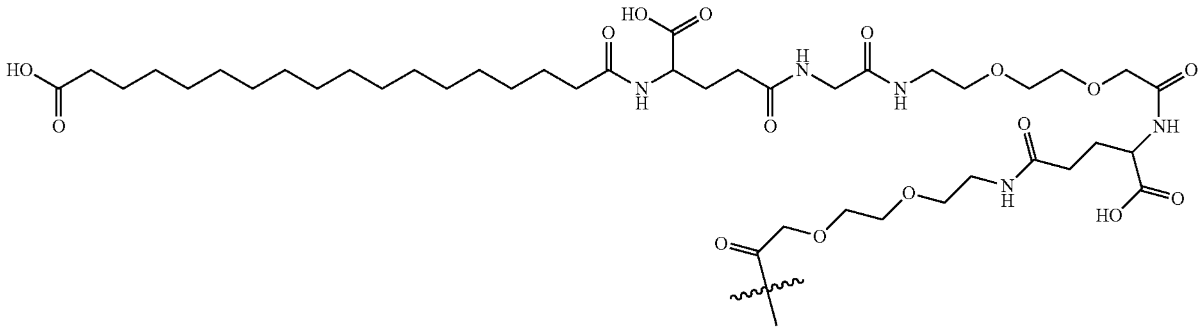

[17-carboxy-heptadecanoyl][γGlu]KG[γGlu] (SEQ ID NO: 267):

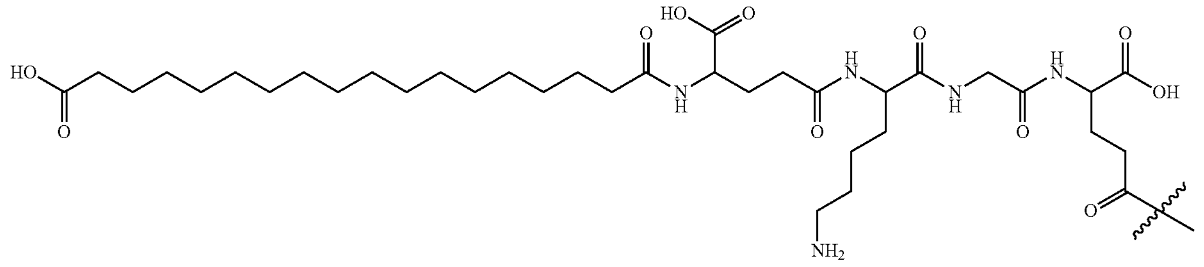

[17-carboxy-heptadecanoyl][γGlu]K[γGlu]:

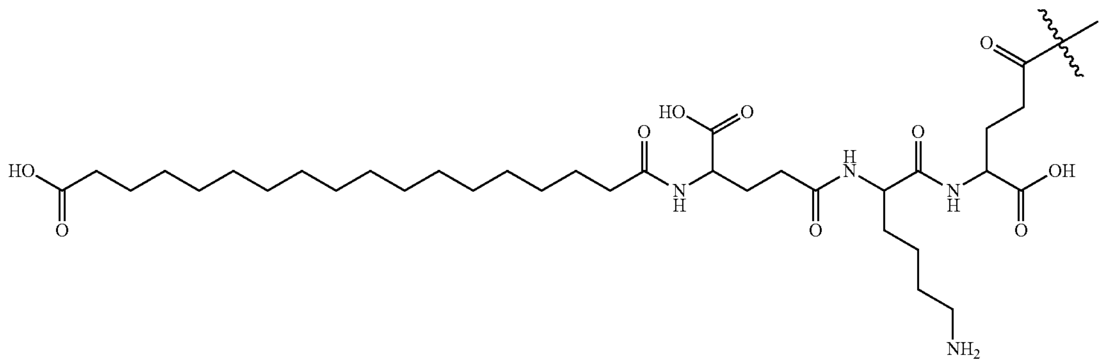

[17-carboxy-heptadecanoyl][γGlu][Peg3][Peg3]:

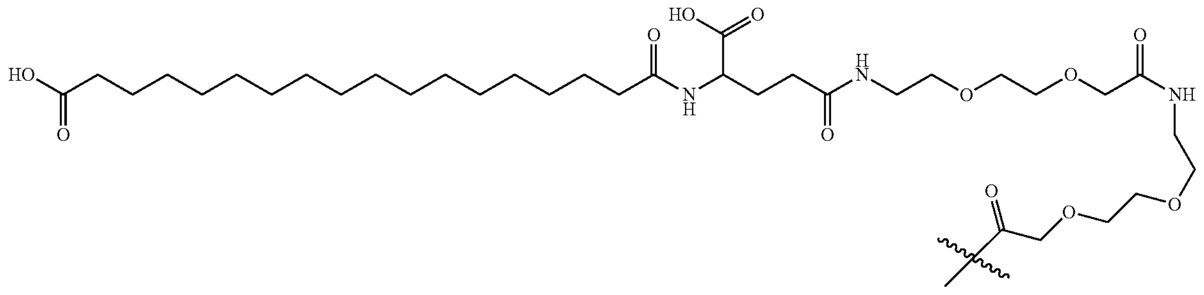

The skilled person will be well aware of suitable techniques for preparing the compounds employed in the context of the invention. For examples of suitable chemistry, see WO98/08871, WO00/55184, WO00/55119, Madsen et al., J. Med. Chem. 50:6126-32 (2007), and Knudsen et al., J. Med Chem. 43:1664-1669 (2000), incorporated herein by reference.

In some embodiments, the compstatin analogue has a lipophilic group ϕ as described above conjugated to an amino acid at one or more of positions corresponding to positions 1, 3, 4, 5, 6, 7, 8, 9, 10, 11 or 13 of the compstatin-like sequence, i.e. positions X1-X13.

In certain embodiments, the compstatin analogue has a lipophilic substituent as described above conjugated to an amino acid at one or more of positions corresponding to positions X1, X11 or X13, or to an amino acid within R1 or R2, or at the N-terminus as group Y1.

For C-terminal acylation or lipidation of peptides, well-established conjugation strategies have been developed. For example, such conjugation could be performed by click chemistry (i.e. the biorthogonal azide-alkyne conjugation reaction catalyzed by Cu(I)) or by other conjugation strategies known to the person skilled in the art of peptide chemistry.

The compstatin analogue may comprise one of the following sequences:

(SEQ ID NO: 35)
IC(1)IWQDWGAHRC(1)T (SEQ ID NO: 41)
IC(1)IWQDWGEHRC(1)T (SEQ ID NO: 140)
ESSAIC(1)IWQDWGEHRC(1)T (SEQ ID NO: 141)
IC(1)|[1MeTrp]QDWGEHRC(1)T (SEQ ID NO: 43)
IC(1)IWQDWGKHRC(1)T (SEQ ID NO: 45)
IC(1)IWQDWGSHRC(1)T (SEQ ID NO: 48)
IC(1)IWQKWGEHRC(1)T (SEQ ID NO: 142)
IC(1)IWQKWGAHRC(1)TGAES (SEQ ID NO: 53)
YC(1)IWQDWGEHRC(1)T (SEQ ID NO: 143)
ESSAYC(1)IWQDWGEHRC(1)T (SEQ ID NO: 17)
[Sar]C(1)IWQDWGEHRC(1)T (SEQ ID NO: 34)
IC(1)IWQDWGAHRC(1)E (SEQ ID NO: 38)
IC(1)IWQDWGEHRC(1)[Sar]

(SEQ ID NO: 144)
ESSAIC(1)IWQDWGEHRC(1)TGAES (SEQ ID NO: 145)
IC(1)IWQDWGEHRC(1)TGAES (SEQ ID NO: 46)
IC(1)IWQEWGEHRC(1)T (SEQ ID NO: 37)
IC(1)IWQDWGDHRC(1)T (SEQ ID NO: 44)
IC(1)IWQDWGRHRC(1)T (SEQ ID NO: 36)
IC(1)IWQDWGAHSC(1)T (SEQ ID NO: 42)
IC(1)IWQDWGEHSC(1)T (SEQ ID NO: 40)
IC(1)IWQDWGEHRC(1)S (SEQ ID NO: 39)
IC(1)IWQDWGEHRC(1)E (SEQ ID NO: 29)
FC(1)IWQDWGEHRC(1)T (SEQ ID NO: 146)
IC(1)IWQDWGEHRC(1)TEGE (SEQ ID NO: 147)
IC(1)IWQDWGEHRC(1)TEA

-continued (SEQ ID NO: 148)
IC(1)IWQDWGEHRC(1)TE (SEQ ID NO: 149)
IC(1)IWQDWGEHRC(1)EGE (SEQ ID NO: 150)
EGSAIC(1)IWQDWGEHRC(1)[Sar]E (SEQ ID NO: 151)
EGSAIC(1)IWQDWGEHRC(1)T (SEQ ID NO: 152)
EGEIC(1)IWQDWGEHRC(1)T (SEQ ID NO: 153)
ESEIC(1)IWQDWGEHRC(1)T (SEQ ID NO: 154)
SEIC(1)IWQDWGEHRC(1)TEA (SEQ ID NO: 155)
EIC(1)IWQDWGEHRC(1)TE (SEQ ID NO: 156)
EIC(1)IWQDWGEHRC(1)TEGE (SEQ ID NO: 157)
EGEIC(1)IWQDWGEHRC(1)EGE (SEQ ID NO: 158)
ESEIC(1)IWQDWGEHRC(1)EGE (SEQ ID NO: 159)
KEKIC(1)IWQDWGEHRC(1)TEKE (SEQ ID NO: 160)
EKGIC(1)IWQDWGEHRC(1)TEKP (SEQ ID NO: 161)
IC(1)IWQDWGEHRC(1)TEGK (SEQ ID NO: 162)
GSAIC(1)IWQDWGEHRC(1)[Sar]E (SEQ ID NO: 163)
SAIC(1)IWQDWGEHRC(1)[Sar]E (SEQ ID NO: 164)
SAIC(1)IWQDWGEHRC(1)TEG (SEQ ID NO: 165)
FC(1)IWQDWGEHRC(1)TGAE (SEQ ID NO: 166)
EGSAIC(1)IWQDWGEHRC(1)[Sar]EGE (SEQ ID NO: 167)
EGSAFC(1)IWQDWGEHRC(1)[Sar]E (SEQ ID NO: 168)
ESSAIC(1)IWQDWGAHRC(1)T (SEQ ID NO: 169)
IC(1)IWQDWGAHRC(1)TGAES (SEQ ID NO: 170)
{d}YIC(1)|[1-Me-Trp]QDW[Sar]AHRC(1)-[N-Me-Ile]

(SEQ ID NO: 171)
EGSAIC(1)|[1-Me-Trp]QDWGEHRC(1)[Sar]E (SEQ ID NO: 172)
EGSAIC(1)|[2-Nal]QDWGEHRC(1)[Sar]E (SEQ ID NO: 173)
IC(1)|[1-Me-Trp]QDWGEHRC(1)TGAES (SEQ ID NO: 174)
IC(1)|[2-Nal]QDWGEHRC(1)TGAES

-continued (SEQ ID NO: 175)
EGSAFC(1)|[1-Me-Trp]QDWGEHRC(1)[Sar]E (SEQ ID NO: 176)
EGSAYC(1)|[1-Me-Trp]QDWGEHRC(1)[Sar]E (SEQ ID NO: 177)
EGSAIC(1)IWQDWGEHRC(1)TE (SEQ ID NO: 178)
EGSAFC(1)|[1-Nal]QDWGEHRC(1)TE (SEQ ID NO: 179)
EGSAFC(1)|[1-Me-Trp]QDWGEHRC(1)TE (SEQ ID NO: 180)
EGSAFC(1)|[1-Me-Trp]QDWGEHRC(1)EGE (SEQ ID NO: 181)
EGSAYC(1)|[1-Me-Trp]QDWGEHRC(1)TE (SEQ ID NO: 182)
EGSAFC(1)|[2-Nal]QDWGEHRC(1)TE (SEQ ID NO: 183)
FC(1)|[1-Me-Trp]QDWGEHRC(1)TGAES (SEQ ID NO: 184)
YC(1)|[1-Me-Trp]QDWGEHRC(1)TGAES (SEQ ID NO: 185)
FC(1)|[1-Nal]QDWGEHRC(1)TGAES (SEQ ID NO: 186)
FC(1)|[2-Nal]QDWGEHRC(1)TGAES (SEQ ID NO: 187)
YC(1)|[2-Nal]QDWGEHRC(1)TGAES (SEQ ID NO: 188)
YC(1)IWQDWGEHRC(1)TGAES (SEQ ID NO: 189)
SEFC(1)|[1-Me-Trp]QDWGEHRC(1)TGAES (SEQ ID NO: 190)
YC(1)|[1-Me-Trp]QDWGEHRC(1)TEAGS (SEQ ID NO: 191)
YC(1)|[1-Me-Trp]QDWGEHRC(1)TESGA (SEQ ID NO: 192)
EGSAYC(1)[1-Me-Trp]QEWGEHRC(1)[Sar]E (SEQ ID NO: 193)
SEYC(1)|[1-Me-Trp]QDWGEHRC(1)[Sar]EA (SEQ ID NO: 194)
FC(1)|[1-Me-Trp]QDW[Sar]EHRC(1)TGAES (SEQ ID NO: 195)
{d}YFC(1)|[1-Me-Trp]QDW[Sar]EHRC(1)TGAES (SEQ ID NO: 196)
SEFC(1)[1-Me-Trp]QDWGEHRC(1)[Sar]GAES (SEQ ID NO: 197)
SEFC(1)|[1-Me-Trp]QDWGEHRC(1)[Sar]EA (SEQ ID NO: 198)
SEFC(1)|[1-Me-Trp]QDW[Sar]EHRC(1)[Sar]EA (SEQ ID NO: 199)
SEFC(1)|[1-Me-Trp]QDW[Sar]EHRC(1)TEA (SEQ ID NO: 200)
SEFC(1)|[1-Me-Trp]QDWGEHRC(1)[Sar]E (SEQ ID NO: 201)
SEFC(1)|[1-Me-Trp]QDW[Sar]EHRC(1)[Sar]E -continued (SEQ ID NO: 202)
EFC(1)|[1-Me-Trp]QDWGEHRC(1)[Sar]EA (SEQ ID NO: 203)
SE[Sar]C(1)|[1-Me-Trp]QDWGEHRC(1)[Sar]EA (SEQ ID NO: 204)
SE[Sar]C(1)|[1-Me-Trp]QDWGEHRC(1)TEA (SEQ ID NO: 205)
SEFC(1)|[1-Me-Trp]QEWGEHRC(1)[Sar]EA (SEQ ID NO: 206)
SEFC(1)|[1-Me-Trp]QDWGEHRC(1)SEA (SEQ ID NO: 207)
EFC(1)|[1-Me-Trp]QDWGEHRC(1)ES (SEQ ID NO: 208)
SEFC(1)|[1-Me-Trp]QDWGEHKC(1)[Sar]EA (SEQ ID NO: 209)
GEFC(1)|[1-Me-Trp]QDWGEHRC(1)[Sar]EA (SEQ ID NO: 210)
GE[Sar]C(1)|[1-Me-Trp]QDWGEHRC(1)TEA (SEQ ID NO: 211)
SE[Sar]C(1)|[1-Me-Trp]QEW[Sar]EHRC(1)TEA (SEQ ID NO: 212)
SE[Sar]C(1)|[1-Me-Trp]QEWGEHRC(1)[Sar]EA (SEQ ID NO: 213)
{d}Y[Sar]C(1)|[1-Me-Trp]QDWGEHRC(1)TEA For example, the compstatin analogue may be:

(Compound 1)
(SEQ ID NO: 35)
Ac-IC(1)IWQDWGAHRC(1)T-NH2

(Compound 2)
(SEQ ID NO: 41)
Ac-IC(1)IWQDWGEHRC(1)T-NH2

(Compound 3)
(SEQ ID NO: 140)
Ac-ESSAIC(1)IWQDWGEHRC(1)T-NH2

(Compound 4)
(SEQ ID NO: 32)
Ac-IC(1)|[1-Me-Trp]QDWGEHRC(1)T-NH2

(Compound 5)
(SEQ ID NO: 43)
Ac-IC(1)IWQDWGKHRC(1)T-NH2

(Compound 6)
(SEQ ID NO: 45)
Ac-IC(1)IWQDWGSHRC(1)T-NH2

(Compound 7)
(SEQ ID NO: 48)
Ac-IC(1)IWQKWGEHRC(1)T-NH2

(Compound 8)
(SEQ ID NO: 142)
Ac-IC(1)IWQKWGAHRC(1)TGAES-NH2

(Compound 9)
(SEQ ID NO: 53)
Ac-YC(1)IWQDWGEHRC(1)T-NH2

(Compound 10)
(SEQ ID NO: 143)
Ac-ESSAYC(1)IWQDWGEHRC(1)T-NH2

-continued (Compound 11)
(SEQ ID NO: 17)
Ac-[Sar]C(1)IWQDWGEHRC(1)T-NH2

(Compound 12)
(SEQ ID NO: 34)
Ac-IC(1)IWQDWGAHRC(1)E-NH2

(Compound 13)
(SEQ ID NO: 38)
Ac-IC(1)IWQDWGEHRC(1)[Sar]-NH2

(Compound 14)
(SEQ ID NO: 144)
Ac-ESSAIC(1)IWQDWGEHRC(1)TGAES-NH2

(Compound 15)
(SEQ ID NO: 145)
Ac-IC(1)IWQDWGEHRC(1)TGAES-NH2

(Compound 16)
(SEQ ID NO: 46)
Ac-IC(1)IWQEWGEHRC(1)T-NH2

(Compound 17)
(SEQ ID NO: 37)
Ac-IC(1)IWQDWGDHRC(1)T-NH2

(Compound 18)
(SEQ ID NO: 44)
Ac-IC(1)IWQDWGRHRC(1)T-NH2

(Compound 19)
(SEQ ID NO: 36)
Ac-IC(1)IWQDWGAHSC(1)T-NH2

(Compound 20)
(SEQ ID NO: 42)
Ac-IC(1)IWQDWGEHSC(1)T-NH2

(Compound 21)
(SEQ ID NO: 40)
Ac-IC(1)IWQDWGEHRC(1)S-NH2

(Compound 22)
(SEQ ID NO: 39)
Ac-IC(1)IWQDWGEHRC(1)E-NH2

(Compound 23)
(SEQ ID NO: 29)
Ac-FC(1)IWQDWGEHRC(1)T-NH2

(Compound 24)
(SEQ ID NO: 146)
Ac-IC(1)IWQDWGEHRC(1)TEGE-NH2

(Compound 25)
(SEQ ID NO: 147)
Ac-IC(1)IWQDWGEHRC(1)TEA-NH2

(Compound 26)
(SEQ ID NO: 148)
Ac-IC(1)IWQDWGEHRC(1)TE-NH2

(Compound 27)
(SEQ ID NO: 149)
Ac-IC(1)IWQDWGEHRC(1)EGE-NH2

(Compound 28)
(SEQ ID NO: 150)
Ac-EGSAIC(1)IWQDWGEHRC(1)[Sar]E-NH2

(Compound 29)
(SEQ ID NO: 151)
Ac-EGSAIC(1)IWQDWGEHRC(1)T-NH2

(Compound 30)
(SEQ ID NO: 152)
Ac-EGEIC(1)IWQDWGEHRC(1)T-NH2

-continued (Compound 31)
(SEQ ID NO: 153)
Ac-ESEIC(1)IWQDWGEHRC(1)T-NH2

(Compound 32)
(SEQ ID NO: 154)
Ac-SEIC(1)IWQDWGEHRC(1)TEA-NH2

(Compound 33)
(SEQ ID NO: 155)
Ac-EIC(1)IWQDWGEHRC(1)TE-NH2

(Compound 34)
(SEQ ID NO: 156)
Ac-EIC(1)IWQDWGEHRC(1)TEGE-NH2

(Compound 35)
(SEQ ID NO: 157)
Ac-EGEIC(1)IWQDWGEHRC(1)EGE-NH2

(Compound 36)
(SEQ ID NO: 158)
Ac-ESEIC(1)IWQDWGEHRC(1)EGE-NH2

(Compound 37)
(SEQ ID NO: 159)
Ac-KEKIC(1)IWQDWGEHRC(1)TEKE-NH2

(Compound 38)
(SEQ ID NO: 160)
Ac-EKGIC(1)IWQDWGEHRC(1)TEKP-NH2

(Compound 39)
(SEQ ID NO: 161)
Ac-IC(1)IWQDWGEHRC(1)TEGK-NH2

(Compound 40)
(SEQ ID NO: 162)
Ac-GSAIC(1)IWQDWGEHRC(1)[Sar]E-NH2

(Compound 41)
(SEQ ID NO: 163)
Ac-SAIC(1)IWQDWGEHRC(1)[Sar]E-NH2

(Compound 42)
(SEQ ID NO: 164)
Ac-SAIC(1)IWQDWGEHRC(1)TEG-NH2

(Compound 43)
(SEQ ID NO: 165)
Ac-FC(1)IWQDWGEHRC(1)TGAE-NH2

(Compound 44)
(SEQ ID NO: 166)
Ac-EGSAIC(1)IWQDWGEHRC(1)[Sar]EGE-NH2

(Compound 45)
(SEQ ID NO: 167)
Ac-EGSAFC(1)IWQDWGEHRC(1)[Sar]E-NH2

(Compound 46)
(SEQ ID NO: 168)
Ac-ESSAIC(1)IWQDWGAHRC(1)T-NH2

(Compound 47)
(SEQ ID NO: 169)
Ac-IC(1)IWQDWGAHRC(1)TGAES-NH2

(Compound 48)
(SEQ ID NO: 170)
H-{d}YIC(1)|[1-Me-Trp]QDW[Sar]AHRC(1)[N-Me-Ile]-NH2

(Compound 49)
(SEQ ID NO: 171)
Ac-EGSAIC(1)|[1-Me-Trp]QDWGEHRC(1)[Sar]E-NH2

-continued (Compound 50)
(SEQ ID NO: 172)
Ac-EGSAIC(1)|[2-Nal]QDWGEHRC(1)[Sar]E-NH2

(Compound 51)
(SEQ ID NO: 173)
Ac-IC(1)|[1-Me-Trp]QDWGEHRC(1)TGAES-NH2

(Compound 52)
(SEQ ID NO: 174)
Ac-IC(1)|[2-Nal]QDWGEHRC(1)TGAES-NH2

(Compound 53)
(SEQ ID NO: 175)
Ac-EGSAFC(1)|[1-Me-Trp]QDWGEHRC(1)[Sar]E-NH2

(Compound 54)
(SEQ ID NO: 176)
Ac-EGSAYC(1)|[1-Me-Trp]QDWGEHRC(1)[Sar]E-NH2

(Compound 55)
(SEQ ID NO: 177)
Ac-EGSAIC(1)IWQDWGEHRC(1)TE-NH2

(Compound 56)
(SEQ ID NO: 178)
Ac-EGSAFC(1)|[1-Nal]QDWGEHRC(1)TE-NH2

(Compound 57)
(SEQ ID NO: 179)
Ac-EGSAFC(1)|[1-Me-Trp]QDWGEHRC(1)TE-NH2

(Compound 58)
(SEQ ID NO: 180)
Ac-EGSAFC(1)|[1-Me-Trp]QDWGEHRC(1)EGE-NH2

(Compound 59)
(SEQ ID NO: 181)
Ac-EGSAYC(1)|[1-Me-Trp]QDWGEHRC(1)TE-NH2

(Compound 60)
(SEQ ID NO: 182)
Ac-EGSAFC(1)|[2-Nal]QDWGEHRC(1)TE-NH2

(Compound 61)
(SEQ ID NO: 183)
Ac-FC(1)|[1-Me-Trp]QDWGEHRC(1)TGAES-NH2

(Compound 62)
(SEQ ID NO: 184)
Ac-YC(1)|[1-Me-Trp]QDWGEHRC(1)TGAES-NH2

(Compound 63)
(SEQ ID NO: 185)
Ac-FC(1)|[1-Nal]QDWGEHRC(1)TGAES-NH2

(Compound 64)
(SEQ ID NO: 186)
Ac-FC(1)|[2-Nal]QDWGEHRC(1)TGAES-NH2

(Compound 65)
(SEQ ID NO: 187)
Ac-YC(1)|[2-Nal]QDWGEHRC(1)TGAES-NH2

(Compound 66)
(SEQ ID NO: 188)
Ac-YC(1)IWQDWGEHRC(1)TGAES-NH2

(Compound 67)
(SEQ ID NO: 189)
Ac-SEFC(1)|[1-Me-Trp]QDWGEHRC(1)TGAES-NH2

(Compound 68)
(SEQ ID NO: 190)
Ac-YC(1)|[1-Me-Trp]QDWGEHRC(1)TEAGS-NH2

(Compound 69)
(SEQ ID NO: 191)
Ac-YC(1)|[1-Me-Trp]QDWGEHRC(1)TESGA-NH2

(Compound 70)
(SEQ ID NO: 192)
Ac-EGSAYC(1)|[1-Me-Trp]QEWGEHRC(1)[Sar]E-NH2

(Compound 71)
(SEQ ID NO: 193)
Ac-SEYC(1)|[1-Me-Trp]QDWGEHRC(1)[Sar]EA-NH2

(Compound 72)
(SEQ ID NO: 194)
Ac-FC(1)|[1-Me-Trp]QDW[Sar]EHRC(1)TGAES-NH2

(Compound 73)
(SEQ ID NO: 195)
H-{d}YFC(1)|[1-Me-Trp]QDW[Sar]EHRC(1)TGAES-NH2

(Compound 74)
(SEQ ID NO: 196)
Ac-SEFC(1)|[1-Me-Trp]QDWGEHRC(1)[Sar]GAES-NH2

(Compound 75)
(SEQ ID NO: 197)
Ac-SEFC(1)|[1-Me-Trp]QDWGEHRC(1)[Sar]EA-NH2

(Compound 76)
(SEQ ID NO: 198)
Ac-SEFC(1)|[1-Me-Trp]QDW[Sar]EHRC(1)[Sar]EA-NH2

(Compound 77)
(SEQ ID NO: 199)
Ac-SEFC(1)|[1-Me-Trp]QDW[Sar]EHRC(1)TEA-NH2

(Compound 78)
(SEQ ID NO: 200)
Ac-SEFC(1)|[1-Me-Trp]QDWGEHRC(1)[Sar]E-NH2

(Compound 79)
(SEQ ID NO: 201)
Ac-SEFC(1)|[1-Me-Trp]QDW[Sar]EHRC(1)[Sar]E-NH2

(Compound 80)
(SEQ ID NO: 202)
Ac-EFC(1)|[1-Me-Trp]QDWGEHRC(1)[Sar]EA-NH2

(Compound 81)
(SEQ ID NO: 203)
Ac-SE[Sar]C(1)|[1-Me-Trp]QDWGEHRC(1)[Sar]EA-NH2

(Compound 82)
(SEQ ID NO: 204)
Ac-SE[Sar]C(1)|[1-Me-Trp]QDWGEHRC(1)TEA-NH2

(Compound 83)
(SEQ ID NO: 205)
Ac-SEFC(1)|[1-Me-Trp]QEWGEHRC(1)[Sar]EA-NH2

(Compound 84)
(SEQ ID NO: 206)
Ac-SEFC(1)[1-Me-Trp]QDWGEHRC(1)SEA-NH2

(Compound 85)
(SEQ ID NO: 207)
Ac-EFC(1)|[1-Me-Trp]QDWGEHRC(1)ES-NH2

(Compound 86)
(SEQ ID NO: 208)
Ac-SEFC(1)|[1-Me-Trp]QDWGEHKC(1)[Sar]EA-NH2

(Compound 87)
(SEQ ID NO: 209)
Ac-GEFC(1)|[1-Me-Trp]QDWGEHRC(1)[Sar]EA-NH2

(Compound 88)
(SEQ ID NO: 210)
Ac-GE[Sar]C(1)|[1-Me-Trp]QDWGEHRC(1)TEA-NH2

(Compound 89)
(SEQ ID NO: 211)
Ac-SE[Sar]C(1)|[1-Me-Trp]QEW[Sar]EHRC(1)TEA-NH2

-continued

```
(Compound 90)
                                          (SEQ ID NO: 212)
Ac-SE[Sar]C(1)|[1-Me-Trp]QEWGEHRC(1)[Sar]EA-NH2

(Compound 91)
                                          (SEQ ID NO: 213)
H-{d}Y[Sar]C(1)|[1-Me-Trp]QDWGEHRC(1)TEA-NH2
```

Alternatively, the compstatin analogue may comprise one of the following sequences:[K*]GSAIC(1)IWQDWGEHRC(1)TEGE (Compound 100) (SEQ ID NO: 214)

ASGEYC(1)I[1-Me-Trp]QDWGEHRC(1)[Sar]EGE-[K*] (Compound 113) (SEQ ID NO: 215)

EFC(1)I[1-Me-Trp]QDWGEHRC(1)EGE-[K*] (Compound 134) (SEQ ID NO: 216)

EGSAIC(1)IWQDWGEHRC(1)TEG[K*] (Compound 101) (SEQ ID NO: 217)

EGSAYC(1)I[1-Me-Trp]QDWGEH[K*]C(1)[Sar]E (Compound 103) (SEQ ID NO: 218)

EGSAYC(1)I[1-Me-Trp]QDWGEHRC(1)[Sar]EG-[K*] (Compound 104) (SEQ ID NO: 219)

EGSAYC(1)I[1-Me-Trp]QDWGEHRC(1)[Sar]EGE-[K*] (Compound 109) (SEQ ID NO: 220)

EGSAYC(1)I[1-Me-Trp]QDWGEHRC(1)[Sar]EGK-[K*] (Compound 110) (SEQ ID NO: 221)

EGSAYC(1)I[1-Me-Trp]QDWGEHRC(1)[Sar]EK[γGlu]-[K*] (Compound 111) (SEQ ID NO: 222)

FC(1)I[1-Me-Trp]QDWGEHRC(1)TGAES-[K*] (Compound 102) (SEQ ID NO: 223)

IC(1)/WQDWGEHRC(1)TEG-[K*] (Compound 92) (SEQ ID NO: 224)

IC(1)IWQDWGEHRC(1)TEGE-[K*] (Compound 94) (SEQ ID NO: 225)

SAYC(1)I[1-Me-Trp]QDWGEHRC(1)[Sar]E-[K*] (Compound 105) (SEQ ID NO: 226)

SEFC(1)I[1-Me-Trp]QDWGEHRC(1)[Sar]EGA-[K*] (Compound 119) (SEQ ID NO: 227)

SEFC(1)I[1-Me-Trp]QDWGEHRC(1)[Sar]EGE[Peg3][Peg3]-[K*] (Compound 123) (SEQ ID NO: 228)

SEFC(1)I[1-Me-Trp]QDWGEHRC(1)[Sar]EGEGGG-[K*] (Compound 129) (SEQ ID NO: 229)

SEFC(1)I[1-Me-Trp]QDWGEHRC(1)[Sar]EGE[Peg3]-[K*] (Compound 138) (SEQ ID NO: 230)

SEFC(1)I[1-Me-Trp]QDWGEHRC(1)[Sar]EGE[Peg3]ES-[K*] (Compound 140) (SEQ ID NO: 231)

SEFC(1)I[1-Me-Trp]QDWGEHRC(1)[Sar]EGE[Peg3][Peg3]-[K*] (Compound 127) (SEQ ID NO: 232)

SEFC(1)I[1-Me-Trp]QDWGEHRC(1)[Sar]EGESES-[K*] (Compound 139) (SEQ ID NO: 233)

SEFC(1)I[1-Me-Trp]QDWGEHRC(1)[Sar]EK[γGlu]GGG-[K*] (Compound 132) (SEQ ID NO: 234)

SEFC(1)I[1-Me-Trp]QDWGEHRC(1)TEGE[8-aminooctanoyl]-[K*] (Compound 136) (SEQ ID NO: 235)

SEFC(1)I[1-Me-Trp]QDWGEHRC(1)TEGE[8-aminooctanoyl]E-[K*] (Compound 137) (SEQ ID NO: 236)

SEFC(1)I[1-Me-Trp]QDWGEHRC(1)TEGEGGG-[K*] (Compound 130) (SEQ ID NO: 237)

SEFC(1)I[1-Me-Trp]QDWGEHRC(1)TEGE[Peg3]ES-[K*] (Compound 142) (SEQ ID NO: 238)

SEFC(1)I[1-Me-Trp]QDWGEHRC(1)TEGE[Peg3][Peg3]-[K*] (Compound 126) (SEQ ID NO: 239)

SEFC(1)I[1-Me-Trp]QDWGEHRC(1)TEK[γGlu]GGG-[K*] (Compound 133) (SEQ ID NO: 240)

SEFC(1)I[1-Me-Trp]QDWGEHRC(1)TGAES-[K*] (Compound 135) (SEQ ID NO: 241)

SEFC(1)I[1-Me-Trp]QEWGEHRC(1)[Sar]EGA-[K*] (Compound 120) (SEQ ID NO: 242)

SEFC(1)I[1-Me-Trp]QEWGEHRC(1)[Sar]EGE[Peg3][Peg3]-[K*] (Compound 124) (SEQ ID NO: 243)

SEYC(1)I[1-Me-Trp]QDWGEHRC(1)[Sar]EGA-[K*] (Compound 112) (SEQ ID NO: 244)

SEYC(1)I[1-Me-Trp]QDWGEHRC(1)[Sar]EGE[Peg3][Peg3]-[K*] (Compound 117) (SEQ ID NO: 245)

SEYC(1)I[1-Me-Trp]QDWGEHRC(1)[Sar]EGE-[K*] (Compound 114) (SEQ ID NO: 246)

SEYC(1)I[1-Me-Trp]QEW[Sar]EHRC(1)[Sar]EK[γGlu]A-[K*] (Compound 121) (SEQ ID NO: 247)

SEYC(1)I[1-Me-Trp]QEWGEHRC(1)[Sar]EGA-[K*] (Compound 122) (SEQ ID NO: 248)

SEYC(1)I[1-Me-Trp]QEWGEHRC(1)[Sar]EGE[Peg3][Peg3]-[K*] (Compound 125) (SEQ ID NO: 249)

EGSEYC(1)I[1-Me-Trp]QDWGEHRC(1)[Sar]E (Compound 107) (SEQ ID NO: 250)

ESSAIC(1)IWQDWGEHRC(1)TEGE (Compound 99) (SEQ ID NO: 251)

SEFC(1)I[1-Me-Trp]QDWGEHRC(1)[Sar]EGE[Peg3][Peg3][Peg3]-[K*] (Compound 143) (SEQ ID NO: 252)

SEFC(1)I[1-Me-Trp]QDW[Sar]EHRC(1)[Sar]E[Peg3][Peg3]-[K*] (Compound 144) (SEQ ID NO: 253)

EFC(1)I[1-Me-Trp]QDWGEHRC(1)[Sar]EA[Peg3][Peg3]-[K"] (Compound 145) (SEQ ID NO: 254)

For example, the compstatin analogue may comprise one of the following sequences:

```
(Compound 100)
                                          (SEQ ID NO: 214)
Ac-[K*]GSAIC(1)IWQDWGEHRC(1)TEGE-NH2

(Compound 113)
                                          (SEQ ID NO: 215)
Ac-ASGEYC(1)I[1-Me-Trp]QDWGEHRC(1)[Sar]EGE-[K*]-NH2

(Compound 134)
                                          (SEQ ID NO: 216)
Ac-EFC(1)|[1-Me-Trp]QDWGEHRC(1)EGE-[K*]-NH2

(Compound 101)
                                          (SEQ ID NO: 217)
Ac-EGSAIC(1)IWQDWGEHRC(1)TEG[K*]-NH2

(Compound 103)
                                          (SEQ ID NO: 218)
Ac-EGSAYC(1)[1-Me-Trp]QDWGEH[K*]C(1)[Sar]-NH2

(Compound 104)
                                          (SEQ ID NO: 219)
Ac-EGSAYC(1)I[1-Me-Trp]QDWGEHRC(1)[Sar]EG-[K*]-NH2

(Compound 109)
                                          (SEQ ID NO: 220)
Ac-EGSAYC(1)I[1-Me-Trp]QDWGEHRC(1)[Sar]EGE-[K*]-NH2

(Compound 110)
                                          (SEQ ID NO: 221)
Ac-EGSAYC(1)I[1-Me-Trp]QDWGEHRC(1)[Sar]EGK-[K*]-NH2

(Compound 111)
                                          (SEQ ID NO: 222)
Ac-EGSAYC(1)I[1-Me-Trp]QDWGEHRC(1)[Sar]EK[yGlu]-
[K*]-NH2

(Compound 102)
                                          (SEQ ID NO: 223)
Ac-FC(1)[1-Me-Trp]QDWGEHRC(1)TGAES-[K*]-NH2

(Compound 92, 93, 95, 96, 98)
                                          (SEQ ID NO: 224)
Ac-IC(1)IWQDWGEHRC(1)TEG-[K*]-NH2
```

-continued (Compound 94, 97)

(SEQ ID NO: 225)

Ac-IC(1)IWQDWGEHRC(1)TEGE-[K*]-NH2

(Compound 105, 106)

(SEQ ID NO: 226)

Ac-SAYC(1)I[1-Me-Trp]QDWGEHRC(1)[Sar]E-[K*]-NH2

(Compound 119)

(SEQ ID NO: 227)

Ac-SEFC(1)I[1-Me-Trp]QDWGEHRC(1)[Sar]EGA-[K*]-NH2

(Compound 123)

(SEQ ID NO: 228)

Ac-SEFC(1)I[1-Me-Trp]QDWGEHRC(1)[Sar]EGE[Peg3][Peg3]-[K*]-NH2

(Compound 129)

(SEQ ID NO: 229)

Ac-SEFC(1)[1-Me-Trp]QDWGEHRC(1)[Sar]EGEGGG-[K*]-NH2

(Compound 138)

(SEQ ID NO: 230)

Ac-SEFC(1)I[1-Me-Trp]QDWGEHRC(1)[Sar]EGE[Peg3]-[K*]-NH2

(Compound 140)

(SEQ ID NO: 231)

Ac-SEFC(1)I[1-Me-Trp]QDWGEHRC(1)[Sar]EGE[Peg3]ES-[K*]-NH2

(Compound 127, 128)

(SEQ ID NO: 232)

Ac-SEFC(1)I[1-Me-Trp]QDWGEHRC(1)[Sar]EGE[Peg3][Peg3]-[K*]-NH2

(Compound 139, 141)

(SEQ ID NO: 233)

Ac-SEFC(1)[1-Me-Trp]QDWGEHRC(1)[Sar]EGESES-[K*]-NH2

(Compound 132)

(SEQ ID NO: 234)

Ac-SEFC(1)I[1-Me-Trp]QDWGEHRC(1)[Sar]EK[yGlu]GGG-[K*]-NH2

(Compound 136)

(SEQ ID NO: 235)

Ac-SEFC(1)I[1-Me-Trp]QDWGEHRC(1)TEGE[8-aminooctanoyl]-[K*]-NH2

(Compound 137)

(SEQ ID NO: 236)

Ac-SEFC(1)I[1-Me-Trp]QDWGEHRC(1)TEGE[8-aminooctanoyl]E-[K*]-NH2

(Compound 130, 131)

(SEQ ID NO: 237)

Ac-SEFC(1)I[1-Me-Trp]QDWGEHRC(1)TEGEGGG-[K*]-NH2

(Compound 142)

(SEQ ID NO: 238)

Ac-SEFC(1)I[1-Me-Trp]QDWGEHRC(1)TEGE[Peg3]ES-[K*]-NH2

(Compound 126)

(SEQ ID NO: 239)

Ac-SEFC(1) I[1-Me-Trp]QDWGEHRC(1)TEGE[Peg3][Peg3]-[K*]-NH2

-continued (Compound 133)

(SEQ ID NO: 240)

Ac-SEFC(1) I[1-Me-Trp]QDWGEHRC(1)TEK[yGlu]GGG-[K*]-NH2

(Compound 135)

(SEQ ID NO: 241)

Ac-SEFC(1) I[1-Me-Trp]QDWGEHRC(1)TGAES-[K*]-NH2

(Compound 120)

(SEQ ID NO: 242)

Ac-SEFC(1)[1-Me-Trp]QEWGEHRC(1)[Sar]EGA-[K*]-NH2

(Compound 124)

(SEQ ID NO: 243)

Ac-SEFC(1) I[1-Me-Trp]QEWGEHRC(1)[Sar]EGE[Peg3][Peg3]-[K*]-NH2

(Compound 112, 118)

(SEQ ID NO: 244)

Ac-SEYC(1) I[1-Me-Trp]QDWGEHRC(1)[Sar]EGA-[K*]-NH2

(Compound 117)

(SEQ ID NO: 245)

Ac-SEYC(1) I[1-Me-Trp]QDWGEHRC(1)[Sar]EGE[Peg3][Peg3]-[K*]-NH2

(Compound 114, 115, 116)

(SEQ ID NO: 246)

Ac-SEYC(1) I[1-Me-Trp]QDWGEHRC(1)[Sar]EGE-[K*]-NH2

(Compound 121)

(SEQ ID NO: 247)

Ac-SEYC(1) I[1-Me-Trp]QEW[Sar]EHRC(1)[Sar]EK[yGlu]A-[K*]-NH2

(Compound 122)

(SEQ ID NO: 248)

Ac-SEYC(1) I[1-Me-Trp]QEWGEHRC(1)[Sar]EGA-[K*]-NH2

(Compound 125)

(SEQ ID NO: 249)

Ac-SEYC(1) I[1-Me-Trp]QEWGEHRC(1)[Sar]EGE[Peg3][Peg3]-[K*]-NH2

(Compound 107, 108)

(SEQ ID NO: 250)

Φ-EGSEYC(1) I[1-Me-Trp]QDWGEHRC(1)[Sar]E-NH2

(Compound 99)

(SEQ ID NO: 251)

Φ-ESSAIC(1)IWQDWGEHRC(1)TEGE-NH2

(Compound 143)

(SEQ ID NO: 252)

Ac-SEFC(1) I[1-Me-Trp]QDWGEHRC(1)[Sar]EGE[Peg3][Peg3][Peg3]-[K*]-NH2

(Compound 144)

(SEQ ID NO: 253)

Ac-SEFC(1) I[1-Me-Trp]QDW[Sar]EHRC(1)[Sar]E[Peg3][Peg3]-[K*]-NH2

(Compound 145)

(SEQ ID NO: 254)

Ac-EFC(1) I[1-Me-Trp]QDWGEHRC(1)[Sar]EA[Peg3][Peg3]-[K*]-NH2

For example, the compstatin analogue may be:

(Compound 92) (SEQ ID NO: 278)
Ac-IC(1)IWQDWGEHRC(1)TEG-K([15-carboxy-pentadecanoyl][Glu])-NH2

(Compound 93) (SEQ ID NO: 279)
Ac-IC(1)IWQDWGEHRC(1) TEG-K([15-carboxy-pentadecanoyl][γGlu][Peg3][Peg3])-NH2

(Compound 94) (SEQ ID NO: 283)
Ac-IC(1)IWQDWGEHRC(1)TEGE-K([15-carboxy-pentadecanoyl][γGlu][Peg3][Peg3])-NH2

(Compound 95) (SEQ ID NO: 280)
Ac-IC(1)IWQDWGEHRC(1)TEG-K((15-carboxy-pentadecanoyl)-[(Piperazine-1-yl)-acetyl][Peg3][Peg3])-NH2

(Compound 96) (SEQ ID NO: 281)
Ac-IC(1)IWQDWGEHRC(1)TEG-K([17-carboxy-heptadecanoyl][γGlu][Peg3][Peg3])-NH2

(Compound 97) (SEQ ID NO: 284)
Ac-IC(1)IWQDWGEHRC(1) TEGE-K([17-carboxy-heptadecanoyl][γGlu][Peg3][Peg3])-NH2

(Compound 98) (SEQ ID NO: 282)
Ac-IC(1)IWQDWGEHRC(1) TEG-K([19-carboxy-nonadecanoyl][γGlu][Peg3][Peg3])-NH2

(Compound 99) (SEQ ID NO: 318)
[15-Carboxy-pentadecanoyl]-ESSAIC(1)IWQDWGEHRC(1)TEGE-NH2

(Compound 100) (SEQ ID NO: 268)
Ac-[K([15-carboxy-pentadecanoyl][γGlu][Peg3][Peg3])]-GSAIC(1)IWQDWGEHRC(1)TEGE-NH2

(Compound 101) (SEQ ID NO: 271)
Ac-EGSAIC(1)IWQDWGEHRC(1)TEG-K([15-carboxy-pentadecanoyl][γGlu])-NH2

(Compound 102) (SEQ ID NO: 277)
Ac-FC(1)|[1-Me-Trp]QDWGEHRC(1)TGAES-K([15-carboxy-pentadecanoyl][γGlu][Peg3][Peg3])-NH2

(Compound 103) (SEQ ID NO: 272)
Ac-EGSAYC(1)|[1-Me-Trp]QDWGEH-K([15-carboxy-pentadecanoyl][γGlu][Peg3][Peg3])-C(1)[Sar]E-NH2

(Compound 104) (SEQ ID NO: 273)
Ac-EGSAYC(1)|[1-Me-Trp]QDWGEHRC(1)[Sar]EG-K([15-carboxy-pentadecanoyl][γGlu][Peg3][Peg3])-NH2

(Compound 105) (SEQ ID NO: 285)
Ac-SAYC(1)|[1-Me-Trp]QDWGEHRC(1)[Sar]E-K([17-carboxy-heptadecanoyl][γGlu]KG[γGlu])-NH2

(Compound 106) (SEQ ID NO: 286)
Ac-SAYC(1)|[1-Me-Trp]QDWGEHRC(1)[Sar]E-K([17-carboxy-heptadecanoyl][γGlu]G[γGlu])-NH2

(Compound 107) (SEQ ID NO: 316)
[15-Carboxy-pentadecanoyl]-EGSEYC(1)|[1-Me-Trp]QDWGEHRC(1)[Sar]E-NH2

-continued (Compound 108)
(SEQ ID NO: 317)
[17-Carboxy-heptadecanoyl]-EGSEYC(1)|[1-Me-Trp]QDWGEHRC(1)[Sar]E-NH2

(Compound 109)
(SEQ ID NO: 274)
Ac-EGSAYC(1)|[1-Me-Trp]QDWGEHRC(1)[Sar]EGE-K([17-carboxy-heptadecanoyl]
[γGlu]G[γGlu])-NH2

(Compound 110)
(SEQ ID NO: 275)
Ac-EGSAYC(1)|[1-Me-Trp]QDWGEHRC(1)[Sar]EGK-K([17-carboxy-heptadecanoyl]
[γGlu]G[γGlu])-NH2

(Compound 111)
(SEQ ID NO: 276)
Ac-EGSAYC(1)|[1-Me-Trp]QDWGEHRC(1)[Sar]EK([yGlu]-K([17-carboxy-heptadecanoyl]
[γGlu](peg3)(peg3))-NH2

(Compound 112)
(SEQ ID NO: 307)
Ac-SEYC(1)|[1-Me-Trp]QDWGEHRC(1)[Sar]EGA-K([17-carboxy-heptadecanoyl][γGlu]-G
[γGlu])-NH2

(Compound 113)
(SEQ ID NO: 269)
Ac-ASGEYC(1)|[1-Me-Trp]QDWGEHRC(1)[Sar]EGE-K([17-carboxy-heptadecanoyl][γGlu]-G
[γGlu])-NH2

(Compound 114)
(SEQ ID NO: 310)
Ac-SEYC(1)|[1-Me-Trp]QDWGEHRC(1)[Sar]EGE-K([17-carboxy-heptadecanoyl][γGlu]-G
[γGlu])-NH2

(Compound 115)
(SEQ ID NO: 311)
Ac-SEYC(1)|[1-Me-Trp]QDWGEHRC(1)[Sar]EGK-K([17-carboxy-heptadecanoyl][γGlu]-G
[γGlu])-NH2

(Compound 116)
(SEQ ID NO: 312)
Ac-SEYC(1)|[1-Me-Trp]QDWGEHRC(1)[Sar]EGE-K([17-carboxy-heptadecanoyl][γGlu]-K
[γGlu])-NH2

(Compound 117)
(SEQ ID NO: 309)
Ac-SEYC(1)|[1-Me-Trp]QDWGEHRC(1)[Sar]EGE[Peg3][Peg3]-K([17-carboxy-heptadecanoyl]
[yGlu]-G[γGlu])-NH2

(Compound 118)
(SEQ ID NO: 308)
Ac-SEYC(1)|[1-Me-Trp]QDWGEHRC(1)[Sar]EGA-K([17-carboxy-heptadecanoyl]-
[γGlu]G[Peg3][γGlu][Peg3])-NH2

(Compound 119)
(SEQ ID NO: 287)
Ac-SEFC(1)|[1-Me-Trp]QDWGEHRC(1)[Sar]EGA-K([17-carboxy-heptadecanoyl]-
[γGlu]G[Peg3][γGlu][Peg3])-NH2

(Compound 120)
(SEQ ID NO: 305)
Ac-SEFC(1)|[1-Me-Trp]QEWGEHRC(1)[Sar]EGA-K([17-carboxy-heptadecanoyl]-
[γGlu]G[Peg3][γGlu][Peg3])-NH2

(Compound 121)
(SEQ ID NO: 313)
Ac-SEYC(1)|[1-Me-Trp]QEW[Sar]EHRC(1)[Sar]EK[yGlu]A-K([17-carboxy-heptadecanoyl]-
[γGlu]G[Peg3][γGlu][Peg3])-NH2

-continued (Compound 122)
(SEQ ID NO: 314)
Ac-SEYC(1)|[1-Me-Trp]QEWGEHRC(1)[Sar]EGA-K([17-carboxy-heptadecanoyl]-[γGlu]G[Peg3][γGlu][Peg3])-NH2

(Compound 123)
(SEQ ID NO: 288)
Ac-SEFC(1)|[1-Me-Trp]QDWGEHRC(1)[Sar]EGE[Peg3][Peg3]-K([17-carboxy-heptadecanoyl][γGlu]G[γGlu])-NH2

(Compound 124)
(SEQ ID NO: 306)
Ac-SEFC(1)|[1-Me-Trp]QEWGEHRC(1)[Sar]EGE[Peg3[Peg3]-K([17-carboxy-heptadecanoyl]-[γGlu]G[γGlu])-NH2

(Compound 125)
(SEQ ID NO: 315)
Ac-SEYC(1)|[1-Me-Trp]QEWGEHRC(1)[Sar]EGE[Peg3][Peg3]-K([17-carboxy-heptadecanoyl][γGlu]G[γGlu])-NH2

(Compound 126)
(SEQ ID NO: 302)
Ac-SEFC(1)|[1-Me-Trp]QDWGEHRC(1)TEGE[Peg3][Peg3]-K([17-carboxy-heptadecanoyl)[γGlu]G[γGlu])-NH2

(Compound 127)
(SEQ ID NO: 292)
Ac-SEFC(1)|[1-Me-Trp]QDWGEHRC(1)[Sar]-EGE-[Peg3][Peg3]-K([15-carboxy-pentadecanoyl][γGlu]G[γGlu])-NH2

(Compound 128)
(SEQ ID NO: 293)
Ac-SEFC(1)|[1-Me-Trp]QDWGEHRC(1)[Sar]EGE[Peg3][Peg3]-K([19-carboxy-nonadecanoyl][γGlu]G[γGlu])-NH2

(Compound 129)
(SEQ ID NO: 289)
Ac-SEFC(1)|[1-Me-Trp]QDWGEHRC(1)[Sar]EGEGGG-K([17-carboxy-heptadecanoyl]-[γGlu]G[γGlu])-NH2

(Compound 130)
(SEQ ID NO: 299)
Ac-SEFC(1)|[1-Me-Trp]QDWGEHRC(1)TEGEGGG-K([17-carboxy-heptadecanoyl]-[γGlu]G[γGlu])-NH2

(Compound 131)
(SEQ ID NO: 300)
Ac-SEFC(1)|[1-Me-Trp]-QDWGEHRC(1)TEGEGGG-K([15-carboxy-pentadecanoyl][γGlu]-G[γGlu])-NH2

(Compound 132)
(SEQ ID NO: 296)
Ac-SEFC(1)|[1-Me-Trp]-QDWGEHRC(1)[Sar]EK[γGlu]GGG-K([17-carboxy-heptadecanoyl][γGlu]-G[γGlu])-NH2

(Compound 133)
(SEQ ID NO: 303)
Ac-SEFC(1)|[1-Me-Trp]QDWGEHRC(1)TEK[γGlu]GGG-K([17-carboxy-heptadecanoyl][γGlu]-G[γGlu])-NH2

(Compound 134)
(SEQ ID NO: 270)
Ac-EFC(1)|[1-Me-Trp]QDWGEHRC(1)EGE-K([17-carboxy-heptadecanoyl][γGlu]G[γGlu])-NH2

-continued (Compound 135)

(SEQ ID NO: 304)

Ac-SEFC(1)|[1-Me-Trp]QDWGEHRC(1)TGAES-K([15-carboxy-hexadecanoyl][γGlu]G[γGlu])-NH2

(Compound 136)

(SEQ ID NO: 297)

Ac-SEFC(1)|[1-Me-Trp]QDWGEHRC(1)TEGE[8-aminooctanoyl]-K([17-carboxy-heptadecanoyl][γGlu]-G[γGlu])-NH2

(Compound 137)

(SEQ ID NO: 298)

Ac-SEFC(1)|[1-Me-Trp]QDWGEHRC(1)TEGE[8-aminooctanoyl]E-K([17-carboxy-heptadecanoyl][γGlu]G[γGlu]])-NH2

(Compound 138)

(SEQ ID NO: 290)

Ac-SEFC(1)|[1-Me-Trp]QDWGEHRC(1)[Sar]EGE[Peg3]-K([17-carboxy-heptadecanoyl]-[γGlu]G[γGlu])-NH2

(Compound 139)

(SEQ ID NO: 294)

Ac-SEFC(1)|[1-Me-Trp]QDWGEHRC(1)[Sar]EGESES-K([17-carboxy-heptadecanoyl]-[γGlu]G[γGlu])-NH2

(Compound 140)

(SEQ ID NO: 291)

Ac-SEFC(1)|[1-Me-Trp]QDWGEHRC(1)[Sar]EGE[Peg3]ES-K([17-carboxy-heptadecanoyl]-[γGlu]G[γGlu])-NH2

(Compound 141)

(SEQ ID NO: 295)

Ac-SEFC(1)|[1-Me-Trp]QDWGEHRC(1)[Sar]EGESES-K([17-carboxy-heptadecanoyl][γGlu])-NH2

(Compound 142)

(SEQ ID NO: 301)

Ac-SEFC(1)|[1-Me-Trp]QDWGEHRC(1)TEGE[Peg3]ES-K([17-carboxy-heptadecanoyl][γGlu])-NH2

(Compound 143)

(SEQ ID NO: 319)

Ac-SEFC(1)|[1-Me-Trp]QDWGEHR[C(1)[Sar]EGE[Peg3][Peg3][Peg3]-K([17-carboxy-heptadecanoyl][γGlu]G[γGlu])-NH2

(Compound 144)

(SEQ ID NO: 320)

Ac-SEFC(1)|[1-Me-Trp]QDW[Sar]EHRC(1)[Sar]E[Peg3][Peg3]-K([17-carboxy-heptadecanoyl][γGlu]G[γGlu])-NH2

(Compound 145)

(SEQ ID NO: 321)

Ac-EF[C(1)|[1-Me-Trp]QDWGEHRC(1)[Sar]EA[Peg3][Peg3]-K([17-carboxy-heptadecanoyl][γGlu]G[γGlu])-NH2.

Compstatin analogues made in the prior art have been shown to possess improved activity as compared with the parent peptide, i.e., up to about 99-fold (Mallik, B. et al, 2005, supra; WO 2004/026328), and up to about 264-fold (Katragadda et al., 2006, supra; WO2007/062249).

In accordance with the present invention, information about the biological and physicochemical characteristics of Ac-compstatin binding to C3 have been employed to design compstatin analogues with significantly improved activity compared to the parent compstatin analogues.

Preferably, the compstatin analogs have greater activity than Ac-compstatin, e.g. at least 10-fold greater activity, at least 20-fold greater activity, at least 30-fold greater activity than Ac-compstatin. In other embodiments, the analogs have at least 40-, 50-, 60-, 70-, 80-, 90-, 100-, 110-, 120-, 130-, 140-, 150-fold or greater activity than Ac-compstatin, as compared utilizing the assays described in the examples.

A compound of the invention typically has greater activity than an otherwise identical compound having valine instead of isoleucine at the position corresponding to Val3 of compstatin.

The compstatin analogues are capable of binding to C3 and/or C3b, and of inhbiting activation of the complement cascade, particularly downstream of C3, e.g. by inhibiting cleavage of C3 by C3 convertases.

The compstatin analogues are also typically capable of inhibiting complement-driven haemolysis. Complement-driven haemolysis is typically assessed (in a "haemolysis assay") by contacting serum from a first mammalian species (e.g. human serum) with erythrocytes (red blood cells; RBC) from a second mammalian species (e.g. sheep or any other suitable species), typically in the presence of mammalian immunoglobulin capable of binding to the erythrocytes. Complement in the serum is activated by the cell-bound immunoglobulin, leading to lysis of the erythrocytes, i.e. haemolysis. The immunoglobulin may be from the first species, or may be from a third mammalian species as long as it is capable of activating complement from the first species.

In such an assay, a test compound will typically be pre-incubated with the serum before the serum is contacted with the erythroctes. The erythrocytes may also be pre-incubated with the immunoglobulin before contacting with the serum.

In the examples below, human serum is pre-incubated with a test compound, and sheep erythroctes are pre-incubated with rabbit anti-serum against sheep erythrocytes, before the serum and erythrocytes are combined.

Thus, the activity of the compstatin analogues may be determined with reference to one or more biological activities selected from (1) binding to C3 protein, (2) binding to C3b protein, (3) inhibiting the cleavage of native C3 by C3 convertases, and (4) inhibiting the activation of the complement system.

Thus a compstatin analogue of the invention may bind C3 or C3b with a higher affinity than that of compstatin. For example, they may have a Kd at least 10-fold lower, at least 20-fold lower, or at least 30-fold lower than Ac-compstatin, e.g. at least 40-, 50-, 60-, 70-, 80-, 90-, 100-, 110-, 120-, 130-, 140-, or 150-fold lower than Ac-compstatin. The Kd may be determined by surface plasmon resonance (SPR), e.g. using an assay as described in Example 4.

A compstatin analogue of the invention typically binds C3 or C3b with a greater affinity (i.e. a lower Kd) than that of an otherwise identical compound having valine instead of isoleucine at the position corresponding to Val3 of compstatin.

A compstatin analogue of the invention may have a greater ability to inhibit haemolysis than Ac-compstatin. For example, it may inhibit haemolysis with an $IC_{50}$ at least 10-fold, at least 20-fold, or at least 30-fold lower than Ac-compstatin, e.g. at least 40-, 50-, 60-, 70-, 80-, 90-, 100-, 110-, 120-, 130-, 140-, 150-, 200-, 250-, 300-350-, 400-, 450-, 500-fold lower than Ac-compstatin.

A compstatin analogue of the invention typically has a greater ability to inhibit haemolysis (i.e. a lower $IC_{50}$) than an otherwise identical compound having valine instead of isoleucine at the position corresponding to Val3 of compstatin.

Preferably, the in vitro effect of the compounds of the present invention are assessed by measuring their inhibitory effect on the classical complement pathway in a haemolysis assay, e.g. using the assay described in Example 2.

Compstatin analogues having acylation may have a lower absolute activity than an otherwise identical compound lacking acylation, but have additional benefits including prolonged in vivo half life which may offset any apparent reduction of absolute activity.

Synthesis of Compstatin Analogues

It is preferred to synthesize compstatin analogues of the present invention by means of solid-phase or liquid-phase peptide synthesis methodology. In this context, reference may be made to WO 98/11125 and, among many others, Fields, G. B. et al., 2002, "Principles and practice of solid-phase peptide synthesis". In: Synthetic Peptides (2nd Edition), and the Examples herein.

In accordance with the present invention, a compstatin analogue of the invention may be synthesized or produced in a number of ways, including for example, a method which comprises:

(a) synthesizing the compstatin analogues by means of solid-phase or liquid-phase peptide synthesis methodology and recovering the synthesized compstatin analogues thus obtained; or (b) expressing a precursor peptide sequence from a nucleic acid construct that encodes the precursor peptide, recovering the expression product, and modifying the precursor peptide to yield a compound of the invention.

The precursor peptide may be modified by introduction of one or more non-proteinogenic amino acids, e.g. Aib, Orn, Dap, 1-Me-Trp, 1-Nal, 2-Nal, Sar, γGlu or Dab, or by the introduction of an appropriate terminal groups Y1 and/or Y2.

Expression is typically performed from a nucleic acid encoding the precursor peptide, which may be performed in a cell or a cell-free expression system comprising such a nucleic acid.

It is preferred to synthesize the analogues of the invention by means of solid-phase or liquid-phase peptide synthesis. In this context, reference is made to WO 98/11125 and, among many others, Fields, G B et al., 2002, "Principles and practice of solid-phase peptide synthesis". In: Synthetic Peptides (2nd Edition), and the Examples herein.

For recombinant expression, the nucleic acid fragments encoding the precursor peptide will normally be inserted in suitable vectors to form cloning or expression vectors. The vectors can, depending on purpose and type of application, be in the form of plasmids, phages, cosmids, mini-chromosomes, or virus, but also naked DNA which is only expressed transiently in certain cells is an important vector. Preferred cloning and expression vectors (plasmid vectors) are capable of autonomous replication, thereby enabling high copy-numbers for the purposes of high-level expression or high-level replication for subsequent cloning.

In general outline, an expression vector comprises the following features in the 5'→3' direction and in operable linkage: a promoter for driving expression of the nucleic acid fragment, optionally a nucleic acid sequence encoding a leader peptide enabling secretion (to the extracellular phase or, where applicable, into the periplasma), the nucleic acid fragment encoding the precursor peptide, and optionally a nucleic acid sequence encoding a terminator.

They may comprise additional features such as selectable markers and origins of replication. When operating with expression vectors in producer strains or cell lines it may be preferred that the vector is capable of integrating into the host cell genome. The skilled person is very familiar with suitable vectors and is able to design one according to their specific requirements.

The vectors of the invention are used to transform host cells to produce the precursor peptide. Such transformed cells can be cultured cells or cell lines used for propagation of the nucleic acid fragments and vectors, and/or used for recombinant production of the precursor peptides.

Preferred transformed cells are micro-organisms such as bacteria [such as the species *Escherichia* (e.g. *E. coli*), *Bacillus* (e.g. *Bacillus subtilis*), *Salmonella*, or *Mycobacte-*

*rium*(preferably non-pathogenic, e.g. *M. bovis* BCG), yeasts (e.g., *Saccharomyces cerevisiae* and *Pichia pastoris*), and protozoans. Alternatively, the transformed cells may be derived from a multicellular organism, i.e. it may be fungal cell, an insect cell, an algal cell, a plant cell, or an animal cell such as a mammalian cell. For the purposes of cloning and/or optimised expression it is preferred that the transformed cell is capable of replicating the nucleic acid fragment of the invention. Cells expressing the nucleic fragment can be used for small-scale or large-scale preparation of the peptides of the invention.

When producing the precursor peptide by means of transformed cells, it is convenient, although far from essential, that the expression product is secreted into the culture medium.

Medical Conditions

In a broad aspect, the present invention provides compstatin analogues of the present invention for use as a medicament or for use in therapy.

The compstatin analogues described herein have biological activities of binding to C3 protein and/or inhibiting complement activation. Generally, the compstatin analogues of the present invention may be used for the treatment or prevention conditions associated with excessive or unwanted activation of the complement system. Complement can be activated through three different pathways: the classical, lectin and alternative pathways. The major activation event that is shared by all three pathways is the proteolytic cleavage of the central protein of the complement system, C3, into its activation products C3a and C3b by C3 convertases.

Generation of these fragments leads to the opsonization of pathogenic cells by C3b and iC3b, a process that renders them susceptible to phagocytosis or clearance, and to the activation of immune cells through an interaction with complement receptors (Markiewski & Lambris, 2007, Am. J. Pathol., 171: 715-727). Deposition of C3b on target cells also induces the formation of new convertase complexes and thereby initiates a self-amplification loop. An ensemble of plasma and cell surface-bound proteins carefully regulates complement activation to prevent host cells from self-attack by the complement cascade. The 13 amino acid cyclic tridecapeptide used as a reference point for the design of the compstatin analogues of the present invention inhibits complement activation by binding to C3 and/or C3b, preventing the cleavage of native C3 by the C3 convertases. Without wishing to be bound by any particular theory, the present inventors believe that the compstatin analogues of the present invention also function in this way and may share one or more biological activities selected from (1) binding to C3 protein, (2) binding to C3b protein, (3) inhibiting the cleavage of native C3 by C3 convertases, and/or (4) inhibiting the activation of the complement system. The biological activity of the compstatin analogues of the present invention may be determined in vitro by measuring their inhibitory effect of the classical complement pathway in a haemolysis assay, for example using a protocol set out in the examples below.

Excessive activation or inappropriate regulation of complement can lead to a number of pathologic conditions, ranging from autoimmune diseases to inflammatory diseases (Holers, 2003, Clin. Immunol., 107: 140-51; Markiewski & Lambris, 2007, supra; Ricklin & Lambris, 2007, Nat. Biotechnol., 25: 1265-75; Sahu et al., 2000, J. Immunol., 165: 2491-9). These conditions include: (1) inhibiting complement activation to facilitate treatment of diseases or conditions including age-related macular degeneration, Stargardt disease, periodontitis, diabetic retinopathy, glaucoma, uveitis, rheumatoid arthritis, spinal cord injury, stroke, multiple sclerosis, Parkinson's disease, Alzheimer's disease, cancer, and respiratory disorders such as asthma, chronic obstructive pulmonary disease (COPD), allergic inflammation, emphysema, bronchitis, bronchiecstasis, cystic fibrosis, tuberculosis, pneumonia, respiratory distress syndrome (RDS—neonatal and adult), rhinitis and sinusitis; bacterial infections such as sepsis, ischemia-reperfusion injury in various tissues, myocardial infarction, anaphylaxis, paroxysmal nocturnal hemoglobinuria, autoimmune hemolytic anemias, psoriasis, hidradentitis suppurativa, myasthenia gravis, systemic lupus erythematosus, CHAPLE syndrome, C3 glomeropathy, IgA nephropathy, atypical hemolytic uremic syndrome, Crohn's disease, ulcerative colitis, antiphospholipid syndrome, or (2) inhibiting complement activation that occurs during cell or solid organ transplantation, or in the use of artificial organs or implants (e.g., by coating or otherwise treating the cells, organs, artificial organs or implants with a peptide of the invention); or (3) inhibiting complement activation that occurs during extracorporeal shunting of physiological fluids (blood, urine) (e.g., by coating the tubing through which the fluids are shunted with a compstatin analogue of the present invention).

Pharmaceutical Compositions and Administration

In a further aspect, the present invention relates to a composition comprising a compstatin analogue according to the invention, or a pharmaceutically acceptable salt or solvate thereof, together with a carrier. In one embodiment of the invention, the composition is a pharmaceutical composition and the carrier is a pharmaceutically acceptable carrier. The present invention also relates to a pharmaceutical composition comprising a compstatin analogue according to the invention, or a salt and/or solvate thereof, together with a carrier, excipient or vehicle. Accordingly, the compstatin analogue of the present invention, or salts or solvates thereof, especially pharmaceutically acceptable salts and/or solvates thereof, may be formulated as compositions or pharmaceutical compositions prepared for storage or administration, and which comprise a therapeutically effective amount of a compstatin analogue of the present invention, or a salt or solvate thereof.

Suitable salts formed with bases include metal salts, such as alkali metal or alkaline earth metal salts.

In one embodiment, a pharmaceutical composition of the invention is one wherein the compstatin analogue is in the form of a pharmaceutically acceptable acid addition salt.

As will be apparent to one skilled in the medical art, a "therapeutically effective amount" of a compstatin analogue compound or pharmaceutical composition thereof of the present invention will vary depending upon, inter alia, the age, weight and/or gender of the subject (patient) to be treated. Other factors that may be of relevance include the physical characteristics of the specific patient under consideration, the patient's diet, the nature of any concurrent medication, the particular compound(s) employed, the particular mode of administration, the desired pharmacological effect(s) and the particular therapeutic indication. Because these factors and their relationship in determining this amount are well known in the medical arts, the determination of therapeutically effective dosage levels, the amount necessary to achieve the desired result of treating and/or preventing and/or remedying malabsorption and/or low-grade inflammation described herein, as well as other medical indications disclosed herein, will be within the ambit of the skilled person.

As used herein, the term "a therapeutically effective amount" refers to an amount which reduces symptoms of a given condition or pathology, and preferably which normalizes physiological responses in an individual with that condition or pathology. Reduction of symptoms or normalization of physiological responses can be determined using methods routine in the art and may vary with a given condition or pathology. In one aspect, a therapeutically effective amount of one or more compstatin analogues, or pharmaceutical compositions thereof, is an amount which restores a measurable physiological parameter to substantially the same value (preferably to within 30%, more preferably to within 20%, and still more preferably to within 10% of the value) of the parameter in an individual without the condition or pathology in question.

In one embodiment of the invention, administration of a compound or pharmaceutical composition of the present invention is commenced at lower dosage levels, with dosage levels being increased until the desired effect of preventing/treating the relevant medical indication is achieved. This would define a therapeutically effective amount. For the compstatin analogues of the present invention, alone or as part of a pharmaceutical composition, such human doses of the active compstatin analogue may be between about 0.01 μmol/kg and 500 μmol/kg body weight, between about 0.01 μmol/kg and 300 μmol/kg body weight, between 0.01 μmol/kg and 100 μmol/kg body weight, between 0.1 μmol/kg and 50 μmol/kg body weight, between 1 pmol/kg and 10 μmol/kg body weight, between 5 pmol/kg and 5 μmol/kg body weight, between 10 pmol/kg and 1 μmol/kg body weight, between 50 pmol/kg and 0.1 μmol/kg body weight, between 100 pmol/kg and 0.01 μmol/kg body weight, between 0.001 μmol/kg and 0.5 μmol/kg body weight, between 0.05 μmol/kg and 0.1 μmol/kg body weight.

The therapeutic dosing and regimen most appropriate for patient treatment will of course vary with the disease or condition to be treated, and according to the patient's weight and other parameters. Without wishing to be bound by any particular theory, it is expected that doses, in the mg/kg range, and shorter or longer duration or frequency of treatment may produce therapeutically useful results, such as a statistically significant inhibition of the alternative and classical complement pathways. The dosage sizes and dosing regimen most appropriate for human use may be guided by the results obtained by the present invention, and may be confirmed in properly designed clinical trials.

An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject.

For local delivery to the eye, the pharmaceutically acceptable compositions may be formulated in isotonic, pH adjusted sterile saline or water, either with or without a preservative such as benzylalkonium chloride. Alternatively, for ophthalmic uses, the pharmaceutically acceptable compositions may be formulated in an ointment such as petrolatum or as eyedrops. Methods of local administration to the eye include, e.g., choroidal injection, transscleral injection or placing a scleral patch, selective arterial catheterization, eyedrops or eye ointments, intraocular administration including transretinal, subconjunctival bulbar, intravitreous injection, suprachoroidal injection, subtenon injection, scleral pocket and scleral cutdown injection, by osmotic pump, etc. The agent can also be alternatively administered intravascularly, such as intravenously (IV) or intraarterially. In choroidal injection and scleral patching, the clinician uses a local approach to the eye after initiation of appropriate anesthesia, including painkillers and ophthalmoplegics. A needle containing the therapeutic compound is directed into the subject's choroid or sclera and inserted under sterile conditions. When the needle is properly positioned the compound is injected into either or both of the choroid or sclera. When using either of these methods, the clinician can choose a sustained release or longer acting formulation. Thus, the procedure can be repeated only every several months or several years, depending on the subject's tolerance of the treatment and response.

The following examples are provided to describe the invention in greater detail. They are intended to illustrate, not to limit, the invention.

Example 1: Synthesis of Compstatin Analogues

General Peptide Synthesis

List of abbreviations and suppliers

| | Abbreviation | Name | Brand/Supplier |
|---|---|---|---|
| Resins | | | |
| | | TentaGel ™ PHB AA(Proct)-Fmoc | Rapp Polymere |
| | | TentaGel ™ SRAM | Rapp Polymere |
| Amino acids | | | |
| | | Pseudoprolines (E.g. YS, FS, FT) | Jupiter Bioscience Ltd. |
| | | Fmoc-L-Aaa-OH | Senn Chemicals AG |
| Coupling reagents | | | |
| | Oxyma Pure | Ethyl cyanoglyoxylate-2-oxime | Chem Impex international |
| | DIC | Diisopropylcarbodiimide | Fluka/Sigma Aldrich Co. |
| | HATU | N-[(dimethylamino)-1H-1,2,3-triazol[4,5-b]pyridine-1-ylmethylene]-N-methylmethanaminium | ChemPep Inc. |

-continued

List of abbreviations and suppliers

| | Abbreviation | Name | Brand/Supplier |
|---|---|---|---|
| | | hexafluorophosphate N-oxide | |
| | HOBt | Hydroxybenzotriazole | Sigma-Aldrich Co. |
| Solvents and reagents | | | |
| | $Boc_2O$ | Di-tert-butyl pyrocarbonate | Advanced ChemTech |
| | DCM | Dichloromethane | Prolabo (VWR) |
| | DIPEA | Diisopropylethylamine | Fluka/Sigma Aldrich Co. |
| | DMF | N,N-dimethylformamide | Taminco |
| | $Et_2O$ | Diethyl ether | Prolabo (VWR) |
| | EtOH | Ethanol | CCS Healthcare AB |
| | HCOOH | Formic acid (HPLC grade) | Sigma-Aldrich Co. |
| | $H_2O$ | Water, Milli-Q water | Millipore |
| | MeCN | Acetonitrile (HPLC) | Sigma-Aldrich Co. |
| | NMP | N-methylpyrrolidone | Sigma-Aldrich Co. |
| | | Piperidine | Jubliant Life Sciences Ltd. |
| | TFA | Trifluoroacetic acid (HPLC) | Chemicals Raw Materials Ltd. |
| | TIS | Triisopropylsilane | Sigma-Aldrich Co. |
| | DODT | 2,2'-(ethylenedioxy)diethanethiol | Sigma-Aldrich Co |
| Other | MeOH | Methanol | Sigma-Aldrich Co. |
| | | Ascorbic acid | Sigma-Aldrich Co. |
| | $I_2$ | Iodine | Sigma-Aldrich Co |

Apparatus and Synthetic Strategy

Peptides were synthesized batchwise on a peptide synthesiser, such as a CEM Liberty Peptide Synthesizer or a Symphony X Synthesizer, according to solid phase peptide synthetic procedures using 9-fluorenylmethyloxycarbonyl (Fmoc) as N-α-amino protecting group and suitable common protection groups for side-chain functionalities.

As polymeric support based resins, such as e.g. TentaGel™, was used. The synthesizer was loaded with resin that prior to usage was swelled in DMF.

Coupling

CEM Liberty Peptide Synthesizer

A solution of Fmoc-protected amino acid (4 equiv.) was added to the resin together with a coupling reagent solution (4 equiv.) and a solution of base (8 equiv.). The mixture was either heated by the microwave unit to 70-75° C. and coupled for 5 minutes or coupled with no heat for 60 minutes. During the coupling nitrogen was bubbled through the mixture.

Symphony X Synthesizer

The coupling solutions were transferred to the reaction vessels in the following order: amino acid (4 equiv.), HATU (4 equiv.) and DIPEA (8 equiv.). The coupling time was 10 min at room temperature (RT) unless otherwise stated. The resin was washed with DMF (5×0.5 min). In case of repeated couplings the coupling time was in all cases 45 min at RT.

Deprotection

CEM Liberty Peptide Synthesizer

The Fmoc group was deprotected using piperidine in DMF or other suitable solvents. The deprotection solution was added to the reaction vessel and the mixture was heated for 30 sec. reaching approx. 40° C. The reaction vessel was drained and fresh deprotection solution was added and subsequently heated to 70-75° C. for 3 min. After draining the reaction vessel the resin was washed with DMF or other suitable solvents.

Symphony X Synthesizer

Fmoc deprotection was performed for 2.5 minutes using 40% piperidine in DMF and repeated using the same conditions. The resin was washed with DMF (5×0.5 min).

Side Chain Acylation

Fmoc-Lys(Dde)-OH or alternatively another amino acid with an orthogonal side chain protective group was introduced at the position of the acylation (side-chain lipidation). The N-terminal of the linier peptide was protected with Ac or Boc. While the peptide was still attached to the resin, the orthogonal side chain protective group was selectively cleaved using freshly prepared hydrazine hydrate (2-4%) in NMP for 2×15 min. The unprotected lysine side chain was then elongated using standard coupling conditions and Fmoc-deprotections with the desired building block. The lipidation moiety was coupled as the last step.

Cleavage

The dried peptide resin was treated with TFA and suitable scavengers for approximately 2 hours. The volume of the filtrate was reduced and the crude peptide was precipitated after addition of diethylether. The crude peptide precipitate was washed several times with diethylether and finally dried.

HPLC Purification of the Crude Peptide

The crude peptide was purified by preparative reverse phase HPLC using a conventional HPLC apparatus, such as a Gilson GX-281 with 331/332 pump combination, for binary gradient application equipped with a column, such as 5×25 cm Gemini NX 5u C18 110A column, and a fraction collector using a flow 20-40 ml/min with a suitable gradient of buffer A (0.1% Fomic acid, aq.) or A (0.1% TFA, aq.) and buffer B (0.1% Formic acid, 90% MeCN, aq.) or B (0.1% TFA, 90% MeCN, aq.). Fractions were analyzed by analytical HPLC and MS and selected fractions were pooled and lyophilized. The final product was characterized by HPLC and MS.

Oxidation

Following purification and lyophilisation of the crude linear peptide, the peptide was redissolved in 0.1% TFA in water, acetonitrile and acetic acids until a clear solution. The concentration of the peptide solution was kept at approx. 1-2 mg/ml depending on the peptides ability to solubilize. The peptide solution was stirred, while a solution of iodine in methanol (approx. 1.5 equiv.) was added drop-wise until the peptide solution obtain an orange colour. After 10-15 minutes, the oxidation was finished and excess iodine was reduced with a solution of ascorbic acid in water (1 equiv.) until a colourless peptide solution. The peptide solution was diluted with water before preparative HPLC purification.

Analytical HPLC

Final purities were determined by analytic HPLC (Agilent 1100/1200 series) equipped with auto sampler, degasser, 20 μl flow cell and Chromeleon software. The HPLC was operated with a flow of 1.2 ml/min at 40° C. using an analytical column, such as Kinetex 2.6 μm XB-C18 100A 100×8.6 mm column. The compound was detected and quantified at 215 nm. Buffers A (0.1% TFA, aq.) and buffer B (0.1% TFA, 90% MeCN, aq.).

Mass Spectroscopy

Final MS analysis were determined on a conventional mass spectroscopy, e.g. Waters Xevo G2 TOF, equipped with electrospray detector with lock-mass calibration and MassLynx software. It was operated in positive mode using direct injection and a cone voltage of 15V (1 TOF), 30 V (2 TOF) or 45 V (3 TOF) as specified on the chomatogram. Precision was 5 ppm with a typical resolution of 15,000-20,000.

Synthesis of Compound No 24

(SEQ ID NO: 146)

$Ac-IC(1)IWQDWGEHRC(1)TEGE-NH_2$

Solid phase peptide synthesis was performed on a Symphony X Synthesizer using standard Fmoc chemistry. TentaGel S RAM (2.51 g; 0.23 mmol/g) was swelled in DMF (20 ml) prior to use and the Fmoc-group was deprotected according to the procedure described above.

Coupling

Suitable protected Fmoc-amino acids according to the sequence were coupled as described above using HATU as coupling reagent. All couplings were performed at R.T.

Deprotection

Fmoc deprotection was performed according to the procedure described above.

Cleavage of the Peptide from the Solid Support

The peptide-resin was washed with EtOH (3×10 ml) and Et2O (3×10 ml) and dried to constant weight at room temperature (r.t.). The peptide was cleaved from the resin by treatment with TFA/DODT (95/5; 60 ml, 2 h; r.t). The volume of the filtrate was reduced and the crude peptide was precipitated after addition of diethylether. The crude peptide precipitate was washed several times with diethylether and finally dried to constant weight at room temperature yield 760 mg crude peptide product (purity ~30%).

HPLC Purification of the Crude Linear Peptide

The crude peptide was purified by preparative reverse phase HPLC using a Gilson GX-281 with 331/332 pump combination for binary gradient application equipped with a 5×25 cm Gemini NX 5u C18 110A, column and a fraction collector and run at 35 ml/min with a gradient of buffer A (0.1% TFA, aq.) and buffer B (0.1% TFA, 90% MeCN, aq.) gradient from 20% B to 45% B in 47 min. Fractions were analyzed by analytical HPLC and MS and relevant fractions were pooled and lyophilized to yield 190 mg, with a purity of 85% as characterized by HPLC and MS as described above. Calculated monoisotopic MW=2001.58 found 2001.81.

Oxidation of the Crude Linear Peptide

The 190 mg purified linear peptide was dissolved in 220 ml 0.1% TFA in water (65%) and acetonitrile (35%) until a clear solution. The peptide solution was stirred, while a solution of iodine in methanol (2.2 mL, approx. 1.5 equiv. iodine) was added drop-wise until the peptide solution obtain an orange colour. The reaction was followed by analytic HPLC but already after 10-15 minutes, the oxidation was finished. Excess iodine was reduced with a solution of ascorbic acid in water (220 μL, approx. 1 equiv.) until a colourless peptide solution. The peptide solution was reduced slightly by rota evaporation before purification on preparative HPLC.

HPLC Purification of the Oxidized Peptide

The crude peptide was purified by preparative reverse phase HPLC using a Gilson GX-281 with 331/332 pump combination for binary gradient application equipped with a 5×25 cm Gemini NX 5u C18 110A, column and a fraction collector and run at 35 ml/min with a gradient of buffer A (0.1% TFA, aq.) and buffer B (0.1% TFA, 90% MeCN, aq.) gradient from 20% B to 45% B in 47 min. Fractions were analyzed by analytical HPLC and MS and relevant fractions were pooled and lyophilized to yield 138 mg, with a purity of 92% as characterized by HPLC and MS as described above. Calculated monoisotopic MW=1999.83 found 1999.54.

Synthesis of Compound No 119

(SEQ ID NO: 287)
Ac-SEFC(1)|[1-Me-Trp]QDWGEHRC(1)[Sar]EGA-K([17-carboxy-heptadecanoyl][yGlu]G[Peg3][yGlu][Peg3])-$NH_2$ Solid phase peptide synthesis was performed on a Symphony X Synthesizer using standard Fmoc chemistry. TentaGel S RAM (3×~1.3 g; 0.22 mmol/g) was swelled in DMF (3×10 ml) prior to use and the Fmoc-group was deprotected according to the procedure described above.

Coupling

Suitable protected Fmoc-amino acids according to the sequence were coupled as described above using HATU as coupling reagent. All couplings were performed at R.T. The lysine used for the incorporation of the branched moiety was incorporated as Fmoc-Lys(Dde)-OH for orthogonal coupling Deprotection Fmoc deprotection was performed according to the procedure described above.

Side Chain Acylation

While the peptide was still attached to the resin, the orthogonal side-chain protective group (Dde) was selectively cleaved using freshly prepared hydrazine hydrate (2-4%) in NMP for 2×15 min. The unprotected lysine side-chain was doubled coupled with Fmoc-Peg3-OH followed by single couplings with Fmoc-Glu-OtBu, Fmoc-Peg3-OH, Fmoc-Gly-OH, Fmoc-Glu-OtBu and lastly the fatty acid moiety 17-carboxy-heptadecanoic acid mono tert-butyl ester using standard coupling conditions.

Cleavage of the Peptide from the Solid Support

The peptide-resin was washed with EtOH (3×15 ml) and Et2O (3×150 ml) and dried to constant weight at room temperature (r.t.). The peptide was cleaved from the resin by treatment with TFA/DODT (95/5; 120 ml, 2 h; r.t.). The volume of the filtrate was reduced and the crude peptide was precipitated after addition of diethylether. The crude peptide precipitate was washed several times with diethylether and finally dried to constant weight at room temperature yield 2.36 g crude peptide product (purity ~41-48%).

HPLC Purification of the Crude Linear Peptide

The crude peptide was purified by preparative reverse phase HPLC using a Gilson GX-281 with 331/332 pump combination for binary gradient application equipped with a 5×25 cm Gemini NX 5u C18 110A, column and a fraction collector and run at 35 ml/min with a gradient of buffer A (0.1% TFA, aq.) and buffer B (0.1% TFA, 90% MeCN, aq.) gradient from 30% B to 60% B in 47 min. Fractions were analyzed by analytical HPLC and MS and relevant fractions were pooled and lyophilized to yield 744 mg, with a purity of 84% as characterized by HPLC and MS as described above. Calculated monoisotopic MW=3207.47 found 3207.32.

Oxidation of the Crude Linear Peptide

The 744 mg purified linear peptide was dissolved in 350 ml 0.1% TFA in water, 150 ml acetonitrile and 100 ml acetic acid until a clear solution (total volume 600 ml). The peptide solution was stirred, while a solution of iodine in methanol (4.7 mL, approx. 1.5 equiv. iodine) was added drop-wise until the peptide solution obtain an orange colour. The reaction was followed by analytic HPLC but already after 10-15 minutes, the oxidation was finished. Excess iodine was reduced with a solution of ascorbic acid in water (150 μL, approx. 1 equiv.) until a colourless peptide solution. The peptide solution was reduced slightly by rota evaporation before purification on preparative HPLC.

HPLC Purification of the Oxidized Peptide

The crude peptide was purified by preparative reverse phase HPLC using a Gilson GX-281 with 331/332 pump combination for binary gradient application equipped with a 5×25 cm Gemini NX 5u C18 110A, column and a fraction collector and run at 35 ml/min with a gradient of buffer A (0.1% TFA, aq.) and buffer B (0.1% TFA, 90% MeCN, aq.) gradient from 30% B to 60% B in 47 min. Fractions were analysed by analytical HPLC and MS and relevant fractions were pooled and lyophilized to yield 510 mg, with a purity of 91% as characterized by HPLC and MS as described above. Calculated monoisotopic MW=3205.47 found 3205.23.

TABLE 1

Synthesized compounds:

| Compound | Sequence |
|---|---|
| Compstatin | 1-13H-IC(1)VVQDWGHHRC(1)T-NH2 (SEQ ID NO: 1) |
| Ac-compstatin | Ac-IC(1)VVQDWGHHRC(1)T-NH2 (SEQ ID NO: 1) |
| 4W9A* | Ac-IC(1)VWQDWGAHRC(1)T-NH2 (SEQ ID NO: 255) |
| Cp40* | H-{d}YIC(1)V[1-Me-Trp]QDW[Sar]AHRC(1)[N-Me-Ile]-NH2 (SEQ ID NO: 256) |
| A | Ac-IC(1)VWQDWGEHRC(1)T-NH2 (SEQ ID NO: 257) |
| B | Ac-IC(1)VWQDWGSHRC(1)T-NH2 (SEQ ID NO: 258) |
| C | Ac-ESSAIC(1)VWQDWGEHRC(1)T-NH2 (SEQ ID NO: 259) |

TABLE 1-continued

| Synthesized compounds: | |
|---|---|
| Compound | Sequence |
| D | Ac-IC(1)VWQDWGEHRC(1)TGAES-NH2 (SEQ ID NO: 260) |
| E | Ac-IC(1)VWQDWGAHSC(1)T-NH2 (SEQ ID NO: 261) |
| F | Ac-IC(1)VWQDWGEHSC(1)T-NH2 (SEQ ID NO: 262) |
| G | Ac-IC(1)VWQDWGEHRC(1)S-NH2 (SEQ ID NO: 263) |
| H | Ac-EGSAIC(1)VWQDWGEHRC(1)[Sar]E-NH2 (SEQ ID NO: 264) |
| J | Ac-IC(1)VWQDWGEHRC(1)TEGE-NH2 (SEQ ID NO: 265) |
| 1 | Ac-IC(1)IWQDWGAHRC(1)T-NH2 (SEQ ID NO: 35) |
| 2 | Ac-IC(1)IWQDWGEHRC(1)T-NH2 (SEQ ID NO: 41) |
| 3 | Ac-ESSAIC(1)IWQDWGEHRC(1)T-NH2 (SEQ ID NO: 140) |
| 4 | Ac-IC(1)I[1-Me-Trp]QDWGEHRC(1)T-NH2 (SEQ ID NO: 32) |
| 5 | Ac-IC(1)IWQDWGKHRC(1)T-NH2 (SEQ ID NO: 43) |
| 6 | Ac-IC(1)IWQDWGSHRC(1)T-NH2 (SEQ ID NO: 45) |
| 7 | Ac-IC(1)IWQKWGEHRC(1)T-NH2 (SEQ ID NO: 48) |
| 8 | Ac-IC(1)IWQKWGAHRC(1)TGAES-NH2 (SEQ ID NO: 142) |
| 9 | Ac-YC(1)IWQDWGEHRC(1)T-NH2 (SEQ ID NO: 53) |
| 10 | Ac-ESSAYC(1)IWQDWGEHRC(1)T-NH2 (SEQ ID NO: 143) |
| 11 | Ac-[Sar]C(1)IWQDWGEHRC(1)T-NH2 (SEQ ID NO: 17) |
| 12 | Ac-IC(1)IWQDWGAHRC(1)E-NH2 (SEQ ID NO: 34) |
| 13 | Ac-IC(1)IWQDWGEHRC(1)[Sar]-NH2 (SEQ ID NO: 38) |
| 14 | Ac-ESSAIC(1)IWQDWGEHRC(1)TGAES-NH2 (SEQ ID NO: 144) |
| 15 | Ac-IC(1)IWQDWGEHRC(1)TGAES-NH2 (SEQ ID NO: 145) |
| 16 | Ac-IC(1)IWQEWGEHRC(1)T-NH2 (SEQ ID NO: 46) |
| 17 | Ac-IC(1)IWQDWGDHRC(1)T-NH2 (SEQ ID NO: 37) |
| 18 | Ac-IC(1)IWQDWGRHRC(1)T-NH2 (SEQ ID NO: 44) |
| 19 | Ac-IC(1)IWQDWGAHSC(1)T-NH2 (SEQ ID NO: 36) |
| 20 | Ac-IC(1)IWQDWGEHSC(1)T-NH2 (SEQ ID NO: 42) |
| 21 | Ac-IC(1)IWQDWGEHRC(1)S-NH2 (SEQ ID NO: 40) |
| 22 | Ac-IC(1)IWQDWGEHRC(1)E-NH2 (SEQ ID NO: 39) |
| 23 | Ac-FC(1)IWQDWGEHRC(1)T-NH2 (SEQ ID NO: 29) |
| 24 | Ac-IC(1)IWQDWGEHRC(1)TEGE-NH2 (SEQ ID NO: 146) |
| 25 | Ac-IC(1)IWQDWGEHRC(1)TEA-NH2 (SEQ ID NO: 147) |
| 26 | Ac-IC(1)IWQDWGEHRC(1)TE-NH2 (SEQ ID NO: 148) |
| 27 | Ac-IC(1)IWQDWGEHRC(1)EGE-NH2 (SEQ ID NO: 149) |
| 28 | Ac-EGSAIC(1)IWQDWGEHRC(1)[Sar]E-NH2 (SEQ ID NO: 150) |
| 29 | Ac-EGSAIC(1)IWQDWGEHRC(1)T-NH2 (SEQ ID NO: 151) |
| 30 | Ac-EGEIC(1)IWQDWGEHRC(1)T-NH2 (SEQ ID NO: 152) |
| 31 | Ac-ESEIC(1)IWQDWGEHRC(1)T-NH2 (SEQ ID NO: 153) |
| 32 | Ac-SEIC(1)IWQDWGEHRC(1)TEA-NH2 (SEQ ID NO: 154) |

TABLE 1-continued

Synthesized compounds:

| Compound | Sequence |
|---|---|
| 33 | Ac-EIC(1)IWQDWGEHRC(1)TE-NH2 (SEQ ID NO: 155) |
| 34 | Ac-EIC(1)IWQDWGEHRC(1)TEGE-NH2 (SEQ ID NO: 156) |
| 35 | Ac-EGEIC(1)IWQDWGEHRC(1)EGE-NH2 (SEQ ID NO: 157) |
| 36 | Ac-ESEIC(1)IWQDWGEHRC(1)EGE-NH2 (SEQ ID NO: 158) |
| 37 | Ac-KEKIC(1)IWQDWGEHRC(1)TEKE-NH2 (SEQ ID NO: 159) |
| 38 | Ac-EKGIC(1)IWQDWGEHRC(1)TEKP-NH2 (SEQ ID NO: 160) |
| 39 | Ac-IC(1)IWQDWGEHRC(1)TEGK-NH2 (SEQ ID NO: 161) |
| 40 | Ac-GSAIC(1)IWQDWGEHRC(1)[Sar]E-NH2 (SEQ ID NO: 162) |
| 41 | Ac-SAIC(1)IWQDWGEHRC(1)[Sar]E-NH2 (SEQ ID NO: 163) |
| 42 | Ac-SAIC(1)IWQDWGEHRC(1)TEG-NH2 (SEQ ID NO: 164) |
| 43 | Ac-FC(1)IWQDWGEHRC(1)TGAE-NH2 (SEQ ID NO: 165) |
| 44 | Ac-EGSAIC(1)IWQDWGEHRC(1)[Sar]EGE-NH2 (SEQ ID NO: 166) |
| 45 | Ac-EGSAFC(1)IWQDWGEHRC(1)[Sar]E-NH2 (SEQ ID NO: 167) |
| 46 | Ac-ESSAIC(1)IWQDWGAHRC(1)T-NH2 (SEQ ID NO: 168) |
| 47 | Ac-IC(1)IWQDWGAHRC(1)TGAES-NH2 (SEQ ID NO: 169) |
| 48 | H-{d}YIC(1)I[1-Me-Trp]QDW[Sar]AHRC(1)[N-Me-Ile]-NH2 (SEQ ID NO: 170) |
| 49 | Ac-EGSAIC(1)I[1-Me-Trp]QDWGEHRC(1)[Sar]E-NH2 (SEQ ID NO: 171) |
| 50 | Ac-EGSAIC(1)I[2-Nal]QDWGEHRC(1)[Sar]E-NH2 (SEQ ID NO: 172) |
| 51 | Ac-IC(1)I[1-Me-Trp]QDWGEHRC(1)TGAES-NH2 (SEQ ID NO: 173) |
| 52 | Ac-IC(1)I[2-Nal]QDWGEHRC(1)TGAES-NH2 (SEQ ID NO: 174) |
| 53 | Ac-EGSAFC(1)I[1-Me-Trp]QDWGEHRC(1)[Sar]E-NH2 (SEQ ID NO: 175) |
| 54 | Ac-EGSAYC(1)I[1-Me-Trp]QDWGEHRC(1)[Sar]E-NH2 (SEQ ID NO: 176) |
| 55 | Ac-EGSAIC(1)IWQDWGEHRC(1)TE-NH2 (SEQ ID NO: 177) |
| 56 | Ac-EGSAFC(1)I[1-Nal]QDWGEHRC(1)TE-NH2 (SEQ ID NO: 178) |
| 57 | Ac-EGSAFC(1)I[1-Me-Trp]QDWGEHRC(1)TE-NH2 (SEQ ID NO: 179) |
| 58 | Ac-EGSAFC(1)I[1-Me-Trp]QDWGEHRC(1)EGE-NH2 (SEQ ID NO: 180) |
| 59 | Ac-EGSAYC(1)I[1-Me-Trp]QDWGEHRC(1)TE-NH2 (SEQ ID NO: 181) |
| 60 | Ac-EGSAFC(1)I[2-Nal]QDWGEHRC(1)TE-NH2 (SEQ ID NO: 182) |
| 61 | Ac-FC(1)I[1-Me-Trp]QDWGEHRC(1)TGAES-NH2 (SEQ ID NO: 183) |
| 62 | Ac-YC(1)I[1-Me-Trp]QDWGEHRC(1)TGAES-NH2 (SEQ ID NO: 184) |
| 63 | Ac-FC(1)I[1-Nal]QDWGEHRC(1)TGAES-NH2 (SEQ ID NO: 185) |
| 64 | Ac-FC(1)I[2-Nal]QDWGEHRC(1)TGAES-NH2 (SEQ ID NO: 186) |
| 65 | Ac-YC(1)I[2-Nal]QDWGEHRC(1)TGAES-NH2 (SEQ ID NO: 187) |
| 66 | Ac-YC(1)IWQDWGEHRC(1)TGAES-NH2 (SEQ ID NO: 188) |
| 67 | Ac-SEFC(1)I[1-Me-Trp]QDWGEHRC(1)TGAES-NH2 (SEQ ID NO: 189) |
| 68 | Ac-YC(1)I[1-Me-Trp]QDWGEHRC(1)TEAGS-NH2 (SEQ ID NO: 190) |

TABLE 1-continued

| Synthesized compounds: | |
|---|---|
| Compound | Sequence |
| 69 | Ac-YC(1)I[1-Me-Trp]QDWGEHRC(1)TESGA-NH2 (SEQ ID NO: 191) |
| 70 | Ac-EGSAYC(1)I[1-Me-Trp]QEWGEHRC(1)[Sar]E-NH2 (SEQ ID NO: 192) |
| 71 | Ac-SEYC(1)I[1-Me-Trp]QDWGEHRC(1)[Sar]EA-NH2 (SEQ ID NO: 193) |
| 72 | Ac-FC(1)I[1-Me-Trp]QDW[Sar]EHRC(1)TGAES-NH2 (SEQ ID NO: 194) |
| 73 | H-{d}YFC(1)I[1-Me-Trp]QDW[Sar]EHRC(1)TGAES-NH2 (SEQ ID NO: 195) |
| 74 | Ac-SEFC(1)I[1-Me-Trp]QDWGEHRC(1)[Sar]GAES-NH2 (SEQ ID NO: 196) |
| 75 | Ac-SEFC(1)I[1-Me-Trp]QDWGEHRC(1)[Sar]EA-NH2 (SEQ ID NO: 197) |
| 76 | Ac-SEFC(1)I[1-Me-Trp]QDW[Sar]EHRC(1)[Sar]EA-NH2 (SEQ ID NO: 198) |
| 77 | Ac-SEFC(1)I[1-Me-Trp]QDW[Sar]EHRC(1)TEA-NH2 (SEQ ID NO: 199) |
| 78 | Ac-SEFC(1)I[1-Me-Trp]QDWGEHRC(1)[Sar]E-NH2 (SEQ ID NO: 200) |
| 79 | Ac-SEFC(1)I[1-Me-Trp]QDW[Sar]EHRC(1)[Sar]E-NH2 (SEQ ID NO: 201) |
| 80 | Ac-EFC(1)I[1-Me-Trp]QDWGEHRC(1)[Sar]EA-NH2 (SEQ ID NO: 202) |
| 81 | Ac-SE[Sar]C(1)I[1-Me-Trp]QDWGEHRC(1)[Sar]EA-NH2 (SEQ ID NO: 203) |
| 82 | Ac-SE[Sar]C(1)I[1-Me-Trp]QDWGEHRC(1)TEA-NH2 (SEQ ID NO: 204) |
| 83 | Ac-SEFC(1)I[1-Me-Trp]QEWGEHRC(1)[Sar]EA-NH2 (SEQ ID NO: 205) |
| 84 | Ac-SEFC(1)I[1-Me-Trp]QDWGEHRC(1)SEA-NH2 (SEQ ID NO: 206) |
| 85 | Ac-EFC(1)I[1-Me-Trp]QDWGEHRC(1)ES-NH2 (SEQ ID NO: 207) |
| 86 | Ac-SEFC(1)I[1-Me-Trp]QDWGEHKC(1)[Sar]EA-NH2 (SEQ ID NO: 208) |
| 87 | Ac-GEFC(1)I[1-Me-Trp]QDWGEHRC(1)[Sar]EA-NH2 (SEQ ID NO: 209) |
| 88 | Ac-GE[Sar]C(1)I[1-Me-Trp]QDWGEHRC(1)TEA-NH2 (SEQ ID NO: 210) |
| 89 | Ac-SE[Sar]C(1)I[1-Me-Trp]QEW[Sar]EHRC(1)TEA-NH2 (SEQ ID NO: 211) |
| 90 | Ac-SE[Sar]C(1)I[1-Me-Trp]QEWGEHRC(1)[Sar]EA-NH2 (SEQ ID NO: 212) |
| 91 | H-{d}Y[Sar]C(1)I[1-Me-Trp]QDWGEHRC(1)TEA-NH2 (SEQ ID NO: 213) |
| 92 | Ac-IC(1)IWQDWGEHRC(1)TEG-K([15-carboxy-pentadecanoyl][γGlu])-NH2 (SEQ ID NO: 278) |
| 93 | Ac-IC(1)IWQDWGEHRC(1)TEG-K([15-carboxy-pentadecanoyl][γGlu][Peg3][Peg3])-NH2 (SEQ ID NO: 279) |
| 94 | Ac-IC(1)IWQDWGEHRC(1)TEGE-K([15-carboxy-pentadecanoyl][γGlu][Peg3][Peg3])-NH2 (SEQ ID NO: 283) |
| 95 | Ac-IC(1)IWQDWGEHRC(1)TEG-K((15-carboxy-pentadecanoyl)-[(Piperazine-1-yl)-acetyl][Peg3][Peg3])-NH2 (SEQ ID NO: 280) |
| 96 | Ac-IC(1)IWQDWGEHRC(1)TEG-K([17-carboxy-heptadecanoyl][γGlu][Peg3][Peg3])-NH2 (SEQ ID NO: 281) |
| 97 | Ac-IC(1)IWQDWGEHRC(1)TEGE-K([17-carboxy-heptadecanoyl][γGlu][Peg3][Peg3])-NH2 (SEQ ID NO: 284) |
| 98 | Ac-IC(1)IWQDWGEHRC(1)TEG-K([19-carboxy-nonadecanoyl][γGlu][Peg3][Peg3])-NH2 (SEQ ID NO: 282) |
| 99 | [15-Carboxy-pentadecanoyl]-ESSAIC(1)IWQDWGEHRC(1)TEGE-NH2 (SEQ ID NO: 318) |
| 100 | Ac-[K([15-carboxy-pentadecanoyl][γGlu][Peg3]-[Peg3]GSAIC(1)IWQDWGEHRC(1)TEGE-NH2 (SEQ ID NO: 268) |
| 101 | Ac-EGSAIC(1)IWQDWGEHRC(1)TEG-K([15-carboxy-pentadecanoyl][γGlu])-NH2 (SEQ ID NO: 271) |

TABLE 1-continued

| Synthesized compounds: | |
|---|---|
| Compound | Sequence |
| 102 | Ac-FC(1)I[1-Me-Trp]QDWGEHRC(1)TGAES-K([15-carboxy-pentadecanoyl][γGlu][Peg3][Peg3])-NH2 (SEQ ID NO: 277) |
| 103 | Ac-EGSAYC(1)I[1-Me-Trp]QDWGEH-[K([15-carboxy-pentadecanoyl][γGlu][Peg3][Peg3])]-C(1)[Sar]E-NH2 (SEQ ID NO: 272) |
| 104 | Ac-EGSAYC(1)I[1-Me-Trp]QDWGEHRC(1)[Sar]EG-K([15-carboxy-pentadecanoyl][γGlu][Peg3][Peg3])-NH2 (SEQ ID NO: 273) |
| 105 | Ac-SAYC(1)I[1-Me-Trp]QDWGEHRC(1)[Sar]E-K([17-carboxy-heptadecanoyl][γGlu]KG[γGlu])-NH2 (SEQ ID NO: 285) |
| 106 | Ac-SAYC(1)I[1-Me-Trp]QDWGEHRC(1)[Sar]EK([17-carboxy-heptadecanoyl][γGlu]G[γGlu])-NH2 (SEQ ID NO: 286) |
| 107 | [15-Carboxy-pentadecanoyl]-EGSEYC(1)I[1-Me-Trp]QDWGEHRC(1)[Sar]E-NH2 (SEQ ID NO: 316) |
| 108 | [17-Carboxy-heptadecanoyl]-EGSEYC(1)I[1-Me-Trp]QDWGEHRC(1)[Sar]E-NH2 (SEQ ID NO: 317) |
| 109 | Ac-EGSAYC(1)I[1-Me-Trp]QDWGEHRC(1)[Sar]EGE-K([17-carboxy-heptadecanoyl][γGlu]G[γGlu])-NH2 (SEQ ID NO: 274) |
| 110 | Ac-EGSAYC(1)I[1-Me-Trp]QDWGEHRC(1)[Sar]EGK-K([17-carboxy-heptadecanoyl][γGlu]G[γGlu])-NH2 (SEQ ID NO: 275) |
| 111 | Ac-EGSAYC(1)I[1-Me-Trp]QDWGEHRC(1)[Sar]EK[γGlu]-K([17-carboxy-heptadecanoyl][γGlu][Peg3][Peg3])]-NH2 (SEQ ID NO: 276) |
| 112 | Ac-SEYC(1)I[1-Me-Trp]QDWGEHRC(1)[Sar]EGA-K([17-carboxy-heptadecanoyl][γGlu]G[γGlu])-NH2 (SEQ ID NO: 307) |
| 113 | Ac-ASGEYC(1)I[1-Me-Trp]QDWGEHRC(1)[Sar]EGE-K([17-carboxy-heptadecanoyl][γGlu]G[γGlu])-NH2 (SEQ ID NO: 269) |
| 114 | Ac-SEYC(1)I[1-Me-Trp]QDWGEHRC(1)[Sar]EGE-K([17-carboxy-heptadecanoyl][γGlu]G[γGlu])-NH2 (SEQ ID NO: 310) |
| 115 | Ac-SEYC(1)I[1-Me-Trp]QDWGEHRC(1)[Sar]EGK-K[17-carboxy-heptadecanoyl][γGlu]G[γGlu])]-NH2 (SEQ ID NO: 311) |
| 116 | Ac-SEYC(1)I[1-Me-Trp]QDWGEHRC(1)[Sar]EGE-K([17-carboxy-heptadecanoyl][γGlu]K[γGlu])-NH2 (SEQ ID NO: 312) |
| 117 | Ac-SEYC(1)I[1-Me-Trp]QDWGEHRC(1)[Sar]EGE[Peg3][Peg3]-K([17-carboxy-heptadecanoyl][γGlu]G[γGlu])-NH2 (SEQ ID NO: 309) |
| 118 | Ac-SEYC(1)I[1-Me-Trp]QDWGEHRC(1)[Sar]EGA-K([17-carboxy-heptadecanoyl][γGlu]G[Peg3][γGlu][Peg3])-NH2 (SEQ ID NO: 308) |
| 119 | Ac-SEFC(1)I[1-Me-Trp]QDWGEHRC(1)[Sar]EGA-K([17-carboxy-heptadecanoyl][γGlu]G[Peg3][γGlu][Peg3])-NH2 (SEQ ID NO: 287) |
| 120 | Ac-SEFC(1)I[1-Me-Trp]QEWGEHRC(1)[Sar]EGA-K([17-carboxy-heptadecanoyl][γGlu]G[Peg3][γGlu][Peg3])-NH2 (SEQ ID NO: 305) |
| 121 | Ac-SEYC(1)I[1-Me-Trp]QEW[Sar]EHRC(1)[Sar]EK[γGlu]A-K([17-carboxy-heptadecanoyl][γGlu]G[Peg3][γGlu][Peg3])-NH2 (SEQ ID NO: 313) |
| 122 | Ac-SEYC(1)I[1-Me-Trp]QEWGEHRC(1)[Sar]EGA-K([17-carboxy-heptadecanoyl][γGlu]G[Peg3][γGlu][Peg3])-NH2 (SEQ ID NO: 314) |
| 123 | Ac-SEFC(1)I[1-Me-Trp]QDWGEHRC(1)[Sar]EGE-[Peg3][Peg3]-K([17-carboxy-heptadecanoyl][γGlu]G[γGlu])-NH2 (SEQ ID NO: 288) |

TABLE 1-continued

| Synthesized compounds: | |
|---|---|
| Compound | Sequence |
| 124 | Ac-SEFC(1)I[1-Me-Trp]QEWGEHRC(1)[Sar]EGE-[Peg3][Peg3]-K([17-carboxy-heptadecanoyl][γGlu]-G[γGlu])]-NH2 (SEQ ID NO: 306) |
| 125 | Ac-SEYC(1)I[1-Me-Trp]QEWGEHRC(1)[Sar]EGE[Peg3][Peg3]-K([17-carboxy-heptadecanoyl][γGlu]G[γGlu])-NH2 (SEQ ID NO: 315) |
| 126 | Ac-SEFC(1)I[1-Me-Trp]QDWGEHRC(1)TEGE[Peg3][Peg3]-K([17-carboxy-heptadecanoyl][γGlu]G[γGlu])-NH2 (SEQ ID NO: 302) |
| 127 | Ac-SEFC(1)I[1-Me-Trp]QDWGEHRC(1)-[Sar]EGE[Peg3][Peg3]-K([15-carboxy-pentadecanoyl][γGlu]-G[γGlu])-NH2 (SEQ ID NO: 292) |
| 128 | Ac-SEFC(1)I[1-Me-Trp]QDWGEHRC(1)[Sar]EGE-[Peg3][Peg3]-K([19-carboxy-nonadecanoyl][γGlu]G[γGlu])-NH2 (SEQ ID NO: 293) |
| 129 | Ac-SEFC(1)I[1-Me-Trp]QDWGEHRC(1)[Sar]EGEGGG-K([17-carboxy-heptadecanoyl][γGlu]G[γGlu])-NH2 (SEQ ID NO: 289) |
| 130 | Ac-SEFC(1)I[1-Me-Trp]QDWGEHRC(1)TEGEGGG-K([17-carboxy-heptadecanoyl][γGlu]G[γGlu])-NH2 (SEQ ID NO: 299) |
| 131 | Ac-SEFC(1)I[1-Me-Trp]QDWGEHRC(1)TEGEGGG-K([15-carboxy-pentadecanoyl][γGlu]G[γGlu])-NH2 (SEQ ID NO: 300) |
| 132 | Ac-SEFC(1)I[1-Me-Trp]QDWGEHRC(1)[Sar]EK[γGlu]GGG-K([17-carboxy-heptadecanoyl][γGlu]G[γGlu])-NH2 (SEQ ID NO: 296) |
| 133 | Ac-SEFC(1)I[1-Me-Trp]QDWGEHRC(1)TEK[γGlu]GGG-K([17-carboxy-heptadecanoyl][γGlu]G[γGlu])-NH2 (SEQ ID NO: 303) |
| 134 | Ac-EFC(1)I[1-Me-Trp]QDWGEHRC(1)EGE-K([17-carboxy-heptadecanoyl][γGlu]G[γGlu])-NH2 (SEQ ID NO: 270) |
| 135 | Ac-SEFC(1)I[1-Me-Trp]QDWGEHRC(1)TGAES-K([15-carboxy-hexadecanoyl][γGlu]G[γGlu])-NH2 (SEQ ID NO: 304) |
| 136 | Ac-SEFC(1)I[1-Me-Trp]-QDWGEHRC(1)TEGE-[8-aminooctanoyl]-K([17-carboxy-heptadecanoyl]-[γGlu]G[γGlu])-NH2 (SEQ ID NO: 297) |
| 137 | Ac-SEFC(1)I[1-Me-Trp]QDWGEHRC(1)TEGE-[8-aminooctanoyl]-E-K([17-carboxy-heptadecanoyl]-[γGlu]G[γGlu])-NH2 (SEQ ID NO: 298) |
| 138 | Ac-SEFC(1)I[1-Me-Trp]QDWGEHRC(1)[Sar]EGE-[Peg3]-K([17-carboxy-heptadecanoyl][γGlu]G[γGlu])-NH2 (SEQ ID NO: 290) |
| 139 | Ac-SEFC(1)I[1-Me-Trp]QDWGEHRC(1)[Sar]EGESES-K([17-carboxy-heptadecanoyl][γGlu]G[γGlu]])-NH2 (SEQ ID NO: 294) |
| 140 | Ac-SEFC(1)I[1-Me-Trp]QDWGEHRC(1)[Sar]EGE[Peg3]ES-K([17-carboxy-heptadecanoyl][γGlu]G[γGlu])-NH2 (SEQ ID NO: 291) |
| 141 | Ac-SEFC(1)I[1-Me-Trp]QDWGEHRC(1)[Sar]EGESES-K([17-carboxy-heptadecanoyl][γGlu])-NH2 (SEQ ID NO: 295) |
| 142 | Ac-SEFC(1)I[1-Me-Trp]QDWGEHRC(1)TEGE[Peg3]ES-K([17-carboxy-heptadecanoyl][γGlu])-NH2 (SEQ ID NO: 301) |
| 143 | Ac-SEFC(1)I[1-Me-Trp] QDWGEHR[C(1)[Sar]EGE[Peg3][Peg3][Peg3]-K([17-carboxy-heptadecanoyl][γGlu]G[γGlu])-NH2 (SEQ ID NO: 319) |

TABLE 1-continued

| Synthesized compounds: | |
|---|---|
| Compound | Sequence |
| 144 | Ac-SEFC(1)I[1-Me-Trp]QDW[Sar]EHRC(1)[Sar]E[Peg3][Peg3]-K([17-carboxy-heptadecanoyl][γGlu]G[γGlu])-NH2 (SEQ ID NO: 320) |
| 145 | Ac-EF[C(1)I[1-Me-Trp]QDWGEHRC(1)[Sar]EA-[Peg3][Peg3]-K([17-carboxy-heptadecanoyl][γGlu]G[γGlu])-NH2 (SEQ ID NO: 321) |

*4W9A—described by Mallik et al., J. Med. Chem. 2005, 48, 274-286 ("V4W/H9A").
Cp40—decribed by Qu et al., Immunobiology 2013, 281(4): 496-505 (also referred to in that paper as "peptide 14).

Example 2: In Vitro Haemolysis Assay

Method

The in vitro effect of the compounds of the present invention was assessed by measuring their inhibitory effect of the classical complement pathway in a haemolysis assay.

Briefly, compounds of the present invention and reference compounds were dissolved in DMSO and diluted in Tris/Casein Assay Buffer (10 mM Tris, 145 mM NaCl, 0.5 mM $MgCl_2$, 0.15 mM $CaCl_2$, and 0.1% W/V Casein, adjusted to pH 7.4) as 9-point serial dilutions in a 96 well plate. Sensitized sheep red blood cells (RBC) coated with rabbit anti-sheep erythrocyte antiserum (Complement Technology, Inc., TX, USA) were washed in Tris/Casein Assay Buffer. 50 μL from each well of diluted compound was added to a 96-well plate containing 50 μL diluted human serum (Complement Technology, Inc., TX, USA) and incubated for 15 minutes at room temperature. The serum dilution factor was optimized for every serum batch to obtain 70-90% of maximal haemolysis using the protocol. Then 50 μL sensitized sheep red blood cells were added to all wells ($10^7$ per well).

After 30 minutes of incubation at 37° C. with gentle agitation, the reaction was stopped by addition of 50 μL Tris STOP Buffer per well (10 mM EDTA, 10 mM Tris, 145 mM NaCl adjusted to pH 7.4). The RBCs were then removed by centrifugation and the resulting supernatant measured for hemolysis by absorbance at 405 nm.

The response was normalized relative to a positive and negative control (vehicle) to calculate the IC50 from the concentration response curve using the 4-parameter logistic (4PL) nonlinear model for curve fitting. All values are based on n=>2 independent determinations.

TABLE 2

Effect of exchange from valine to isoleucine. Compound 1 differs from the prior art compound 4W9A only by the presence of Ile instead of Val at position 3.

| Comp no | CP hemolysis IC50 (nM) | | 1 | 2 | 3 | 4 | 5 | 6 | 7 | 8 | 9 | 10 | 11 | 12 | 13 | | |
|---|---|---|---|---|---|---|---|---|---|---|---|---|---|---|---|---|---|
| 1 | 150 | Ac | I | C(1) | I | W | Q | D | W | G | A | H | R | C(1) | T | $NH_2$ | (SEQ ID NO: 322) |
| 4W9A | 250 | | | | V | | | | | | | | | | | | (SEQ ID NO: 323) |

Further compounds were tested as shown below.

TABLE 3

| in vitro analysis of inhibition of hemolysis | |
|---|---|
| Compound | IC50[nM] |
| Compstatin | >5 μM |
| Ac-compstatin | >5 μM |
| 4W9A | <500 |
| Cp40 | <100 |
| 1 | <250 |
| 2 | <100 |
| 3 | <100 |
| 4 | <100 |
| 5 | <250 |
| 6 | <250 |
| 7 | <1000 |
| 8 | <500 |
| 9 | <100 |
| 10 | <100 |
| 11 | <100 |
| 12 | <100 |
| 13 | <100 |
| 14 | <100 |
| 15 | <100 |
| 16 | <100 |
| 17 | <100 |
| 18 | <100 |
| 19 | <250 |
| 20 | <100 |
| 21 | <100 |
| 22 | <100 |
| 23 | <100 |
| 24 | <100 |
| 25 | <100 |
| 26 | <100 |
| 27 | <100 |
| 28 | <100 |
| 29 | <100 |
| 30 | <100 |

TABLE 3-continued in vitro analysis of inhibition of hemolysis

| Compound | IC50[nM] |
|---|---|
| 31 | <100 |
| 32 | <100 |
| 33 | <100 |
| 34 | <250 |
| 35 | <500 |
| 36 | <250 |
| 37 | <250 |
| 38 | <250 |
| 39 | <100 |
| 40 | <250 |
| 41 | <250 |
| 42 | <250 |
| 43 | <100 |
| 44 | <250 |
| 45 | <100 |
| 46 | <100 |
| 47 | <100 |
| 48 | <100 |
| 49 | <100 |
| 50 | <100 |
| 51 | <100 |
| 52 | <100 |
| 53 | <100 |
| 54 | <100 |
| 55 | <250 |
| 56 | <100 |
| 57 | <100 |
| 58 | <100 |
| 59 | <100 |
| 60 | <100 |
| 61 | <100 |
| 62 | <100 |
| 63 | <100 |
| 64 | <100 |
| 65 | <100 |
| 66 | <100 |
| 67 | <100 |
| 68 | <100 |
| 69 | <100 |
| 70 | <100 |
| 71 | <100 |
| 72 | <100 |
| 73 | <100 |
| 74 | <100 |
| 75 | <100 |
| 76 | <100 |
| 77 | <100 |
| 78 | <100 |
| 79 | <100 |
| 80 | <100 |
| 81 | <100 |
| 82 | <100 |
| 83 | <100 |
| 84 | <100 |
| 85 | <100 |
| 86 | <100 |
| 87 | <100 |
| 88 | <100 |
| 89 | <100 |
| 90 | <250 |
| 91 | <100 |
| 92 | <1000 |
| 93 | <500 |
| 94 | <500 |
| 95 | <500 |
| 96 | <1000 |
| 97 | <250 |
| 98 | <500 |
| 99 | <250 |
| 100 | <500 |
| 101 | <500 |
| 102 | <100 |
| 103 | <100 |
| 104 | <100 |
| 105 | <100 |
| 106 | <250 |
| 107 | <100 |
| 108 | <500 |
| 109 | <250 |
| 110 | <250 |
| 111 | <100 |
| 112 | <500 |
| 113 | <500 |
| 114 | <500 |
| 115 | <250 |
| 116 | <500 |
| 117 | <250 |
| 118 | <100 |
| 119 | <100 |
| 120 | <250 |
| 121 | <250 |
| 122 | <500 |
| 123 | <100 |
| 124 | <100 |
| 125 | <500 |
| 126 | <100 |
| 127 | <100 |
| 128 | <100 |
| 129 | <100 |
| 130 | <100 |
| 131 | <100 |
| 132 | <100 |
| 133 | <100 |
| 134 | <100 |
| 135 | <100 |
| 136 | <100 |
| 137 | <100 |
| 138 | <100 |
| 139 | <100 |
| 140 | <100 |
| 141 | <100 |
| 142 | <100 |
| 143 | <100 |
| 144 | <100 |
| 145 | <100 |

The following pairs of compounds, each of which differ only at position 3, show that the effects of replacing valine by isoleucine are seen in compounds having a variety of peptide backbone sequences.

TABLE 4

Direct comparison of valine 3 to isoleucine 3 in combination with modification at position 9, 11 and/or 13.

| Compound | CP hemolysis IC50 (nM) | | | 1 | 2 | 3 | 4 | 5 | 6 | 7 | 8 | 9 | 10 | 11 | 12 | 13 | | | |
|---|---|---|---|---|---|---|---|---|---|---|---|---|---|---|---|---|---|---|---|
| 2 | 94 | Ac | | I | C(1) | **I** | W | Q | D | W | G | **E** | H | R | C(1) | T | | $NH_2$ | (SEQ ID NO: 41) |
| A | 350 | | | | | **V** | | | | | | | | | | | | | (SEQ ID NO: 257) |
| 6 | 140 | Ac | | I | C(1) | **I** | W | Q | D | W | G | **S** | H | R | C(1) | T | | $NH_2$ | (SEQ ID NO: 45) |
| B | 360 | | | | | **V** | | | | | | | | | | | | | (SEQ ID NO: 258) |
| 3 | 69 | Ac | ESSA | I | C(1) | **I** | W | Q | D | W | G | **E** | H | R | C(1) | T | | $NH_2$ | (SEQ ID NO: 140) |
| C | 300 | | | | | **V** | | | | | | | | | | | | | (SEQ ID NO: 259) |
| 15 | 47 | Ac | | I | C(1) | **I** | W | Q | D | W | G | **E** | H | R | C(1) | T | GAES | $NH_2$ | (SEQ ID NO: 145) |
| D | 210 | | | | | **V** | | | | | | | | | | | | | (SEQ ID NO: 260) |
| 19 | 140 | Ac | | I | C(1) | **I** | W | Q | D | W | G | **A** | H | **S** | C(1) | T | | $NH_2$ | (SEQ ID NO: 36) |
| E | >1000 | | | | | **V** | | | | | | | | | | | | | (SEQ ID NO: 261) |
| 20 | 59 | Ac | | I | C(1) | **I** | W | Q | D | W | G | **E** | H | **S** | C(1) | T | | $NH_2$ | (SEQ ID NO: 42) |
| F | 540 | | | | | **V** | | | | | | | | | | | | | (SEQ ID NO: 262) |
| 21 | 77 | Ac | | I | C(1) | **I** | W | Q | D | W | G | **E** | H | R | C(1) | **S** | | $NH_2$ | (SEQ ID NO: 40) |
| G | 180 | | | | | **V** | | | | | | | | | | | | | (SEQ ID NO: 263) |
| 28 | 88 | Ac | EGSA | I | C(1) | **I** | W | Q | D | W | G | **E** | H | R | C(1) | **Sar** | E | $NH_2$ | (SEQ ID NO: 150) |
| H | 330 | | | | | **V** | | | | | | | | | | | | | (SEQ ID NO: 264) |
| 24 | 90 | Ac | | I | C(1) | **I** | W | Q | D | W | G | **E** | H | R | C(1) | **T** | EGE | $NH_2$ | (SEQ ID NO: 146) |
| J | 240 | | | | | **V** | | | | | | | | | | | | | (SEQ ID NO: 265) |

Isoleucine at position 3 was also demonstrated to be superior compared to other residues often considered to be "conservative" replacements for isoleucine.

TABLE 5

Effect on hemolysis of different residues at position 3
Ac-IC(1)XWQDWGEHRC(1)T-NH2 (SEQ ID NO: 324)

| Compound | Position 3 (X) | IC50, CP hemolysis (nM) |
|---|---|---|
| A | Valine | 350 |
| 2 | Isoleucine | <100 |
| — | Leucine | 500 |
| — | Norvaline | >1000 |
| — | Norleucine | 480 |
| — | Phenylalanine | >10000 |
| — | Beta-Homo-Isoleucine | >10000 |

Due to the high concentration of C3 found in serum, it may be difficult to use the hemolysis assay to differentiate between compounds having very high affinity for C3.

In such circumstances, it may be possible to determine a more accurate hierarchy of binding affinity to C3 by SPR measurements using immobilized C3, as described below.

Example 3: Solubility Test

Materials and Method

Compound solubility at 10 mg/ml

The solubility of compounds was assessed by measuring light scattering over a pH interval from pH 4 to pH 7.5.

Compounds were dissolved in a stock solution of 20 mg/mL in $H_2O$ at pH 2.5 or pH 10. These stock solutions were diluted 1:1 with 200 mM buffered solution to reach a final solution of 10 mg/mL compound in 100 mM buffer. The 5 investigated conditions were (1) acetate pH 4.0, (2) acetate pH 5.0, (3) phosphate pH 6.0, (4) phosphate pH 7 and (5) phosphate pH 7.5.

These samples were equilibrated for 15 minutes at ambient temperature, before evaluating solubility by visual inspection and absorbance measurements in a SpectraMax 190 microplate reader (Molecular Devices).

Visual Inspection

Visual inspection included manually checking the 96 well plate for wells that are clear or non-clear. In addition to this a picture of the 96 well plate is taken.

Microplate Reader and Light Scattering

Absorbance was measured at four wavelengths: 280 nm, 325 nm, 340 nm and 360 nm in an UV transparent 96 well microplate in a SpectraMax 190 microplate reader (Molecular Devices). The compounds do not absorb at 325-360 nm and signal at these wavelengths are therefore an expression of light scattering, which reflects the presence of visible or sub-visible particles that are detected as increased signal.

The light scattering was normalized to the signal from pure buffer solutions (100 mM) and compound solubility was evaluated as good (+) or poor (–). The criteria for this was a combination of visual inspection and light scattering not exceeding 0.1 AU, where values below 0.1 AU are good in visually clear samples.

Solubility of Comp No 24

Stock Solution

Comp No 24 was carefully weighed out and dissolved in pH 2.5 $H_2O$—Cl. The stock solution was equilibrated 15 minutes at ambient temperature, at which point no visible particles were present. 200 mM buffer stock solutions were prepared for each pH condition.

Solubility Assay

The formulations for solubility testing were made by mixing 50 μL Comp No 24 stock solution and 50 μL buffer stock solution with gentle mixing by pipetting the solution a couple of times. This was done for each buffer/pH condition in a UV transparent 96 well microplate (Corning 96 well REF 3635). Reference samples without Comp No 24 were made by mixing 50 μL pH 2.5 $H_2O$—Cl and 50 μL buffer stock solution. The plate was covered with a lid and left 15 minutes at ambient temperature before assessing solubility.

Measuring Solubility

Solubility was assessed by visual inspection of each formulation and a picture taken in a photo box. Light scattering was measured at 280 nm, 325 nm, 340 nm and 360 nm in a SpectraMax 190 microplate reader (Molecular Devices).

The visual inspection revealed that condition 1, 2 and 3 were cloudy and condition 2 additionally contained visible precipitates. The absorbance measurement confirmed the visual evaluation with condition 1, 2 and 3 all exceeding 0.1 AU threshold. Condition 4 and 5 were thus deemed good conditions for solubility of 10 mg/mL Comp No 24.

Similarly, additional compounds were tested for solubility (Table 6).

TABLE 6

Table of most soluble compounds, as tested at 10 mg/mL.

| Comp No | Buffer & pH | | | | |
|---|---|---|---|---|---|
| | Condition 1 Acetate pH 4 | Condition 2 Acetate pH 5 | Condition 3 Phosphate pH 6 | Condition 4 Phosphate pH 7 | Condition 5 Phosphate pH 7.5 |
| 1 | + | – | – | – | – |
| 3 | + | – | – | + | + |
| 14 | + | – | – | + | + |
| 15 | + | – | – | + | + |
| 22 | + | – | – | + | + |
| 24 | – | – | – | + | + |
| 25 | + | – | – | + | + |
| 27 | – | – | – | + | + |
| 28 | + | + | + | + | + |
| 30 | – | – | | + | + |
| 31 | + | + | + | + | + |
| 32 | – | – | – | + | + |
| 33 | – | – | + | + | + |
| 36 | – | – | – | + | + |
| 40 | – | – | + | + | + |
| 41 | – | – | + | + | + |
| 44 | – | – | + | + | + |
| 45 | – | + | + | + | + |
| 49 | – | – | + | + | + |
| 50 | – | – | + | + | + |
| 51 | – | – | + | + | + |
| 52 | – | – | + | + | + |
| 53 | – | – | + | + | + |
| 54 | – | – | + | + | + |
| 55 | – | – | + | + | + |
| 56 | – | – | + | + | + |
| 57 | – | – | + | + | + |
| 60 | – | – | + | + | + |
| 61 | – | – | + | + | + |
| 62 | – | – | + | + | + |
| 63 | – | – | + | + | + |
| 65 | – | – | + | + | + |
| 66 | – | – | + | + | + |
| 67 | – | – | + | + | + |
| 68 | – | – | + | + | + |
| 72 | – | – | + | + | + |
| 73 | + | – | – | + | + |
| 74 | – | + | + | + | + |
| 76 | – | – | + | + | + |
| 77 | – | – | + | + | + |
| 78 | – | – | + | + | + |
| 79 | – | – | + | + | + |
| 80 | – | – | + | + | + |
| 81 | – | – | + | + | + |
| 102 | – | + | + | + | + |
| 103 | – | + | + | + | + |
| 104 | – | + | + | + | + |
| 105 | – | – | + | + | + |
| 107 | – | – | + | + | + |
| 108 | – | – | + | + | + |
| 109 | – | + | + | + | + |
| 111 | – | – | + | + | + |
| 114 | + | + | + | + | + |
| 115 | – | – | + | + | + |
| 116 | – | – | + | + | + |
| 118 | – | + | + | + | + |

"+" denotes solubility at the given condition, as determined by UV absorbance being less than 0.1 AU at 340 nm and the sample being clear when manually inspected.

"–" denotes lack of solubility at the given condition, as UV absorbance at 340 nm exceeds 0.1 AU and/or it is visibly turbid or contains particles.

Example 4: Affinity Measurements by Surface Plasmon Resonance (SPR)

Method

Surface plasmon resonance (SPR) was used to characterize peptides with respect to their binding affinity (Kd) for C3. Human C3 (Complement tech cat #A113c) was immobilised on individual flow cells of CM5 sensor chips (GE Healthcare) using standard amine coupling to a density of approximately 3000 resonance units (RU) in a buffer consisting of 10 mM phosphate pH 7.4, 150 mM NaCl, 0.05% Tween20.

For interaction experiments a multi-cycle experiment approach was used and performed using a BiacoreT200™ instrument (GE Healthcare) at 25° C. Peptides were injected in increasing concentration series (6-8 different concentrations) for 60-120 s at a flow rate of 30 μL/min in a buffer consisting of 10 mM Tris buffer at pH 7.4, with 150 mM NaCl and 0.05% Tween20. This was followed by a dissociation period for up to 10 min. The C3 surface was regenerated between runs by a 45 s injection of 3 M $MgCl_2$.

Sensorgrams were double-referenced (reference surface, blanks) prior to analysis of the kinetic profiles by globally fitting data to a 1:1 Langmuir binding model to obtain association and dissociation rates for calculation of the equilibrium dissociation constant Kd. Each peptide was tested at in a least 3 independent experiments.

TABLE 7

Compstatin analogues binding affinities for C3 as determined by a surface plasmon resonance assay with immobilized C3.

| Comp. no. | Kd [nM] | N |
|---|---|---|
| 2 | 16 | 3 |
| 4 | 1.5 | 3 |
| 15 | 14 | 3 |
| 20 | 37 | 3 |
| 21 | 16 | 3 |
| 23 | 2.8 | 3 |
| 24 | 28 | 5 |
| 28 | 44 | 3 |
| 29 | 21 | 3 |
| 43 | 3.3 | 3 |
| 48 | 0.12 | 3 |
| 49 | 3.2 | 3 |
| 50 | 13 | 3 |
| 53 | 1.4 | 3 |
| 54 | 3.0 | 3 |
| 61 | 0.33 | 3 |
| 63 | 4.3 | 3 |
| 67 | 0.68 | 7 |
| 73 | 0.30 | 3 |
| 75 | 1.5 | 3 |

TABLE 7-continued

Compstatin analogues binding affinities for C3 as determined by a surface plasmon resonance assay with immobilized C3.

| Comp. no. | Kd [nM] | N |
|---|---|---|
| 81 | 9.7 | 3 |
| 82 | 5.4 | 3 |
| 85 | 1.3 | 3 |
| 86 | 2.6 | 3 |
| 102 | 1.7 | 3 |
| 104 | 34 | 2 |
| 106 | 5.4 | 5 |
| 107 | 6.1 | 5 |
| 111 | 8.2 | 5 |
| 117 | 24 | 3 |
| 118 | 11 | 5 |
| 119 | 9.8 | 3 |
| 120 | 28 | 3 |
| 121 | 30 | 3 |
| 122 | 63 | 3 |
| 123 | 11 | 3 |
| 124 | 31 | 3 |
| 125 | 71 | 3 |
| 126 | 5.2 | 3 |
| 127 | 8.5 | 3 |
| 128 | 6.5 | 3 |
| 130 | 4.4 | 3 |
| 139 | 7.4 | 3 |
| 140 | 7.6 | 3 |
| 141 | 6.6 | 3 |
| 142 | 4.8 | 3 |

The following pairs of compounds, which differ only at position 3, show the effects of replacing valine by isoleucine in different peptide backbones.

TABLE 8

Binding affinity of compstatin analogues to immobilized C3 determined by a surface plasmon resonance (SPR) assay.

| Comp no | spr Kd (nM) | | | 1 | 2 | 3 | 4 | 5 | 6 | 7 | 8 | 9 | 10 | 11 | 12 | 13 | | | |
|---|---|---|---|---|---|---|---|---|---|---|---|---|---|---|---|---|---|---|---|
| 2 | 16 | Ac | | I | C(1) | **I** | W | Q | D | W | G | **E** | H | R | C(1) | T | | $NH_2$ | (SEQ ID NO: 41) |
| A | 130 | | | | | **V** | | | | | | | | | | | | | (SEQ ID NO: 257) |
| 15 | 14 | Ac | | I | C(1) | **I** | W | Q | D | W | G | **E** | H | R | C(1) | T | GAES | $NH_2$ | (SEQ ID NO: 145) |
| D | 230 | | | | | **V** | | | | | | | | | | | | | (SEQ ID NO: 260) |
| 21 | 16 | Ac | | I | C(1) | **I** | W | Q | D | W | G | **E** | H | R | C(1) | **S** | | $NH_2$ | (SEQ ID NO: 40) |
| G | 160 | | | | | **V** | | | | | | | | | | | | | (SEQ ID NO: 263) |
| 48 | 0.12 | H | dTyr | I | C(1) | **I** | 1MeTrp | Q | D | W | Sar | A | H | R | C(1) | NMeIle | | $NH_2$ | (SEQ ID NO: 170) |
| Cp40 | 0.31 | | | | | **V** | | | | | | | | | | | | | (SEQ ID NO: 326) |

Example 5: Profiling of Test Compounds in Non-Human Primates (NHP)

Healthy male Cynomolgus monkeys (*Macaca fascicularis*) received single subcutaneous administrations of each test substance. Compounds were formulated in 20 mM phosphate adjusted with NaOH to pH 7.5 and mannitol for isotonicity and dosed at 1840 nmol/kg. Blood was collected from a femoral vein from each animal at the following times: Pre-dose, 1, 2, 4, 8, 24, 48, 72, 96 and 120 h (10 sampling times). Blood was collected into serum separation tubes and allowed to clot at room temperature. The tubes were centrifuged and resulting serum was aliquoted and snap-frozen over dry-ice and stored at nominally −80° C. until analysis. All NHP studies were performed in accordance with animal welfare laws and regulations, including approval of the study by a local ethical review process.

Serum isolated from non-human primates at specific time points after dosing were analyzed for alternative pathway complement activity using the Complement system Alternative Pathway WIESLAB® kit from Svar Life Science (previously Euro diagnostic AB, Sweden) following the manufacturer's protocol. Briefly, serum samples or controls were diluted in buffer and incubated in microtitre strips coated with specific activators of the alternative pathway. The wells were washed and formed C5b-9 was detected using included colorimetric reagents. Absorbance at 405 nm was measured. The percent activity of the alternative complement pathway was calculated for each animal and timepoint relative to the pre-dose activity (0 hours) of the individual animal with subtraction of the negative control. This reflects the pharmacological activity of the compounds.

Figure 1E:
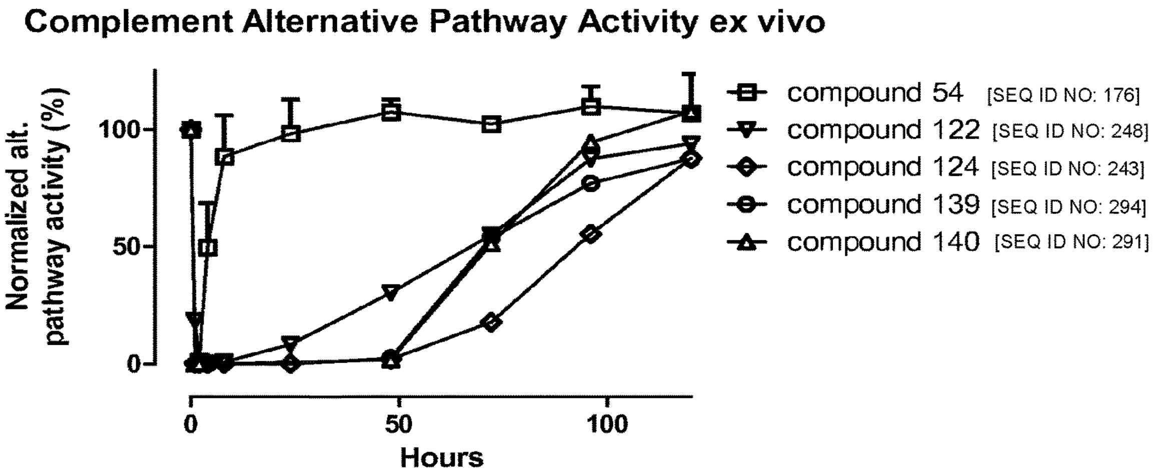
Figure 1F:
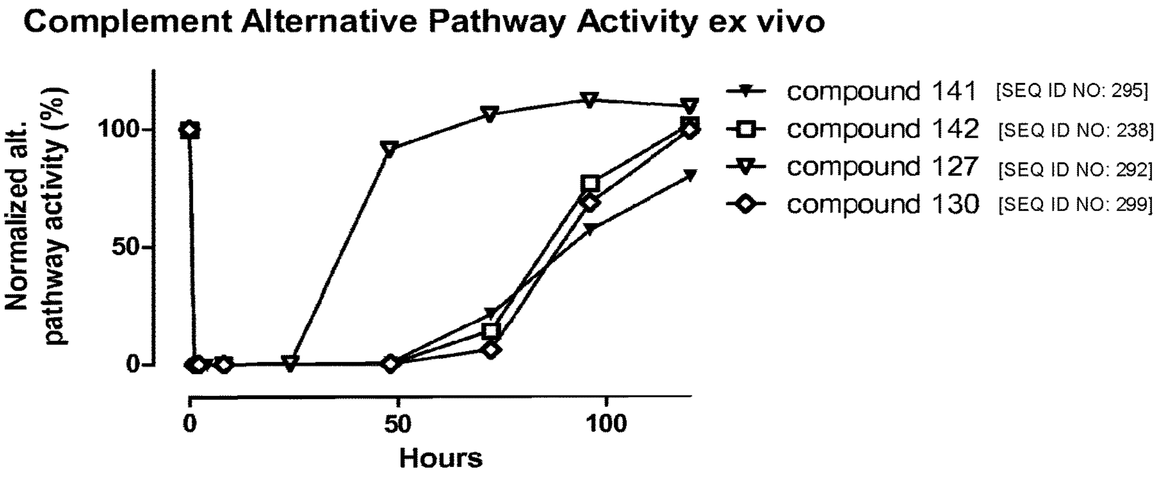

The results from the Alternative Pathway WIESLAB® kit are shown in FIGS. 1*a-f*. In FIG. 1*a*, the non-acylated compound 61 had a relatively short duration of action despite high affinity for C3. The same is seen for the non-acylated compounds Cp40 (FIG. 1*b*) and compound 54 (FIG. 1*e*). By contrast, the acylated compounds in FIGS. 1*b*, 1*c*, 1*d*, 1*e* and 1*f* in general possessed a longer-lasting pharmacological activity in vivo when compared to the non-acylated compounds despite lower affinity. Although acylation of peptides is generally known to increase the in vivo half-life, it was surprisingly found that the in vivo duration of the pharmacological efficacy was prolonged to this extent.

In order to assess pharmacokinetic half-life (t½), serum samples isolated from non-human primates at specific time points after dosing were analysed for total drug compound after sample preparation by solid phase extraction (SPE) and liquid chromatography mass spectrometry (LC-MS/MS) using analogue internal standard. Single measurement of serum concentrations were used for calculation of the pharmacokinetic parameters using the non-compartmental approach in Phoenix WinNonlin 6.3. Plasma terminal elimination half-life ($t_{1/2}$) was determined as ln(2)/λz where λz is the magnitude of the slope of the log linear regression of the log concentration versus time profile during the terminal phase.

Pharmacokinetic (PK) data are shown in Table 9.

TABLE 9

PK data in NHP:

| Compound | $t_{1/2}$ hours |
|---|---|
| Cp40 | 31.8 |
| 54 | 9.71 |
| 61 | 23.3 |
| 104 | 96.3* |
| 106 | 93.9* |
| 107 | 20.1 |
| 111 | 157* |
| 118 | 78.7* |
| 118 | 155 |
| 119 | 139 |
| 122 | 127 |
| 123 | 105 |
| 124 | 112 |
| 139 | 82 |
| 140 | 100 |
| 141 | 145 |
| 142 | 143 |

*Approximate determination, as t½ determined over less than three times the expected half-life.

The invention claimed is:

1. A method of inhibiting complement activation for treating a subject in need thereof, the method comprising administering to the subject a compstatin analogue of Formula I:

```
(SEQ ID NO: 2)
Y1-R1-X1-C-I-X4-Q-X6-W-X8-E-H-X11-C-X13-R2-Y2
(Formula I)
```

wherein:

Y1 is hydrogen, acetyl or a lipophilic group ϕ;

X1 is I, Y, F or Sar;

X4 is W, F, V, Y, 1-Me-Trp, D-Trp, N-Me-Trp, 1-For-Trp, 1-Nal, 2-Nal, 5-Me-Trp, Bpa or 2-Igl;

X6 is E, K or D;

X8 is G or Sar;

X11 is R, S or K;

X13 is T, S, E, F, H, K, Sar, G, I, D, N-Me-Ile or N-Me-Thr;

Y2 is $NH_2$, OH or a lipophilic group ϕ;

R1 is absent or is a sequence of 1 to 6 amino acid residues selected from the group consisting of A, E, G, L, K, F, P, S, T, W, Y, R, V, Sar, εLys, γGlu, βAsp, βAla, or a corresponding D form thereof; Peg3, Peg4, and 8-aminooctanoyl; and R2 is absent or is a sequence of 1 to 8 amino acid residues selected from the group consisting of A, E, G, L, K, F, P, S, T, W, Y, R, V, Sar, εLys, γGlu, βAsp, βAla, or a corresponding D form thereof; Peg3, Peg4, and 8-aminooctanoyl;

wherein the compstatin analogue has a disulphide bond between the cysteine residues at positions 2 and 12;

and wherein the compstatin analogue optionally has a lipophilic group ϕ covalently linked to the side chain of one or more amino acid residues;

or a pharmaceutically acceptable salt thereof, thereby to inhibit complement activation in the subject.

2. The method of claim 1, wherein the compstatin analogue comprises at least one lipophilic group ϕ, wherein:

(a) Y1 or Y2 is a lipophilic group ϕ; and/or (b) the compstatin analogue comprises a lipophilic group ϕ linked to the side chain of an amino acid residue at position X1, X11 or X13, or an amino acid residue in R1 or R2, wherein said amino acid residue is a lysine residue.

3. The method of claim 1, wherein the compstatin analogue does not comprise a lipophilic group ϕ.

4. The method of claim 1, wherein the 13-mer peptide portion (X1-X13) of the compstatin analogue has a sequence selected from:

```
(SEQ ID NO: 13)
[Sar]C(1)|[1-Me-Trp]QDWGEHRC(1)[Sar];

(SEQ ID NO: 14)
[Sar]C(1)|[1-Me-Trp]QDWGEHRC(1)T;

(SEQ ID NO: 15)
[Sar]C(1)|[1-Me-Trp]QEW[Sar]EHRC(1)T;

(SEQ ID NO: 16)
[Sar]C(1)|[1-Me-Trp]QEWGEHRC(1)[Sar];

(SEQ ID NO: 17)
[Sar]C(1)IWQDWGEHRC(1)T;
```

-continued

```
(SEQ ID NO: 18)
FC(1)|[1-Me-Trp]QDW[Sar]EHRC(1)[Sar];

(SEQ ID NO: 19)
FC(1)|[1-Me-Trp]QDW[Sar]EHRC(1)T;

(SEQ ID NO: 20)
FC(1)|[1-Me-Trp]QDWGEHKC(1)[Sar];

(SEQ ID NO: 21)
FC(1)|[1-Me-Trp]QDWGEHRC(1)[Sar];

(SEQ ID NO: 22)
FC(1)|[1-Me-Trp]QDWGEHRC(1)E;

(SEQ ID NO: 23)
FC(1)|[1-Me-Trp]QDWGEHRC(1)S;

(SEQ ID NO: 24)
FC(1)|[1-Me-Trp]QDWGEHRC(1)T;

(SEQ ID NO: 25)
FC(1)|[1-Me-Trp]QEWGEHRC(1)[Sar];

(SEQ ID NO: 26)
FC(1)|[1-Nal]QDWGEHRC(1)T;

(SEQ ID NO: 27)
FC(1)|[2-Nal]QDWGEHRC(1)T;

(SEQ ID NO: 28)
FC(1)IWQDWGEHRC(1)[Sar];

(SEQ ID NO: 29)
FC(1)IWQDWGEHRC(1)T;

(SEQ ID NO: 30)
IC(1)|[1-Me-Trp]QDW[Sar]AHRC(1)[N-Me-Ile];

(SEQ ID NO: 31)
IC(1)|[1-Me-Trp]QDWGEHRC(1)[Sar];

(SEQ ID NO: 32)
IC(1)|[1-Me-Trp]QDWGEHRC(1)T;

(SEQ ID NO: 33)
IC(1)|[2-Nal]QDWGEHRC(1)[Sar];

(SEQ ID NO: 34)
IC(1)IWQDWGAHRC(1)E;

(SEQ ID NO: 35)
IC(1)IWQDWGAHRC(1)T;

(SEQ ID NO: 36)
IC(1)IWQDWGAHSC(1)T;

(SEQ ID NO: 37)
IC(1)IWQDWGDHRC(1)T;

(SEQ ID NO: 38)
IC(1)IWQDWGEHRC(1)[Sar];

(SEQ ID NO: 39)
IC(1)IWQDWGEHRC(1)E;

(SEQ ID NO: 40)
IC(1)IWQDWGEHRC(1)S;

(SEQ ID NO: 41)
IC(1)IWQDWGEHRC(1)T;

(SEQ ID NO: 42)
IC(1)IWQDWGEHSC(1)T;

(SEQ ID NO: 43)
IC(1)IWQDWGKHRC(1)T;

(SEQ ID NO: 44)
IC(1)IWQDWGRHRC(1)T;
```

-continued (SEQ ID NO: 45)
IC(1)IWQDWGSHRC(1)T;

(SEQ ID NO: 46)
IC(1)IWQEWGEHRC(1)T;

(SEQ ID NO: 47)
IC(1)IWQKWGAHRC(1)T;

(SEQ ID NO: 48)
IC(1)IWQKWGEHRC(1)T;

(SEQ ID NO: 49)
YC(1)|[1-Me-Trp]QDWGEHRC(1)[Sar];

(SEQ ID NO: 50)
YC(1)|[1-Me-Trp]QDWGEHRC(1)T;

(SEQ ID NO: 51)
YC(1)|[1-Me-Trp]QEWGEHRC(1)[Sar];

(SEQ ID NO: 52)
YC(1)|[2-Nal]QDWGEHRC(1)T;

(SEQ ID NO: 53)
YC(1)IWQDWGEHRC(1)T;

(SEQ ID NO: 54)
YC(1)|[1-Me-Trp]QDWGEH[K*]C(1)[Sar];
and (SEQ ID NO: 55)
YC(1)|[1-Me-Trp]QEW[Sar]EHRC(1)[Sar].

5. The method of claim 1, wherein the compstatin analogue comprises:

(a) R1 has a sequence selected from the group consisting of:

{d}Y, EGSE (SEQ ID NO: 82), AGSE (SEQ ID NO: 83), SASE (SEQ ID NO: 84), EYSE (SEQ ID NO: 85), GSE, ASE, ESSA (SEQ ID NO: 56), KGSA (SEQ ID NO: 86), AKGE (SEQ ID NO: 57), ASGE (SEQ ID NO: 87), ASSE (SEQ ID NO: 58), ASES (SEQ ID NO: 59), GSAE (SEQ ID NO: 60), ESSE (SEQ ID NO: 61), ESGA (SEQ ID NO: 62), SEG, GES, ESS, EGSA (SEQ ID NO: 63), ESE, EGE, ESA, SAE, SGA, YLEA (SEQ ID NO: 64), GSA, KEK, EKG, ES, AE, TE, KE, GE, FE, YE, AS, SE, RS, SR, SA, GE, Y, S and E; and/or (b) R2 has a sequence selected from the group consisting of:

EGASGSG (SEQ ID NO: 88), EGAGSG (SEQ ID NO: 89), EGASAG (SEQ ID NO: 90), EGAGAG (SEQ ID NO: 91), EGESGSG (SEQ ID NO: 92), EGEGSG (SEQ ID NO: 93), EGESAG (SEQ ID NO: 94), EGEGAG (SEQ ID NO: 95), EK [γGlu] AK (SEQ ID NO: 96), EGEGG (SEQ ID NO: 97), EGAGG (SEQ ID NO: 98), EGESS (SEQ ID NO: 99), GAESK (SEQ ID NO: 100), EGAK (SEQ ID NO: 101), EGEK (SEQ ID NO: 102), EGG, EGK, EGKK (SEQ ID NO: 103), EGS, EK, EGA, EGAK (SEQ ID NO: 101), EK [γGlu], EK [γGlu]-K (SEQ ID NO: 104), EGE-[Peg3, EGE [Peg3]-K (SEQ ID NO: 105), EGE [Peg3][Peg3], EGE [Peg3][Peg3]-K (SEQ ID NO: 106), EGE [Peg3][Peg3][Peg3], GESESE (SEQ ID NO: 107), GAESES (SEQ ID NO: 108), EGESES (SEQ ID NO: 109), EGESESK (SEQ ID NO: 110), EGE [Peg3]-ES (SEQ ID NO: 111), EGE [Peg3]-ESK (SEQ ID NO: 112), GESESE (SEQ ID NO: 107), EGE-[8-aminooctanoyl], EGE-[8-aminooctanoyl]-K (SEQ ID NO: 113), EGE-[8-aminooctanoyl]-EK (SEQ ID NO: 114), EGEGGG (SEQ ID NO: 115), EGEGGGK (SEQ ID NO: 116), EK [γGlu]GGG (SEQ ID NO: 117), EK [γGlu]GGGK (SEQ ID NO: 118), EGE-[8-aminooctanoyl]-E (SEQ ID NO: 119), GAES (SEQ ID NO: 65), EYGS (SEQ ID NO: 66), EGYA (SEQ ID NO: 67), EAGS (SEQ ID NO: 68), EAKS (SEQ ID NO: 69), EKSA (SEQ ID NO: 70), ESGA (SEQ ID NO: 62), EGGS (SEQ ID NO: 71), EGGA (SEQ ID NO: 72), ESSG (SEQ ID NO: 73), ESAG (SEQ ID NO: 74), GEES (SEQ ID NO: 75), AEES (SEQ ID NO: 76), ESEG (SEQ ID NO: 77), AEGS (SEQ ID NO: 78), ESGS (SEQ ID NO: 79), SEGA (SEQ ID NO: 80), SEG, EGK, ESG, EAG, GAE, EGEA (SEQ ID NO: 81), EGE, EA, E, S, GE, GEK, EG, EA, EKE and EKP.

6. The method of claim 5, wherein the compstatin analogue comprises a lipophilic group ϕ covalently linked to an amino acid side chain of R1 and/or R2.

7. The method of claim 5, wherein the compstatin analogue comprises:

(a) R1 has the sequence K*GSA (SEQ ID NO: 325); and/or (b) R2 has the sequence EK [γGlu] AK* (SEQ ID NO: 121), EGKK* (SEQ ID NO: 122), EK [γGlu]K* (SEQ ID NO: 123), EGE [Peg3]-K* (SEQ ID NO: 124), EGESESK* (SEQ ID NO: 125), EGE [Peg3]-ESK* (SEQ ID NO: 126), EGE-[8-aminooctanoyl]-K* (SEQ ID NO: 127), EGE-[8-aminooctanoyl]-EK* (SEQ ID NO: 128), EGEGGGK* (SEQ ID NO: 129), EK [γGlu] GGGK* (SEQ ID NO: 130), EGE [Peg3][Peg3]-K* (SEQ ID NO: 131), GAESK* (SEQ ID NO: 132), EGAK* (SEQ ID NO: 133), EGEK* (SEQ ID NO: 134), EGK* EGE [Peg3]-ESK* (SEQ ID NO: 135), GESESEK* (SEQ ID NO: 136), GEK* or EK*.

8. The method of claim 1, wherein the compstatin analogue comprises a sequence selected from the group consisting of:

(SEQ ID NO: 41)
IC(1)IWQDWGEHRC(1)T;

(SEQ ID NO: 140)
ESSAIC(1)IWQDWGEHRC(1)T;

(SEQ ID NO: 141)
IC(1)|[1MeTrp]QDWGEHRC(1)T;

(SEQ ID NO: 43)
IC(1)IWQDWGKHRC(1)T;

(SEQ ID NO: 45)
IC(1)IWQDWGSHRC(1)T (SEQ ID NO: 48)
IC(1)IWQKWGEHRC(1)T;

(SEQ ID NO: 142)
IC(1)IWQKWGAHRC(1)TGAES;

(SEQ ID NO: 53)
YC(1)IWQDWGEHRC(1)T;

(SEQ ID NO: 143)
ESSAYC(1)IWQDWGEHRC(1)T;

(SEQ ID NO: 17)
[Sar]C(1)IWQDWGEHRC(1)T;

(SEQ ID NO: 34)
IC(1)IWQDWGAHRC(1)E;

(SEQ ID NO: 38)
IC(1)IWQDWGEHRC(1)[Sar];

(SEQ ID NO: 144)
ESSAIC(1)IWQDWGEHRC(1)TGAES;

(SEQ ID NO: 145)
IC(1)IWQDWGEHRC(1)TGAES;

-continued (SEQ ID NO: 46)
IC(1)IWQEWGEHRC(1)T;

(SEQ ID NO: 37)
IC(1)IWQDWGDHRC(1)T;

(SEQ ID NO: 44)
IC(1)IWQDWGRHRC(1)T;

(SEQ ID NO: 36)
IC(1)IWQDWGAHSC(1)T;

(SEQ ID NO: 42)
IC(1)IWQDWGEHSC(1)T;

(SEQ ID NO: 40)
IC(1)IWQDWGEHRC(1)S;

(SEQ ID NO: 39)
IC(1)IWQDWGEHRC(1)E;

(SEQ ID NO: 29)
FC(1)IWQDWGEHRC(1)T;

(SEQ ID NO: 146)
IC(1)IWQDWGEHRC(1)TEGE;

(SEQ ID NO: 147)
IC(1)IWQDWGEHRC(1)TEA;

(SEQ ID NO: 148)
IC(1)IWQDWGEHRC(1)TE;

(SEQ ID NO: 149)
IC(1)IWQDWGEHRC(1)EGE;

(SEQ ID NO: 150)
EGSAIC(1)IWQDWGEHRC(1)[Sar]E;

(SEQ ID NO: 151)
EGSAIC(1)IWQDWGEHRC(1)T;

(SEQ ID NO: 152)
EGEIC(1)IWQDWGEHRC(1)T;

(SEQ ID NO: 153)
ESEIC(1)IWQDWGEHRC(1)T;

(SEQ ID NO: 154)
SEIC(1)IWQDWGEHRC(1)TEA;

(SEQ ID NO: 155)
EIC(1)IWQDWGEHRC(1)TE;

(SEQ ID NO: 156)
EIC(1)IWQDWGEHRC(1)TEGE;

(SEQ ID NO: 157)
EGEIC(1)IWQDWGEHRC(1)EGE;

(SEQ ID NO: 158)
ESEIC(1)IWQDWGEHRC(1)EGE;

(SEQ ID NO: 159)
KEKIC(1)IWQDWGEHRC(1)TEKE;

(SEQ ID NO: 160)
EKGIC(1)IWQDWGEHRC(1)TEKP;

(SEQ ID NO: 161)
IC(1)IWQDWGEHRC(1)TEGK;

(SEQ ID NO: 162)
GSAIC(1)IWQDWGEHRC(1)[Sar]E;

(SEQ ID NO: 163)
SAIC(1)IWQDWGEHRC(1)[Sar]E;

(SEQ ID NO: 164)
SAIC(1)IWQDWGEHRC(1)TEG;

-continued (SEQ ID NO: 165)
FC(1)IWQDWGEHRC(1)TGAE;

(SEQ ID NO: 166)
EGSAIC(1)IWQDWGEHRC(1)[Sar]EGE;

(SEQ ID NO: 167)
EGSAFC(1)IWQDWGEHRC(1)[Sar]E;

(SEQ ID NO: 168)
ESSAIC(1)IWQDWGAHRC(1)T;

(SEQ ID NO: 169)
IC(1)IWQDWGAHRC(1)TGAES;

(SEQ ID NO: 170)
{d}YIC(1)|[1-Me-Trp]QDW[Sar]AHRC(1)-[N-Me-Ile];

(SEQ ID NO: 171)
EGSAIC(1)|[1-Me-Trp]QDWGEHRC(1)[Sar]E;

(SEQ ID NO: 172)
EGSAIC(1)|[2-Nal]QDWGEHRC(1)[Sar]E;

(SEQ ID NO: 173)
IC(1)|[1-Me-Trp]QDWGEHRC(1)TGAES;

(SEQ ID NO: 174)
IC(1)|[2-Nal]QDWGEHRC(1)TGAES;

(SEQ ID NO: 175)
EGSAFC(1)|[1-Me-Trp]QDWGEHRC(1)[Sar]E;

(SEQ ID NO: 176)
EGSAYC(1)|[1-Me-Trp]QDWGEHRC(1)[Sar]E;

(SEQ ID NO: 177)
EGSAIC(1)IWQDWGEHRC(1)TE;

(SEQ ID NO: 178)
EGSAFC(1)|[1-Nal]QDWGEHRC(1)TE;

(SEQ ID NO: 179)
EGSAFC(1)|[1-Me-Trp]QDWGEHRC(1)TE;

(SEQ ID NO: 180)
EGSAFC(1)|[1-Me-Trp]QDWGEHRC(1)EGE;

(SEQ ID NO: 181)
EGSAYC(1)|[1-Me-Trp]QDWGEHRC(1)TE;

(SEQ ID NO: 182)
EGSAFC(1)|[2-Nal]QDWGEHRC(1)TE;

(SEQ ID NO: 183)
FC(1)|[1-Me-Trp]QDWGEHRC(1)TGAES;

(SEQ ID NO: 184)
YC(1)|[1-Me-Trp]QDWGEHRC(1)TGAES;

(SEQ ID NO: 185)
FC(1)|[1-Nal]QDWGEHRC(1)TGAES;

(SEQ ID NO: 186)
FC(1)|[2-Nal]QDWGEHRC(1)TGAES;

(SEQ ID NO: 187)
YC(1)|[2-Nal]QDWGEHRC(1)TGAES;

(SEQ ID NO: 188)
YC(1)IWQDWGEHRC(1)TGAES;

(SEQ ID NO: 189)
SEFC(1)|[1-Me-Trp]QDWGEHRC(1)TGAES;

(SEQ ID NO: 190)
YC(1)|[1-Me-Trp]QDWGEHRC(1)TEAGS;

(SEQ ID NO: 191)
YC(1)|[1-Me-Trp]QDWGEHRC(1)TESGA;

-continued (SEQ ID NO: 192)
EGSAYC(1)[1-Me-Trp]QEWGEHRC(1)[Sar]E;

(SEQ ID NO: 193)
SEYC(1)I[1-Me-Trp]QDWGEHRC(1)[Sar]EA;

(SEQ ID NO: 194)
FC(1)I[1-Me-Trp]QDW[Sar]EHRC(1)TGAES;

(SEQ ID NO: 195)
{d}YFC(1)I[1-Me-Trp]QDW[Sar]EHRC(1)TGAES;

(SEQ ID NO: 196)
SEFC(1)[1-Me-Trp]QDWGEHRC(1)[Sar]GAES;

(SEQ ID NO: 197)
SEFC(1)I[1-Me-Trp]QDWGEHRC(1)[Sar]EA;

(SEQ ID NO: 198)
SEFC(1)I[1-Me-Trp]QDW[Sar]EHRC(1)[Sar]EA;

(SEQ ID NO: 199)
SEFC(1)I[1-Me-Trp]QDW[Sar]EHRC(1)TEA;

(SEQ ID NO: 200)
SEFC(1)I[1-Me-Trp]QDWGEHRC(1)[Sar]E;

(SEQ ID NO: 201)
SEFC(1)I[1-Me-Trp]QDW[Sar]EHRC(1)[Sar]E;

(SEQ ID NO: 202)
EFC(1)I[1-Me-Trp]QDWGEHRC(1)[Sar]EA;

-continued (SEQ ID NO: 203)
SE[Sar]C(1)I[1-Me-Trp]QDWGEHRC(1)[Sar]EA;

(SEQ ID NO: 204)
SE[Sar]C(1)I[1-Me-Trp]QDWGEHRC(1)TEA;

(SEQ ID NO: 205)
SEFC(1)I[1-Me-Trp]QEWGEHRC(1)[Sar]EA;

(SEQ ID NO: 206)
SEFC(1)I[1-Me-Trp]QDWGEHRC(1)SEA;

(SEQ ID NO: 207)
EFC(1)I[1-Me-Trp]QDWGEHRC(1)ES;

(SEQ ID NO: 208)
SEFC(1)I[1-Me-Trp]QDWGEHKC(1)[Sar]EA;

(SEQ ID NO: 209)
GEFC(1)I[1-Me-Trp]QDWGEHRC(1)[Sar]EA;

(SEQ ID NO: 210)
GE[Sar]C(1)I[1-Me-Trp]QDWGEHRC(1)TEA;

(SEQ ID NO: 211)
SE[Sar]C(1)I[1-Me-Trp]QEW[Sar]EHRC(1)TEA;

(SEQ ID NO: 212)
SE[Sar]C(1)I[1-Me-Trp]QEWGEHRC(1)[Sar]EA; and (SEQ ID NO: 213)
{d}Y[Sar]C(1)I[1-Me-Trp]QDWGEHRC(1)TEA.

9. The method of claim 1, wherein the compstatin analogue is:

(SEQ ID NO: 35)
Ac-IC(1)IWQDWGAHRC(1)T-NH2 (Compound 1);

(SEQ ID NO: 41)
Ac-IC(1)IWQDWGEHRC(1)T-NH2 (Compound 2);

(SEQ ID NO: 140)
Ac-ESSAIC(1)IWQDWGEHRC(1)T-NH2 (Compound 3);

(SEQ ID NO: 32)
Ac-IC(1)I[1-Me-Trp]QDWGEHRC(1)T-NH2 (Compound 4);

(SEQ ID NO: 43)
Ac-IC(1)IWQDWGKHRC(1)T-NH2 (Compound 5);

(SEQ ID NO: 45)
Ac-IC(1)IWQDWGSHRC(1)T-NH2 (Compound 6);

(SEQ ID NO: 48)
Ac-IC(1)IWQKWGEHRC(1)T-NH2 (Compound 7);

(SEQ ID NO: 142)
Ac-IC(1)IWQKWGAHRC(1)TGAES-NH2 (Compound 8);

(SEQ ID NO: 53)
Ac-YC(1)IWQDWGEHRC(1)T-NH2 (Compound 9);

(SEQ ID NO: 143)
Ac-ESSAYC(1)IWQDWGEHRC(1)T-NH2 (Compound 10);

(SEQ ID NO: 17)
Ac-[Sar]C(1)IWQDWGEHRC(1)T-NH2 (Compound 11);

(SEQ ID NO: 34)
Ac-IC(1)IWQDWGAHRC(1)E-NH2 (Compound 12);

(SEQ ID NO: 38)
Ac-IC(1)IWQDWGEHRC(1)[Sar]-NH2 (Compound 13);

(SEQ ID NO: 144)
Ac-ESSAIC(1)IWQDWGEHRC(1)TGAES-NH2 (Compound 14);

-continued (SEQ ID NO: 145)
Ac-IC(1)IWQDWGEHRC(1)TGAES-NH2 (Compound 15);

(SEQ ID NO: 46)
Ac-IC(1)IWQEWGEHRC(1)T-NH2 (Compound 16);

(SEQ ID NO: 37)
Ac-IC(1)IWQDWGDHRC(1)T-NH2 (Compound 17);

(SEQ ID NO: 44)
Ac-IC(1)IWQDWGRHRC(1)T-NH2 (Compound 18);

(SEQ ID NO: 36)
Ac-IC(1)IWQDWGAHSC(1)T-NH2 (Compound 19);

(SEQ ID NO: 42)
Ac-IC(1)IWQDWGEHSC(1)T-NH2 (Compound 20);

(SEQ ID NO: 40)
Ac-IC(1)IWQDWGEHRC(1)S-NH2 (Compound 21);

(SEQ ID NO: 39)
Ac-IC(1)IWQDWGEHRC(1)E-NH2 (Compound 22);

(SEQ ID NO: 29)
Ac-FC(1)IWQDWGEHRC(1)T-NH2 (Compound 23);

(SEQ ID NO: 146)
Ac-IC(1)IWQDWGEHRC(1)TEGE-NH2 (Compound 24);

(SEQ ID NO: 147)
Ac-IC(1)IWQDWGEHRC(1)TEA-NH2 (Compound 25);

(SEQ ID NO: 148)
Ac-IC(1)IWQDWGEHRC(1)TE-NH2 (Compound 26);

(SEQ ID NO: 149)
Ac-IC(1)IWQDWGEHRC(1)EGE-NH2 (Compound 27);

(SEQ ID NO: 150)
Ac-EGSAIC(1)IWQDWGEHRC(1)[Sar]E-NH2 (Compound 28);

(SEQ ID NO: 151)
Ac-EGSAIC(1)IWQDWGEHRC(1)T-NH2 (Compound 29);

(SEQ ID NO: 152)
Ac-EGEIC(1)IWQDWGEHRC(1)T-NH2 (Compound 30);

(SEQ ID NO: 153)
Ac-ESEIC(1)IWQDWGEHRC(1)T-NH2 (Compound 31);

(SEQ ID NO: 154)
Ac-SEIC(1)IWQDWGEHRC(1)TEA-NH2 (Compound 32);

(SEQ ID NO: 155)
Ac-EIC(1)IWQDWGEHRC(1)TE-NH2 (Compound 33);

(SEQ ID NO: 156)
Ac-EIC(1)IWQDWGEHRC(1)TEGE-NH2 (Compound 34);

(SEQ ID NO: 157)
Ac-EGEIC(1)IWQDWGEHRC(1)EGE-NH2 (Compound 35);

(SEQ ID NO: 158)
Ac-ESEIC(1)IWQDWGEHRC(1)EGE-NH2 (Compound 36);

(SEQ ID NO: 159)
Ac-KEKIC(1)IWQDWGEHRC(1)TEKE-NH2 (Compound 37);

(SEQ ID NO: 160)
Ac-EKGIC(1)IWQDWGEHRC(1)TEKP-NH2 (Compound 38);

(SEQ ID NO: 161)
Ac-IC(1)IWQDWGEHRC(1)TEGK-NH2 (Compound 39);

(SEQ ID NO: 162)
Ac-GSAIC(1)IWQDWGEHRC(1)[Sar]E-NH2 (Compound 40);

(SEQ ID NO: 163)
Ac-SAIC(1)IWQDWGEHRC(1)[Sar]E-NH2 (Compound 41);

-continued (SEQ ID NO: 164)
Ac-SAIC(1)IWQDWGEHRC(1)TEG-NH2 (Compound 42);

(SEQ ID NO: 165)
Ac-FC(1)IWQDWGEHRC(1)TGAE-NH2 (Compound 43);

(SEQ ID NO: 166)
Ac-EGSAIC(1)IWQDWGEHRC(1)[Sar]EGE-NH2 (Compound 44);

(SEQ ID NO: 167)
Ac-EGSAFC(1)IWQDWGEHRC(1)[Sar]E-NH2 (Compound 45);

(SEQ ID NO: 168)
Ac-ESSAIC(1)IWQDWGAHRC(1)T-NH2 (Compound 46);

(SEQ ID NO: 169)
Ac-IC(1)IWQDWGAHRC(1)TGAES-NH2 (Compound 47);

(SEQ ID NO: 170)
H-{d}YIC(1)|[1-Me-Trp]QDW[Sar]AHRC(1)[N-Me-Ile]-NH2 (Compound 48) ;

(SEQ ID NO: 171)
Ac-EGSAIC(1)|[1-Me-Trp]QDWGEHRC(1)[Sar]E-NH2 (Compound 49);

(SEQ ID NO: 172)
Ac-EGSAIC(1)|[2-Nal]QDWGEHRC(1)[Sar]E-NH2 (Compound 50);

(SEQ ID NO: 173)
Ac-IC(1)|[1-Me-Trp]QDWGEHRC(1)TGAES-NH2 (Compound 51);

(SEQ ID NO: 174)
Ac-IC(1)|[2-Nal]QDWGEHRC(1)TGAES-NH2 (Compound 52);

(SEQ ID NO: 175)
Ac-EGSAFC(1)|[1-Me-Trp]QDWGEHRC(1)[Sar]E-NH2 (Compound 53);

(SEQ ID NO: 176)
Ac-EGSAYC(1)|[1-Me-Trp]QDWGEHRC(1)[Sar]E-NH2 (Compound 54);

(SEQ ID NO: 177)
Ac-EGSAIC(1)IWQDWGEHRC(1)TE-NH2 (Compound 55);

(SEQ ID NO: 178)
Ac-EGSAFC(1)|[1-Nal]QDWGEHRC(1)TE-NH2 (Compound 56);

(SEQ ID NO: 179)
Ac-EGSAFC(1)|[1-Me-Trp]QDWGEHRC(1)TE-NH2 (Compound 57);

(SEQ ID NO: 180)
Ac-EGSAFC(1)|[1-Me-Trp]QDWGEHRC(1)EGE-NH2 (Compound 58);

(SEQ ID NO: 181)
Ac-EGSAYC(1)|[1-Me-Trp]QDWGEHRC(1)TE-NH2 (Compound 59);

(SEQ ID NO: 182)
Ac-EGSAFC(1)|[2-Nal]QDWGEHRC(1)TE-NH2 (Compound 60);

(SEQ ID NO: 183)
Ac-FC(1)|[1-Me-Trp]QDWGEHRC(1)TGAES-NH2 (Compound 61);

(SEQ ID NO: 184)
Ac-YC(1)|[1-Me-Trp]QDWGEHRC(1)TGAES-NH2 (Compound 62);

(SEQ ID NO: 185)
Ac-FC(1)|[1-Nal]QDWGEHRC(1)TGAES-NH2 (Compound 63);

(SEQ ID NO: 186)
Ac-FC(1)|[2-Nal]QDWGEHRC(1)TGAES-NH2 (Compound 64);

(SEQ ID NO: 187)
Ac-YC(1)|[2-Nal]QDWGEHRC(1)TGAES-NH2 (Compound 65);

(SEQ ID NO: 188)
Ac-YC(1)IWQDWGEHRC(1)TGAES-NH2 (Compound 66);

(SEQ ID NO: 189)
Ac-SEFC(1)|[1-Me-Trp]QDWGEHRC(1)TGAES-NH2 (Compound 67);

(SEQ ID NO: 190)
Ac-YC(1)|[1-Me-Trp]QDWGEHRC(1)TEAGS-NH2 (Compound 68);

-continued (SEQ ID NO: 191)
Ac-YC(1)|[1-Me-Trp]QDWGEHRC(1)TESGA-NH2 (Compound 69);

(SEQ ID NO: 192)
Ac-EGSAYC(1)|[1-Me-Trp]QEWGEHRC(1)[Sar]E-NH2 (Compound 70);

(SEQ ID NO: 193)
Ac-SEYC(1)|[1-Me-Trp]QDWGEHRC(1)[Sar]EA-NH2 (Compound 71);

(SEQ ID NO: 194)
Ac-FC(1)|[1-Me-Trp]QDW[Sar]EHRC(1)TGAES-NH2 (Compound 72);

(SEQ ID NO: 195)
H-{d}YFC(1)|[1-Me-Trp]QDW[Sar]EHRC(1)TGAES-NH2 (Compound 73);

(SEQ ID NO: 196)
Ac-SEFC(1)|[1-Me-Trp]QDWGEHRC(1)[Sar]GAES-NH2 (Compound 74);

(SEQ ID NO: 197)
Ac-SEFC(1)|[1-Me-Trp]QDWGEHRC(1)[Sar]EA-NH2 (Compound 75);

(SEQ ID NO: 198)
Ac-SEFC(1)|[1-Me-Trp]QDW[Sar]EHRC(1)[Sar]EA-NH2 (Compound 76);

(SEQ ID NO: 199)
Ac-SEFC(1)|[1-Me-Trp]QDW[Sar]EHRC(1)TEA-NH2 (Compound 77);

(SEQ ID NO: 200)
Ac-SEFC(1)|[1-Me-Trp]QDWGEHRC(1)[Sar]E-NH2 (Compound 78);

(SEQ ID NO: 201)
Ac-SEFC(1)|[1-Me-Trp]QDW[Sar]EHRC(1)[Sar]E-NH2 (Compound 79);

(SEQ ID NO: 202)
Ac-EFC(1)|[1-Me-Trp]QDWGEHRC(1)[Sar]EA-NH2 (Compound 80);

(SEQ ID NO: 203)
Ac-SE[Sar]C(1)|[1-Me-Trp]QDWGEHRC(1)[Sar]EA-NH2 (Compound 81);

(SEQ ID NO: 204)
Ac-SE[Sar]C(1)|[1-Me-Trp]QDWGEHRC(1)TEA-NH2 (Compound 82);

(SEQ ID NO: 205)
Ac-SEFC(1)|[1-Me-Trp]QEWGEHRC(1)[Sar]EA-NH2 (Compound 83);

(SEQ ID NO: 206)
Ac-SEFC(1)[1-Me-Trp]QDWGEHRC(1)SEA-NH2 (Compound 84);

(SEQ ID NO: 207)
Ac-EFC(1)|[1-Me-Trp]QDWGEHRC(1)ES-NH2 (Compound 85);

(SEQ ID NO: 208)
Ac-SEFC(1)|[1-Me-Trp]QDWGEHKC(1)[Sar]EA-NH2 (Compound 86);

(SEQ ID NO: 209)
Ac-GEFC(1)|[1-Me-Trp]QDWGEHRC(1)[Sar]EA-NH2 (Compound 87);

(SEQ ID NO: 210)
Ac-GE[Sar]C(1)|[1-Me-Trp]QDWGEHRC(1)TEA-NH2 (Compound 88);

(SEQ ID NO: 211)
Ac-SE[Sar]C(1)|[1-Me-Trp]QEW[Sar]EHRC(1)TEA-NH2 (Compound 89);

(SEQ ID NO: 212)
Ac-SE[Sar]C(1)|[1-Me-Trp]QEWGEHRC(1)[Sar]EA-NH2 (Compound 90); or (SEQ ID NO: 213)
H-{d}Y[Sar]C(1)|[1-Me-Trp]QDWGEHRC(1)TEA-NH2 (Compound 91).

10. The method of claim 1, wherein the compstatin analogue comprises a sequence selected from the group consisting of:

(SEQ ID NO: 214)
[K*]GSAIC(1)IWQDWGEHRC(1)TEGE (Compound 100);

(SEQ ID NO: 215)
ASGEYC(1)|[1-Me-Trp]QDWGEHRC(1)[Sar]EGE-[K*] (Compound 113);

-continued (SEQ ID NO: 216)
EFC(1)|[1-Me-Trp]QDWGEHRC(1)EGE-[K*] (Compound 134);

(SEQ ID NO: 217)
EGSAIC(1)IWQDWGEHRC(1)TEG[K*] (Compound 101);

(SEQ ID NO: 218)
EGSAYC(1)[1-Me-Trp]QDWGEH[K*]C(1)[Sar]E (Compound 103);

(SEQ ID NO: 219)
EGSAYC(1)|[1-Me-Trp]QDWGEHRC(1)[Sar]EG-[K*] (Compound 104);

(SEQ ID NO: 220)
EGSAYC(1)|[1-Me-Trp]QDWGEHRC(1)[Sar]EGE-[K*] (Compound 109);

(SEQ ID NO: 221)
EGSAYC(1)|[1-Me-Trp]QDWGEHRC(1)[Sar]EGK-[K*] (Compound 110);

(SEQ ID NO: 222)
EGSAYC(1)|[1-Me-Trp]QDWGEHRC(1)[Sar]EK[yGlu]-[K*] (Compound 111);

(SEQ ID NO: 223)
FC(1)[1-Me-Trp]QDWGEHRC(1)TGAES-[K*] (Compound 102);

(SEQ ID NO: 224)
IC(1)IWQDWGEHRC(1)TEG-[K*] (Compound 92);

(SEQ ID NO: 225)
IC(1)IWQDWGEHRC(1)TEGE-[K*] (Compound 94);

(SEQ ID NO: 226)
SAYC(1)|[1-Me-Trp]QDWGEHRC(1)[Sar]E-[K*] (Compound 105);

(SEQ ID NO: 227)
SEFC(1)|[1-Me-Trp]QDWGEHRC(1)[Sar]EGA-[K*] (Compound 119);

(SEQ ID NO: 228)
SEFC(1)|[1-Me-Trp]QDWGEHRC(1)[Sar]EGE[Peg3][Peg3]-[K*] (Compound 123);

(SEQ ID NO: 229)
SEFC(1)[1-Me-Trp]QDWGEHRC(1)[Sar]EGEGGG-[K*] (Compound 129);

(SEQ ID NO: 230)
SEFC(1)|[1-Me-Trp]QDWGEHRC(1)[Sar]EGE[Peg3]-[K*] (Compound 138);

(SEQ ID NO: 231)
SEFC(1)|[1-Me-Trp]QDWGEHRC(1)[Sar]EGE[Peg3]ES-[K*] (Compound 140);

(SEQ ID NO: 232)
SEFC(1)|[1-Me-Trp]QDWGEHRC(1)[Sar]EGE[Peg3][Peg3]-[K*] (Compound 127);

(SEQ ID NO: 233)
SEFC(1)[1-Me-Trp]QDWGEHRC(1)[Sar]EGESES-[K*] (Compound 139);

(SEQ ID NO: 234)
SEFC(1)|[1-Me-Trp]QDWGEHRC(1)[Sar]EK[yGlu]GGG-[K*] (Compound 132);

(SEQ ID NO: 235)
SEFC(1)|[1-Me-Trp]QDWGEHRC(1)TEGE[8-aminooctanoyl]-[K*] (Compound 136);

(SEQ ID NO: 236)
SEFC(1)|[1-Me-Trp]QDWGEHRC(1)TEGE[8-aminooctanoyl]E-[K*] (Compound 137);

(SEQ ID NO: 237)
SEFC(1)|[1-Me-Trp]QDWGEHRC(1)TEGEGGG-[K*] (Compound 130);

(SEQ ID NO: 238)
SEFC(1)|[1-Me-Trp]QDWGEHRC(1)TEGE[Peg3]ES-[K*] (Compound 142);

(SEQ ID NO: 239)
SEFC(1)|[1-Me-Trp]QDWGEHRC(1)TEGE[Peg3][Peg3]-[K*] (Compound 126);

(SEQ ID NO: 240)
SEFC(1)|[1-Me-Trp]QDWGEHRC(1)TEK[yGlu]GGG-[K*] (Compound 133);

(SEQ ID NO: 241)
SEFC(1)|[1-Me-Trp]QDWGEHRC(1)TGAES-[K*] (Compound 135);

(SEQ ID NO: 242)
SEFC(1)[1-Me-Trp]QEWGEHRC(1)[Sar]EGA-[K*] (Compound 120);

-continued (SEQ ID NO: 243)
SEFC(1)||[1-Me-Trp]QEWGEHRC(1)[Sar]EGE[Peg3][Peg3]-[K*] (Compound 124);

(SEQ ID NO: 244)
SEYC(1)||[1-Me-Trp]QDWGEHRC(1)[Sar]EGA-[K*] (Compound 112);

(SEQ ID NO: 245)
SEYC(1)||[1-Me-Trp]QDWGEHRC(1)[Sar]EGE[Peg3][Peg3]-[K*] (Compound 117);

(SEQ ID NO: 246)
SEYC(1)||[1-Me-Trp]QDWGEHRC(1)[Sar]EGE-[K*] (Compound 114);

(SEQ ID NO: 247)
SEYC(1)||[1-Me-Trp]QEW[Sar]EHRC(1)[Sar]EK[yGlu]A-[K*] (Compound 121);

(SEQ ID NO: 248)
SEYC(1)||[1-Me-Trp]QEWGEHRC(1)[Sar]EGA-[K*] (Compound 122);

(SEQ ID NO: 249)
SEYC(1)||[1-Me-Trp]QEWGEHRC(1)[Sar]EGE[Peg3][Peg3]-[K*] (Compound 125);

(SEQ ID NO: 250)
EGSEYC(1)||[1-Me-Trp]QDWGEHRC(1)[Sar]E (Compound 107);

(SEQ ID NO: 251)
ESSAIC(1)IWQDWGEHRC(1)TEGE (Compound 99);

(SEQ ID NO: 252)
SEFC(1)||[1-Me-Trp]QDWGEHRC(1)[Sar]EGE[Peg3][Peg3][Peg3]-[K*] (Compound 143);

(SEQ ID NO: 253)
SEFC(1)||[1-Me-Trp]QDW[Sar]EHRC(1)[Sar]E[Peg3][Peg3]-[K*] (Compound 144); and (SEQ ID NO: 254)
EFC(1)||[1-Me-Trp]QDWGEHRC(1)[Sar]EA[Peg3][Peg3]-[K*] (Compound 145).

11. The method of claim 10, wherein the compstatin analogue comprises a sequence selected from the group consisting of:

(SEQ ID NO: 214)
Ac-[K*]GSAIC(1)IWQDWGEHRC(1)TEGE-NH2 (Compound 100), (SEQ ID NO: 215)
Ac-ASGEYC(1)||[1-Me-Trp]QDWGEHRC(1)[Sar]EGE-[K*]-NH2 (Compound 113);

(SEQ ID NO: 216)
Ac-EFC(1)||[1-Me-Trp]QDWGEHRC(1)EGE-[K*]-NH2 (Compound 134);

(SEQ ID NO: 217)
Ac-EGSAIC(1)IWQDWGEHRC(1)TEG-[K*]-NH2 (Compound 101);

(SEQ ID NO: 218)
Ac-EGSAYC(1)||[1-Me-Trp]QDWGEH[K*]C(1)[Sar]E-NH2 (Compound 103);

(SEQ ID NO: 219)
Ac-EGSAYC(1)||[1-Me-Trp]QDWGEHRC(1)[Sar]EG-[K*]-NH2 (Compound 104);

(SEQ ID NO: 220)
Ac-EGSAYC(1)||[1-Me-Trp]QDWGEHRC(1)[Sar]EGE-[K*]-NH2 (Compound 109);

(SEQ ID NO: 221)
Ac-EGSAYC(1)||[1-Me-Trp]QDWGEHRC(1)[Sar]EGK-[K*]-NH2 (Compound 110);

(SEQ ID NO: 222)
Ac-EGSAYC(1)||[1-Me-Trp]QDWGEHRC(1)[Sar]EK[yGlu]-[K*]-NH2 (Compound 111);

(SEQ ID NO: 223)
Ac-FC(1)[1-Me-Trp]QDWGEHRC(1)TGAES-[K*]-NH2 (Compound 102);

(SEQ ID NO: 224)
Ac-IC(1)IWQDWGEHRC(1)TEG-[K*]-NH2 (Compound 92, 93, 95, 96, 98);

(SEQ ID NO: 225)
Ac-IC(1)IWQDWGEHRC(1)TEGE-[K*]-NH2 (Compound 94, 97);

-continued (SEQ ID NO: 226)
Ac-SAYC(1)|[1-Me-Trp]QDWGEHRC(1)[Sar]E-[K*]-NH2 (Compound 105, 106);

(SEQ ID NO: 227)
Ac-SEFC(1)|[1-Me-Trp]QDWGEHRC(1)[Sar]EGA-[K*]-NH2 (Compound 119);

(SEQ ID NO: 228)
Ac-SEFC(1)|[1-Me-Trp]QDWGEHRC(1)[Sar]EGE[Peg3][Peg3]-[K*]-NH2 (Compound 123);

(SEQ ID NO: 229)
Ac-SEFC(1)|[1-Me-Trp]QDWGEHRC(1)[Sar]EGEGGG-[K*]-NH2 (Compound 129);

(SEQ ID NO: 230)
Ac-SEFC(1)|[1-Me-Trp]QDWGEHRC(1)[Sar]EGE[Peg3]-[K*]-NH2 (Compound 138);

(SEQ ID NO: 231)
Ac-SEFC(1)|[1-Me-Trp]QDWGEHRC(1)[Sar]EGE[Peg3]ES-[K*]-NH2 (Compound 140);

(SEQ ID NO: 232)
Ac-SEFC(1)|[1-Me-Trp]QDWGEHRC(1)[Sar]EGE[Peg3][Peg3]-[K*]-NH2 (Compound 127, 128);

(SEQ ID NO: 233)
Ac-SEFC(1)|[1-Me-Trp]QDWGEHRC(1)[Sar]EGESES-[K*]-NH2 (Compound 139, 141);

(SEQ ID NO: 234)
Ac-SEFC(1)|[1-Me-Trp]QDWGEHRC(1)[Sar]EK[yGlu]GGG-[K*]-NH2 (Compound 132);

(SEQ ID NO: 235)
Ac-SEFC(1)|[1-Me-Trp]QDWGEHRC(1)TEGE[8-aminooctanoyl]-[K*]-NH2 (Compound 136);

(SEQ ID NO: 236)
Ac-SEFC(1)|[1-Me-Trp]QDWGEHRC(1)TEGE[8-aminooctanoyl]E-[K*]-NH2 (Compound 137);

(SEQ ID NO: 237)
Ac-SEFC(1)|[1-Me-Trp]QDWGEHRC(1)TEGEGGG-[K*]-NH2 (Compound 130, 131);

(SEQ ID NO: 238)
Ac-SEFC(1)[1-Me-Trp]QDWGEHRC(1)TEGE-[Peg3]ES-[K*]-NH2 (Compound 142);

(SEQ ID NO: 239)
Ac-SEFC(1)|[1-Me-Trp]QDWGEHRC(1)TEGE-[Peg3][Peg3]-[K*]-NH2 (Compound 126);

(SEQ ID NO: 240)
Ac-SEFC(1)|[1-Me-Trp]QDWGEHRC(1)TEK[yGlu]GGG-[K*]-NH2 (Compound 133);

(SEQ ID NO: 241)
Ac-SEFC(1)[1-Me-Trp]QDWGEHRC(1)TGAES-[K*]-NH2 (Compound 135);

(SEQ ID NO: 242)
Ac-SEFC(1)|[1-Me-Trp]QEWGEHRC(1)[Sar]EGA-[K*]-NH2 (Compound 120);

(SEQ ID NO: 243)
Ac-SEFC(1)|[1-Me-Trp]QEWGEHRC(1)[Sar]EGE[Peg3][Peg3]-[K*]-NH2 (Compound 124);

(SEQ ID NO: 244)
Ac-SEYC(1)|[1-Me-Trp]QDWGEHRC(1)[Sar]EGA-[K*]-NH2 (Compound 112, 118);

(SEQ ID NO: 245)
Ac-SEYC(1)|[1-Me-Trp]QDWGEHRC(1)[Sar]EGE[Peg3][Peg3]-[K*]-NH2 (Compound 117);

(SEQ ID NO: 246)
Ac-SEYC(1)|[1-Me-Trp]QDWGEHRC(1)[Sar]EGE-[K*]-NH2 (Compound 114, 115, 116);

(SEQ ID NO: 247)
Ac-SEYC(1)|[1-Me-Trp]QEW[Sar]EHRC(1)[Sar]EK[yGlu]A-[K*]-NH2 (Compound 121);

(SEQ ID NO: 248)
Ac-SEYC(1)|[1-Me-Trp]QEWGEHRC(1)[Sar]EGA-[K*]-NH2 (Compound 122);

(SEQ ID NO: 249)
Ac-SEYC(1)|[1-Me-Trp]QEWGEHRC(1)[Sar]EGE[Peg3][Peg3]-[K*]-NH2 (Compound 125);

(SEQ ID NO: 250)
Φ-EGSEYC(1)|[1-Me-Trp]QDWGEHRC(1)[Sar]E-NH2 (Compound 107, 108);

(SEQ ID NO: 251)
Φ-ESSAIC(1)IWQDWGEHRC(1)TEGE-NH2 (Compound 99);

(SEQ ID NO: 252)
Ac-SEFC(1)|[1-Me-Trp]QDWGEHRC(1)[Sar]EGE[Peg3][Peg3][Peg3]-[K*]-NH2 (Compound 143);

-continued (SEQ ID NO: 253)
Ac-SEFC(1)|[1-Me-Trp]QDW[Sar]EHRC(1)[Sar]E[Peg3][Peg3]-[K*]-NH2 (Compound 144); and (SEQ ID NO: 254)
Ac-EFC(1)|[1-Me-Trp]QDWGEHRC(1)[Sar]EA[Peg3][Peg3]-[K*]-NH2 (Compound 145).

12. The method of claim 1, wherein the compstatin analogue comprises a lipophilic group ϕ, and wherein the lipophilic group ϕ is $Z^1$— or $Z^1$-$Z^2$—; wherein $Z^1$ is A-$C_{12-22}$alkylene-(CO)—;

where A is H or —COOH, and wherein the alkylene may be linear or branched and may be saturated or unsaturated, and may optionally incorporate a phenylene or piperazinylene moiety in its length; and $Z^2$ is a sequence of 1 to 6 residues of compounds selected from γ-Glu, E, K, Orn, S, T, A, B-Ala, G, P, V, L, I, Y, Q, N, Dapa, Gaba, or Aib, or a corresponding D form thereof, 5-aminopentanoyl, 6-aminohexanoyl, 7-aminoheptanoyl, 8-aminooctanoyl, 9-aminononanoyl, and 10-aminodecanoyl, 8-amino-3,6-dioxaoctanoic acid (Peg3), 11-amino-3,6,9-trioxaundecanoic acid (Peg4) and (piperazine-1-yl)-carboxylic acid.

13. The method of claim 12, wherein $Z^1$ is selected from the group consisting of:

Dodecanoyl, H—$(CH_2)_{11}$—(CO)—;
Tetradecanoyl, H—$(CH_2)_{13}$—(CO)—;
Hexadecanoyl, H—$(CH_2)_{15}$—(CO)—;
13-carboxytridecanoyl, i.e., HOOC—$(CH_2)_{12}$—(CO)—;
15-carboxypentadecanoyl, i.e., HOOC—$(CH_2)_{14}$—(CO)—;
17-carboxyheptadecanoyl, i.e., HOOC—$(CH_2)_{16}$—(CO)—;
19-carboxynonadecanoyl, i.e., HOOC—$(CH_2)_{18}$—(CO)—; or
21-carboxyheneicosanoyl, i.e., HOOC—$(CH_2)_{20}$—(CO)—.

14. The method of claim 12, wherein $Z^2$ is selected from the group consisting of:

[γGlu],
[γGlu][Peg3][Peg3]-;
[(Piperazine-1-yl)-acetyl][Peg3][Peg3];
[γGlu]G[γGlu];
[γGlu]K[γGlu];
[γGlu]KG[γGlu]; or
[γGlu]G[Peg3][γGlu][Peg3].

15. The method of claim 12, wherein $Z^1$— or $Z^1$—$Z^2$— is selected from the group consisting of:

15-carboxy-pentadecanoyl;
15-carboxy-pentadecanoyl[γGlu]-,
15-carboxy-pentadecanoyl[γGlu][Peg3][Peg3]-;
19-carboxy-nonadecanoyl[γGlu][Peg3][Peg3]-;
15-carboxy-pentadecanoyl-[(Piperazine-1-yl)-acetyl][Peg3][Peg3]);
17-carboxy-heptadecanoyl[γGlu]G[γGlu];
17-carboxy-heptadecanoyl[γGlu]K[γGlu];
17-carboxy-heptadecanoyl[γGlu]KG[γGlu];
17-carboxy-heptadecanoyl[γGlu]G(Peg3) [γGlu]-(Peg3);
15-carboxy-hexadecanoyl[γGlu]G[γGlu];
17-carboxy-heptadecanoyl;
17-carboxy-heptadecanoyl[γGlu]
19-carboxy-nonadecanoyl[γGlu]G[γGlu]; and
17-carboxy-heptadecanoyl[γGlu][Peg3][Peg3].

16. The method of claim 1, wherein the compstatin analogue is:

(SEQ ID NO: 278)
Ac-IC(1)IWQDWGEHRC(1)TEG-K([15-carboxy-pentadecanoyl][Glu])-NH2 (Compound 92);

(SEQ ID NO: 279)
Ac-IC(1)IWQDWGEHRC(1) TEG-K([15-carboxy-pentadecanoyl][γGlu][Peg3][Peg3])-NH2 (Compound 93);

(SEQ ID NO: 283)
Ac-IC(1)IWQDWGEHRC(1)TEGE-K([15-carboxy-pentadecanoyl][γGlu][Peg3][Peg3])-NH2 (Compound 94);

(SEQ ID NO: 280)
Ac-IC(1)IWQDWGEHRC(1)TEG-K((15-carboxy-pentadecanoyl)-[(Piperazine-1-yl)-acetyl][Peg3][Peg3])-NH2 (Compound 95);

(SEQ ID NO: 281)
Ac-IC(1)IWQDWGEHRC(1)TEG-K([17-carboxy-heptadecanoyl][γGlu][Peg3][Peg3])-NH2 (Compound 96);

(SEQ ID NO: 284)
Ac-IC(1)IWQDWGEHRC(1) TEGE-K([17-carboxy-heptadecanoyl][γGlu][Peg3][Peg3])-NH2 (Compound 97);

(SEQ ID NO: 282)
Ac-IC(1)IWQDWGEHRC(1) TEG-K([19-carboxy-nonadecanoyl][γGlu][Peg3][Peg3])-NH2 (Compound 98);

(SEQ ID NO: 318)
[15-Carboxy-pentadecanoyl]-ESSAIC(1)IWQDWGEHRC(1)TEGE-NH2 (Compound 99);

(SEQ ID NO: 268)
Ac-[K([15-carboxy-pentadecanoyl][γGlu][Peg3][Peg3])]-GSAIC(1)IWQDWGEHRC(1) TEGE-NH2 (Compound 100);

-continued (SEQ ID NO: 271)
Ac-EGSAIC(1)IWQDWGEHRC(1)TEG-K([15-carboxy-pentadecanoyl][γGlu])-NH2 (Compound 101);

(SEQ ID NO: 277)
Ac-FC(1)|[1-Me-Trp]QDWGEHRC(1)TGAES-K([15-carboxy-pentadecanoyl][γGlu][Peg3][Peg3])-NH2 (Compound 102);

(SEQ ID NO: 272)
Ac-EGSAYC(1)|[1-Me-Trp]QDWGEH-K([15-carboxy-pentadecanoyl][γGlu][Peg3][Peg3])-C(1)[Sar]E-NH2 (Compound 103);

(SEQ ID NO: 273)
Ac-EGSAYC(1)|[1-Me-Trp]QDWGEHRC(1)[Sar]EG-K([15-carboxy-pentadecanoyl][γGlu][Peg3][Peg3])-NH2 (Compound 104);

(SEQ ID NO: 285)
Ac-SAYC(1)|[1-Me-Trp]QDWGEHRC(1)[Sar]E-K([17-carboxy-heptadecanoyl][γGlu]KG[γGlu])-NH2 (Compound 105);

(SEQ ID NO: 286)
Ac-SAYC(1)|[1-Me-Trp]QDWGEHRC(1)[Sar]E-K([17-carboxy-heptadecanoyl][γGlu]G[γGlu])-NH2 (Compound 106);

(SEQ ID NO: 316)
[15-Carboxy-pentadecanoyl]-EGSEYC(1)|[1-Me-Trp]QDWGEHRC(1)[Sar]E-NH2 (Compound 107);

(SEQ ID NO: 317)
[17-Carboxy-heptadecanoyl]-EGSEYC(1)|[1-Me-Trp]QDWGEHRC(1)[Sar]E-NH2 (Compound 108);

(SEQ ID NO: 274)
Ac-EGSAYC(1)|[1-Me-Trp]QDWGEHRC(1)[Sar]EGE-K([17-carboxy-heptadecanoyl][γGlu]G[γGlu])-NH2 (Compound 109);

(SEQ ID NO: 275)
Ac-EGSAYC(1)|[1-Me-Trp]QDWGEHRC(1)[Sar]EGK-K([17-carboxy-heptadecanoyl][γGlu]G[γGlu])-NH2 (Compound 110);

(SEQ ID NO: 276)
Ac-EGSAYC(1)|[1-Me-Trp]QDWGEHRC(1)[Sar]EK([yGlu]-K([17-carboxy-heptadecanoyl][γGlu](peg3)(peg3))-NH2 (Compound 111);

(SEQ ID NO: 307)
Ac-SEYC(1)|[1-Me-Trp]QDWGEHRC(1)[Sar]EGA-K([17-carboxy-heptadecanoyl][γGlu]-G[γGlu])-NH2 (Compound 112);

(SEQ ID NO: 269)
Ac-ASGEYC(1)|[1-Me-Trp]QDWGEHRC(1)[Sar]EGE-K([17-carboxy-heptadecanoyl][γGlu]-G[γGlu])-NH2 (Compound 113);

(SEQ ID NO: 310)
Ac-SEYC(1)|[1-Me-Trp]QDWGEHRC(1)[Sar]EGE-K([17-carboxy-heptadecanoyl][γGlu]-G[γGlu])-NH2 (Compound 114);

(SEQ ID NO: 311)
Ac-SEYC(1)|[1-Me-Trp]QDWGEHRC(1)[Sar]EGK-K([17-carboxy-heptadecanoyl][γGlu]-G[γGlu])-NH2 (Compound 115);

(SEQ ID NO: 312)
Ac-SEYC(1)|[1-Me-Trp]QDWGEHRC(1)[Sar]EGE-K([17-carboxy-heptadecanoyl][γGlu]-K[γGlu])-NH2 (Compound 116);

(SEQ ID NO: 309)
Ac-SEYC(1)|[1-Me-Trp]QDWGEHRC(1)[Sar]EGE[Peg3][Peg3]-K([17-carboxy-heptadecanoyl][yGlu]-G[γGlu])-NH2 (Compound 117);

(SEQ ID NO: 308)
Ac-SEYC(1)|[1-Me-Trp]QDWGEHRC(1)[Sar]EGA-K([17-carboxy-heptadecanoyl]-[γGlu]G[Peg3][γGlu][Peg3])-NH2 (Compound 118);

(SEQ ID NO: 287)
Ac-SEFC(1)|[1-Me-Trp]QDWGEHRC(1)[Sar]EGA-K([17-carboxy-heptadecanoyl]-[γGlu]G[Peg3][γGlu][Peg3])-NH2 (Compound 119);

-continued (SEQ ID NO: 305)
Ac-SEFC(1)|[1-Me-Trp]QEWGEHRC(1)[Sar]EGA-K([17-carboxy-heptadecanoyl]-[γGlu]G[Peg3][γGlu][Peg3])-NH2 (Compound 120);

(SEQ ID NO: 313)
Ac-SEYC(1)|[1-Me-Trp]QEW[Sar]EHRC(1)[Sar]EK[yGlu]A-K([17-carboxy-heptadecanoyl]-[γGlu]G[Peg3][γGlu][Peg3])-NH2 (Compound 121);

(SEQ ID NO: 314)
Ac-SEYC(1)|[1-Me-Trp]QEWGEHRC(1)[Sar]EGA-K([17-carboxy-heptadecanoyl]-[γGlu]G[Peg3][γGlu][Peg3])-NH2 (Compound 122);

(SEQ ID NO: 288)
Ac-SEFC(1)|[1-Me-Trp]QDWGEHRC(1)[Sar]EGE[Peg3][Peg3]-K([17-carboxy-heptadecanoyl][γGlu]G[γGlu])-NH2 (Compound 123);

(SEQ ID NO: 306)
Ac-SEFC(1)|[1-Me-Trp]QEWGEHRC(1)[Sar]EGE[Peg3[Peg3]-K([17-carboxy-heptadecanoyl]-[γGlu]G[γGlu])-NH2 (Compound 124);

(SEQ ID NO: 315)
Ac-SEYC(1)|[1-Me-Trp]QEWGEHRC(1)[Sar]EGE[Peg3][Peg3]-K([17-carboxy-heptadecanoyl][γGlu]G[γGlu])-NH2 (Compound 125);

(SEQ ID NO: 302)
Ac-SEFC(1)|[1-Me-Trp]QDWGEHRC(1)TEGE[Peg3][Peg3]-K([17-carboxy-heptadecanoyl)[γGlu]G[γGlu])-NH2 (Compound 126);

(SEQ ID NO: 292)
Ac-SEFC(1)|[1-Me-Trp]QDWGEHRC(1)[Sar]-EGE-[Peg3][Peg3]-K([15-carboxy-pentadecanoyl][γGlu]G[γGlu])-NH2 (Compound 127);

(SEQ ID NO: 293)
Ac-SEFC(1)|[1-Me-Trp]QDWGEHRC(1)[Sar]EGE[Peg3][Peg3]-K([19-carboxy-nonadecanoyl][γGlu]G[γGlu])-NH2 (Compound 128);

(SEQ ID NO: 289)
Ac-SEFC(1)|[1-Me-Trp]QDWGEHRC(1)[Sar]EGEGGG-K([17-carboxy-heptadecanoyl]-[γGlu]G[γGlu])-NH2 (Compound 129);

(SEQ ID NO: 299)
Ac-SEFC(1)|[1-Me-Trp]QDWGEHRC(1)TEGEGGG-K([17-carboxy-heptadecanoyl]-[γGlu]G[γGlu])-NH2 (Compound 130);

(SEQ ID NO: 300)
Ac-SEFC(1)|[1-Me-Trp]-QDWGEHRC(1)TEGEGGG-K([15-carboxy-pentadecanoyl][γGlu]-G[γGlu])-NH2 (Compound 131);

(SEQ ID NO: 296)
Ac-SEFC(1)|[1-Me-Trp]-QDWGEHRC(1)[Sar]EK[γGlu]GGG-K([17-carboxy-heptadecanoyl][γGlu]-G[γGlu])-NH2 (Compound 132);

(SEQ ID NO: 303)
Ac-SEFC(1)|[1-Me-Trp]QDWGEHRC(1)TEK[γGlu]GGG-K([17-carboxy-heptadecanoyl][γGlu]-G[γGlu])-NH2 (Compound 133);

(SEQ ID NO: 270)
Ac-EFC(1)|[1-Me-Trp]QDWGEHRC(1)EGE-K([17-carboxy-heptadecanoyl][γGlu]G[γGlu])-NH2(Compound 134);

(SEQ ID NO: 304)
Ac-SEFC(1)|[1-Me-Trp]QDWGEHRC(1)TGAES-K([15-carboxy-hexadecanoyl][γGlu]G[γGlu])-NH2 (Compound 135);

(SEQ ID NO: 297)
Ac-SEFC(1)|[1-Me-Trp]QDWGEHRC(1)TEGE[8-aminooctanoyl]-K([17-carboxy-heptadecanoyl][γGlu]-G[γGlu])-NH2 (Compound 136);

(SEQ ID NO: 298)
Ac-SEFC(1)|[1-Me-Trp]QDWGEHRC(1)TEGE[8-aminooctanoyl]E-K([17-carboxy-heptadecanoyl][γGlu]G[γGlu]])-NH2 (Compound 137);

(SEQ ID NO: 290)
Ac-SEFC(1)|[1-Me-Trp]QDWGEHRC(1)[Sar]EGE[Peg3]-K([17-carboxy-heptadecanoyl]-[γGlu]G[γGlu])-NH2 (Compound 138);

-continued (SEQ ID NO: 294)
Ac-SEFC(1)|[1-Me-Trp]QDWGEHRC(1)[Sar]EGESES-K([17-carboxy-heptadecanoyl]-[γGlu]G[γGlu])-NH2 (Compound 139);

(SEQ ID NO: 291)
Ac-SEFC(1)|[1-Me-Trp]QDWGEHRC(1)[Sar]EGE[Peg3]ES-K([17-carboxy-heptadecanoyl]-[γGlu]G[γGlu])-NH2 (Compound 140);

(SEQ ID NO: 295)
Ac-SEFC(1)|[1-Me-Trp]QDWGEHRC(1)[Sar]EGESES-K([17-carboxy-heptadecanoyl][γGlu])-NH2 (Compound 141);

(SEQ ID NO: 301)
Ac-SEFC(1)|[1-Me-Trp]QDWGEHRC(1)TEGE[Peg3]ES-K([17-carboxy-heptadecanoyl][γGlu])-NH2 (Compound 142);

(SEQ ID NO: 319)
Ac-SEFC(1)|[1-Me-Trp]QDWGEHR[C(1)[Sar]EGE[Peg3][Peg3][Peg3]-K([17-carboxy-heptadecanoyl][γGlu]G[γGlu])-NH2 (Compound 143);

(SEQ ID NO: 320)
Ac-SEFC(1)|[1-Me-Trp]QDW[Sar]EHRC(1)[Sar]E[Peg3][Peg3]-K([17-carboxy-heptadecanoyl][γGlu]G[γGlu])-NH2 (Compound 144); and (SEQ ID NO: 321)
Ac-EF[C(1)|[1-Me-Trp]QDWGEHRC(1)[Sar]EA[Peg3][Peg3]-K([17-carboxy-heptadecanoyl][γGlu]G[γGlu])-NH2 (Compound 145).

17. The method of claim 1, wherein the compstatin analogue, or a pharmaceutically acceptable salt thereof, is in admixture with a carrier.

18. The method of claim 1, wherein the compstatin analogue, or a pharmaceutically acceptable salt thereof, is in a pharmaceutical composition comprising an admixture with a pharmaceutically acceptable carrier, excipient or vehicle.

19. The method of claim 1, wherein the subject has age-related macular degeneration, Stargardt disease, periodontitis, diabetic retinopathy, glaucoma, uveitis, rheumatoid arthritis, spinal cord injury, stroke, multiple sclerosis, Parkinson's disease, Alzheimer's disease, cancer, and respiratory disorders including asthma, chronic obstructive pulmonary disease (COPD), allergic inflammation, emphysema, bronchitis, bronchiecstasis, cystic fibrosis, tuberculosis, pneumonia, respiratory distress syndrome (RDS-neonatal and adult), rhinitis and sinusitis; bacterial infections such as sepsis, ischemia-reperfusion injury in various tissues, myocardial infarction, anaphylaxis, paroxysmal nocturnal hemoglobinuria, autoimmune hemolytic anemias, psoriasis, hidradentitis suppurativa, myasthenia gravis, systemic lupus erythematosus, CHAPLE syndrome, C3 glomeropathy, IgA nephropathy, atypical hemolytic uremic syndrome, Crohn's disease, ulcerative colitis or antiphospholipid syndrome.

* * * * *

SEQUENCE LISTING

```
Sequence total quantity: 334
SEQ ID NO: 1          moltype = AA  length = 13
FEATURE               Location/Qualifiers
REGION                1..13
                      note = Description of Artificial Sequence: Synthetic peptide
REGION                1..13
                      note = core compstatin peptide
DISULFID              2..12
                      note = Intrachain disulfide bond
source                1..13
                      mol_type = protein
                      organism = synthetic construct
SEQUENCE: 1
ICVVQDWGHH RCT                                                      13

SEQ ID NO: 2          moltype = AA  length = 27
FEATURE               Location/Qualifiers
REGION                1..27
                      note = Description of Artificial Sequence: Synthetic peptide
REGION                1..27
                      note = compstatin analogue
VARIANT               1..6
```

-continued

```
                        note = A, E, G, L, K, F, P, S, T, W, Y, R, V, Sar,
                         epsilonLys, gammaGlu, betaAsp, or betaAla, or a
                         corresponding D form thereof or Peg3, Peg4,
                         8-aminooctanoyl derivatives thereof or may be absent
VARIANT                 1..6
                        note = This region may encompass 1 to 6 amino acid residues
VARIANT                 7
                        note = I, Y, F or Sar
DISULFID                8..18
                        note = Intrachain disulfide bond
VARIANT                 10
                        note = W, F, V, Y, 1-Me-Trp, D-Trp, N-Me-Trp, 1-For-Trp,
                         1-Nal, 2-Nal, 5-Me-Trp, Bpa or 2-Igl
VARIANT                 12
                        note = E, K or D
VARIANT                 14
                        note = G or Sar
VARIANT                 15
                        note = H, A, E, D, K, R or S
VARIANT                 17
                        note = R, S or K
VARIANT                 19
                        note = T, S, E, F, H, K, Sar, G, I, D, N-Me-Ile or N-Me-Thr
VARIANT                 20..27
                        note = A, E, G, L, K, F, P, S, T, W, Y, R, V, Sar,
                         epsilonLys, gammaGlu, betaAsp, or betaAla, or a
                         corresponding D form thereof or Peg3, Peg4,
                         8-aminooctanoyl derivatives thereof or may be absent
VARIANT                 20..27
                        note = This region may encompass 1 to 8 amino acid residues
source                  1..27
                        mol_type = protein
                        organism = synthetic construct
SEQUENCE: 2
XXXXXXXCIX QXWXXHXCXX XXXXXXX                                     27

SEQ ID NO: 3            moltype = AA  length = 27
FEATURE                 Location/Qualifiers
REGION                  1..27
                        note = Description of Artificial Sequence: Synthetic peptide
REGION                  1..27
                        note = compstatin analogue
VARIANT                 1..6
                        note = A, E, G, L, K, F, P, S, T, W, Y, R, V, Sar,
                         epsilonLys, gammaGlu, betaAsp, or betaAla, or a
                         corresponding D form thereof, or Peg3, Peg4,
                         8-aminooctanoyl derivatives thereof or may be absent
VARIANT                 1..6
                        note = This region may encompass 1 to 6 amino acid residues
VARIANT                 7
                        note = I, Y, F or Sar
DISULFID                8..18
                        note = Intrachain disulfide bond
VARIANT                 10
                        note = W, V, Y, 2-Nal, 1-Nal or 1-Me-Trp
VARIANT                 12
                        note = E or D
VARIANT                 14
                        note = G or Sar
VARIANT                 15
                        note = A, E, D, K or S
VARIANT                 17
                        note = R, S or K
VARIANT                 19
                        note = T, S, E, I, Sar, K, G or N-Me-Ile
VARIANT                 20..27
                        note = A, E, G, L, K, F, P, S, T, W, Y, R, V, Sar,
                         epsilonLys, gammaGlu, betaAsp, or betaAla, or a
                         corresponding D form thereof or Peg3 or Peg4,
                         8-aminooctanoyl derivatives thereof or may be absent
VARIANT                 20..27
                        note = This region may encompass 1 to 8 amino acid residues
source                  1..27
                        mol_type = protein
                        organism = synthetic construct
SEQUENCE: 3
XXXXXXXCIX QXWXXHXCXX XXXXXXX                                     27

SEQ ID NO: 4            moltype = AA  length = 27
```

-continued

```
FEATURE                 Location/Qualifiers
REGION                  1..27
                        note = Description of Artificial Sequence: Synthetic peptide
REGION                  1..27
                        note = compstatin analogue
VARIANT                 1..6
                        note = A, E, G, L, K, F, P, S, T, W, Y, R, V, Sar,
                         epsilonLys, gammaGlu, betaAsp, or betaAla, or a
                         corresponding D form thereof, or Peg3, Peg4,
                         8-aminooctanoyl derivatives thereof or may be absent
VARIANT                 1..6
                        note = This region may encompass 1 to 6 amino acid residues
VARIANT                 7
                        note = I, Y, F or Sar
DISULFID                8..18
                        note = Intrachain disulfide bond
VARIANT                 10
                        note = W, V, Y,1-Nal, 2-Nal or 1-Me-Trp
VARIANT                 12
                        note = E or D
VARIANT                 15
                        note = A, E, D, K or S
VARIANT                 17
                        note = R, S or K
VARIANT                 19
                        note = T, I, S, E, K or Sar
VARIANT                 20..27
                        note = A, E, G, L, K, F, P, S, T, W, Y, R, V, Sar,
                         epsilonLys, gammaGlu, betaAsp, or betaAla, or a
                         corresponding D form thereof or Peg3 or Peg4,
                         8-aminooctanoyl derivatives thereof or may be absent
VARIANT                 20..27
                        note = This region may encompass 1 to 8 amino acid residues
source                  1..27
                        mol_type = protein
                        organism = synthetic construct
SEQUENCE: 4
XXXXXXXCIX QXWGXHXCXX XXXXXXX                                       27

SEQ ID NO: 5            moltype = AA  length = 27
FEATURE                 Location/Qualifiers
REGION                  1..27
                        note = Description of Artificial Sequence: Synthetic peptide
REGION                  1..27
                        note = compstatin analogue
VARIANT                 1..6
                        note = A, E, G, L, K, F, P, S, T, W, Y, R, V, Sar,
                         epsilonLys, gammaGlu, betaAsp, or betaAla, or a
                         corresponding D form thereof, or Peg3, Peg4,
                         8-aminooctanoyl derivatives thereof or may be absent
VARIANT                 1..6
                        note = This region may encompass 1 to 6 amino acid residues
VARIANT                 7
                        note = I, Y, F or Sar
DISULFID                8..18
                        note = Intrachain disulfide bond
VARIANT                 10
                        note = W, V, Y, 1-Nal, 2-Nal or 1-Me-Trp
VARIANT                 12
                        note = E or D
VARIANT                 15
                        note = A, E, D, K or S
VARIANT                 19
                        note = T, S, E or Sar
VARIANT                 20..27
                        note = A, E, G, L, K, F, P, S, T, W, Y, R, V, Sar,
                         epsilonLys, gammaGlu, betaAsp, or betaAla, or a
                         corresponding D form thereof or Peg3 or Peg4,
                         8-aminooctanoyl derivatives thereof or may be absent
VARIANT                 20..27
                        note = This region may encompass 1 to 8 amino acid residues
source                  1..27
                        mol_type = protein
                        organism = synthetic construct
SEQUENCE: 5
XXXXXXXCIX QXWGXHRCXX XXXXXXX                                       27

SEQ ID NO: 6            moltype = AA  length = 25
FEATURE                 Location/Qualifiers
```

-continued

```
REGION                  1..25
                        note = Description of Artificial Sequence: Synthetic peptide
REGION                  1..25
                        note = compstatin analogue
VARIANT                 1..6
                        note = A, E, G, L, K, F, P, S, T, W, Y, R, V, Sar,
                         epsilonLys, gammaGlu, betaAsp, or betaAla, or a
                         corresponding D form thereof, or Peg3, Peg4,
                         8-aminooctanoyl derivatives thereof or may be absent
VARIANT                 1..6
                        note = This region may encompass 1 to 6 amino acid residues
VARIANT                 7
                        note = Y or F
DISULFID                8..18
                        note = Intrachain disulfide bond
VARIANT                 10
                        note = W, Y, or 1-Me-Trp
VARIANT                 12
                        note = E or D
VARIANT                 15
                        note = A, E or K
VARIANT                 19
                        note = T, E or Sar
VARIANT                 20..25
                        note = A, E, G, L, K, F, P, S, T, W, Y, R, V, Sar,
                         epsilonLys, gammaGlu, betaAsp, or betaAla, or a
                         corresponding D form thereof or Peg3 or Peg4,
                         8-aminooctanoyl derivatives thereof or may be absent
VARIANT                 20..25
                        note = This region may encompass 1 to 6 amino acid residues
source                  1..25
                        mol_type = protein
                        organism = synthetic construct
SEQUENCE: 6
XXXXXXXCIX QXWGXHRCXX XXXXX                                       25

SEQ ID NO: 7            moltype = AA  length = 25
FEATURE                 Location/Qualifiers
REGION                  1..25
                        note = Description of Artificial Sequence: Synthetic peptide
REGION                  1..25
                        note = compstatin analogue
VARIANT                 1..6
                        note = A, E, G, L, K, F, P, S, T, W, Y, R, V, Sar,
                         epsilonLys, gammaGlu, betaAsp, or betaAla, or a
                         corresponding D form thereof, or Peg3, Peg4,
                         8-aminooctanoyl derivatives thereof or may be absent
VARIANT                 1..6
                        note = This region may encompass 1 to 6 amino acid residues
VARIANT                 7
                        note = Y or F
DISULFID                8..18
                        note = Intrachain disulfide bond
MOD_RES                 10
                        note = 1-methyl-tryptophan
VARIANT                 12
                        note = E or D
VARIANT                 19
                        note = T, E or Sar
VARIANT                 20..25
                        note = A, E, G, L, K, F, P, S, T, W, Y, R, V, Sar,
                         epsilonLys, gammaGlu, betaAsp, or betaAla, or a
                         corresponding D form thereof or Peg3 or Peg4,
                         8-aminooctanoyl derivatives thereof or may be absent
VARIANT                 20..25
                        note = This region may encompass 1 to 6 amino acid residues
source                  1..25
                        mol_type = protein
                        organism = synthetic construct
SEQUENCE: 7
XXXXXXXCIX QXWGEHRCXX XXXXX                                       25

SEQ ID NO: 8            moltype = AA  length = 27
FEATURE                 Location/Qualifiers
REGION                  1..27
                        note = Description of Artificial Sequence: Synthetic peptide
REGION                  1..27
                        note = compstatin analogue
VARIANT                 1..6
```

```
                     note = A, E, G, K, K covalently linked to a lipophilic
                      group via its side chain, S, Y, a corresponding D form
                      thereof or may be absent
VARIANT              1..6
                     note = This region may encompass 1 to 6 amino acid residues
VARIANT              7
                     note = I, Y, F or Sar
VARIANT              10
                     note = W, V, 1-Me-Trp, 1-Nal or 2-Nal
VARIANT              12
                     note = E, K or D
VARIANT              14
                     note = G or Sar
VARIANT              15
                     note = H, A, E, D, K, R or S
VARIANT              17
                     note = R, S, K or K covalently linked to a lipophilic group
                      via its side chain
VARIANT              19
                     note = T, S, E, Sar or N-Me-Ile
VARIANT              20..27
                     note = A, E, G, K, K covalently linked to a lipophilic
                      group via its side chain, P, S, Peg3, gammaGlu,
                      8-aminooctanoyl, a corresponding D form thereof or may be
                      absent
VARIANT              20..27
                     note = This region may encompass 1 to 8 amino acid residues
source               1..27
                     mol_type = protein
                     organism = synthetic construct
SEQUENCE: 8
XXXXXXXCIX QXWXXHXCXX XXXXXXX                                          27

SEQ ID NO: 9         moltype = AA  length = 27
FEATURE              Location/Qualifiers
REGION               1..27
                     note = Description of Artificial Sequence: Synthetic peptide
REGION               1..27
                     note = compstatin analogue
VARIANT              1..6
                     note = A, E, G, L, K, K covalently linked to a lipophilic
                      group via its side chain, F, P, S, T, W, Y, R, V or Sar, a
                      corresponding D form thereof or may be absent
VARIANT              1..6
                     note = This region may encompass 1 to 6 amino acid residues
VARIANT              7
                     note = I, Y, F or Sar
DISULFID             8..18
                     note = Intrachain disulfide bond
VARIANT              10
                     note = W, V, Y, 2-Nal, 1-Nal or 1-Me-Trp
VARIANT              12
                     note = E or D
VARIANT              14
                     note = G or Sar
VARIANT              15
                     note = A, E, D, K or S
VARIANT              17
                     note = R, S or K covalently linked to a lipophilic group
                      via its side chain
VARIANT              19
                     note = T, S, E, I, Sar, K, G or N-Me-Ile
VARIANT              20..27
                     note = A, E, G, L, K, K covalently linked to a lipophilic
                      group via its side chain, F, P, S, T, W, Y, R, V, Sar,
                      epsilonLys, gammaGlu, betaAsp, betaAla, or a corresponding
                      D form thereof or Peg 3 or Peg4, or 8-aminooctanoyl
                      derivatives thereof or may be absent
VARIANT              20..27
                     note = This region may encompass 1 to 8 amino acid residues
source               1..27
                     mol_type = protein
                     organism = synthetic construct
SEQUENCE: 9
XXXXXXXCIX QXWXXHXCXX XXXXXXX                                          27

SEQ ID NO: 10        moltype = AA  length = 27
FEATURE              Location/Qualifiers
REGION               1..27
```

-continued

```
                        note = Description of Artificial Sequence: Synthetic peptide
REGION                  1..27
                        note = compstatin analogue
VARIANT                 1..6
                        note = A, E, G, L, K, K covalently linked to a lipophilic
                         group via its side chain, F, P, S, T, W, Y, R, V or Sar, a
                         corresponding D form thereof or may be absent
VARIANT                 1..6
                        note = This region may encompass 1 to 6 amino acid residues
VARIANT                 7
                        note = I, Y, F or Sar
DISULFID                8..18
                        note = Intrachain disulfide bond
VARIANT                 10
                        note = W, V, Y, 1-Nal, 2-Nal or 1-Me-Trp
VARIANT                 12
                        note = E or D
VARIANT                 15
                        note = A, E, D, K or S
VARIANT                 17
                        note = R, S or K covalently linked to a lipophilic group
                         via its side chain
VARIANT                 19
                        note = T, I, S, E, K or Sar
VARIANT                 20..27
                        note = A, E, G, L, K, K covalently linked to a lipophilic
                         group via its side chain F, P, S, T, W, Y, R, V, Sar,
                         epsilonLys, gammaGlu, betaAsp, or betaAla, or a
                         corresponding D form thereof or Peg3 or Peg4, or
                         8-aminooctanoyl derivatives thereof or may be absent
VARIANT                 20..27
                        note = This region may encompass 1 to 8 amino acid residues
source                  1..27
                        mol_type = protein
                        organism = synthetic construct
SEQUENCE: 10
XXXXXXXCIX QXWGXHXCXX XXXXXXX                                      27

SEQ ID NO: 11           moltype = AA  length = 27
FEATURE                 Location/Qualifiers
REGION                  1..27
                        note = Description of Artificial Sequence: Synthetic peptide
REGION                  1..27
                        note = compstatin analogue
VARIANT                 1..6
                        note = A, E, G, L, K, K covalently linked to a lipophilic
                         group via its side chain, F, P, S, T, W, Y, R, V or Sar, a
                         corresponding D form thereof or may be absent
VARIANT                 1..6
                        note = This region may encompass 1 to 6 amino acid residues
VARIANT                 7
                        note = I, Y, F or Sar
DISULFID                8..18
                        note = Intrachain disulfide bond
VARIANT                 10
                        note = W, V, 1-Nal, 2-Nal or 1-Me-Trp
VARIANT                 12
                        note = E or D
VARIANT                 15
                        note = A, E, D, K or S
VARIANT                 19
                        note = T, S, E or Sar
VARIANT                 20..27
                        note = A, E, G, L, K, K covalently linked to a lipophilic
                         group via its side chain, F, P, S, T, W, Y, R, V, Sar,
                         epsilonLys, gammaGlu, betaAsp, or betaAla, or a
                         corresponding D form thereof or Peg3 or Peg4, or
                         8-aminooctanoyl derivatives thereof or may be absent
VARIANT                 20..27
                        note = This region may encompass 1 to 8 amino acid residues
source                  1..27
                        mol_type = protein
                        organism = synthetic construct
SEQUENCE: 11
XXXXXXXCIX QXWGXHRCXX XXXXXXX                                      27

SEQ ID NO: 12           moltype = AA  length = 27
FEATURE                 Location/Qualifiers
REGION                  1..27
```

```
                         note = Description of Artificial Sequence: Synthetic peptide
REGION                   1..27
                         note = compstatin analogue
VARIANT                  1..6
                         note = A, E, G, L, K, K covalently linked to a lipophilic
                          group via its side chain, F, P, S, T, W, Y, R, V or Sar, a
                          corresponding D form thereof or may be absent
VARIANT                  1..6
                         note = This region may encompass 1 to 6 amino acid residues
VARIANT                  7
                         note = Y or F
DISULFID                 8..18
                         note = Intrachain disulfide bond
MOD_RES                  10
                         note = 1-methyl-tryptophan
VARIANT                  12
                         note = E or D
VARIANT                  19
                         note = T, E or Sar
VARIANT                  20..27
                         note = A, E, G, L, K, K covalently linked to a lipophilic
                          group via its side chain F, P, S, T, W, Y, R, V, Sar,
                          epsilonLys, gammaGlu, betaAsp, or betaAla, or a
                          corresponding D form thereof or Peg3 or Peg4, or
                          8-aminooctanoyl derivatives thereof or may be absent
VARIANT                  20..27
                         note = This region may encompass 1 to 8 amino acid residues
source                   1..27
                         mol_type = protein
                         organism = synthetic construct
SEQUENCE: 12
XXXXXXXCIX QXWGEHRCXX XXXXXXX                                          27

SEQ ID NO: 13            moltype = AA  length = 13
FEATURE                  Location/Qualifiers
REGION                   1..13
                         note = Description of Artificial Sequence: Synthetic peptide
REGION                   1..13
                         note = 13-mer peptide portion of the compstatin analogue
MOD_RES                  1
                         note = sarcosine
DISULFID                 2..12
                         note = Intrachain disulfide bond
MOD_RES                  4
                         note = 1-methyl-tryptophan
MOD_RES                  13
                         note = sarcosine
source                   1..13
                         mol_type = protein
                         organism = synthetic construct
SEQUENCE: 13
XCIWQDWGEH RCX                                                         13

SEQ ID NO: 14            moltype = AA  length = 13
FEATURE                  Location/Qualifiers
REGION                   1..13
                         note = Description of Artificial Sequence: Synthetic peptide
REGION                   1..13
                         note = 13-mer peptide portion of the compstatin analogue
MOD_RES                  1
                         note = sarcosine
DISULFID                 2..12
                         note = Intrachain disulfide bond
MOD_RES                  4
                         note = 1-methyl-tryptophan
source                   1..13
                         mol_type = protein
                         organism = synthetic construct
SEQUENCE: 14
XCIWQDWGEH RCT                                                         13

SEQ ID NO: 15            moltype = AA  length = 13
FEATURE                  Location/Qualifiers
REGION                   1..13
                         note = Description of Artificial Sequence: Synthetic peptide
REGION                   1..13
                         note = 13-mer peptide portion of the compstatin analogue
MOD_RES                  1
                         note = sarcosine
```

-continued

```
DISULFID              2..12
                      note = Intrachain disulfide bond
MOD_RES               4
                      note = 1-methyl-tryptophan
MOD_RES               8
                      note = sarcosine
source                1..13
                      mol_type = protein
                      organism = synthetic construct
SEQUENCE: 15
XCIWQEWXEH RCT                                                        13

SEQ ID NO: 16         moltype = AA  length = 13
FEATURE               Location/Qualifiers
REGION                1..13
                      note = Description of Artificial Sequence: Synthetic peptide
REGION                1..13
                      note = 13-mer peptide portion of the compstatin analogue
MOD_RES               1
                      note = sarcosine
DISULFID              2..12
                      note = Intrachain disulfide bond
MOD_RES               4
                      note = 1-methyl-tryptophan
MOD_RES               13
                      note = sarcosine
source                1..13
                      mol_type = protein
                      organism = synthetic construct
SEQUENCE: 16
XCIWQEWGEH RCX                                                        13

SEQ ID NO: 17         moltype = AA  length = 13
FEATURE               Location/Qualifiers
REGION                1..13
                      note = Description of Artificial Sequence: Synthetic peptide
REGION                1..13
                      note = 13-mer peptide portion of the compstatin analogue
MOD_RES               1
                      note = sarcosine
DISULFID              2..12
                      note = Intrachain disulfide bond
source                1..13
                      mol_type = protein
                      organism = synthetic construct
SEQUENCE: 17
XCIWQDWGEH RCT                                                        13

SEQ ID NO: 18         moltype = AA  length = 13
FEATURE               Location/Qualifiers
REGION                1..13
                      note = Description of Artificial Sequence: Synthetic peptide
REGION                1..13
                      note = 13-mer peptide portion of the compstatin analogue
DISULFID              2..12
                      note = Intrachain disulfide bond
MOD_RES               4
                      note = 1-methyl-tryptophan
MOD_RES               8
                      note = sarcosine
MOD_RES               13
                      note = sarcosine
source                1..13
                      mol_type = protein
                      organism = synthetic construct
SEQUENCE: 18
FCIWQDWXEH RCX                                                        13

SEQ ID NO: 19         moltype = AA  length = 13
FEATURE               Location/Qualifiers
REGION                1..13
                      note = Description of Artificial Sequence: Synthetic peptide
REGION                1..13
                      note = 13-mer peptide portion of the compstatin analogue
DISULFID              2..12
                      note = Intrachain disulfide bond
MOD_RES               4
                      note = 1-methyl-tryptophan
MOD_RES               8
```

-continued

```
                        note = sarcosine
source                  1..13
                        mol_type = protein
                        organism = synthetic construct
SEQUENCE: 19
FCIWQDWXEH RCT                                                   13

SEQ ID NO: 20           moltype = AA  length = 13
FEATURE                 Location/Qualifiers
REGION                  1..13
                        note = Description of Artificial Sequence: Synthetic peptide
REGION                  1..13
                        note = 13-mer peptide portion of the compstatin analogue
DISULFID                2..12
                        note = Intrachain disulfide bond
MOD_RES                 4
                        note = 1-methyl-tryptophan
MOD_RES                 13
                        note = sarcosine
source                  1..13
                        mol_type = protein
                        organism = synthetic construct
SEQUENCE: 20
FCIWQDWGEH KCX                                                   13

SEQ ID NO: 21           moltype = AA  length = 13
FEATURE                 Location/Qualifiers
REGION                  1..13
                        note = Description of Artificial Sequence: Synthetic peptide
REGION                  1..13
                        note = 13-mer peptide portion of the compstatin analogue
DISULFID                2..12
                        note = Intrachain disulfide bond
MOD_RES                 4
                        note = 1-methyl-tryptophan
MOD_RES                 13
                        note = sarcosine
source                  1..13
                        mol_type = protein
                        organism = synthetic construct
SEQUENCE: 21
FCIWQDWGEH RCX                                                   13

SEQ ID NO: 22           moltype = AA  length = 13
FEATURE                 Location/Qualifiers
REGION                  1..13
                        note = Description of Artificial Sequence: Synthetic peptide
REGION                  1..13
                        note = 13-mer peptide portion of the compstatin analogue
DISULFID                2..12
                        note = Intrachain disulfide bond
MOD_RES                 4
                        note = 1-methyl-tryptophan
source                  1..13
                        mol_type = protein
                        organism = synthetic construct
SEQUENCE: 22
FCIWQDWGEH RCE                                                   13

SEQ ID NO: 23           moltype = AA  length = 13
FEATURE                 Location/Qualifiers
REGION                  1..13
                        note = Description of Artificial Sequence: Synthetic peptide
REGION                  1..13
                        note = 13-mer peptide portion of the compstatin analogue
DISULFID                2..12
                        note = Intrachain disulfide bond
MOD_RES                 4
                        note = 1-methyl-tryptophan
source                  1..13
                        mol_type = protein
                        organism = synthetic construct
SEQUENCE: 23
FCIWQDWGEH RCS                                                   13

SEQ ID NO: 24           moltype = AA  length = 13
FEATURE                 Location/Qualifiers
REGION                  1..13
                        note = Description of Artificial Sequence: Synthetic peptide
```

-continued

```
REGION                  1..13
                        note = 13-mer peptide portion of the compstatin analogue
DISULFID                2..12
                        note = Intrachain disulfide bond
MOD_RES                 4
                        note = 1-methyl-tryptophan
source                  1..13
                        mol_type = protein
                        organism = synthetic construct
SEQUENCE: 24
FCIWQDWGEH RCT                                                              13

SEQ ID NO: 25           moltype = AA  length = 13
FEATURE                 Location/Qualifiers
REGION                  1..13
                        note = Description of Artificial Sequence: Synthetic peptide
REGION                  1..13
                        note = 13-mer peptide portion of the compstatin analogue
DISULFID                2..12
                        note = Intrachain disulfide bond
MOD_RES                 4
                        note = 1-methyl-tryptophan
MOD_RES                 13
                        note = sarcosine
source                  1..13
                        mol_type = protein
                        organism = synthetic construct
SEQUENCE: 25
FCIWQEWGEH RCX                                                              13

SEQ ID NO: 26           moltype = AA  length = 13
FEATURE                 Location/Qualifiers
REGION                  1..13
                        note = Description of Artificial Sequence: Synthetic peptide
REGION                  1..13
                        note = 13-mer peptide portion of the compstatin analogue
DISULFID                2..12
                        note = Intrachain disulfide bond
MOD_RES                 4
                        note = 1-naphathalin
source                  1..13
                        mol_type = protein
                        organism = synthetic construct
SEQUENCE: 26
FCIXQDWGEH RCT                                                              13

SEQ ID NO: 27           moltype = AA  length = 13
FEATURE                 Location/Qualifiers
REGION                  1..13
                        note = Description of Artificial Sequence: Synthetic peptide
REGION                  1..13
                        note = 13-mer peptide portion of the compstatin analogue
DISULFID                2..12
                        note = Intrachain disulfide bond
MOD_RES                 4
                        note = 2-naphathalin
source                  1..13
                        mol_type = protein
                        organism = synthetic construct
SEQUENCE: 27
FCIXQDWGEH RCT                                                              13

SEQ ID NO: 28           moltype = AA  length = 13
FEATURE                 Location/Qualifiers
REGION                  1..13
                        note = Description of Artificial Sequence: Synthetic peptide
REGION                  1..13
                        note = 13-mer peptide portion of the compstatin analogue
DISULFID                2..12
                        note = Intrachain disulfide bond
MOD_RES                 13
                        note = sarcosine
source                  1..13
                        mol_type = protein
                        organism = synthetic construct
SEQUENCE: 28
FCIWQDWGEH RCX                                                              13

SEQ ID NO: 29           moltype = AA  length = 13
```

-continued

```
FEATURE                Location/Qualifiers
REGION                 1..13
                       note = Description of Artificial Sequence: Synthetic peptide
REGION                 1..13
                       note = 13-mer peptide portion of the compstatin analogue
DISULFID               2..12
                       note = Intrachain disulfide bond
source                 1..13
                       mol_type = protein
                       organism = synthetic construct
SEQUENCE: 29
FCIWQDWGEH RCT                                                           13

SEQ ID NO: 30          moltype = AA  length = 13
FEATURE                Location/Qualifiers
REGION                 1..13
                       note = Description of Artificial Sequence: Synthetic peptide
REGION                 1..13
                       note = 13-mer peptide portion of the compstatin analogue
DISULFID               2..12
                       note = Intrachain disulfide bond
MOD_RES                4
                       note = 1-methyl-tryptophan
MOD_RES                8
                       note = sarcosine
MOD_RES                13
                       note = N-methyl-isoleucine
source                 1..13
                       mol_type = protein
                       organism = synthetic construct
SEQUENCE: 30
ICIWQDWXAH RCI                                                           13

SEQ ID NO: 31          moltype = AA  length = 13
FEATURE                Location/Qualifiers
REGION                 1..13
                       note = Description of Artificial Sequence: Synthetic peptide
REGION                 1..13
                       note = 13-mer peptide portion of the compstatin analogue
DISULFID               2..12
                       note = Intrachain disulfide bond
MOD_RES                4
                       note = 1-methyl-tryptophan
MOD_RES                13
                       note = sarcosine
source                 1..13
                       mol_type = protein
                       organism = synthetic construct
SEQUENCE: 31
ICIWQDWGEH RCX                                                           13

SEQ ID NO: 32          moltype = AA  length = 13
FEATURE                Location/Qualifiers
REGION                 1..13
                       note = Description of Artificial Sequence: Synthetic peptide
REGION                 1..13
                       note = 13-mer peptide portion of the compstatin analogue
DISULFID               2..12
                       note = Intrachain disulfide bond
MOD_RES                4
                       note = 1-methyl-tryptophan
source                 1..13
                       mol_type = protein
                       organism = synthetic construct
SEQUENCE: 32
ICIWQDWGEH RCT                                                           13

SEQ ID NO: 33          moltype = AA  length = 13
FEATURE                Location/Qualifiers
REGION                 1..13
                       note = Description of Artificial Sequence: Synthetic peptide
REGION                 1..13
                       note = 13-mer peptide portion of the compstatin analogue
DISULFID               2..12
                       note = Intrachain disulfide bond
MOD_RES                4
                       note = 2-naphathalin
MOD_RES                13
                       note = sarcosine
```

```
source                 1..13
                       mol_type = protein
                       organism = synthetic construct
SEQUENCE: 33
ICIXQDWGEH RCX                                                      13

SEQ ID NO: 34          moltype = AA  length = 13
FEATURE                Location/Qualifiers
REGION                 1..13
                       note = Description of Artificial Sequence: Synthetic peptide
REGION                 1..13
                       note = 13-mer peptide portion of the compstatin analogue
DISULFID               2..12
                       note = Intrachain disulfide bond
source                 1..13
                       mol_type = protein
                       organism = synthetic construct
SEQUENCE: 34
ICIWQDWGAH RCE                                                      13

SEQ ID NO: 35          moltype = AA  length = 13
FEATURE                Location/Qualifiers
REGION                 1..13
                       note = Description of Artificial Sequence: Synthetic peptide
REGION                 1..13
                       note = 13-mer peptide portion of the compstatin analogue
DISULFID               2..12
                       note = Intrachain disulfide bond
source                 1..13
                       mol_type = protein
                       organism = synthetic construct
SEQUENCE: 35
ICIWQDWGAH RCT                                                      13

SEQ ID NO: 36          moltype = AA  length = 13
FEATURE                Location/Qualifiers
REGION                 1..13
                       note = Description of Artificial Sequence: Synthetic peptide
REGION                 1..13
                       note = 13-mer peptide portion of the compstatin analogue
DISULFID               2..12
                       note = Intrachain disulfide bond
source                 1..13
                       mol_type = protein
                       organism = synthetic construct
SEQUENCE: 36
ICIWQDWGAH SCT                                                      13

SEQ ID NO: 37          moltype = AA  length = 13
FEATURE                Location/Qualifiers
REGION                 1..13
                       note = Description of Artificial Sequence: Synthetic peptide
REGION                 1..13
                       note = 13-mer peptide portion of the compstatin analogue
DISULFID               2..12
                       note = Intrachain disulfide bond
source                 1..13
                       mol_type = protein
                       organism = synthetic construct
SEQUENCE: 37
ICIWQDWGDH RCT                                                      13

SEQ ID NO: 38          moltype = AA  length = 13
FEATURE                Location/Qualifiers
REGION                 1..13
                       note = Description of Artificial Sequence: Synthetic peptide
REGION                 1..13
                       note = 13-mer peptide portion of the compstatin analogue
DISULFID               2..12
                       note = Intrachain disulfide bond
MOD_RES                13
                       note = sarcosine
source                 1..13
                       mol_type = protein
                       organism = synthetic construct
SEQUENCE: 38
ICIWQDWGEH RCX                                                      13

SEQ ID NO: 39          moltype = AA  length = 13
```

-continued

```
FEATURE                 Location/Qualifiers
REGION                  1..13
                        note = Description of Artificial Sequence: Synthetic peptide
REGION                  1..13
                        note = 13-mer peptide portion of the compstatin analogue
DISULFID                2..12
                        note = Intrachain disulfide bond
source                  1..13
                        mol_type = protein
                        organism = synthetic construct
SEQUENCE: 39
ICIWQDWGEH RCE                                                             13

SEQ ID NO: 40           moltype = AA  length = 13
FEATURE                 Location/Qualifiers
REGION                  1..13
                        note = Description of Artificial Sequence: Synthetic peptide
REGION                  1..13
                        note = 13-mer peptide portion of the compstatin analogue
DISULFID                2..12
                        note = Intrachain disulfide bond
source                  1..13
                        mol_type = protein
                        organism = synthetic construct
SEQUENCE: 40
ICIWQDWGEH RCS                                                             13

SEQ ID NO: 41           moltype = AA  length = 13
FEATURE                 Location/Qualifiers
REGION                  1..13
                        note = Description of Artificial Sequence: Synthetic peptide
REGION                  1..13
                        note = 13-mer peptide portion of the compstatin analogue
DISULFID                2..12
                        note = Intrachain disulfide bond
source                  1..13
                        mol_type = protein
                        organism = synthetic construct
SEQUENCE: 41
ICIWQDWGEH RCT                                                             13

SEQ ID NO: 42           moltype = AA  length = 13
FEATURE                 Location/Qualifiers
REGION                  1..13
                        note = Description of Artificial Sequence: Synthetic peptide
REGION                  1..13
                        note = 13-mer peptide portion of the compstatin analogue
DISULFID                2..12
                        note = Intrachain disulfide bond
source                  1..13
                        mol_type = protein
                        organism = synthetic construct
SEQUENCE: 42
ICIWQDWGEH SCT                                                             13

SEQ ID NO: 43           moltype = AA  length = 13
FEATURE                 Location/Qualifiers
REGION                  1..13
                        note = Description of Artificial Sequence: Synthetic peptide
REGION                  1..13
                        note = 13-mer peptide portion of the compstatin analogue
DISULFID                2..12
                        note = Intrachain disulfide bond
source                  1..13
                        mol_type = protein
                        organism = synthetic construct
SEQUENCE: 43
ICIWQDWGKH RCT                                                             13

SEQ ID NO: 44           moltype = AA  length = 13
FEATURE                 Location/Qualifiers
REGION                  1..13
                        note = Description of Artificial Sequence: Synthetic peptide
REGION                  1..13
                        note = 13-mer peptide portion of the compstatin analogue
DISULFID                2..12
                        note = Intrachain disulfide bond
source                  1..13
                        mol_type = protein
```

-continued

```
                        organism = synthetic construct
SEQUENCE: 44
ICIWQDWGRH RCT                                                            13

SEQ ID NO: 45           moltype = AA  length = 13
FEATURE                 Location/Qualifiers
REGION                  1..13
                        note = Description of Artificial Sequence: Synthetic peptide
REGION                  1..13
                        note = 13-mer peptide portion of the compstatin analogue
DISULFID                2..12
                        note = Intrachain disulfide bond
source                  1..13
                        mol_type = protein
                        organism = synthetic construct
SEQUENCE: 45
ICIWQDWGSH RCT                                                            13

SEQ ID NO: 46           moltype = AA  length = 13
FEATURE                 Location/Qualifiers
REGION                  1..13
                        note = Description of Artificial Sequence: Synthetic peptide
REGION                  1..13
                        note = 13-mer peptide portion of the compstatin analogue
DISULFID                2..12
                        note = Intrachain disulfide bond
source                  1..13
                        mol_type = protein
                        organism = synthetic construct
SEQUENCE: 46
ICIWQEWGEH RCT                                                            13

SEQ ID NO: 47           moltype = AA  length = 13
FEATURE                 Location/Qualifiers
REGION                  1..13
                        note = Description of Artificial Sequence: Synthetic peptide
REGION                  1..13
                        note = 13-mer peptide portion of the compstatin analogue
DISULFID                2..12
                        note = Intrachain disulfide bond
source                  1..13
                        mol_type = protein
                        organism = synthetic construct
SEQUENCE: 47
ICIWQKWGAH RCT                                                            13

SEQ ID NO: 48           moltype = AA  length = 13
FEATURE                 Location/Qualifiers
REGION                  1..13
                        note = Description of Artificial Sequence: Synthetic peptide
REGION                  1..13
                        note = 13-mer peptide portion of the compstatin analogue
DISULFID                2..12
                        note = Intrachain disulfide bond
source                  1..13
                        mol_type = protein
                        organism = synthetic construct
SEQUENCE: 48
ICIWQKWGEH RCT                                                            13

SEQ ID NO: 49           moltype = AA  length = 13
FEATURE                 Location/Qualifiers
REGION                  1..13
                        note = Description of Artificial Sequence: Synthetic peptide
REGION                  1..13
                        note = 13-mer peptide portion of the compstatin analogue
DISULFID                2..12
                        note = Intrachain disulfide bond
MOD_RES                 4
                        note = 1-methyl-tryptophan
MOD_RES                 13
                        note = sarcosine
source                  1..13
                        mol_type = protein
                        organism = synthetic construct
SEQUENCE: 49
YCIWQDWGEH RCX                                                            13

SEQ ID NO: 50           moltype = AA  length = 13
```

-continued

```
FEATURE                 Location/Qualifiers
REGION                  1..13
                        note = Description of Artificial Sequence: Synthetic peptide
REGION                  1..13
                        note = 13-mer peptide portion of the compstatin analogue
DISULFID                2..12
                        note = Intrachain disulfide bond
MOD_RES                 4
                        note = 1-methyl-tryptophan
source                  1..13
                        mol_type = protein
                        organism = synthetic construct
SEQUENCE: 50
YCIWQDWGEH RCT                                                         13

SEQ ID NO: 51           moltype = AA  length = 13
FEATURE                 Location/Qualifiers
REGION                  1..13
                        note = Description of Artificial Sequence: Synthetic peptide
REGION                  1..13
                        note = 13-mer peptide portion of the compstatin analogue
DISULFID                2..12
                        note = Intrachain disulfide bond
MOD_RES                 4
                        note = 1-methyl-tryptophan
MOD_RES                 13
                        note = sarcosine
source                  1..13
                        mol_type = protein
                        organism = synthetic construct
SEQUENCE: 51
YCIWQEWGEH RCX                                                         13

SEQ ID NO: 52           moltype = AA  length = 13
FEATURE                 Location/Qualifiers
REGION                  1..13
                        note = Description of Artificial Sequence: Synthetic peptide
REGION                  1..13
                        note = 13-mer peptide portion of the compstatin analogue
DISULFID                2..12
                        note = Intrachain disulfide bond
MOD_RES                 4
                        note = 2-naphathalin
source                  1..13
                        mol_type = protein
                        organism = synthetic construct
SEQUENCE: 52
YCIXQDWGEH RCT                                                         13

SEQ ID NO: 53           moltype = AA  length = 13
FEATURE                 Location/Qualifiers
REGION                  1..13
                        note = Description of Artificial Sequence: Synthetic peptide
REGION                  1..13
                        note = 13-mer peptide portion of the compstatin analogue
DISULFID                2..12
                        note = Intrachain disulfide bond
source                  1..13
                        mol_type = protein
                        organism = synthetic construct
SEQUENCE: 53
YCIWQDWGEH RCT                                                         13

SEQ ID NO: 54           moltype = AA  length = 13
FEATURE                 Location/Qualifiers
REGION                  1..13
                        note = Description of Artificial Sequence: Synthetic peptide
REGION                  1..13
                        note = 13-mer peptide portion of the compstatin analogue
DISULFID                2..12
                        note = Intrachain disulfide bond
MOD_RES                 4
                        note = 1-methyl-tryptophan
SITE                    11
                        note = Lysine residue covalently linked to a lipophilic
                         group via its side chain
MOD_RES                 13
                        note = sarcosine
source                  1..13
```

-continued

```
                        mol_type = protein
                        organism = synthetic construct
SEQUENCE: 54
YCIWQDWGEH KCX                                                              13

SEQ ID NO: 55           moltype = AA  length = 13
FEATURE                 Location/Qualifiers
REGION                  1..13
                        note = Description of Artificial Sequence: Synthetic peptide
REGION                  1..13
                        note = 13-mer peptide portion of the compstatin analogue
DISULFID                2..12
                        note = Intrachain disulfide bond
MOD_RES                 4
                        note = 1-methyl-tryptophan
MOD_RES                 8
                        note = sarcosine
MOD_RES                 13
                        note = sarcosine
source                  1..13
                        mol_type = protein
                        organism = synthetic construct
SEQUENCE: 55
YCIWQEWXEH RCX                                                              13

SEQ ID NO: 56           moltype = AA  length = 4
FEATURE                 Location/Qualifiers
REGION                  1..4
                        note = Description of Artificial Sequence: Synthetic peptide
REGION                  1..4
                        note = N-terminal and/or C-terminal flanking sequence
source                  1..4
                        mol_type = protein
                        organism = synthetic construct
SEQUENCE: 56
ESSA                                                                        4

SEQ ID NO: 57           moltype = AA  length = 4
FEATURE                 Location/Qualifiers
REGION                  1..4
                        note = Description of Artificial Sequence: Synthetic peptide
REGION                  1..4
                        note = N-terminal and/or C-terminal flanking sequence
source                  1..4
                        mol_type = protein
                        organism = synthetic construct
SEQUENCE: 57
AKGE                                                                        4

SEQ ID NO: 58           moltype = AA  length = 4
FEATURE                 Location/Qualifiers
REGION                  1..4
                        note = Description of Artificial Sequence: Synthetic peptide
REGION                  1..4
                        note = N-terminal and/or C-terminal flanking sequence
source                  1..4
                        mol_type = protein
                        organism = synthetic construct
SEQUENCE: 58
ASSE                                                                        4

SEQ ID NO: 59           moltype = AA  length = 4
FEATURE                 Location/Qualifiers
REGION                  1..4
                        note = Description of Artificial Sequence: Synthetic peptide
REGION                  1..4
                        note = N-terminal and/or C-terminal flanking sequence
source                  1..4
                        mol_type = protein
                        organism = synthetic construct
SEQUENCE: 59
ASES                                                                        4

SEQ ID NO: 60           moltype = AA  length = 4
FEATURE                 Location/Qualifiers
REGION                  1..4
                        note = Description of Artificial Sequence: Synthetic peptide
REGION                  1..4
                        note = N-terminal and/or C-terminal flanking sequence
```

```
source                  1..4
                        mol_type = protein
                        organism = synthetic construct
SEQUENCE: 60
GSAE                                                                        4

SEQ ID NO: 61           moltype = AA  length = 4
FEATURE                 Location/Qualifiers
REGION                  1..4
                        note = Description of Artificial Sequence: Synthetic peptide
REGION                  1..4
                        note = N-terminal and/or C-terminal flanking sequence
source                  1..4
                        mol_type = protein
                        organism = synthetic construct
SEQUENCE: 61
ESSE                                                                        4

SEQ ID NO: 62           moltype = AA  length = 4
FEATURE                 Location/Qualifiers
REGION                  1..4
                        note = Description of Artificial Sequence: Synthetic peptide
REGION                  1..4
                        note = N-terminal and/or C-terminal flanking sequence
source                  1..4
                        mol_type = protein
                        organism = synthetic construct
SEQUENCE: 62
ESGA                                                                        4

SEQ ID NO: 63           moltype = AA  length = 4
FEATURE                 Location/Qualifiers
REGION                  1..4
                        note = Description of Artificial Sequence: Synthetic peptide
REGION                  1..4
                        note = N-terminal and/or C-terminal flanking sequence
source                  1..4
                        mol_type = protein
                        organism = synthetic construct
SEQUENCE: 63
EGSA                                                                        4

SEQ ID NO: 64           moltype = AA  length = 4
FEATURE                 Location/Qualifiers
REGION                  1..4
                        note = Description of Artificial Sequence: Synthetic peptide
REGION                  1..4
                        note = N-terminal and/or C-terminal flanking sequence
source                  1..4
                        mol_type = protein
                        organism = synthetic construct
SEQUENCE: 64
YLEA                                                                        4

SEQ ID NO: 65           moltype = AA  length = 4
FEATURE                 Location/Qualifiers
REGION                  1..4
                        note = Description of Artificial Sequence: Synthetic peptide
REGION                  1..4
                        note = N-terminal and/or C-terminal flanking sequence
source                  1..4
                        mol_type = protein
                        organism = synthetic construct
SEQUENCE: 65
GAES                                                                        4

SEQ ID NO: 66           moltype = AA  length = 4
FEATURE                 Location/Qualifiers
REGION                  1..4
                        note = Description of Artificial Sequence: Synthetic peptide
REGION                  1..4
                        note = N-terminal and/or C-terminal flanking sequence
source                  1..4
                        mol_type = protein
                        organism = synthetic construct
SEQUENCE: 66
EYGS                                                                        4

SEQ ID NO: 67           moltype = AA  length = 4
```

-continued

```
FEATURE                 Location/Qualifiers
REGION                  1..4
                        note = Description of Artificial Sequence: Synthetic peptide
REGION                  1..4
                        note = N-terminal and/or C-terminal flanking sequence
source                  1..4
                        mol_type = protein
                        organism = synthetic construct
SEQUENCE: 67
EGYA                                                                       4

SEQ ID NO: 68           moltype = AA  length = 4
FEATURE                 Location/Qualifiers
REGION                  1..4
                        note = Description of Artificial Sequence: Synthetic peptide
REGION                  1..4
                        note = N-terminal and/or C-terminal flanking sequence
source                  1..4
                        mol_type = protein
                        organism = synthetic construct
SEQUENCE: 68
EAGS                                                                       4

SEQ ID NO: 69           moltype = AA  length = 4
FEATURE                 Location/Qualifiers
REGION                  1..4
                        note = Description of Artificial Sequence: Synthetic peptide
REGION                  1..4
                        note = N-terminal and/or C-terminal flanking sequence
source                  1..4
                        mol_type = protein
                        organism = synthetic construct
SEQUENCE: 69
EAKS                                                                       4

SEQ ID NO: 70           moltype = AA  length = 4
FEATURE                 Location/Qualifiers
REGION                  1..4
                        note = Description of Artificial Sequence: Synthetic peptide
REGION                  1..4
                        note = N-terminal and/or C-terminal flanking sequence
source                  1..4
                        mol_type = protein
                        organism = synthetic construct
SEQUENCE: 70
EKSA                                                                       4

SEQ ID NO: 71           moltype = AA  length = 4
FEATURE                 Location/Qualifiers
REGION                  1..4
                        note = Description of Artificial Sequence: Synthetic peptide
REGION                  1..4
                        note = N-terminal and/or C-terminal flanking sequence
source                  1..4
                        mol_type = protein
                        organism = synthetic construct
SEQUENCE: 71
EGGS                                                                       4

SEQ ID NO: 72           moltype = AA  length = 4
FEATURE                 Location/Qualifiers
REGION                  1..4
                        note = Description of Artificial Sequence: Synthetic peptide
REGION                  1..4
                        note = N-terminal and/or C-terminal flanking sequence
source                  1..4
                        mol_type = protein
                        organism = synthetic construct
SEQUENCE: 72
EGGA                                                                       4

SEQ ID NO: 73           moltype = AA  length = 4
FEATURE                 Location/Qualifiers
REGION                  1..4
                        note = Description of Artificial Sequence: Synthetic peptide
REGION                  1..4
                        note = N-terminal and/or C-terminal flanking sequence
source                  1..4
                        mol_type = protein
```

```
                        organism = synthetic construct
SEQUENCE: 73
ESSG                                                                            4

SEQ ID NO: 74           moltype = AA  length = 4
FEATURE                 Location/Qualifiers
REGION                  1..4
                        note = Description of Artificial Sequence: Synthetic peptide
REGION                  1..4
                        note = N-terminal and/or C-terminal flanking sequence
source                  1..4
                        mol_type = protein
                        organism = synthetic construct
SEQUENCE: 74
ESAG                                                                            4

SEQ ID NO: 75           moltype = AA  length = 4
FEATURE                 Location/Qualifiers
REGION                  1..4
                        note = Description of Artificial Sequence: Synthetic peptide
REGION                  1..4
                        note = N-terminal and/or C-terminal flanking sequence
source                  1..4
                        mol_type = protein
                        organism = synthetic construct
SEQUENCE: 75
GEES                                                                            4

SEQ ID NO: 76           moltype = AA  length = 4
FEATURE                 Location/Qualifiers
REGION                  1..4
                        note = Description of Artificial Sequence: Synthetic peptide
REGION                  1..4
                        note = N-terminal and/or C-terminal flanking sequence
source                  1..4
                        mol_type = protein
                        organism = synthetic construct
SEQUENCE: 76
AEES                                                                            4

SEQ ID NO: 77           moltype = AA  length = 4
FEATURE                 Location/Qualifiers
REGION                  1..4
                        note = Description of Artificial Sequence: Synthetic peptide
REGION                  1..4
                        note = N-terminal and/or C-terminal flanking sequence
source                  1..4
                        mol_type = protein
                        organism = synthetic construct
SEQUENCE: 77
ESEG                                                                            4

SEQ ID NO: 78           moltype = AA  length = 4
FEATURE                 Location/Qualifiers
REGION                  1..4
                        note = Description of Artificial Sequence: Synthetic peptide
REGION                  1..4
                        note = N-terminal and/or C-terminal flanking sequence
source                  1..4
                        mol_type = protein
                        organism = synthetic construct
SEQUENCE: 78
AEGS                                                                            4

SEQ ID NO: 79           moltype = AA  length = 4
FEATURE                 Location/Qualifiers
REGION                  1..4
                        note = Description of Artificial Sequence: Synthetic peptide
REGION                  1..4
                        note = N-terminal and/or C-terminal flanking sequence
source                  1..4
                        mol_type = protein
                        organism = synthetic construct
SEQUENCE: 79
ESGS                                                                            4

SEQ ID NO: 80           moltype = AA  length = 4
FEATURE                 Location/Qualifiers
REGION                  1..4
```

-continued

```
                        note = Description of Artificial Sequence: Synthetic peptide
REGION                  1..4
                        note = N-terminal and/or C-terminal flanking sequence
source                  1..4
                        mol_type = protein
                        organism = synthetic construct
SEQUENCE: 80
SEGA                                                                             4

SEQ ID NO: 81           moltype = AA  length = 4
FEATURE                 Location/Qualifiers
REGION                  1..4
                        note = Description of Artificial Sequence: Synthetic peptide
REGION                  1..4
                        note = N-terminal and/or C-terminal flanking sequence
source                  1..4
                        mol_type = protein
                        organism = synthetic construct
SEQUENCE: 81
EGEA                                                                             4

SEQ ID NO: 82           moltype = AA  length = 4
FEATURE                 Location/Qualifiers
REGION                  1..4
                        note = Description of Artificial Sequence: Synthetic peptide
REGION                  1..4
                        note = N-terminal and/or C-terminal flanking sequence
source                  1..4
                        mol_type = protein
                        organism = synthetic construct
SEQUENCE: 82
EGSE                                                                             4

SEQ ID NO: 83           moltype = AA  length = 4
FEATURE                 Location/Qualifiers
REGION                  1..4
                        note = Description of Artificial Sequence: Synthetic peptide
REGION                  1..4
                        note = N-terminal and/or C-terminal flanking sequence
source                  1..4
                        mol_type = protein
                        organism = synthetic construct
SEQUENCE: 83
AGSE                                                                             4

SEQ ID NO: 84           moltype = AA  length = 4
FEATURE                 Location/Qualifiers
REGION                  1..4
                        note = Description of Artificial Sequence: Synthetic peptide
REGION                  1..4
                        note = N-terminal and/or C-terminal flanking sequence
source                  1..4
                        mol_type = protein
                        organism = synthetic construct
SEQUENCE: 84
SASE                                                                             4

SEQ ID NO: 85           moltype = AA  length = 4
FEATURE                 Location/Qualifiers
REGION                  1..4
                        note = Description of Artificial Sequence: Synthetic peptide
REGION                  1..4
                        note = N-terminal and/or C-terminal flanking sequence
source                  1..4
                        mol_type = protein
                        organism = synthetic construct
SEQUENCE: 85
EYSE                                                                             4

SEQ ID NO: 86           moltype = AA  length = 4
FEATURE                 Location/Qualifiers
REGION                  1..4
                        note = Description of Artificial Sequence: Synthetic peptide
REGION                  1..4
                        note = N-terminal and/or C-terminal flanking sequence
source                  1..4
                        mol_type = protein
                        organism = synthetic construct
SEQUENCE: 86
```

-continued

```
KGSA                                                                    4

SEQ ID NO: 87          moltype = AA  length = 4
FEATURE                Location/Qualifiers
REGION                 1..4
                       note = Description of Artificial Sequence: Synthetic peptide
REGION                 1..4
                       note = N-terminal and/or C-terminal flanking sequence
source                 1..4
                       mol_type = protein
                       organism = synthetic construct
SEQUENCE: 87
ASGE                                                                    4

SEQ ID NO: 88          moltype = AA  length = 7
FEATURE                Location/Qualifiers
REGION                 1..7
                       note = Description of Artificial Sequence: Synthetic peptide
REGION                 1..7
                       note = N-terminal and/or C-terminal flanking sequence
source                 1..7
                       mol_type = protein
                       organism = synthetic construct
SEQUENCE: 88
EGASGSG                                                                 7

SEQ ID NO: 89          moltype = AA  length = 6
FEATURE                Location/Qualifiers
REGION                 1..6
                       note = Description of Artificial Sequence: Synthetic peptide
REGION                 1..6
                       note = N-terminal and/or C-terminal flanking sequence
source                 1..6
                       mol_type = protein
                       organism = synthetic construct
SEQUENCE: 89
EGAGSG                                                                  6

SEQ ID NO: 90          moltype = AA  length = 6
FEATURE                Location/Qualifiers
REGION                 1..6
                       note = Description of Artificial Sequence: Synthetic peptide
REGION                 1..6
                       note = N-terminal and/or C-terminal flanking sequence
source                 1..6
                       mol_type = protein
                       organism = synthetic construct
SEQUENCE: 90
EGASAG                                                                  6

SEQ ID NO: 91          moltype = AA  length = 6
FEATURE                Location/Qualifiers
REGION                 1..6
                       note = Description of Artificial Sequence: Synthetic peptide
REGION                 1..6
                       note = N-terminal and/or C-terminal flanking sequence
source                 1..6
                       mol_type = protein
                       organism = synthetic construct
SEQUENCE: 91
EGAGAG                                                                  6

SEQ ID NO: 92          moltype = AA  length = 7
FEATURE                Location/Qualifiers
REGION                 1..7
                       note = Description of Artificial Sequence: Synthetic peptide
REGION                 1..7
                       note = N-terminal and/or C-terminal flanking sequence
source                 1..7
                       mol_type = protein
                       organism = synthetic construct
SEQUENCE: 92
EGESGSG                                                                 7

SEQ ID NO: 93          moltype = AA  length = 6
FEATURE                Location/Qualifiers
REGION                 1..6
                       note = Description of Artificial Sequence: Synthetic peptide
REGION                 1..6
```

-continued

```
                        note = N-terminal and/or C-terminal flanking sequence
source                  1..6
                        mol_type = protein
                        organism = synthetic construct
SEQUENCE: 93
EGEGSG                                                            6

SEQ ID NO: 94           moltype = AA  length = 6
FEATURE                 Location/Qualifiers
REGION                  1..6
                        note = Description of Artificial Sequence: Synthetic peptide
REGION                  1..6
                        note = N-terminal and/or C-terminal flanking sequence
source                  1..6
                        mol_type = protein
                        organism = synthetic construct
SEQUENCE: 94
EGESAG                                                            6

SEQ ID NO: 95           moltype = AA  length = 6
FEATURE                 Location/Qualifiers
REGION                  1..6
                        note = Description of Artificial Sequence: Synthetic peptide
REGION                  1..6
                        note = N-terminal and/or C-terminal flanking sequence
source                  1..6
                        mol_type = protein
                        organism = synthetic construct
SEQUENCE: 95
EGEGAG                                                            6

SEQ ID NO: 96           moltype = AA  length = 5
FEATURE                 Location/Qualifiers
REGION                  1..5
                        note = Description of Artificial Sequence: Synthetic peptide
REGION                  1..5
                        note = N-terminal and/or C-terminal flanking sequence
SITE                    3
                        note = glutamate participating in the peptide bond via the
                         gamma-carboxylic acid
source                  1..5
                        mol_type = protein
                        organism = synthetic construct
SEQUENCE: 96
EKEAK                                                             5

SEQ ID NO: 97           moltype = AA  length = 5
FEATURE                 Location/Qualifiers
REGION                  1..5
                        note = Description of Artificial Sequence: Synthetic peptide
REGION                  1..5
                        note = N-terminal and/or C-terminal flanking sequence
source                  1..5
                        mol_type = protein
                        organism = synthetic construct
SEQUENCE: 97
EGEGG                                                             5

SEQ ID NO: 98           moltype = AA  length = 5
FEATURE                 Location/Qualifiers
REGION                  1..5
                        note = Description of Artificial Sequence: Synthetic peptide
REGION                  1..5
                        note = N-terminal and/or C-terminal flanking sequence
source                  1..5
                        mol_type = protein
                        organism = synthetic construct
SEQUENCE: 98
EGAGG                                                             5

SEQ ID NO: 99           moltype = AA  length = 5
FEATURE                 Location/Qualifiers
REGION                  1..5
                        note = Description of Artificial Sequence: Synthetic peptide
REGION                  1..5
                        note = N-terminal and/or C-terminal flanking sequence
source                  1..5
                        mol_type = protein
                        organism = synthetic construct
```

```
SEQUENCE: 99
EGESS                                                                    5

SEQ ID NO: 100          moltype = AA  length = 5
FEATURE                 Location/Qualifiers
REGION                  1..5
                        note = Description of Artificial Sequence: Synthetic peptide
REGION                  1..5
                        note = N-terminal and/or C-terminal flanking sequence
source                  1..5
                        mol_type = protein
                        organism = synthetic construct
SEQUENCE: 100
GAESK                                                                    5

SEQ ID NO: 101          moltype = AA  length = 4
FEATURE                 Location/Qualifiers
REGION                  1..4
                        note = Description of Artificial Sequence: Synthetic peptide
REGION                  1..4
                        note = N-terminal and/or C-terminal flanking sequence
source                  1..4
                        mol_type = protein
                        organism = synthetic construct
SEQUENCE: 101
EGAK                                                                     4

SEQ ID NO: 102          moltype = AA  length = 4
FEATURE                 Location/Qualifiers
REGION                  1..4
                        note = Description of Artificial Sequence: Synthetic peptide
REGION                  1..4
                        note = N-terminal and/or C-terminal flanking sequence
source                  1..4
                        mol_type = protein
                        organism = synthetic construct
SEQUENCE: 102
EGEK                                                                     4

SEQ ID NO: 103          moltype = AA  length = 4
FEATURE                 Location/Qualifiers
REGION                  1..4
                        note = Description of Artificial Sequence: Synthetic peptide
REGION                  1..4
                        note = N-terminal and/or C-terminal flanking sequence
source                  1..4
                        mol_type = protein
                        organism = synthetic construct
SEQUENCE: 103
EGKK                                                                     4

SEQ ID NO: 104          moltype = AA  length = 4
FEATURE                 Location/Qualifiers
REGION                  1..4
                        note = Description of Artificial Sequence: Synthetic peptide
REGION                  1..4
                        note = N-terminal and/or C-terminal flanking sequence
SITE                    3
                        note = glutamate participating in the peptide bond via the
                         gamma-carboxylic acid
source                  1..4
                        mol_type = protein
                        organism = synthetic construct
SEQUENCE: 104
EKEK                                                                     4

SEQ ID NO: 105          moltype =   length =
SEQUENCE: 105
000

SEQ ID NO: 106          moltype =   length =
SEQUENCE: 106
000

SEQ ID NO: 107          moltype = AA  length = 6
FEATURE                 Location/Qualifiers
REGION                  1..6
                        note = Description of Artificial Sequence: Synthetic peptide
REGION                  1..6
```

-continued

```
                        note = N-terminal and/or C-terminal flanking sequence
source                  1..6
                        mol_type = protein
                        organism = synthetic construct
SEQUENCE: 107
GESESE                                                              6

SEQ ID NO: 108          moltype = AA  length = 6
FEATURE                 Location/Qualifiers
REGION                  1..6
                        note = Description of Artificial Sequence: Synthetic peptide
REGION                  1..6
                        note = N-terminal and/or C-terminal flanking sequence
source                  1..6
                        mol_type = protein
                        organism = synthetic construct
SEQUENCE: 108
GAESES                                                              6

SEQ ID NO: 109          moltype = AA  length = 6
FEATURE                 Location/Qualifiers
REGION                  1..6
                        note = Description of Artificial Sequence: Synthetic peptide
REGION                  1..6
                        note = N-terminal and/or C-terminal flanking sequence
source                  1..6
                        mol_type = protein
                        organism = synthetic construct
SEQUENCE: 109
EGESES                                                              6

SEQ ID NO: 110          moltype = AA  length = 7
FEATURE                 Location/Qualifiers
REGION                  1..7
                        note = Description of Artificial Sequence: Synthetic peptide
REGION                  1..7
                        note = N-terminal and/or C-terminal flanking sequence
source                  1..7
                        mol_type = protein
                        organism = synthetic construct
SEQUENCE: 110
EGESESK                                                             7

SEQ ID NO: 111          moltype =   length =
SEQUENCE: 111
000

SEQ ID NO: 112          moltype =   length =
SEQUENCE: 112
000

SEQ ID NO: 113          moltype =   length =
SEQUENCE: 113
000

SEQ ID NO: 114          moltype =   length =
SEQUENCE: 114
000

SEQ ID NO: 115          moltype = AA  length = 6
FEATURE                 Location/Qualifiers
REGION                  1..6
                        note = Description of Artificial Sequence: Synthetic peptide
REGION                  1..6
                        note = N-terminal and/or C-terminal flanking sequence
source                  1..6
                        mol_type = protein
                        organism = synthetic construct
SEQUENCE: 115
EGEGGG                                                              6

SEQ ID NO: 116          moltype = AA  length = 7
FEATURE                 Location/Qualifiers
REGION                  1..7
                        note = Description of Artificial Sequence: Synthetic peptide
REGION                  1..7
                        note = N-terminal and/or C-terminal flanking sequence
source                  1..7
                        mol_type = protein
```

-continued

```
                        organism = synthetic construct
SEQUENCE: 116
EGEGGGK                                                            7

SEQ ID NO: 117          moltype = AA  length = 6
FEATURE                 Location/Qualifiers
REGION                  1..6
                        note = Description of Artificial Sequence: Synthetic peptide
REGION                  1..6
                        note = N-terminal and/or C-terminal flanking sequence
SITE                    3
                        note = glutamate participating in the peptide bond via the
                         gamma-carboxylic acid
source                  1..6
                        mol_type = protein
                        organism = synthetic construct
SEQUENCE: 117
EKEGGG                                                             6

SEQ ID NO: 118          moltype = AA  length = 7
FEATURE                 Location/Qualifiers
REGION                  1..7
                        note = Description of Artificial Sequence: Synthetic peptide
REGION                  1..7
                        note = N-terminal and/or C-terminal flanking sequence
SITE                    3
                        note = glutamate participating in the peptide bond via the
                         gamma-carboxylic acid
source                  1..7
                        mol_type = protein
                        organism = synthetic construct
SEQUENCE: 118
EKEGGGK                                                            7

SEQ ID NO: 119          moltype =   length =
SEQUENCE: 119
000

SEQ ID NO: 120          moltype =   length =
SEQUENCE: 120
000

SEQ ID NO: 121          moltype = AA  length = 5
FEATURE                 Location/Qualifiers
REGION                  1..5
                        note = Description of Artificial Sequence: Synthetic peptide
REGION                  1..5
                        note = a sequence linked to the C terminus of the peptide
SITE                    3
                        note = glutamate participating in the peptide bond via the
                         gamma-carboxylic acid
SITE                    5
                        note = Lysine residue covalently linked to a lipophilic
                         group via its side chain
source                  1..5
                        mol_type = protein
                        organism = synthetic construct
SEQUENCE: 121
EKEAK                                                              5

SEQ ID NO: 122          moltype = AA  length = 4
FEATURE                 Location/Qualifiers
REGION                  1..4
                        note = Description of Artificial Sequence: Synthetic peptide
REGION                  1..4
                        note = a sequence linked to the C terminus of the peptide
SITE                    4
                        note = Lysine residue covalently linked to a lipophilic
                         group via its side chain
source                  1..4
                        mol_type = protein
                        organism = synthetic construct
SEQUENCE: 122
EGKK                                                               4

SEQ ID NO: 123          moltype = AA  length = 4
FEATURE                 Location/Qualifiers
REGION                  1..4
                        note = Description of Artificial Sequence: Synthetic peptide
```

-continued

```
REGION                  1..4
                        note = a sequence linked to the C terminus of the peptide
SITE                    3
                        note = glutamate participating in the peptide bond via the
                         gamma-carboxylic acid
SITE                    4
                        note = Lysine residue covalently linked to a lipophilic
                         group via its side chain
source                  1..4
                        mol_type = protein
                        organism = synthetic construct
SEQUENCE: 123
EKEK                                                                             4

SEQ ID NO: 124          moltype =   length =
SEQUENCE: 124
000

SEQ ID NO: 125          moltype = AA  length = 7
FEATURE                 Location/Qualifiers
REGION                  1..7
                        note = Description of Artificial Sequence: Synthetic peptide
REGION                  1..7
                        note = a sequence linked to the C terminus of the peptide
SITE                    7
                        note = Lysine residue covalently linked to a lipophilic
                         group via its side chain
source                  1..7
                        mol_type = protein
                        organism = synthetic construct
SEQUENCE: 125
EGESESK                                                                          7

SEQ ID NO: 126          moltype =   length =
SEQUENCE: 126
000

SEQ ID NO: 127          moltype =   length =
SEQUENCE: 127
000

SEQ ID NO: 128          moltype =   length =
SEQUENCE: 128
000

SEQ ID NO: 129          moltype = AA  length = 7
FEATURE                 Location/Qualifiers
REGION                  1..7
                        note = Description of Artificial Sequence: Synthetic peptide
REGION                  1..7
                        note = a sequence linked to the C terminus of the peptide
SITE                    7
                        note = Lysine residue covalently linked to a lipophilic
                         group via its side chain
source                  1..7
                        mol_type = protein
                        organism = synthetic construct
SEQUENCE: 129
EGEGGGK                                                                          7

SEQ ID NO: 130          moltype = AA  length = 7
FEATURE                 Location/Qualifiers
REGION                  1..7
                        note = Description of Artificial Sequence: Synthetic peptide
REGION                  1..7
                        note = a sequence linked to the C terminus of the peptide
SITE                    3
                        note = glutamate participating in the peptide bond via the
                         gamma-carboxylic acid
SITE                    7
                        note = Lysine residue covalently linked to a lipophilic
                         group via its side chain
source                  1..7
                        mol_type = protein
                        organism = synthetic construct
SEQUENCE: 130
EKEGGGK                                                                          7

SEQ ID NO: 131          moltype =   length =
```

```
SEQUENCE: 131
000

SEQ ID NO: 132          moltype = AA  length = 5
FEATURE                 Location/Qualifiers
REGION                  1..5
                        note = Description of Artificial Sequence: Synthetic peptide
REGION                  1..5
                        note = a sequence linked to the C terminus of the peptide
SITE                    5
                        note = Lysine residue covalently linked to a lipophilic
                         group via its side chain
source                  1..5
                        mol_type = protein
                        organism = synthetic construct
SEQUENCE: 132
GAESK                                                                       5

SEQ ID NO: 133          moltype = AA  length = 4
FEATURE                 Location/Qualifiers
REGION                  1..4
                        note = Description of Artificial Sequence: Synthetic peptide
REGION                  1..4
                        note = a sequence linked to the C terminus of the peptide
SITE                    4
                        note = Lysine residue covalently linked to a lipophilic
                         group via its side chain
source                  1..4
                        mol_type = protein
                        organism = synthetic construct
SEQUENCE: 133
EGAK                                                                        4

SEQ ID NO: 134          moltype = AA  length = 4
FEATURE                 Location/Qualifiers
REGION                  1..4
                        note = Description of Artificial Sequence: Synthetic peptide
REGION                  1..4
                        note = a sequence linked to the C terminus of the peptide
SITE                    4
                        note = Lysine residue covalently linked to a lipophilic
                         group via its side chain
source                  1..4
                        mol_type = protein
                        organism = synthetic construct
SEQUENCE: 134
EGEK                                                                        4

SEQ ID NO: 135          moltype = AA  length = 6
FEATURE                 Location/Qualifiers
REGION                  1..6
                        note = Description of Artificial Sequence: Synthetic peptide
REGION                  1..6
                        note = a sequence linked to the C terminus of the peptide
SITE                    3
                        note = Lysine residue covalently linked to a lipophilic
                         group via its side chain
source                  1..6
                        mol_type = protein
                        organism = synthetic construct
SEQUENCE: 135
EGKEGE                                                                      6

SEQ ID NO: 136          moltype = AA  length = 7
FEATURE                 Location/Qualifiers
REGION                  1..7
                        note = Description of Artificial Sequence: Synthetic peptide
REGION                  1..7
                        note = a sequence linked to the C terminus of the peptide
SITE                    7
                        note = Lysine residue covalently linked to a lipophilic
                         group via its side chain
source                  1..7
                        mol_type = protein
                        organism = synthetic construct
SEQUENCE: 136
GESESEK                                                                     7

SEQ ID NO: 137          moltype =   length =
```

-continued

```
SEQUENCE: 137
000

SEQ ID NO: 138         moltype = AA  length = 27
FEATURE                Location/Qualifiers
REGION                 1..27
                       note = Description of Artificial Sequence: Synthetic peptide
REGION                 1..27
                       note = full length compstatin
DISULFID               2..12
                       note = Intrachain disulfide bond
source                 1..27
                       mol_type = protein
                       organism = synthetic construct
SEQUENCE: 138
ICVVQDWGHH RCTAGHMANL TSHASAI                                    27

SEQ ID NO: 139         moltype = AA  length = 4
FEATURE                Location/Qualifiers
REGION                 1..4
                       note = Description of Artificial Sequence: Synthetic peptide
REGION                 1..4
                       note = spacer
SITE                   1
                       note = glutamate participating in the peptide bond via the
                        gamma-carboxylic acid
SITE                   4
                       note = glutamate participating in the peptide bond via the
                        gamma-carboxylic acid
source                 1..4
                       mol_type = protein
                       organism = synthetic construct
SEQUENCE: 139
EKGE                                                             4

SEQ ID NO: 140         moltype = AA  length = 17
FEATURE                Location/Qualifiers
REGION                 1..17
                       note = Description of Artificial Sequence: Synthetic peptide
REGION                 1..17
                       note = compstatin analogue
DISULFID               6..16
                       note = Intrachain disulfide bond
source                 1..17
                       mol_type = protein
                       organism = synthetic construct
SEQUENCE: 140
ESSAICIWQD WGEHRCT                                               17

SEQ ID NO: 141         moltype = AA  length = 13
FEATURE                Location/Qualifiers
REGION                 1..13
                       note = Description of Artificial Sequence: Synthetic peptide
REGION                 1..13
                       note = compstatin analogue
DISULFID               2..12
                       note = Intrachain disulfide bond
MOD_RES                4
                       note = 1-methyl-tryptophan
source                 1..13
                       mol_type = protein
                       organism = synthetic construct
SEQUENCE: 141
ICIWQDWGEH RCT                                                   13

SEQ ID NO: 142         moltype = AA  length = 17
FEATURE                Location/Qualifiers
REGION                 1..17
                       note = Description of Artificial Sequence: Synthetic peptide
REGION                 1..17
                       note = compstatin analogue
DISULFID               2..12
                       note = Intrachain disulfide bond
source                 1..17
                       mol_type = protein
                       organism = synthetic construct
SEQUENCE: 142
ICIWQKWGAH RCTGAES                                               17
```

-continued

```
SEQ ID NO: 143          moltype = AA  length = 17
FEATURE                 Location/Qualifiers
REGION                  1..17
                        note = Description of Artificial Sequence: Synthetic peptide
REGION                  1..17
                        note = compstatin analogue
DISULFID                6..16
                        note = Intrachain disulfide bond
source                  1..17
                        mol_type = protein
                        organism = synthetic construct
SEQUENCE: 143
ESSAYCIWQD WGEHRCT                                                17

SEQ ID NO: 144          moltype = AA  length = 21
FEATURE                 Location/Qualifiers
REGION                  1..21
                        note = Description of Artificial Sequence: Synthetic peptide
REGION                  1..21
                        note = compstatin analogue
DISULFID                6..16
                        note = Intrachain disulfide bond
source                  1..21
                        mol_type = protein
                        organism = synthetic construct
SEQUENCE: 144
ESSAICIWQD WGEHRCTGAE S                                           21

SEQ ID NO: 145          moltype = AA  length = 17
FEATURE                 Location/Qualifiers
REGION                  1..17
                        note = Description of Artificial Sequence: Synthetic peptide
REGION                  1..17
                        note = compstatin analogue
DISULFID                2..12
                        note = Intrachain disulfide bond
source                  1..17
                        mol_type = protein
                        organism = synthetic construct
SEQUENCE: 145
ICIWQDWGEH RCTGAES                                                17

SEQ ID NO: 146          moltype = AA  length = 16
FEATURE                 Location/Qualifiers
REGION                  1..16
                        note = Description of Artificial Sequence: Synthetic peptide
REGION                  1..16
                        note = compstatin analogue
DISULFID                2..12
                        note = Intrachain disulfide bond
source                  1..16
                        mol_type = protein
                        organism = synthetic construct
SEQUENCE: 146
ICIWQDWGEH RCTEGE                                                 16

SEQ ID NO: 147          moltype = AA  length = 15
FEATURE                 Location/Qualifiers
REGION                  1..15
                        note = Description of Artificial Sequence: Synthetic peptide
REGION                  1..15
                        note = compstatin analogue
DISULFID                2..12
                        note = Intrachain disulfide bond
source                  1..15
                        mol_type = protein
                        organism = synthetic construct
SEQUENCE: 147
ICIWQDWGEH RCTEA                                                  15

SEQ ID NO: 148          moltype = AA  length = 14
FEATURE                 Location/Qualifiers
REGION                  1..14
                        note = Description of Artificial Sequence: Synthetic peptide
REGION                  1..14
                        note = compstatin analogue
DISULFID                2..12
                        note = Intrachain disulfide bond
source                  1..14
```

-continued

```
                        mol_type = protein
                        organism = synthetic construct
SEQUENCE: 148
ICIWQDWGEH RCTE                                                          14

SEQ ID NO: 149          moltype = AA  length = 15
FEATURE                 Location/Qualifiers
REGION                  1..15
                        note = Description of Artificial Sequence: Synthetic peptide
REGION                  1..15
                        note = compstatin analogue
DISULFID                2..12
                        note = Intrachain disulfide bond
source                  1..15
                        mol_type = protein
                        organism = synthetic construct
SEQUENCE: 149
ICIWQDWGEH RCEGE                                                         15

SEQ ID NO: 150          moltype = AA  length = 18
FEATURE                 Location/Qualifiers
REGION                  1..18
                        note = Description of Artificial Sequence: Synthetic peptide
REGION                  1..18
                        note = compstatin analogue
DISULFID                6..16
                        note = Intrachain disulfide bond
MOD_RES                 17
                        note = sarcosine
source                  1..18
                        mol_type = protein
                        organism = synthetic construct
SEQUENCE: 150
EGSAICIWQD WGEHRCXE                                                      18

SEQ ID NO: 151          moltype = AA  length = 17
FEATURE                 Location/Qualifiers
REGION                  1..17
                        note = Description of Artificial Sequence: Synthetic peptide
REGION                  1..17
                        note = compstatin analogue
DISULFID                6..16
                        note = Intrachain disulfide bond
source                  1..17
                        mol_type = protein
                        organism = synthetic construct
SEQUENCE: 151
EGSAICIWQD WGEHRCT                                                       17

SEQ ID NO: 152          moltype = AA  length = 16
FEATURE                 Location/Qualifiers
REGION                  1..16
                        note = Description of Artificial Sequence: Synthetic peptide
REGION                  1..16
                        note = compstatin analogue
DISULFID                5..15
                        note = Intrachain disulfide bond
source                  1..16
                        mol_type = protein
                        organism = synthetic construct
SEQUENCE: 152
EGEICIWQDW GEHRCT                                                        16

SEQ ID NO: 153          moltype = AA  length = 16
FEATURE                 Location/Qualifiers
REGION                  1..16
                        note = Description of Artificial Sequence: Synthetic peptide
REGION                  1..16
                        note = compstatin analogue
DISULFID                5..15
                        note = Intrachain disulfide bond
source                  1..16
                        mol_type = protein
                        organism = synthetic construct
SEQUENCE: 153
ESEICIWQDW GEHRCT                                                        16

SEQ ID NO: 154          moltype = AA  length = 17
FEATURE                 Location/Qualifiers
```

```
REGION                1..17
                      note = Description of Artificial Sequence: Synthetic peptide
REGION                1..17
                      note = compstatin analogue
DISULFID              4..14
                      note = Intrachain disulfide bond
source                1..17
                      mol_type = protein
                      organism = synthetic construct
SEQUENCE: 154
SEICIWQDWG EHRCTEA                                                    17

SEQ ID NO: 155        moltype = AA  length = 15
FEATURE               Location/Qualifiers
REGION                1..15
                      note = Description of Artificial Sequence: Synthetic peptide
REGION                1..15
                      note = compstatin analogue
DISULFID              3..13
                      note = Intrachain disulfide bond
source                1..15
                      mol_type = protein
                      organism = synthetic construct
SEQUENCE: 155
EICIWQDWGE HRCTE                                                      15

SEQ ID NO: 156        moltype = AA  length = 17
FEATURE               Location/Qualifiers
REGION                1..17
                      note = Description of Artificial Sequence: Synthetic peptide
REGION                1..17
                      note = compstatin analogue
DISULFID              3..13
                      note = Intrachain disulfide bond
source                1..17
                      mol_type = protein
                      organism = synthetic construct
SEQUENCE: 156
EICIWQDWGE HRCTEGE                                                    17

SEQ ID NO: 157        moltype = AA  length = 18
FEATURE               Location/Qualifiers
REGION                1..18
                      note = Description of Artificial Sequence: Synthetic peptide
REGION                1..18
                      note = compstatin analogue
DISULFID              5..15
                      note = Intrachain disulfide bond
source                1..18
                      mol_type = protein
                      organism = synthetic construct
SEQUENCE: 157
EGEICIWQDW GEHRCEGE                                                   18

SEQ ID NO: 158        moltype = AA  length = 18
FEATURE               Location/Qualifiers
REGION                1..18
                      note = Description of Artificial Sequence: Synthetic peptide
REGION                1..18
                      note = compstatin analogue
DISULFID              5..15
                      note = Intrachain disulfide bond
source                1..18
                      mol_type = protein
                      organism = synthetic construct
SEQUENCE: 158
ESEICIWQDW GEHRCEGE                                                   18

SEQ ID NO: 159        moltype = AA  length = 19
FEATURE               Location/Qualifiers
REGION                1..19
                      note = Description of Artificial Sequence: Synthetic peptide
REGION                1..19
                      note = compstatin analogue
DISULFID              5..15
                      note = Intrachain disulfide bond
source                1..19
                      mol_type = protein
                      organism = synthetic construct
```

-continued

```
SEQUENCE: 159
KEKICIWQDW GEHRCTEKE                                       19

SEQ ID NO: 160         moltype = AA  length = 19
FEATURE                Location/Qualifiers
REGION                 1..19
                       note = Description of Artificial Sequence: Synthetic peptide
REGION                 1..19
                       note = compstatin analogue
DISULFID               5..15
                       note = Intrachain disulfide bond
source                 1..19
                       mol_type = protein
                       organism = synthetic construct
SEQUENCE: 160
EKGICIWQDW GEHRCTEKP                                       19

SEQ ID NO: 161         moltype = AA  length = 16
FEATURE                Location/Qualifiers
REGION                 1..16
                       note = Description of Artificial Sequence: Synthetic peptide
REGION                 1..16
                       note = compstatin analogue
DISULFID               2..12
                       note = Intrachain disulfide bond
source                 1..16
                       mol_type = protein
                       organism = synthetic construct
SEQUENCE: 161
ICIWQDWGEH RCTEGK                                          16

SEQ ID NO: 162         moltype = AA  length = 17
FEATURE                Location/Qualifiers
REGION                 1..17
                       note = Description of Artificial Sequence: Synthetic peptide
REGION                 1..17
                       note = compstatin analogue
DISULFID               5..15
                       note = Intrachain disulfide bond
MOD_RES                16
                       note = sarcosine
source                 1..17
                       mol_type = protein
                       organism = synthetic construct
SEQUENCE: 162
GSAICIWQDW GEHRCXE                                         17

SEQ ID NO: 163         moltype = AA  length = 16
FEATURE                Location/Qualifiers
REGION                 1..16
                       note = Description of Artificial Sequence: Synthetic peptide
REGION                 1..16
                       note = compstatin analogue
DISULFID               4..14
                       note = Intrachain disulfide bond
MOD_RES                15
                       note = sarcosine
source                 1..16
                       mol_type = protein
                       organism = synthetic construct
SEQUENCE: 163
SAICIWQDWG EHRCXE                                          16

SEQ ID NO: 164         moltype = AA  length = 17
FEATURE                Location/Qualifiers
REGION                 1..17
                       note = Description of Artificial Sequence: Synthetic peptide
REGION                 1..17
                       note = compstatin analogue
DISULFID               4..14
                       note = Intrachain disulfide bond
source                 1..17
                       mol_type = protein
                       organism = synthetic construct
SEQUENCE: 164
SAICIWQDWG EHRCTEG                                         17

SEQ ID NO: 165         moltype = AA  length = 16
FEATURE                Location/Qualifiers
```

```
REGION                1..16
                      note = Description of Artificial Sequence: Synthetic peptide
REGION                1..16
                      note = compstatin analogue
DISULFID              2..12
                      note = Intrachain disulfide bond
source                1..16
                      mol_type = protein
                      organism = synthetic construct
SEQUENCE: 165
FCIWQDWGEH RCTGAE                                             16

SEQ ID NO: 166        moltype = AA  length = 20
FEATURE               Location/Qualifiers
REGION                1..20
                      note = Description of Artificial Sequence: Synthetic peptide
REGION                1..20
                      note = compstatin analogue
DISULFID              6..16
                      note = Intrachain disulfide bond
MOD_RES               17
                      note = sarcosine
source                1..20
                      mol_type = protein
                      organism = synthetic construct
SEQUENCE: 166
EGSAICIWQD WGEHRCXEGE                                         20

SEQ ID NO: 167        moltype = AA  length = 18
FEATURE               Location/Qualifiers
REGION                1..18
                      note = Description of Artificial Sequence: Synthetic peptide
REGION                1..18
                      note = compstatin analogue
DISULFID              6..16
                      note = Intrachain disulfide bond
MOD_RES               17
                      note = sarcosine
source                1..18
                      mol_type = protein
                      organism = synthetic construct
SEQUENCE: 167
EGSAFCIWQD WGEHRCXE                                           18

SEQ ID NO: 168        moltype = AA  length = 17
FEATURE               Location/Qualifiers
REGION                1..17
                      note = Description of Artificial Sequence: Synthetic peptide
REGION                1..17
                      note = compstatin analogue
DISULFID              6..16
                      note = Intrachain disulfide bond
source                1..17
                      mol_type = protein
                      organism = synthetic construct
SEQUENCE: 168
ESSAICIWQD WGAHRCT                                            17

SEQ ID NO: 169        moltype = AA  length = 17
FEATURE               Location/Qualifiers
REGION                1..17
                      note = Description of Artificial Sequence: Synthetic peptide
REGION                1..17
                      note = compstatin analogue
DISULFID              2..12
                      note = Intrachain disulfide bond
source                1..17
                      mol_type = protein
                      organism = synthetic construct
SEQUENCE: 169
ICIWQDWGAH RCTGAES                                            17

SEQ ID NO: 170        moltype = AA  length = 14
FEATURE               Location/Qualifiers
REGION                1..14
                      note = Description of Artificial Sequence: Synthetic peptide
REGION                1..14
                      note = compstatin analogue
SITE                  1
```

-continued

```
                        note = D-Tyrosine
DISULFID                3..13
                        note = Intrachain disulfide bond
MOD_RES                 5
                        note = 1-methyl-tryptophan
MOD_RES                 9
                        note = sarcosine
MOD_RES                 14
                        note = N-methyl-isoleucine
source                  1..14
                        mol_type = protein
                        organism = synthetic construct
SEQUENCE: 170
YICIWQDWXA HRCI                                                       14

SEQ ID NO: 171          moltype = AA  length = 18
FEATURE                 Location/Qualifiers
REGION                  1..18
                        note = Description of Artificial Sequence: Synthetic peptide
REGION                  1..18
                        note = compstatin analogue
DISULFID                6..16
                        note = Intrachain disulfide bond
MOD_RES                 8
                        note = 1-methyl-tryptophan
MOD_RES                 17
                        note = sarcosine
source                  1..18
                        mol_type = protein
                        organism = synthetic construct
SEQUENCE: 171
EGSAICIWQD WGEHRCXE                                                   18

SEQ ID NO: 172          moltype = AA  length = 18
FEATURE                 Location/Qualifiers
REGION                  1..18
                        note = Description of Artificial Sequence: Synthetic peptide
REGION                  1..18
                        note = compstatin analogue
DISULFID                6..16
                        note = Intrachain disulfide bond
MOD_RES                 8
                        note = 2-naphathalin
MOD_RES                 17
                        note = sarcosine
source                  1..18
                        mol_type = protein
                        organism = synthetic construct
SEQUENCE: 172
EGSAICIXQD WGEHRCXE                                                   18

SEQ ID NO: 173          moltype = AA  length = 17
FEATURE                 Location/Qualifiers
REGION                  1..17
                        note = Description of Artificial Sequence: Synthetic peptide
REGION                  1..17
                        note = compstatin analogue
DISULFID                2..12
                        note = Intrachain disulfide bond
MOD_RES                 4
                        note = 1-methyl-tryptophan
source                  1..17
                        mol_type = protein
                        organism = synthetic construct
SEQUENCE: 173
ICIWQDWGEH RCTGAES                                                    17

SEQ ID NO: 174          moltype = AA  length = 17
FEATURE                 Location/Qualifiers
REGION                  1..17
                        note = Description of Artificial Sequence: Synthetic peptide
REGION                  1..17
                        note = compstatin analogue
DISULFID                2..12
                        note = Intrachain disulfide bond
MOD_RES                 4
                        note = 2-naphathalin
source                  1..17
                        mol_type = protein
```

```
                        organism = synthetic construct
SEQUENCE: 174
ICIXQDWGEH RCTGAES                                                17

SEQ ID NO: 175          moltype = AA  length = 18
FEATURE                 Location/Qualifiers
REGION                  1..18
                        note = Description of Artificial Sequence: Synthetic peptide
REGION                  1..18
                        note = compstatin analogue
DISULFID                6..16
                        note = Intrachain disulfide bond
MOD_RES                 8
                        note = 1-methyl-tryptophan
MOD_RES                 17
                        note = sarcosine
source                  1..18
                        mol_type = protein
                        organism = synthetic construct
SEQUENCE: 175
EGSAFCIWQD WGEHRCXE                                               18

SEQ ID NO: 176          moltype = AA  length = 18
FEATURE                 Location/Qualifiers
REGION                  1..18
                        note = Description of Artificial Sequence: Synthetic peptide
REGION                  1..18
                        note = compstatin analogue
DISULFID                6..16
                        note = Intrachain disulfide bond
MOD_RES                 8
                        note = 1-methyl-tryptophan
MOD_RES                 17
                        note = sarcosine
source                  1..18
                        mol_type = protein
                        organism = synthetic construct
SEQUENCE: 176
EGSAYCIWQD WGEHRCXE                                               18

SEQ ID NO: 177          moltype = AA  length = 18
FEATURE                 Location/Qualifiers
REGION                  1..18
                        note = Description of Artificial Sequence: Synthetic peptide
REGION                  1..18
                        note = compstatin analogue
DISULFID                6..16
                        note = Intrachain disulfide bond
source                  1..18
                        mol_type = protein
                        organism = synthetic construct
SEQUENCE: 177
EGSAICIWQD WGEHRCTE                                               18

SEQ ID NO: 178          moltype = AA  length = 18
FEATURE                 Location/Qualifiers
REGION                  1..18
                        note = Description of Artificial Sequence: Synthetic peptide
REGION                  1..18
                        note = compstatin analogue
DISULFID                6..16
                        note = Intrachain disulfide bond
MOD_RES                 8
                        note = 1-naphathalin
source                  1..18
                        mol_type = protein
                        organism = synthetic construct
SEQUENCE: 178
EGSAFCIXQD WGEHRCTE                                               18

SEQ ID NO: 179          moltype = AA  length = 18
FEATURE                 Location/Qualifiers
REGION                  1..18
                        note = Description of Artificial Sequence: Synthetic peptide
REGION                  1..18
                        note = compstatin analogue
DISULFID                6..16
                        note = Intrachain disulfide bond
MOD_RES                 8
```

-continued

```
                      note = 1-methyl-tryptophan
source                1..18
                      mol_type = protein
                      organism = synthetic construct
SEQUENCE: 179
EGSAFCIWQD WGEHRCTE                                            18

SEQ ID NO: 180        moltype = AA  length = 19
FEATURE               Location/Qualifiers
REGION                1..19
                      note = Description of Artificial Sequence: Synthetic peptide
REGION                1..19
                      note = compstatin analogue
DISULFID              6..16
                      note = Intrachain disulfide bond
MOD_RES               8
                      note = 1-methyl-tryptophan
source                1..19
                      mol_type = protein
                      organism = synthetic construct
SEQUENCE: 180
EGSAFCIWQD WGEHRCEGE                                           19

SEQ ID NO: 181        moltype = AA  length = 18
FEATURE               Location/Qualifiers
REGION                1..18
                      note = Description of Artificial Sequence: Synthetic peptide
REGION                1..18
                      note = compstatin analogue
DISULFID              6..16
                      note = Intrachain disulfide bond
MOD_RES               8
                      note = 1-methyl-tryptophan
source                1..18
                      mol_type = protein
                      organism = synthetic construct
SEQUENCE: 181
EGSAYCIWQD WGEHRCTE                                            18

SEQ ID NO: 182        moltype = AA  length = 18
FEATURE               Location/Qualifiers
REGION                1..18
                      note = Description of Artificial Sequence: Synthetic peptide
REGION                1..18
                      note = compstatin analogue
DISULFID              6..16
                      note = Intrachain disulfide bond
MOD_RES               8
                      note = 2-naphathalin
source                1..18
                      mol_type = protein
                      organism = synthetic construct
SEQUENCE: 182
EGSAFCIXQD WGEHRCTE                                            18

SEQ ID NO: 183        moltype = AA  length = 17
FEATURE               Location/Qualifiers
REGION                1..17
                      note = Description of Artificial Sequence: Synthetic peptide
REGION                1..17
                      note = compstatin analogue
DISULFID              2..12
                      note = Intrachain disulfide bond
MOD_RES               4
                      note = 1-methyl-tryptophan
source                1..17
                      mol_type = protein
                      organism = synthetic construct
SEQUENCE: 183
FCIWQDWGEH RCTGAES                                             17

SEQ ID NO: 184        moltype = AA  length = 17
FEATURE               Location/Qualifiers
REGION                1..17
                      note = Description of Artificial Sequence: Synthetic peptide
REGION                1..17
                      note = compstatin analogue
DISULFID              2..12
                      note = Intrachain disulfide bond
```

-continued

```
MOD_RES                4
                       note = 1-methyl-tryptophan
source                 1..17
                       mol_type = protein
                       organism = synthetic construct
SEQUENCE: 184
YCIWQDWGEH RCTGAES                                            17

SEQ ID NO: 185         moltype = AA  length = 17
FEATURE                Location/Qualifiers
REGION                 1..17
                       note = Description of Artificial Sequence: Synthetic peptide
REGION                 1..17
                       note = compstatin analogue
DISULFID               2..12
                       note = Intrachain disulfide bond
MOD_RES                4
                       note = 1-naphathalin
source                 1..17
                       mol_type = protein
                       organism = synthetic construct
SEQUENCE: 185
FCIXQDWGEH RCTGAES                                            17

SEQ ID NO: 186         moltype = AA  length = 17
FEATURE                Location/Qualifiers
REGION                 1..17
                       note = Description of Artificial Sequence: Synthetic peptide
REGION                 1..17
                       note = compstatin analogue
DISULFID               2..12
                       note = Intrachain disulfide bond
MOD_RES                4
                       note = 2-naphathalin
source                 1..17
                       mol_type = protein
                       organism = synthetic construct
SEQUENCE: 186
FCIXQDWGEH RCTGAES                                            17

SEQ ID NO: 187         moltype = AA  length = 17
FEATURE                Location/Qualifiers
REGION                 1..17
                       note = Description of Artificial Sequence: Synthetic peptide
REGION                 1..17
                       note = compstatin analogue
DISULFID               2..12
                       note = Intrachain disulfide bond
MOD_RES                4
                       note = 2-naphathalin
source                 1..17
                       mol_type = protein
                       organism = synthetic construct
SEQUENCE: 187
YCIXQDWGEH RCTGAES                                            17

SEQ ID NO: 188         moltype = AA  length = 17
FEATURE                Location/Qualifiers
REGION                 1..17
                       note = Description of Artificial Sequence: Synthetic peptide
REGION                 1..17
                       note = compstatin analogue
DISULFID               2..12
                       note = Intrachain disulfide bond
source                 1..17
                       mol_type = protein
                       organism = synthetic construct
SEQUENCE: 188
YCIWQDWGEH RCTGAES                                            17

SEQ ID NO: 189         moltype = AA  length = 19
FEATURE                Location/Qualifiers
REGION                 1..19
                       note = Description of Artificial Sequence: Synthetic peptide
REGION                 1..19
                       note = compstatin analogue
DISULFID               4..14
                       note = Intrachain disulfide bond
MOD_RES                6
```

-continued

```
                          note = 1-methyl-tryptophan
source                    1..19
                          mol_type = protein
                          organism = synthetic construct
SEQUENCE: 189
SEFCIWQDWG EHRCTGAES                                                   19

SEQ ID NO: 190            moltype = AA  length = 17
FEATURE                   Location/Qualifiers
REGION                    1..17
                          note = Description of Artificial Sequence: Synthetic peptide
REGION                    1..17
                          note = compstatin analogue
DISULFID                  2..12
                          note = Intrachain disulfide bond
MOD_RES                   4
                          note = 1-methyl-tryptophan
source                    1..17
                          mol_type = protein
                          organism = synthetic construct
SEQUENCE: 190
YCIWQDWGEH RCTEAGS                                                     17

SEQ ID NO: 191            moltype = AA  length = 17
FEATURE                   Location/Qualifiers
REGION                    1..17
                          note = Description of Artificial Sequence: Synthetic peptide
REGION                    1..17
                          note = compstatin analogue
DISULFID                  2..12
                          note = Intrachain disulfide bond
MOD_RES                   4
                          note = 1-methyl-tryptophan
source                    1..17
                          mol_type = protein
                          organism = synthetic construct
SEQUENCE: 191
YCIWQDWGEH RCTESGA                                                     17

SEQ ID NO: 192            moltype = AA  length = 18
FEATURE                   Location/Qualifiers
REGION                    1..18
                          note = Description of Artificial Sequence: Synthetic peptide
REGION                    1..18
                          note = compstatin analogue
DISULFID                  6..16
                          note = Intrachain disulfide bond
MOD_RES                   8
                          note = 1-methyl-tryptophan
MOD_RES                   17
                          note = sarcosine
source                    1..18
                          mol_type = protein
                          organism = synthetic construct
SEQUENCE: 192
EGSAYCIWQE WGEHRCXE                                                    18

SEQ ID NO: 193            moltype = AA  length = 17
FEATURE                   Location/Qualifiers
REGION                    1..17
                          note = Description of Artificial Sequence: Synthetic peptide
REGION                    1..17
                          note = compstatin analogue
DISULFID                  4..14
                          note = Intrachain disulfide bond
MOD_RES                   6
                          note = 1-methyl-tryptophan
MOD_RES                   15
                          note = sarcosine
source                    1..17
                          mol_type = protein
                          organism = synthetic construct
SEQUENCE: 193
SEYCIWQDWG EHRCXEA                                                     17

SEQ ID NO: 194            moltype = AA  length = 17
FEATURE                   Location/Qualifiers
REGION                    1..17
                          note = Description of Artificial Sequence: Synthetic peptide
```

-continued

```
REGION                  1..17
                        note = compstatin analogue
DISULFID                2..12
                        note = Intrachain disulfide bond
MOD_RES                 4
                        note = 1-methyl-tryptophan
MOD_RES                 8
                        note = sarcosine
source                  1..17
                        mol_type = protein
                        organism = synthetic construct
SEQUENCE: 194
FCIWQDWXEH RCTGAES                                                   17

SEQ ID NO: 195          moltype = AA  length = 18
FEATURE                 Location/Qualifiers
REGION                  1..18
                        note = Description of Artificial Sequence: Synthetic peptide
REGION                  1..18
                        note = compstatin analogue
SITE                    1
                        note = D-Tyrosine
DISULFID                3..13
                        note = Intrachain disulfide bond
MOD_RES                 5
                        note = 1-methyl-tryptophan
MOD_RES                 9
                        note = sarcosine
source                  1..18
                        mol_type = protein
                        organism = synthetic construct
SEQUENCE: 195
YFCIWQDWXE HRCTGAES                                                  18

SEQ ID NO: 196          moltype = AA  length = 19
FEATURE                 Location/Qualifiers
REGION                  1..19
                        note = Description of Artificial Sequence: Synthetic peptide
REGION                  1..19
                        note = compstatin analogue
DISULFID                4..14
                        note = Intrachain disulfide bond
MOD_RES                 6
                        note = 1-methyl-tryptophan
MOD_RES                 15
                        note = sarcosine
source                  1..19
                        mol_type = protein
                        organism = synthetic construct
SEQUENCE: 196
SEFCIWQDWG EHRCXGAES                                                 19

SEQ ID NO: 197          moltype = AA  length = 17
FEATURE                 Location/Qualifiers
REGION                  1..17
                        note = Description of Artificial Sequence: Synthetic peptide
REGION                  1..17
                        note = compstatin analogue
DISULFID                4..14
                        note = Intrachain disulfide bond
MOD_RES                 6
                        note = 1-methyl-tryptophan
MOD_RES                 15
                        note = sarcosine
source                  1..17
                        mol_type = protein
                        organism = synthetic construct
SEQUENCE: 197
SEFCIWQDWG EHRCXEA                                                   17

SEQ ID NO: 198          moltype = AA  length = 17
FEATURE                 Location/Qualifiers
REGION                  1..17
                        note = Description of Artificial Sequence: Synthetic peptide
REGION                  1..17
                        note = compstatin analogue
DISULFID                4..14
                        note = Intrachain disulfide bond
MOD_RES                 6
```

-continued

```
                        note = 1-methyl-tryptophan
MOD_RES                 10
                        note = sarcosine
MOD_RES                 15
                        note = sarcosine
source                  1..17
                        mol_type = protein
                        organism = synthetic construct
SEQUENCE: 198
SEFCIWQDWX EHRCXEA                                                17

SEQ ID NO: 199          moltype = AA  length = 17
FEATURE                 Location/Qualifiers
REGION                  1..17
                        note = Description of Artificial Sequence: Synthetic peptide
REGION                  1..17
                        note = compstatin analogue
DISULFID                4..14
                        note = Intrachain disulfide bond
MOD_RES                 6
                        note = 1-methyl-tryptophan
MOD_RES                 10
                        note = sarcosine
source                  1..17
                        mol_type = protein
                        organism = synthetic construct
SEQUENCE: 199
SEFCIWQDWX EHRCTEA                                                17

SEQ ID NO: 200          moltype = AA  length = 16
FEATURE                 Location/Qualifiers
REGION                  1..16
                        note = Description of Artificial Sequence: Synthetic peptide
REGION                  1..16
                        note = compstatin analogue
DISULFID                4..14
                        note = Intrachain disulfide bond
MOD_RES                 6
                        note = 1-methyl-tryptophan
MOD_RES                 15
                        note = sarcosine
source                  1..16
                        mol_type = protein
                        organism = synthetic construct
SEQUENCE: 200
SEFCIWQDWG EHRCXE                                                 16

SEQ ID NO: 201          moltype = AA  length = 16
FEATURE                 Location/Qualifiers
REGION                  1..16
                        note = Description of Artificial Sequence: Synthetic peptide
REGION                  1..16
                        note = compstatin analogue
DISULFID                4..14
                        note = Intrachain disulfide bond
MOD_RES                 6
                        note = 1-methyl-tryptophan
MOD_RES                 10
                        note = sarcosine
MOD_RES                 15
                        note = sarcosine
source                  1..16
                        mol_type = protein
                        organism = synthetic construct
SEQUENCE: 201
SEFCIWQDWX EHRCXE                                                 16

SEQ ID NO: 202          moltype = AA  length = 16
FEATURE                 Location/Qualifiers
REGION                  1..16
                        note = Description of Artificial Sequence: Synthetic peptide
REGION                  1..16
                        note = compstatin analogue
DISULFID                3..13
                        note = Intrachain disulfide bond
MOD_RES                 5
                        note = 1-methyl-tryptophan
MOD_RES                 14
                        note = sarcosine
```

-continued

```
source                  1..16
                        mol_type = protein
                        organism = synthetic construct
SEQUENCE: 202
EFCIWQDWGE HRCXEA                                                   16

SEQ ID NO: 203          moltype = AA  length = 17
FEATURE                 Location/Qualifiers
REGION                  1..17
                        note = Description of Artificial Sequence: Synthetic peptide
REGION                  1..17
                        note = compstatin analogue
MOD_RES                 3
                        note = sarcosine
DISULFID                4..14
                        note = Intrachain disulfide bond
MOD_RES                 6
                        note = 1-methyl-tryptophan
MOD_RES                 15
                        note = sarcosine
source                  1..17
                        mol_type = protein
                        organism = synthetic construct
SEQUENCE: 203
SEXCIWQDWG EHRCXEA                                                  17

SEQ ID NO: 204          moltype = AA  length = 17
FEATURE                 Location/Qualifiers
REGION                  1..17
                        note = Description of Artificial Sequence: Synthetic peptide
REGION                  1..17
                        note = compstatin analogue
MOD_RES                 3
                        note = sarcosine
DISULFID                4..14
                        note = Intrachain disulfide bond
MOD_RES                 6
                        note = 1-methyl-tryptophan
source                  1..17
                        mol_type = protein
                        organism = synthetic construct
SEQUENCE: 204
SEXCIWQDWG EHRCTEA                                                  17

SEQ ID NO: 205          moltype = AA  length = 17
FEATURE                 Location/Qualifiers
REGION                  1..17
                        note = Description of Artificial Sequence: Synthetic peptide
REGION                  1..17
                        note = compstatin analogue
DISULFID                4..14
                        note = Intrachain disulfide bond
MOD_RES                 6
                        note = 1-methyl-tryptophan
MOD_RES                 15
                        note = sarcosine
source                  1..17
                        mol_type = protein
                        organism = synthetic construct
SEQUENCE: 205
SEFCIWQEWG EHRCXEA                                                  17

SEQ ID NO: 206          moltype = AA  length = 17
FEATURE                 Location/Qualifiers
REGION                  1..17
                        note = Description of Artificial Sequence: Synthetic peptide
REGION                  1..17
                        note = compstatin analogue
DISULFID                4..14
                        note = Intrachain disulfide bond
MOD_RES                 6
                        note = 1-methyl-tryptophan
source                  1..17
                        mol_type = protein
                        organism = synthetic construct
SEQUENCE: 206
SEFCIWQDWG EHRCSEA                                                  17

SEQ ID NO: 207          moltype = AA  length = 15
```

-continued

```
FEATURE                 Location/Qualifiers
REGION                  1..15
                        note = Description of Artificial Sequence: Synthetic peptide
REGION                  1..15
                        note = compstatin analogue
DISULFID                3..13
                        note = Intrachain disulfide bond
MOD_RES                 5
                        note = 1-methyl-tryptophan
source                  1..15
                        mol_type = protein
                        organism = synthetic construct
SEQUENCE: 207
EFCIWQDWGE HRCES                                                  15

SEQ ID NO: 208          moltype = AA  length = 17
FEATURE                 Location/Qualifiers
REGION                  1..17
                        note = Description of Artificial Sequence: Synthetic peptide
REGION                  1..17
                        note = compstatin analogue
DISULFID                4..14
                        note = Intrachain disulfide bond
MOD_RES                 6
                        note = 1-methyl-tryptophan
MOD_RES                 15
                        note = sarcosine
source                  1..17
                        mol_type = protein
                        organism = synthetic construct
SEQUENCE: 208
SEFCIWQDWG EHKCXEA                                                17

SEQ ID NO: 209          moltype = AA  length = 17
FEATURE                 Location/Qualifiers
REGION                  1..17
                        note = Description of Artificial Sequence: Synthetic peptide
REGION                  1..17
                        note = compstatin analogue
DISULFID                4..14
                        note = Intrachain disulfide bond
MOD_RES                 6
                        note = 1-methyl-tryptophan
MOD_RES                 15
                        note = sarcosine
source                  1..17
                        mol_type = protein
                        organism = synthetic construct
SEQUENCE: 209
GEFCIWQDWG EHRCXEA                                                17

SEQ ID NO: 210          moltype = AA  length = 17
FEATURE                 Location/Qualifiers
REGION                  1..17
                        note = Description of Artificial Sequence: Synthetic peptide
REGION                  1..17
                        note = compstatin analogue
MOD_RES                 3
                        note = sarcosine
DISULFID                4..14
                        note = Intrachain disulfide bond
MOD_RES                 6
                        note = 1-methyl-tryptophan
source                  1..17
                        mol_type = protein
                        organism = synthetic construct
SEQUENCE: 210
GEXCIWQDWG EHRCTEA                                                17

SEQ ID NO: 211          moltype = AA  length = 17
FEATURE                 Location/Qualifiers
REGION                  1..17
                        note = Description of Artificial Sequence: Synthetic peptide
REGION                  1..17
                        note = compstatin analogue
MOD_RES                 3
                        note = sarcosine
DISULFID                4..14
                        note = Intrachain disulfide bond
```

-continued

```
MOD_RES                 6
                        note = 1-methyl-tryptophan
MOD_RES                 10
                        note = sarcosine
source                  1..17
                        mol_type = protein
                        organism = synthetic construct
SEQUENCE: 211
SEXCIWQEWX EHRCTEA                                                        17

SEQ ID NO: 212          moltype = AA  length = 17
FEATURE                 Location/Qualifiers
REGION                  1..17
                        note = Description of Artificial Sequence: Synthetic peptide
REGION                  1..17
                        note = compstatin analogue
MOD_RES                 3
                        note = sarcosine
DISULFID                4..14
                        note = Intrachain disulfide bond
MOD_RES                 6
                        note = 1-methyl-tryptophan
MOD_RES                 15
                        note = sarcosine
source                  1..17
                        mol_type = protein
                        organism = synthetic construct
SEQUENCE: 212
SEXCIWQEWG EHRCXEA                                                        17

SEQ ID NO: 213          moltype = AA  length = 16
FEATURE                 Location/Qualifiers
REGION                  1..16
                        note = Description of Artificial Sequence: Synthetic peptide
REGION                  1..16
                        note = compstatin analogue
SITE                    1
                        note = D-Tyrosine
MOD_RES                 2
                        note = sarcosine
DISULFID                3..13
                        note = Intrachain disulfide bond
MOD_RES                 5
                        note = 1-methyl-tryptophan
source                  1..16
                        mol_type = protein
                        organism = synthetic construct
SEQUENCE: 213
YXCIWQDWGE HRCTEA                                                         16

SEQ ID NO: 214          moltype = AA  length = 20
FEATURE                 Location/Qualifiers
REGION                  1..20
                        note = Description of Artificial Sequence: Synthetic peptide
REGION                  1..20
                        note = compstatin analogue
SITE                    1
                        note = Lysine residue covalently linked to a lipophilic
                         group via its side chain
DISULFID                6..16
                        note = Intrachain disulfide bond
source                  1..20
                        mol_type = protein
                        organism = synthetic construct
SEQUENCE: 214
KGSAICIWQD WGEHRCTEGE                                                     20

SEQ ID NO: 215          moltype = AA  length = 21
FEATURE                 Location/Qualifiers
REGION                  1..21
                        note = Description of Artificial Sequence: Synthetic peptide
REGION                  1..21
                        note = compstatin analogue
DISULFID                6..16
                        note = Intrachain disulfide bond
MOD_RES                 8
                        note = 1-methyl-tryptophan
MOD_RES                 17
                        note = sarcosine
```

-continued

```
SITE                    21
                        note = Lysine residue covalently linked to a lipophilic
                         group via its side chain
source                  1..21
                        mol_type = protein
                        organism = synthetic construct
SEQUENCE: 215
ASGEYCIWQD WGEHRCXEGE K                                             21

SEQ ID NO: 216          moltype = AA  length = 17
FEATURE                 Location/Qualifiers
REGION                  1..17
                        note = Description of Artificial Sequence: Synthetic peptide
REGION                  1..17
                        note = compstatin analogue
DISULFID                3..13
                        note = Intrachain disulfide bond
MOD_RES                 5
                        note = 1-methyl-tryptophan
SITE                    17
                        note = Lysine residue covalently linked to a lipophilic
                         group via its side chain
source                  1..17
                        mol_type = protein
                        organism = synthetic construct
SEQUENCE: 216
EFCIWQDWGE HRCEGEK                                                  17

SEQ ID NO: 217          moltype = AA  length = 20
FEATURE                 Location/Qualifiers
REGION                  1..20
                        note = Description of Artificial Sequence: Synthetic peptide
REGION                  1..20
                        note = compstatin analogue
DISULFID                6..16
                        note = Intrachain disulfide bond
SITE                    20
                        note = Lysine residue covalently linked to a lipophilic
                         group via its side chain
source                  1..20
                        mol_type = protein
                        organism = synthetic construct
SEQUENCE: 217
EGSAICIWQD WGEHRCTEGK                                               20

SEQ ID NO: 218          moltype = AA  length = 18
FEATURE                 Location/Qualifiers
REGION                  1..18
                        note = Description of Artificial Sequence: Synthetic peptide
REGION                  1..18
                        note = compstatin analogue
DISULFID                6..16
                        note = Intrachain disulfide bond
MOD_RES                 8
                        note = 1-methyl-tryptophan
SITE                    15
                        note = Lysine residue covalently linked to a lipophilic
                         group via its side chain
MOD_RES                 17
                        note = sarcosine
source                  1..18
                        mol_type = protein
                        organism = synthetic construct
SEQUENCE: 218
EGSAYCIWQD WGEHKCXE                                                 18

SEQ ID NO: 219          moltype = AA  length = 20
FEATURE                 Location/Qualifiers
REGION                  1..20
                        note = Description of Artificial Sequence: Synthetic peptide
REGION                  1..20
                        note = compstatin analogue
DISULFID                6..16
                        note = Intrachain disulfide bond
MOD_RES                 8
                        note = 1-methyl-tryptophan
MOD_RES                 17
                        note = sarcosine
SITE                    20
```

```
                       note = Lysine residue covalently linked to a lipophilic
                        group via its side chain
source                 1..20
                       mol_type = protein
                       organism = synthetic construct
SEQUENCE: 219
EGSAYCIWQD WGEHRCXEGK                                              20

SEQ ID NO: 220         moltype = AA  length = 21
FEATURE                Location/Qualifiers
REGION                 1..21
                       note = Description of Artificial Sequence: Synthetic peptide
REGION                 1..21
                       note = compstatin analogue
DISULFID               6..16
                       note = Intrachain disulfide bond
MOD_RES                8
                       note = 1-methyl-tryptophan
MOD_RES                17
                       note = sarcosine
SITE                   21
                       note = Lysine residue covalently linked to a lipophilic
                        group via its side chain
source                 1..21
                       mol_type = protein
                       organism = synthetic construct
SEQUENCE: 220
EGSAYCIWQD WGEHRCXEGE K                                            21

SEQ ID NO: 221         moltype = AA  length = 21
FEATURE                Location/Qualifiers
REGION                 1..21
                       note = Description of Artificial Sequence: Synthetic peptide
REGION                 1..21
                       note = compstatin analogue
DISULFID               6..16
                       note = Intrachain disulfide bond
MOD_RES                8
                       note = 1-methyl-tryptophan
MOD_RES                17
                       note = sarcosine
SITE                   21
                       note = Lysine residue covalently linked to a lipophilic
                        group via its side chain
source                 1..21
                       mol_type = protein
                       organism = synthetic construct
SEQUENCE: 221
EGSAYCIWQD WGEHRCXEGK K                                            21

SEQ ID NO: 222         moltype = AA  length = 21
FEATURE                Location/Qualifiers
REGION                 1..21
                       note = Description of Artificial Sequence: Synthetic peptide
REGION                 1..21
                       note = compstatin analogue
DISULFID               6..16
                       note = Intrachain disulfide bond
MOD_RES                8
                       note = 1-methyl-tryptophan
MOD_RES                17
                       note = sarcosine
SITE                   20
                       note = glutamate participating in the peptide bond via the
                        gamma-carboxylic acid
SITE                   21
                       note = Lysine residue covalently linked to a lipophilic
                        group via its side chain
source                 1..21
                       mol_type = protein
                       organism = synthetic construct
SEQUENCE: 222
EGSAYCIWQD WGEHRCXEKE K                                            21

SEQ ID NO: 223         moltype = AA  length = 18
FEATURE                Location/Qualifiers
REGION                 1..18
                       note = Description of Artificial Sequence: Synthetic peptide
REGION                 1..18
```

```
                        note = compstatin analogue
DISULFID                2..12
                        note = Intrachain disulfide bond
MOD_RES                 4
                        note = 1-methyl-tryptophan
SITE                    18
                        note = Lysine residue covalently linked to a lipophilic
                         group via its side chain
source                  1..18
                        mol_type = protein
                        organism = synthetic construct
SEQUENCE: 223
FCIWQDWGEH RCTGAESK                                                 18

SEQ ID NO: 224          moltype = AA  length = 16
FEATURE                 Location/Qualifiers
REGION                  1..16
                        note = Description of Artificial Sequence: Synthetic peptide
REGION                  1..16
                        note = compstatin analogue
DISULFID                2..12
                        note = Intrachain disulfide bond
SITE                    16
                        note = Lysine residue covalently linked to a lipophilic
                         group via its side chain
source                  1..16
                        mol_type = protein
                        organism = synthetic construct
SEQUENCE: 224
ICIWQDWGEH RCTEGK                                                   16

SEQ ID NO: 225          moltype = AA  length = 17
FEATURE                 Location/Qualifiers
REGION                  1..17
                        note = Description of Artificial Sequence: Synthetic peptide
REGION                  1..17
                        note = compstatin analogue
DISULFID                2..12
                        note = Intrachain disulfide bond
SITE                    17
                        note = Lysine residue covalently linked to a lipophilic
                         group via its side chain
source                  1..17
                        mol_type = protein
                        organism = synthetic construct
SEQUENCE: 225
ICIWQDWGEH RCTEGEK                                                  17

SEQ ID NO: 226          moltype = AA  length = 17
FEATURE                 Location/Qualifiers
REGION                  1..17
                        note = Description of Artificial Sequence: Synthetic peptide
REGION                  1..17
                        note = compstatin analogue
DISULFID                4..14
                        note = Intrachain disulfide bond
MOD_RES                 6
                        note = 1-methyl-tryptophan
MOD_RES                 15
                        note = sarcosine
SITE                    17
                        note = Lysine residue covalently linked to a lipophilic
                         group via its side chain
source                  1..17
                        mol_type = protein
                        organism = synthetic construct
SEQUENCE: 226
SAYCIWQDWG EHRCXEK                                                  17

SEQ ID NO: 227          moltype = AA  length = 19
FEATURE                 Location/Qualifiers
REGION                  1..19
                        note = Description of Artificial Sequence: Synthetic peptide
REGION                  1..19
                        note = compstatin analogue
DISULFID                4..14
                        note = Intrachain disulfide bond
MOD_RES                 6
                        note = 1-methyl-tryptophan
```

-continued

```
MOD_RES                 15
                        note = sarcosine
SITE                    19
                        note = Lysine residue covalently linked to a lipophilic
                         group via its side chain
source                  1..19
                        mol_type = protein
                        organism = synthetic construct
SEQUENCE: 227
SEFCIWQDWG EHRCXEGAK                                                19

SEQ ID NO: 228          moltype = AA  length = 18
FEATURE                 Location/Qualifiers
REGION                  1..18
                        note = Description of Artificial Sequence: Synthetic peptide
REGION                  1..18
                        note = compstatin analogue
DISULFID                4..14
                        note = Intrachain disulfide bond
MOD_RES                 6
                        note = 1-methyl-tryptophan
MOD_RES                 15
                        note = sarcosine
source                  1..18
                        mol_type = protein
                        organism = synthetic construct
SEQUENCE: 228
SEFCIWQDWG EHRCXEGE                                                 18

SEQ ID NO: 229          moltype = AA  length = 22
FEATURE                 Location/Qualifiers
REGION                  1..22
                        note = Description of Artificial Sequence: Synthetic peptide
REGION                  1..22
                        note = compstatin analogue
DISULFID                4..14
                        note = Intrachain disulfide bond
MOD_RES                 6
                        note = 1-methyl-tryptophan
MOD_RES                 15
                        note = sarcosine
SITE                    22
                        note = Lysine residue covalently linked to a lipophilic
                         group via its side chain
source                  1..22
                        mol_type = protein
                        organism = synthetic construct
SEQUENCE: 229
SEFCIWQDWG EHRCXEGEGG GK                                            22

SEQ ID NO: 230          moltype = AA  length = 18
FEATURE                 Location/Qualifiers
REGION                  1..18
                        note = Description of Artificial Sequence: Synthetic peptide
REGION                  1..18
                        note = compstatin analogue
DISULFID                4..14
                        note = Intrachain disulfide bond
MOD_RES                 6
                        note = 1-methyl-tryptophan
MOD_RES                 15
                        note = sarcosine
source                  1..18
                        mol_type = protein
                        organism = synthetic construct
SEQUENCE: 230
SEFCIWQDWG EHRCXEGE                                                 18

SEQ ID NO: 231          moltype = AA  length = 18
FEATURE                 Location/Qualifiers
REGION                  1..18
                        note = Description of Artificial Sequence: Synthetic peptide
REGION                  1..18
                        note = compstatin analogue
DISULFID                4..14
                        note = Intrachain disulfide bond
MOD_RES                 6
                        note = 1-methyl-tryptophan
MOD_RES                 15
```

```
                          note = sarcosine
source                    1..18
                          mol_type = protein
                          organism = synthetic construct
SEQUENCE: 231
SEFCIWQDWG EHRCXEGE                                                18

SEQ ID NO: 232            moltype = AA  length = 18
FEATURE                   Location/Qualifiers
REGION                    1..18
                          note = Description of Artificial Sequence: Synthetic peptide
REGION                    1..18
                          note = compstatin analogue
DISULFID                  4..14
                          note = Intrachain disulfide bond
MOD_RES                   6
                          note = 1-methyl-tryptophan
MOD_RES                   15
                          note = sarcosine
source                    1..18
                          mol_type = protein
                          organism = synthetic construct
SEQUENCE: 232
SEFCIWQDWG EHRCXEGE                                                18

SEQ ID NO: 233            moltype = AA  length = 22
FEATURE                   Location/Qualifiers
REGION                    1..22
                          note = Description of Artificial Sequence: Synthetic peptide
REGION                    1..22
                          note = compstatin analogue
DISULFID                  4..14
                          note = Intrachain disulfide bond
MOD_RES                   6
                          note = 1-methyl-tryptophan
MOD_RES                   15
                          note = sarcosine
SITE                      22
                          note = Lysine residue covalently linked to a lipophilic
                           group via its side chain
source                    1..22
                          mol_type = protein
                          organism = synthetic construct
SEQUENCE: 233
SEFCIWQDWG EHRCXEGESE SK                                           22

SEQ ID NO: 234            moltype = AA  length = 22
FEATURE                   Location/Qualifiers
REGION                    1..22
                          note = Description of Artificial Sequence: Synthetic peptide
REGION                    1..22
                          note = compstatin analogue
DISULFID                  4..14
                          note = Intrachain disulfide bond
MOD_RES                   6
                          note = 1-methyl-tryptophan
MOD_RES                   15
                          note = sarcosine
SITE                      18
                          note = glutamate participating in the peptide bond via the
                           gamma-carboxylic acid
SITE                      22
                          note = Lysine residue covalently linked to a lipophilic
                           group via its side chain
source                    1..22
                          mol_type = protein
                          organism = synthetic construct
SEQUENCE: 234
SEFCIWQDWG EHRCXEKEGG GK                                           22

SEQ ID NO: 235            moltype = AA  length = 18
FEATURE                   Location/Qualifiers
REGION                    1..18
                          note = Description of Artificial Sequence: Synthetic peptide
REGION                    1..18
                          note = compstatin analogue
DISULFID                  4..14
                          note = Intrachain disulfide bond
MOD_RES                   6
```

-continued

```
                        note = 1-methyl-tryptophan
source                  1..18
                        mol_type = protein
                        organism = synthetic construct
SEQUENCE: 235
SEFCIWQDWG EHRCTEGE                                             18

SEQ ID NO: 236          moltype = AA  length = 18
FEATURE                 Location/Qualifiers
REGION                  1..18
                        note = Description of Artificial Sequence: Synthetic peptide
REGION                  1..18
                        note = compstatin analogue
DISULFID                4..14
                        note = Intrachain disulfide bond
MOD_RES                 6
                        note = 1-methyl-tryptophan
source                  1..18
                        mol_type = protein
                        organism = synthetic construct
SEQUENCE: 236
SEFCIWQDWG EHRCTEGE                                             18

SEQ ID NO: 237          moltype = AA  length = 22
FEATURE                 Location/Qualifiers
REGION                  1..22
                        note = Description of Artificial Sequence: Synthetic peptide
REGION                  1..22
                        note = compstatin analogue
DISULFID                4..14
                        note = Intrachain disulfide bond
MOD_RES                 6
                        note = 1-methyl-tryptophan
SITE                    22
                        note = Lysine residue covalently linked to a lipophilic
                         group via its side chain
source                  1..22
                        mol_type = protein
                        organism = synthetic construct
SEQUENCE: 237
SEFCIWQDWG EHRCTEGEGG GK                                        22

SEQ ID NO: 238          moltype = AA  length = 18
FEATURE                 Location/Qualifiers
REGION                  1..18
                        note = Description of Artificial Sequence: Synthetic peptide
REGION                  1..18
                        note = compstatin analogue
DISULFID                4..14
                        note = Intrachain disulfide bond
MOD_RES                 6
                        note = 1-methyl-tryptophan
source                  1..18
                        mol_type = protein
                        organism = synthetic construct
SEQUENCE: 238
SEFCIWQDWG EHRCTEGE                                             18

SEQ ID NO: 239          moltype = AA  length = 18
FEATURE                 Location/Qualifiers
REGION                  1..18
                        note = Description of Artificial Sequence: Synthetic peptide
REGION                  1..18
                        note = compstatin analogue
DISULFID                4..14
                        note = Intrachain disulfide bond
MOD_RES                 6
                        note = 1-methyl-tryptophan
source                  1..18
                        mol_type = protein
                        organism = synthetic construct
SEQUENCE: 239
SEFCIWQDWG EHRCTEGE                                             18

SEQ ID NO: 240          moltype = AA  length = 22
FEATURE                 Location/Qualifiers
REGION                  1..22
                        note = Description of Artificial Sequence: Synthetic peptide
REGION                  1..22
```

```
                        note = compstatin analogue
DISULFID                4..14
                        note = Intrachain disulfide bond
MOD_RES                 6
                        note = 1-methyl-tryptophan
SITE                    18
                        note = glutamate participating in the peptide bond via the
                         gamma-carboxylic acid
SITE                    22
                        note = Lysine residue covalently linked to a lipophilic
                         group via its side chain
source                  1..22
                        mol_type = protein
                        organism = synthetic construct
SEQUENCE: 240
SEFCIWQDWG EHRCTEKEGG GK                                              22

SEQ ID NO: 241          moltype = AA  length = 20
FEATURE                 Location/Qualifiers
REGION                  1..20
                        note = Description of Artificial Sequence: Synthetic peptide
REGION                  1..20
                        note = compstatin analogue
DISULFID                4..14
                        note = Intrachain disulfide bond
MOD_RES                 6
                        note = 1-methyl-tryptophan
SITE                    20
                        note = Lysine residue covalently linked to a lipophilic
                         group via its side chain
source                  1..20
                        mol_type = protein
                        organism = synthetic construct
SEQUENCE: 241
SEFCIWQDWG EHRCTGAESK                                                 20

SEQ ID NO: 242          moltype = AA  length = 19
FEATURE                 Location/Qualifiers
REGION                  1..19
                        note = Description of Artificial Sequence: Synthetic peptide
REGION                  1..19
                        note = compstatin analogue
DISULFID                4..14
                        note = Intrachain disulfide bond
MOD_RES                 6
                        note = 1-methyl-tryptophan
MOD_RES                 15
                        note = sarcosine
SITE                    19
                        note = Lysine residue covalently linked to a lipophilic
                         group via its side chain
source                  1..19
                        mol_type = protein
                        organism = synthetic construct
SEQUENCE: 242
SEFCIWQEWG EHRCXEGAK                                                  19

SEQ ID NO: 243          moltype = AA  length = 18
FEATURE                 Location/Qualifiers
REGION                  1..18
                        note = Description of Artificial Sequence: Synthetic peptide
REGION                  1..18
                        note = compstatin analogue
DISULFID                4..14
                        note = Intrachain disulfide bond
MOD_RES                 6
                        note = 1-methyl-tryptophan
MOD_RES                 15
                        note = sarcosine
source                  1..18
                        mol_type = protein
                        organism = synthetic construct
SEQUENCE: 243
SEFCIWQEWG EHRCXEGE                                                   18

SEQ ID NO: 244          moltype = AA  length = 19
FEATURE                 Location/Qualifiers
REGION                  1..19
                        note = Description of Artificial Sequence: Synthetic peptide
```

-continued

```
REGION                1..19
                      note = compstatin analogue
DISULFID              4..14
                      note = Intrachain disulfide bond
MOD_RES               6
                      note = 1-methyl-tryptophan
MOD_RES               15
                      note = sarcosine
SITE                  19
                      note = Lysine residue covalently linked to a lipophilic
                       group via its side chain
source                1..19
                      mol_type = protein
                      organism = synthetic construct
SEQUENCE: 244
SEYCIWQDWG EHRCXEGAK                                              19

SEQ ID NO: 245        moltype = AA  length = 18
FEATURE               Location/Qualifiers
REGION                1..18
                      note = Description of Artificial Sequence: Synthetic peptide
REGION                1..18
                      note = compstatin analogue
DISULFID              4..14
                      note = Intrachain disulfide bond
MOD_RES               6
                      note = 1-methyl-tryptophan
MOD_RES               15
                      note = sarcosine
source                1..18
                      mol_type = protein
                      organism = synthetic construct
SEQUENCE: 245
SEYCIWQDWG EHRCXEGE                                               18

SEQ ID NO: 246        moltype = AA  length = 19
FEATURE               Location/Qualifiers
REGION                1..19
                      note = Description of Artificial Sequence: Synthetic peptide
REGION                1..19
                      note = compstatin analogue
DISULFID              4..14
                      note = Intrachain disulfide bond
MOD_RES               6
                      note = 1-methyl-tryptophan
MOD_RES               15
                      note = sarcosine
SITE                  19
                      note = Lysine residue covalently linked to a lipophilic
                       group via its side chain
source                1..19
                      mol_type = protein
                      organism = synthetic construct
SEQUENCE: 246
SEYCIWQDWG EHRCXEGEK                                              19

SEQ ID NO: 247        moltype = AA  length = 20
FEATURE               Location/Qualifiers
REGION                1..20
                      note = Description of Artificial Sequence: Synthetic peptide
REGION                1..20
                      note = compstatin analogue
DISULFID              4..14
                      note = Intrachain disulfide bond
MOD_RES               6
                      note = 1-methyl-tryptophan
MOD_RES               10
                      note = sarcosine
MOD_RES               15
                      note = sarcosine
SITE                  18
                      note = glutamate participating in the peptide bond via the
                       gamma-carboxylic acid
SITE                  20
                      note = Lysine residue covalently linked to a lipophilic
                       group via its side chain
source                1..20
                      mol_type = protein
                      organism = synthetic construct
```

```
SEQUENCE: 247
SEYCIWQEWX EHRCXEKEAK                                              20

SEQ ID NO: 248          moltype = AA  length = 19
FEATURE                 Location/Qualifiers
REGION                  1..19
                        note = Description of Artificial Sequence: Synthetic peptide
REGION                  1..19
                        note = compstatin analogue
DISULFID                4..14
                        note = Intrachain disulfide bond
MOD_RES                 6
                        note = 1-methyl-tryptophan
MOD_RES                 15
                        note = sarcosine
SITE                    19
                        note = Lysine residue covalently linked to a lipophilic
                         group via its side chain
source                  1..19
                        mol_type = protein
                        organism = synthetic construct
SEQUENCE: 248
SEYCIWQEWG EHRCXEGAK                                               19

SEQ ID NO: 249          moltype = AA  length = 18
FEATURE                 Location/Qualifiers
REGION                  1..18
                        note = Description of Artificial Sequence: Synthetic peptide
REGION                  1..18
                        note = compstatin analogue
DISULFID                4..14
                        note = Intrachain disulfide bond
MOD_RES                 6
                        note = 1-methyl-tryptophan
MOD_RES                 15
                        note = sarcosine
source                  1..18
                        mol_type = protein
                        organism = synthetic construct
SEQUENCE: 249
SEYCIWQEWG EHRCXEGE                                                18

SEQ ID NO: 250          moltype = AA  length = 18
FEATURE                 Location/Qualifiers
REGION                  1..18
                        note = Description of Artificial Sequence: Synthetic peptide
REGION                  1..18
                        note = compstatin analogue
DISULFID                6..16
                        note = Intrachain disulfide bond
MOD_RES                 8
                        note = 1-methyl-tryptophan
MOD_RES                 17
                        note = sarcosine
source                  1..18
                        mol_type = protein
                        organism = synthetic construct
SEQUENCE: 250
EGSEYCIWQD WGEHRCXE                                                18

SEQ ID NO: 251          moltype = AA  length = 20
FEATURE                 Location/Qualifiers
REGION                  1..20
                        note = Description of Artificial Sequence: Synthetic peptide
REGION                  1..20
                        note = compstatin analogue
DISULFID                6..16
                        note = Intrachain disulfide bond
source                  1..20
                        mol_type = protein
                        organism = synthetic construct
SEQUENCE: 251
ESSAICIWQD WGEHRCTEGE                                              20

SEQ ID NO: 252          moltype = AA  length = 18
FEATURE                 Location/Qualifiers
REGION                  1..18
                        note = Description of Artificial Sequence: Synthetic peptide
REGION                  1..18
```

```
                        note = compstatin analogue
DISULFID                4..14
                        note = Intrachain disulfide bond
MOD_RES                 6
                        note = 1-methyl-tryptophan
MOD_RES                 15
                        note = sarcosine
source                  1..18
                        mol_type = protein
                        organism = synthetic construct
SEQUENCE: 252
SEFCIWQDWG EHRCXEGE                                                    18

SEQ ID NO: 253          moltype = AA  length = 16
FEATURE                 Location/Qualifiers
REGION                  1..16
                        note = Description of Artificial Sequence: Synthetic peptide
REGION                  1..16
                        note = compstatin analogue
DISULFID                4..14
                        note = Intrachain disulfide bond
MOD_RES                 6
                        note = 1-methyl-tryptophan
MOD_RES                 10
                        note = sarcosine
MOD_RES                 15
                        note = sarcosine
source                  1..16
                        mol_type = protein
                        organism = synthetic construct
SEQUENCE: 253
SEFCIWQDWX EHRCXE                                                      16

SEQ ID NO: 254          moltype = AA  length = 16
FEATURE                 Location/Qualifiers
REGION                  1..16
                        note = Description of Artificial Sequence: Synthetic peptide
REGION                  1..16
                        note = compstatin analogue
DISULFID                3..13
                        note = Intrachain disulfide bond
MOD_RES                 5
                        note = 1-methyl-tryptophan
MOD_RES                 14
                        note = sarcosine
source                  1..16
                        mol_type = protein
                        organism = synthetic construct
SEQUENCE: 254
EFCIWQDWGE HRCXEA                                                      16

SEQ ID NO: 255          moltype = AA  length = 13
FEATURE                 Location/Qualifiers
REGION                  1..13
                        note = Description of Artificial Sequence: Synthetic peptide
REGION                  1..13
                        note = 4W9A*
DISULFID                2..12
                        note = Intrachain disulfide bond
source                  1..13
                        mol_type = protein
                        organism = synthetic construct
SEQUENCE: 255
ICVWQDWGAH RCT                                                         13

SEQ ID NO: 256          moltype = AA  length = 14
FEATURE                 Location/Qualifiers
REGION                  1..14
                        note = Description of Artificial Sequence: Synthetic peptide
REGION                  1..14
                        note = compound A
SITE                    1
                        note = D-Tyrosine
DISULFID                3..13
                        note = Intrachain disulfide bond
MOD_RES                 5
                        note = 1-methyl-tryptophan
MOD_RES                 9
                        note = sarcosine
```

-continued

```
MOD_RES                14
                       note = N-methyl-isoleucine
source                 1..14
                       mol_type = protein
                       organism = synthetic construct
SEQUENCE: 256
YICVWQDWXA HRCI                                                  14

SEQ ID NO: 257         moltype = AA  length = 13
FEATURE                Location/Qualifiers
REGION                 1..13
                       note = Description of Artificial Sequence: Synthetic peptide
REGION                 1..13
                       note = Compound A
DISULFID               2..12
                       note = Intrachain disulfide bond
source                 1..13
                       mol_type = protein
                       organism = synthetic construct
SEQUENCE: 257
ICVWQDWGEH RCT                                                   13

SEQ ID NO: 258         moltype = AA  length = 13
FEATURE                Location/Qualifiers
REGION                 1..13
                       note = Description of Artificial Sequence: Synthetic peptide
REGION                 1..13
                       note = Compound B
DISULFID               2..12
                       note = Intrachain disulfide bond
source                 1..13
                       mol_type = protein
                       organism = synthetic construct
SEQUENCE: 258
ICVWQDWGSH RCT                                                   13

SEQ ID NO: 259         moltype = AA  length = 17
FEATURE                Location/Qualifiers
REGION                 1..17
                       note = Description of Artificial Sequence: Synthetic peptide
REGION                 1..17
                       note = Compound C
DISULFID               6..16
                       note = Intrachain disulfide bond
source                 1..17
                       mol_type = protein
                       organism = synthetic construct
SEQUENCE: 259
ESSAICVWQD WGEHRCT                                               17

SEQ ID NO: 260         moltype = AA  length = 17
FEATURE                Location/Qualifiers
REGION                 1..17
                       note = Description of Artificial Sequence: Synthetic peptide
REGION                 1..17
                       note = Compound D
DISULFID               2..12
                       note = Intrachain disulfide bond
source                 1..17
                       mol_type = protein
                       organism = synthetic construct
SEQUENCE: 260
ICVWQDWGEH RCTGAES                                               17

SEQ ID NO: 261         moltype = AA  length = 13
FEATURE                Location/Qualifiers
REGION                 1..13
                       note = Description of Artificial Sequence: Synthetic peptide
REGION                 1..13
                       note = Compound E
DISULFID               2..12
                       note = Intrachain disulfide bond
source                 1..13
                       mol_type = protein
                       organism = synthetic construct
SEQUENCE: 261
ICVWQDWGAH SCT                                                   13

SEQ ID NO: 262         moltype = AA  length = 13
```

```
FEATURE                Location/Qualifiers
REGION                 1..13
                       note = Description of Artificial Sequence: Synthetic peptide
REGION                 1..13
                       note = Compound F
DISULFID               2..12
                       note = Intrachain disulfide bond
source                 1..13
                       mol_type = protein
                       organism = synthetic construct
SEQUENCE: 262
ICVWQDWGEH SCT                                                        13

SEQ ID NO: 263         moltype = AA  length = 13
FEATURE                Location/Qualifiers
REGION                 1..13
                       note = Description of Artificial Sequence: Synthetic peptide
REGION                 1..13
                       note = Compound G
DISULFID               2..12
                       note = Intrachain disulfide bond
source                 1..13
                       mol_type = protein
                       organism = synthetic construct
SEQUENCE: 263
ICVWQDWGEH RCS                                                        13

SEQ ID NO: 264         moltype = AA  length = 18
FEATURE                Location/Qualifiers
REGION                 1..18
                       note = Description of Artificial Sequence: Synthetic peptide
REGION                 1..18
                       note = Compound H
DISULFID               6..16
                       note = Intrachain disulfide bond
MOD_RES                17
                       note = sarcosine
source                 1..18
                       mol_type = protein
                       organism = synthetic construct
SEQUENCE: 264
EGSAICVWQD WGEHRCXE                                                   18

SEQ ID NO: 265         moltype = AA  length = 16
FEATURE                Location/Qualifiers
REGION                 1..16
                       note = Description of Artificial Sequence: Synthetic peptide
REGION                 1..16
                       note = Compound J
DISULFID               2..12
                       note = Intrachain disulfide bond
source                 1..16
                       mol_type = protein
                       organism = synthetic construct
SEQUENCE: 265
ICVWQDWGEH RCTEGE                                                     16

SEQ ID NO: 266         moltype = AA  length = 4
FEATURE                Location/Qualifiers
REGION                 1..4
                       note = Description of Artificial Sequence: Synthetic peptide
REGION                 1..4
                       note = N-terminal and/or C-terminal flanking sequence
SITE                   3
                       note = glutamate participating in the peptide bond via the
                        gamma-carboxylic acid
source                 1..4
                       mol_type = protein
                       organism = synthetic construct
SEQUENCE: 266
EKEA                                                                  4

SEQ ID NO: 267         moltype = AA  length = 4
FEATURE                Location/Qualifiers
REGION                 1..4
                       note = Description of Artificial Sequence: Synthetic peptide
MOD_RES                1
                       note = 17-carboxy-heptadecanoyl-gammaGlu
SITE                   4
```

```
                        note = glutamate participating in the peptide bond via the
                         gamma-carboxylic acid
source                  1..4
                        mol_type = protein
                        organism = synthetic construct
SEQUENCE: 267
EKGE                                                                             4

SEQ ID NO: 268          moltype = AA  length = 20
FEATURE                 Location/Qualifiers
REGION                  1..20
                        note = Description of Artificial Sequence: Synthetic peptide
MOD_RES                 1
                        note = 15-carboxy-pentadecanoyl-gammaGlu-Peg3-Peg3 attached
                         to side chain of Lysine
DISULFID                6..16
                        note = Intrachain disulfide bond
source                  1..20
                        mol_type = protein
                        organism = synthetic construct
SEQUENCE: 268
KGSAICIWQD WGEHRCTEGE                                                            20

SEQ ID NO: 269          moltype = AA  length = 21
FEATURE                 Location/Qualifiers
REGION                  1..21
                        note = Description of Artificial Sequence: Synthetic peptide
DISULFID                6..16
                        note = Intrachain disulfide bond
MOD_RES                 8
                        note = 1-methyl-tryptophan
MOD_RES                 17
                        note = sarcosine
MOD_RES                 21
                        note = 17-carboxy-heptadecanoyl-gammaGlu-Gly-gammaGlu
                         attached to side chain of Lysine
source                  1..21
                        mol_type = protein
                        organism = synthetic construct
SEQUENCE: 269
ASGEYCIWQD WGEHRCXEGE K                                                          21

SEQ ID NO: 270          moltype = AA  length = 17
FEATURE                 Location/Qualifiers
REGION                  1..17
                        note = Description of Artificial Sequence: Synthetic peptide
DISULFID                3..13
                        note = Intrachain disulfide bond
MOD_RES                 5
                        note = 1-methyl-tryptophan
MOD_RES                 17
                        note = 17-carboxy-heptadecanoyl-gammaGlu-Gly-gammaGlu
                         attached to side chain of Lysine
source                  1..17
                        mol_type = protein
                        organism = synthetic construct
SEQUENCE: 270
EFCIWQDWGE HRCEGEK                                                               17

SEQ ID NO: 271          moltype = AA  length = 20
FEATURE                 Location/Qualifiers
REGION                  1..20
                        note = Description of Artificial Sequence: Synthetic peptide
DISULFID                6..16
                        note = Intrachain disulfide bond
MOD_RES                 20
                        note = 15-carboxy-pentadecanoyl-gammaGlu attached to side
                         chain of Lysine
source                  1..20
                        mol_type = protein
                        organism = synthetic construct
SEQUENCE: 271
EGSAICIWQD WGEHRCTEGK                                                            20

SEQ ID NO: 272          moltype = AA  length = 18
FEATURE                 Location/Qualifiers
REGION                  1..18
                        note = Description of Artificial Sequence: Synthetic peptide
DISULFID                6..16
```

-continued

```
                        note = Intrachain disulfide bond
MOD_RES                 8
                        note = 1-methyl-tryptophan
MOD_RES                 15
                        note = 15-carboxy-pentadecanoyl-gammaGlu-Peg3-Peg3 attached
                         to side chain of Lysine
MOD_RES                 17
                        note = sarcosine
source                  1..18
                        mol_type = protein
                        organism = synthetic construct
SEQUENCE: 272
EGSAYCIWQD WGEHKCXE                                                18

SEQ ID NO: 273          moltype = AA  length = 20
FEATURE                 Location/Qualifiers
REGION                  1..20
                        note = Description of Artificial Sequence: Synthetic peptide
DISULFID                6..16
                        note = Intrachain disulfide bond
MOD_RES                 8
                        note = 1-methyl-tryptophan
MOD_RES                 17
                        note = sarcosine
MOD_RES                 20
                        note = 15-carboxy-pentadecanoyl-gammaGlu-Peg3-Peg3 attached
                         to side chain of Lysine
source                  1..20
                        mol_type = protein
                        organism = synthetic construct
SEQUENCE: 273
EGSAYCIWQD WGEHRCXEGK                                              20

SEQ ID NO: 274          moltype = AA  length = 21
FEATURE                 Location/Qualifiers
REGION                  1..21
                        note = Description of Artificial Sequence: Synthetic peptide
DISULFID                6..16
                        note = Intrachain disulfide bond
MOD_RES                 8
                        note = 1-methyl-tryptophan
MOD_RES                 17
                        note = sarcosine
MOD_RES                 21
                        note = 17-carboxy-heptadecanoyl-gammaGlu-Gly-gammaGlu
                         attached to side chain of Lysine
source                  1..21
                        mol_type = protein
                        organism = synthetic construct
SEQUENCE: 274
EGSAYCIWQD WGEHRCXEGE K                                            21

SEQ ID NO: 275          moltype = AA  length = 21
FEATURE                 Location/Qualifiers
REGION                  1..21
                        note = Description of Artificial Sequence: Synthetic peptide
DISULFID                6..16
                        note = Intrachain disulfide bond
MOD_RES                 8
                        note = 1-methyl-tryptophan
MOD_RES                 17
                        note = sarcosine
MOD_RES                 21
                        note = 17-carboxy-heptadecanoyl-gammaGlu-Gly-gammaGlu
                         attached to side chain of Lysine
source                  1..21
                        mol_type = protein
                        organism = synthetic construct
SEQUENCE: 275
EGSAYCIWQD WGEHRCXEGK K                                            21

SEQ ID NO: 276          moltype = AA  length = 21
FEATURE                 Location/Qualifiers
REGION                  1..21
                        note = Description of Artificial Sequence: Synthetic peptide
DISULFID                6..16
                        note = Intrachain disulfide bond
MOD_RES                 8
                        note = 1-methyl-tryptophan
```

-continued

```
MOD_RES              17
                     note = sarcosine
SITE                 20
                     note = glutamate participating in the peptide bond via the
                      gamma-carboxylic acid
MOD_RES              21
                     note = 17-carboxy-heptadecanoyl-gammaGlu-Peg3-Peg3 attached
                      to side chain of Lysine
source               1..21
                     mol_type = protein
                     organism = synthetic construct
SEQUENCE: 276
EGSAYCIWQD WGEHRCXEKE K                                              21

SEQ ID NO: 277       moltype = AA  length = 18
FEATURE              Location/Qualifiers
REGION               1..18
                     note = Description of Artificial Sequence: Synthetic peptide
DISULFID             2..12
                     note = Intrachain disulfide bond
MOD_RES              4
                     note = 1-methyl-tryptophan
MOD_RES              18
                     note = 15-carboxy-pentadecanoyl-gammaGlu-Peg3-Peg3 attached
                      to side chain of Lysine
source               1..18
                     mol_type = protein
                     organism = synthetic construct
SEQUENCE: 277
FCIWQDWGEH RCTGAESK                                                  18

SEQ ID NO: 278       moltype = AA  length = 16
FEATURE              Location/Qualifiers
REGION               1..16
                     note = Description of Artificial Sequence: Synthetic peptide
DISULFID             2..12
                     note = Intrachain disulfide bond
MOD_RES              16
                     note = 15-carboxy-pentadecanoyl-gammaGlu attached to side
                      chain of Lysine
source               1..16
                     mol_type = protein
                     organism = synthetic construct
SEQUENCE: 278
ICIWQDWGEH RCTEGK                                                    16

SEQ ID NO: 279       moltype = AA  length = 16
FEATURE              Location/Qualifiers
REGION               1..16
                     note = Description of Artificial Sequence: Synthetic peptide
DISULFID             2..12
                     note = Intrachain disulfide bond
MOD_RES              16
                     note = 15-carboxy-pentadecanoyl-gammaGlu-Peg3-Peg3 attached
                      to side chain of Lysine
source               1..16
                     mol_type = protein
                     organism = synthetic construct
SEQUENCE: 279
ICIWQDWGEH RCTEGK                                                    16

SEQ ID NO: 280       moltype = AA  length = 16
FEATURE              Location/Qualifiers
REGION               1..16
                     note = Description of Artificial Sequence: Synthetic peptide
DISULFID             2..12
                     note = Intrachain disulfide bond
MOD_RES              16
                     note =
                      15-carboxy-pentadecanoyl-(Piperazine-1-yl)-acetyl-Peg3-Peg3
                       attached to side chain of Lysine
source               1..16
                     mol_type = protein
                     organism = synthetic construct
SEQUENCE: 280
ICIWQDWGEH RCTEGK                                                    16

SEQ ID NO: 281       moltype = AA  length = 16
FEATURE              Location/Qualifiers
```

-continued

```
REGION                  1..16
                        note = Description of Artificial Sequence: Synthetic peptide
DISULFID                2..12
                        note = Intrachain disulfide bond
MOD_RES                 16
                        note = 17-carboxy-heptadecanoyl-gammaGlu-Peg3-Peg3 attached
                         to side chain of Lysine
source                  1..16
                        mol_type = protein
                        organism = synthetic construct
SEQUENCE: 281
ICIWQDWGEH RCTEGK                                                           16

SEQ ID NO: 282          moltype = AA  length = 16
FEATURE                 Location/Qualifiers
REGION                  1..16
                        note = Description of Artificial Sequence: Synthetic peptide
DISULFID                2..12
                        note = Intrachain disulfide bond
MOD_RES                 16
                        note = 19-carboxy-nonadecanoyl-gammaGlu-Peg3-Peg3 attached
                         to side chain of Lysine
source                  1..16
                        mol_type = protein
                        organism = synthetic construct
SEQUENCE: 282
ICIWQDWGEH RCTEGK                                                           16

SEQ ID NO: 283          moltype = AA  length = 17
FEATURE                 Location/Qualifiers
REGION                  1..17
                        note = Description of Artificial Sequence: Synthetic peptide
DISULFID                2..12
                        note = Intrachain disulfide bond
MOD_RES                 17
                        note = 15-carboxy-pentadecanoyl-gammaGlu-Peg3-Peg3 attached
                         to side chain of Lysine
source                  1..17
                        mol_type = protein
                        organism = synthetic construct
SEQUENCE: 283
ICIWQDWGEH RCTEGEK                                                          17

SEQ ID NO: 284          moltype = AA  length = 17
FEATURE                 Location/Qualifiers
REGION                  1..17
                        note = Description of Artificial Sequence: Synthetic peptide
DISULFID                2..12
                        note = Intrachain disulfide bond
MOD_RES                 17
                        note = 17-carboxy-heptadecanoyl-gammaGlu-Peg3-Peg3 attached
                         to side chain of Lysine
source                  1..17
                        mol_type = protein
                        organism = synthetic construct
SEQUENCE: 284
ICIWQDWGEH RCTEGEK                                                          17

SEQ ID NO: 285          moltype = AA  length = 17
FEATURE                 Location/Qualifiers
REGION                  1..17
                        note = Description of Artificial Sequence: Synthetic peptide
DISULFID                4..14
                        note = Intrachain disulfide bond
MOD_RES                 6
                        note = 1-methyl-tryptophan
MOD_RES                 15
                        note = sarcosine
MOD_RES                 17
                        note = 17-carboxy-heptadecanoyl-gammaGlu-Lys-Gly-gammaGlu
                         attached to side chain of Lysine
source                  1..17
                        mol_type = protein
                        organism = synthetic construct
SEQUENCE: 285
SAYCIWQDWG EHRCXEK                                                          17

SEQ ID NO: 286          moltype = AA  length = 17
FEATURE                 Location/Qualifiers
```

-continued

```
REGION                  1..17
                        note = Description of Artificial Sequence: Synthetic peptide
DISULFID                4..14
                        note = Intrachain disulfide bond
MOD_RES                 6
                        note = 1-methyl-tryptophan
MOD_RES                 15
                        note = sarcosine
MOD_RES                 17
                        note = 17-carboxy-heptadecanoyl-gammaGlu-Gly-gammaGlu
                         attached to side chain of Lysine
source                  1..17
                        mol_type = protein
                        organism = synthetic construct
SEQUENCE: 286
SAYCIWQDWG EHRCXEK                                                   17

SEQ ID NO: 287          moltype = AA  length = 19
FEATURE                 Location/Qualifiers
REGION                  1..19
                        note = Description of Artificial Sequence: Synthetic peptide
DISULFID                4..14
                        note = Intrachain disulfide bond
MOD_RES                 6
                        note = 1-methyl-tryptophan
MOD_RES                 15
                        note = sarcosine
MOD_RES                 19
                        note =
                         17-carboxy-heptadecanoyl-gammaGlu-Gly-Peg3-gammaGlu-Peg3
                         attached to side chain of Lysine
source                  1..19
                        mol_type = protein
                        organism = synthetic construct
SEQUENCE: 287
SEFCIWQDWG EHRCXEGAK                                                 19

SEQ ID NO: 288          moltype = AA  length = 18
FEATURE                 Location/Qualifiers
REGION                  1..18
                        note = Description of Artificial Sequence: Synthetic peptide
DISULFID                4..14
                        note = Intrachain disulfide bond
MOD_RES                 6
                        note = 1-methyl-tryptophan
MOD_RES                 15
                        note = sarcosine
source                  1..18
                        mol_type = protein
                        organism = synthetic construct
SEQUENCE: 288
SEFCIWQDWG EHRCXEGE                                                  18

SEQ ID NO: 289          moltype = AA  length = 22
FEATURE                 Location/Qualifiers
REGION                  1..22
                        note = Description of Artificial Sequence: Synthetic peptide
DISULFID                4..14
                        note = Intrachain disulfide bond
MOD_RES                 6
                        note = 1-methyl-tryptophan
MOD_RES                 15
                        note = sarcosine
MOD_RES                 22
                        note = 17-carboxy-heptadecanoyl-gammaGlu-Gly-gammaGlu
                         attached to side chain of Lysine
source                  1..22
                        mol_type = protein
                        organism = synthetic construct
SEQUENCE: 289
SEFCIWQDWG EHRCXEGEGG GK                                             22

SEQ ID NO: 290          moltype = AA  length = 18
FEATURE                 Location/Qualifiers
REGION                  1..18
                        note = Description of Artificial Sequence: Synthetic peptide
DISULFID                4..14
                        note = Intrachain disulfide bond
MOD_RES                 6
```

-continued

```
                        note = 1-methyl-tryptophan
MOD_RES                 15
                        note = sarcosine
source                  1..18
                        mol_type = protein
                        organism = synthetic construct
SEQUENCE: 290
SEFCIWQDWG EHRCXEGE                                              18

SEQ ID NO: 291          moltype = AA  length = 18
FEATURE                 Location/Qualifiers
REGION                  1..18
                        note = Description of Artificial Sequence: Synthetic peptide
DISULFID                4..14
                        note = Intrachain disulfide bond
MOD_RES                 6
                        note = 1-methyl-tryptophan
MOD_RES                 15
                        note = sarcosine
source                  1..18
                        mol_type = protein
                        organism = synthetic construct
SEQUENCE: 291
SEFCIWQDWG EHRCXEGE                                              18

SEQ ID NO: 292          moltype = AA  length = 18
FEATURE                 Location/Qualifiers
REGION                  1..18
                        note = Description of Artificial Sequence: Synthetic peptide
DISULFID                4..14
                        note = Intrachain disulfide bond
MOD_RES                 6
                        note = 1-methyl-tryptophan
MOD_RES                 15
                        note = sarcosine
source                  1..18
                        mol_type = protein
                        organism = synthetic construct
SEQUENCE: 292
SEFCIWQDWG EHRCXEGE                                              18

SEQ ID NO: 293          moltype = AA  length = 18
FEATURE                 Location/Qualifiers
REGION                  1..18
                        note = Description of Artificial Sequence: Synthetic peptide
DISULFID                4..14
                        note = Intrachain disulfide bond
MOD_RES                 6
                        note = 1-methyl-tryptophan
MOD_RES                 15
                        note = sarcosine
source                  1..18
                        mol_type = protein
                        organism = synthetic construct
SEQUENCE: 293
SEFCIWQDWG EHRCXEGE                                              18

SEQ ID NO: 294          moltype = AA  length = 22
FEATURE                 Location/Qualifiers
REGION                  1..22
                        note = Description of Artificial Sequence: Synthetic peptide
DISULFID                4..14
                        note = Intrachain disulfide bond
MOD_RES                 6
                        note = 1-methyl-tryptophan
MOD_RES                 15
                        note = sarcosine
MOD_RES                 22
                        note = 17-carboxy-heptadecanoyl-gammaGlu-Gly-gammaGlu
                         attached to side chain of Lysine
source                  1..22
                        mol_type = protein
                        organism = synthetic construct
SEQUENCE: 294
SEFCIWQDWG EHRCXEGESE SK                                         22

SEQ ID NO: 295          moltype = AA  length = 22
FEATURE                 Location/Qualifiers
REGION                  1..22
```

-continued

```
                        note = Description of Artificial Sequence: Synthetic peptide
DISULFID                4..14
                        note = Intrachain disulfide bond
MOD_RES                 6
                        note = 1-methyl-tryptophan
MOD_RES                 15
                        note = sarcosine
MOD_RES                 22
                        note = 17-carboxy-heptadecanoyl-gammaGlu attached to side
                         chain of Lysine
source                  1..22
                        mol_type = protein
                        organism = synthetic construct
SEQUENCE: 295
SEFCIWQDWG EHRCXEGESE SK                                             22

SEQ ID NO: 296          moltype = AA  length = 22
FEATURE                 Location/Qualifiers
REGION                  1..22
                        note = Description of Artificial Sequence: Synthetic peptide
DISULFID                4..14
                        note = Intrachain disulfide bond
MOD_RES                 6
                        note = 1-methyl-tryptophan
MOD_RES                 15
                        note = sarcosine
SITE                    18
                        note = glutamate participating in the peptide bond via the
                         gamma-carboxylic acid
MOD_RES                 22
                        note = 17-carboxy-heptadecanoyl-gammaGlu-Gly-gammaGlu
                         attached to side chain of Lysine
source                  1..22
                        mol_type = protein
                        organism = synthetic construct
SEQUENCE: 296
SEFCIWQDWG EHRCXEKEGG GK                                             22

SEQ ID NO: 297          moltype = AA  length = 18
FEATURE                 Location/Qualifiers
REGION                  1..18
                        note = Description of Artificial Sequence: Synthetic peptide
DISULFID                4..14
                        note = Intrachain disulfide bond
MOD_RES                 6
                        note = 1-methyl-tryptophan
source                  1..18
                        mol_type = protein
                        organism = synthetic construct
SEQUENCE: 297
SEFCIWQDWG EHRCTEGE                                                  18

SEQ ID NO: 298          moltype = AA  length = 18
FEATURE                 Location/Qualifiers
REGION                  1..18
                        note = Description of Artificial Sequence: Synthetic peptide
DISULFID                4..14
                        note = Intrachain disulfide bond
MOD_RES                 6
                        note = 1-methyl-tryptophan
source                  1..18
                        mol_type = protein
                        organism = synthetic construct
SEQUENCE: 298
SEFCIWQDWG EHRCTEGE                                                  18

SEQ ID NO: 299          moltype = AA  length = 22
FEATURE                 Location/Qualifiers
REGION                  1..22
                        note = Description of Artificial Sequence: Synthetic peptide
DISULFID                4..14
                        note = Intrachain disulfide bond
MOD_RES                 6
                        note = 1-methyl-tryptophan
MOD_RES                 22
                        note = 17-carboxy-heptadecanoyl-gammaGlu-Gly-gammaGlu
                         attached to side chain of Lysine
source                  1..22
                        mol_type = protein
```

```
                         organism = synthetic construct
SEQUENCE: 299
SEFCIWQDWG EHRCTEGEGG GK                                           22

SEQ ID NO: 300           moltype = AA  length = 22
FEATURE                  Location/Qualifiers
REGION                   1..22
                         note = Description of Artificial Sequence: Synthetic peptide
DISULFID                 4..14
                         note = Intrachain disulfide bond
MOD_RES                  6
                         note = 1-methyl-tryptophan
MOD_RES                  22
                         note = 15-carboxy-pentadecanoyl-gammaGlu-Gly-gammaGlu
                          attached to side chain of Lysine
source                   1..22
                         mol_type = protein
                         organism = synthetic construct
SEQUENCE: 300
SEFCIWQDWG EHRCTEGEGG GK                                           22

SEQ ID NO: 301           moltype = AA  length = 18
FEATURE                  Location/Qualifiers
REGION                   1..18
                         note = Description of Artificial Sequence: Synthetic peptide
DISULFID                 4..14
                         note = Intrachain disulfide bond
MOD_RES                  6
                         note = 1-methyl-tryptophan
source                   1..18
                         mol_type = protein
                         organism = synthetic construct
SEQUENCE: 301
SEFCIWQDWG EHRCTEGE                                                18

SEQ ID NO: 302           moltype = AA  length = 18
FEATURE                  Location/Qualifiers
REGION                   1..18
                         note = Description of Artificial Sequence: Synthetic peptide
DISULFID                 4..14
                         note = Intrachain disulfide bond
MOD_RES                  6
                         note = 1-methyl-tryptophan
source                   1..18
                         mol_type = protein
                         organism = synthetic construct
SEQUENCE: 302
SEFCIWQDWG EHRCTEGE                                                18

SEQ ID NO: 303           moltype = AA  length = 22
FEATURE                  Location/Qualifiers
REGION                   1..22
                         note = Description of Artificial Sequence: Synthetic peptide
DISULFID                 4..14
                         note = Intrachain disulfide bond
MOD_RES                  6
                         note = 1-methyl-tryptophan
SITE                     18
                         note = glutamate participating in the peptide bond via the
                          gamma-carboxylic acid
MOD_RES                  22
                         note = 17-carboxy-heptadecanoyl-gammaGlu-Gly-gammaGlu
                          attached to side chain of Lysine
source                   1..22
                         mol_type = protein
                         organism = synthetic construct
SEQUENCE: 303
SEFCIWQDWG EHRCTEKEGG GK                                           22

SEQ ID NO: 304           moltype = AA  length = 20
FEATURE                  Location/Qualifiers
REGION                   1..20
                         note = Description of Artificial Sequence: Synthetic peptide
DISULFID                 4..14
                         note = Intrachain disulfide bond
MOD_RES                  6
                         note = 1-methyl-tryptophan
MOD_RES                  20
                         note = 15-carboxy-hexadecanoyl-gammaGlu-Gly-gammaGlu
```

```
                         attached to side chain of Lysine
source                   1..20
                         mol_type = protein
                         organism = synthetic construct
SEQUENCE: 304
SEFCIWQDWG EHRCTGAESK                                          20

SEQ ID NO: 305           moltype = AA  length = 19
FEATURE                  Location/Qualifiers
REGION                   1..19
                         note = Description of Artificial Sequence: Synthetic peptide
DISULFID                 4..14
                         note = Intrachain disulfide bond
MOD_RES                  6
                         note = 1-methyl-tryptophan
MOD_RES                  15
                         note = sarcosine
MOD_RES                  19
                         note =
                          17-carboxy-heptadecanoyl-gammaGlu-Gly-Peg3-gammaGlu-Peg3
                          attached to side chain of Lysine
source                   1..19
                         mol_type = protein
                         organism = synthetic construct
SEQUENCE: 305
SEFCIWQEWG EHRCXEGAK                                           19

SEQ ID NO: 306           moltype = AA  length = 18
FEATURE                  Location/Qualifiers
REGION                   1..18
                         note = Description of Artificial Sequence: Synthetic peptide
DISULFID                 4..14
                         note = Intrachain disulfide bond
MOD_RES                  6
                         note = 1-methyl-tryptophan
MOD_RES                  15
                         note = sarcosine
source                   1..18
                         mol_type = protein
                         organism = synthetic construct
SEQUENCE: 306
SEFCIWQEWG EHRCXEGE                                            18

SEQ ID NO: 307           moltype = AA  length = 19
FEATURE                  Location/Qualifiers
REGION                   1..19
                         note = Description of Artificial Sequence: Synthetic peptide
DISULFID                 4..14
                         note = Intrachain disulfide bond
MOD_RES                  6
                         note = 1-methyl-tryptophan
MOD_RES                  15
                         note = sarcosine
MOD_RES                  19
                         note = 17-carboxy-heptadecanoyl-gammaGlu-Gly-gammaGlu
                          attached to side chain of Lysine
source                   1..19
                         mol_type = protein
                         organism = synthetic construct
SEQUENCE: 307
SEYCIWQDWG EHRCXEGAK                                           19

SEQ ID NO: 308           moltype = AA  length = 19
FEATURE                  Location/Qualifiers
REGION                   1..19
                         note = Description of Artificial Sequence: Synthetic peptide
DISULFID                 4..14
                         note = Intrachain disulfide bond
MOD_RES                  6
                         note = 1-methyl-tryptophan
MOD_RES                  15
                         note = sarcosine
MOD_RES                  19
                         note =
                          17-carboxy-heptadecanoyl-gammaGlu-Gly-Peg3-gammaGlu-Peg3
                          attached to side chain of Lysine
source                   1..19
                         mol_type = protein
                         organism = synthetic construct
```

-continued

```
SEQUENCE: 308
SEYCIWQDWG EHRCXEGAK                                              19

SEQ ID NO: 309          moltype = AA  length = 18
FEATURE                 Location/Qualifiers
REGION                  1..18
                        note = Description of Artificial Sequence: Synthetic peptide
DISULFID                4..14
                        note = Intrachain disulfide bond
MOD_RES                 6
                        note = 1-methyl-tryptophan
MOD_RES                 15
                        note = sarcosine
source                  1..18
                        mol_type = protein
                        organism = synthetic construct
SEQUENCE: 309
SEYCIWQDWG EHRCXEGE                                               18

SEQ ID NO: 310          moltype = AA  length = 19
FEATURE                 Location/Qualifiers
REGION                  1..19
                        note = Description of Artificial Sequence: Synthetic peptide
DISULFID                4..14
                        note = Intrachain disulfide bond
MOD_RES                 6
                        note = 1-methyl-tryptophan
MOD_RES                 15
                        note = sarcosine
MOD_RES                 19
                        note = 17-carboxy-heptadecanoyl-gammaGlu-Gly-gammaGlu
                         attached to side chain of Lysine
source                  1..19
                        mol_type = protein
                        organism = synthetic construct
SEQUENCE: 310
SEYCIWQDWG EHRCXEGEK                                              19

SEQ ID NO: 311          moltype = AA  length = 19
FEATURE                 Location/Qualifiers
REGION                  1..19
                        note = Description of Artificial Sequence: Synthetic peptide
DISULFID                4..14
                        note = Intrachain disulfide bond
MOD_RES                 6
                        note = 1-methyl-tryptophan
MOD_RES                 15
                        note = sarcosine
MOD_RES                 19
                        note = 17-carboxy-heptadecanoyl-gammaGlu-Gly-gammaGlu
                         attached to side chain of Lysine
source                  1..19
                        mol_type = protein
                        organism = synthetic construct
SEQUENCE: 311
SEYCIWQDWG EHRCXEGKK                                              19

SEQ ID NO: 312          moltype = AA  length = 19
FEATURE                 Location/Qualifiers
REGION                  1..19
                        note = Description of Artificial Sequence: Synthetic peptide
DISULFID                4..14
                        note = Intrachain disulfide bond
MOD_RES                 6
                        note = 1-methyl-tryptophan
MOD_RES                 15
                        note = sarcosine
MOD_RES                 19
                        note = 17-carboxy-heptadecanoyl-gammaGlu-Lys-gammaGlu
                         attached to side chain of Lysine
source                  1..19
                        mol_type = protein
                        organism = synthetic construct
SEQUENCE: 312
SEYCIWQDWG EHRCXEGEK                                              19

SEQ ID NO: 313          moltype = AA  length = 20
FEATURE                 Location/Qualifiers
REGION                  1..20
```

```
                        note = Description of Artificial Sequence: Synthetic peptide
DISULFID                4..14
                        note = Intrachain disulfide bond
MOD_RES                 6
                        note = 1-methyl-tryptophan
MOD_RES                 10
                        note = sarcosine
MOD_RES                 15
                        note = sarcosine
SITE                    18
                        note = glutamate participating in the peptide bond via the
                         gamma-carboxylic acid
MOD_RES                 20
                        note =
                         17-carboxy-heptadecanoyl-gammaGlu-Gly-Peg3-gammaGlu-Peg3
                         attached to side chain of Lysine
source                  1..20
                        mol_type = protein
                        organism = synthetic construct
SEQUENCE: 313
SEYCIWQEWX EHRCXEKEAK                                                20

SEQ ID NO: 314          moltype = AA  length = 19
FEATURE                 Location/Qualifiers
REGION                  1..19
                        note = Description of Artificial Sequence: Synthetic peptide
DISULFID                4..14
                        note = Intrachain disulfide bond
MOD_RES                 6
                        note = 1-methyl-tryptophan
MOD_RES                 15
                        note = sarcosine
MOD_RES                 19
                        note =
                         17-carboxy-heptadecanoyl-gammaGlu-Gly-Peg3-gammaGlu-Peg3
                         attached to side chain of Lysine
source                  1..19
                        mol_type = protein
                        organism = synthetic construct
SEQUENCE: 314
SEYCIWQEWG EHRCXEGAK                                                 19

SEQ ID NO: 315          moltype = AA  length = 18
FEATURE                 Location/Qualifiers
REGION                  1..18
                        note = Description of Artificial Sequence: Synthetic peptide
DISULFID                4..14
                        note = Intrachain disulfide bond
MOD_RES                 6
                        note = 1-methyl-tryptophan
MOD_RES                 15
                        note = sarcosine
source                  1..18
                        mol_type = protein
                        organism = synthetic construct
SEQUENCE: 315
SEYCIWQEWG EHRCXEGE                                                  18

SEQ ID NO: 316          moltype = AA  length = 18
FEATURE                 Location/Qualifiers
REGION                  1..18
                        note = Description of Artificial Sequence: Synthetic peptide
MOD_RES                 1
                        note = 15-Carboxy-pentadecanoyl attached to side chain of
                         Glu
DISULFID                6..16
                        note = Intrachain disulfide bond
MOD_RES                 8
                        note = 1-methyl-tryptophan
MOD_RES                 17
                        note = sarcosine
source                  1..18
                        mol_type = protein
                        organism = synthetic construct
SEQUENCE: 316
EGSEYCIWQD WGEHRCXE                                                  18

SEQ ID NO: 317          moltype = AA  length = 18
FEATURE                 Location/Qualifiers
```

-continued

```
REGION                1..18
                      note = Description of Artificial Sequence: Synthetic peptide
MOD_RES               1
                      note = 17-Carboxy-heptadecanoyl attached to side chain of
                       Glu
DISULFID              6..16
                      note = Intrachain disulfide bond
MOD_RES               8
                      note = 1-methyl-tryptophan
MOD_RES               17
                      note = sarcosine
source                1..18
                      mol_type = protein
                      organism = synthetic construct
SEQUENCE: 317
EGSEYCIWQD WGEHRCXE                                                  18

SEQ ID NO: 318        moltype = AA  length = 20
FEATURE               Location/Qualifiers
REGION                1..20
                      note = Description of Artificial Sequence: Synthetic peptide
MOD_RES               1
                      note = 15-Carboxy-pentadecanoyl attached to side chain of
                       Glu
DISULFID              6..16
                      note = Intrachain disulfide bond
source                1..20
                      mol_type = protein
                      organism = synthetic construct
SEQUENCE: 318
ESSAICIWQD WGEHRCTEGE                                                20

SEQ ID NO: 319        moltype = AA  length = 18
FEATURE               Location/Qualifiers
REGION                1..18
                      note = Description of Artificial Sequence: Synthetic peptide
DISULFID              4..14
                      note = Intrachain disulfide bond
MOD_RES               6
                      note = 1-methyl-tryptophan
MOD_RES               15
                      note = sarcosine
source                1..18
                      mol_type = protein
                      organism = synthetic construct
SEQUENCE: 319
SEFCIWQDWG EHRCXEGE                                                  18

SEQ ID NO: 320        moltype = AA  length = 16
FEATURE               Location/Qualifiers
REGION                1..16
                      note = Description of Artificial Sequence: Synthetic peptide
DISULFID              4..14
                      note = Intrachain disulfide bond
MOD_RES               6
                      note = 1-methyl-tryptophan
MOD_RES               10
                      note = sarcosine
MOD_RES               15
                      note = sarcosine
source                1..16
                      mol_type = protein
                      organism = synthetic construct
SEQUENCE: 320
SEFCIWQDWX EHRCXE                                                    16

SEQ ID NO: 321        moltype = AA  length = 16
FEATURE               Location/Qualifiers
REGION                1..16
                      note = Description of Artificial Sequence: Synthetic peptide
DISULFID              3..13
                      note = Intrachain disulfide bond
MOD_RES               5
                      note = 1-methyl-tryptophan
MOD_RES               14
                      note = sarcosine
source                1..16
                      mol_type = protein
                      organism = synthetic construct
```

```
SEQUENCE: 321
EFCIWQDWGE HRCXEA                                                    16

SEQ ID NO: 322          moltype = AA  length = 13
FEATURE                 Location/Qualifiers
REGION                  1..13
                        note = Description of Artificial Sequence: Synthetic peptide
DISULFID                2..12
                        note = Intrachain disulfide bond
source                  1..13
                        mol_type = protein
                        organism = synthetic construct
SEQUENCE: 322
ICIWQDWGAH RCT                                                       13

SEQ ID NO: 323          moltype = AA  length = 13
FEATURE                 Location/Qualifiers
REGION                  1..13
                        note = Description of Artificial Sequence: Synthetic peptide
DISULFID                2..12
                        note = Intrachain disulfide bond
source                  1..13
                        mol_type = protein
                        organism = synthetic construct
SEQUENCE: 323
ICVWQDWGAH RCT                                                       13

SEQ ID NO: 324          moltype = AA  length = 13
FEATURE                 Location/Qualifiers
REGION                  1..13
                        note = Description of Artificial Sequence: Synthetic peptide
DISULFID                2..12
                        note = Intrachain disulfide bond
MOD_RES                 3
                        note = Any amino acid
source                  1..13
                        mol_type = protein
                        organism = synthetic construct
SEQUENCE: 324
ICXWQDWGEH RCT                                                       13

SEQ ID NO: 325          moltype = AA  length = 4
FEATURE                 Location/Qualifiers
REGION                  1..4
                        note = Description of Artificial Sequence: Synthetic peptide
SITE                    1
                        note = Lysine residue covalently linked to a lipophilic
                         group via its side chain
source                  1..4
                        mol_type = protein
                        organism = synthetic construct
SEQUENCE: 325
KGSA                                                                 4

SEQ ID NO: 326          moltype = AA  length = 14
FEATURE                 Location/Qualifiers
REGION                  1..14
                        note = Description of Artificial Sequence: Synthetic peptide
SITE                    1
                        note = D-Tyrosine
DISULFID                3..13
                        note = Intrachain disulfide bond
MOD_RES                 5
                        note = 1-methyl-tryptophan
MOD_RES                 9
                        note = sarcosine
MOD_RES                 14
                        note = N-methyl-isoleucine
source                  1..14
                        mol_type = protein
                        organism = synthetic construct
SEQUENCE: 326
YICVWQDWXA HRCI                                                      14

SEQ ID NO: 327          moltype = AA  length = 27
FEATURE                 Location/Qualifiers
REGION                  1..27
                        note = Description of Artificial Sequence: Synthetic peptide
REGION                  1..27
```

```
                        note = compstatin analogue
VARIANT                 1..6
                        note = A, E, G, L, K, F, P, S, T, W, Y, R, V, Sar,
                         epsilonLys, gammaGlu, betaAsp, or betaAla, or a
                         corresponding D form thereof or Peg3, Peg4,
                         8-aminooctanoyl derivatives thereof or may be absent
VARIANT                 1..6
                        note = This region may encompass 1 to 6 amino acid residues
VARIANT                 7
                        note = I, Y, F or Sar
DISULFID                8..18
                        note = Intrachain disulfide bond
VARIANT                 10
                        note = W, F, V, Y, 1-Me-Trp, D-Trp, N-Me-Trp, 1-For-Trp,
                         1-Nal, 2-Nal, 5-Me-Trp, Bpa or 2-Igl
VARIANT                 12
                        note = E, K or D
VARIANT                 14
                        note = G or Sar
VARIANT                 17
                        note = R, S or K
VARIANT                 19
                        note = T, S, E, F, H, K, Sar, G, I, D, N-Me-Ile or N-Me-Thr
VARIANT                 20..27
                        note = A, E, G, L, K, F, P, S, T, W, Y, R, V, Sar,
                         epsilonLys, gammaGlu, betaAsp, or betaAla, or a
                         corresponding D form thereof or Peg3, Peg4,
                         8-aminooctanoyl derivatives thereof or may be absent
VARIANT                 20..27
                        note = This region may encompass 1 to 8 amino acid residues
source                  1..27
                        mol_type = protein
                        organism = synthetic construct
SEQUENCE: 327
XXXXXXXCIX QXWXEHXCXX XXXXXXX                                         27

SEQ ID NO: 328          moltype = AA  length = 27
FEATURE                 Location/Qualifiers
REGION                  1..27
                        note = Description of Artificial Sequence: Synthetic peptide
REGION                  1..27
                        note = compstatin analogue
VARIANT                 1..6
                        note = A, E, G, L, K, F, P, S, T, W, Y, R, V, Sar,
                         epsilonLys, gammaGlu, betaAsp, or betaAla, or a
                         corresponding D form thereof, or Peg3, Peg4,
                         8-aminooctanoyl derivatives thereof or may be absent
VARIANT                 1..6
                        note = This region may encompass 1 to 6 amino acid residues
VARIANT                 7
                        note = I, Y, F or Sar
DISULFID                8..18
                        note = Intrachain disulfide bond
VARIANT                 10
                        note = W, V, Y, 2-Nal, 1-Nal or 1-Me-Trp
VARIANT                 12
                        note = E or D
VARIANT                 14
                        note = G or Sar
VARIANT                 17
                        note = R, S or K
VARIANT                 19
                        note = T, S, E, I, Sar, K, G or N-Me-Ile
VARIANT                 20..27
                        note = A, E, G, L, K, F, P, S, T, W, Y, R, V, Sar,
                         epsilonLys, gammaGlu, betaAsp, or betaAla, or a
                         corresponding D form thereof or Peg3 or Peg4,
                         8-aminooctanoyl derivatives thereof or may be absent
VARIANT                 20..27
                        note = This region may encompass 1 to 8 amino acid residues
source                  1..27
                        mol_type = protein
                        organism = synthetic construct
SEQUENCE: 328
XXXXXXXCIX QXWXEHXCXX XXXXXXX                                         27

SEQ ID NO: 329          moltype = AA  length = 27
FEATURE                 Location/Qualifiers
REGION                  1..27
```

-continued

```
                        note = Description of Artificial Sequence: Synthetic peptide
REGION                  1..27
                        note = compstatin analogue
VARIANT                 1..6
                        note = A, E, G, L, K, F, P, S, T, W, Y, R, V, Sar,
                         epsilonLys, gammaGlu, betaAsp, or betaAla, or a
                         corresponding D form thereof, or Peg3, Peg4,
                         8-aminooctanoyl derivatives thereof or may be absent
VARIANT                 1..6
                        note = This region may encompass 1 to 6 amino acid residues
VARIANT                 7
                        note = I, Y, F or Sar
DISULFID                8..18
                        note = Intrachain disulfide bond
VARIANT                 10
                        note = W, V, Y,1-Nal, 2-Nal or 1-Me-Trp
VARIANT                 12
                        note = E or D
VARIANT                 17
                        note = R, S or K
VARIANT                 19
                        note = T, I, S, E, K or Sar
VARIANT                 20..27
                        note = A, E, G, L, K, F, P, S, T, W, Y, R, V, Sar,
                         epsilonLys, gammaGlu, betaAsp, or betaAla, or a
                         corresponding D form thereof or Peg3 or Peg4,
                         8-aminooctanoyl derivatives thereof or may be absent
VARIANT                 20..27
                        note = This region may encompass 1 to 8 amino acid residues
source                  1..27
                        mol_type = protein
                        organism = synthetic construct
SEQUENCE: 329
XXXXXXXCIX QXWGEHXCXX XXXXXXX                                        27

SEQ ID NO: 330          moltype = AA  length = 27
FEATURE                 Location/Qualifiers
REGION                  1..27
                        note = Description of Artificial Sequence: Synthetic peptide
REGION                  1..27
                        note = compstatin analogue
VARIANT                 1..6
                        note = A, E, G, L, K, F, P, S, T, W, Y, R, V, Sar,
                         epsilonLys, gammaGlu, betaAsp, or betaAla, or a
                         corresponding D form thereof, or Peg3, Peg4,
                         8-aminooctanoyl derivatives thereof or may be absent
VARIANT                 1..6
                        note = This region may encompass 1 to 6 amino acid residues
VARIANT                 7
                        note = I, Y, F or Sar
DISULFID                8..18
                        note = Intrachain disulfide bond
VARIANT                 10
                        note = W, V, Y, 1-Nal, 2-Nal or 1-Me-Trp
VARIANT                 12
                        note = E or D
VARIANT                 19
                        note = T, S, E or Sar
VARIANT                 20..27
                        note = A, E, G, L, K, F, P, S, T, W, Y, R, V, Sar,
                         epsilonLys, gammaGlu, betaAsp, or betaAla, or a
                         corresponding D form thereof or Peg3 or Peg4,
                         8-aminooctanoyl derivatives thereof or may be absent
VARIANT                 20..27
                        note = This region may encompass 1 to 8 amino acid residues
source                  1..27
                        mol_type = protein
                        organism = synthetic construct
SEQUENCE: 330
XXXXXXXCIX QXWGEHRCXX XXXXXXX                                        27

SEQ ID NO: 331          moltype = AA  length = 25
FEATURE                 Location/Qualifiers
REGION                  1..25
                        note = Description of Artificial Sequence: Synthetic peptide
REGION                  1..25
                        note = compstatin analogue
VARIANT                 1..6
                        note = A, E, G, L, K, F, P, S, T, W, Y, R, V, Sar,
```

```
                         epsilonLys, gammaGlu, betaAsp, or betaAla, or a
                         corresponding D form thereof, or Peg3, Peg4,
                         8-aminooctanoyl derivatives thereof or may be absent
VARIANT                 1..6
                        note = This region may encompass 1 to 6 amino acid residues
VARIANT                 7
                        note = Y or F
DISULFID                8..18
                        note = Intrachain disulfide bond
VARIANT                 10
                        note = W, Y, or 1-Me-Trp
VARIANT                 12
                        note = E or D
VARIANT                 19
                        note = T, E or Sar
VARIANT                 20..25
                        note = A, E, G, L, K, F, P, S, T, W, Y, R, V, Sar,
                         epsilonLys, gammaGlu, betaAsp, or betaAla, or a
                         corresponding D form thereof or Peg3 or Peg4,
                         8-aminooctanoyl derivatives thereof or may be absent
VARIANT                 20..25
                        note = This region may encompass 1 to 6 amino acid residues
source                  1..25
                        mol_type = protein
                        organism = synthetic construct
SEQUENCE: 331
XXXXXXXCIX QXWGEHRCXX XXXXX                                        25

SEQ ID NO: 332          moltype = AA  length = 27
FEATURE                 Location/Qualifiers
REGION                  1..27
                        note = Description of Artificial Sequence: Synthetic peptide
REGION                  1..27
                        note = compstatin analogue
VARIANT                 1..6
                        note = A, E, G, L, K, K covalently linked to a lipophilic
                         group via its side chain, F, P, S, T, W, Y, R, V or Sar, a
                         corresponding D form thereof or may be absent
VARIANT                 1..6
                        note = This region may encompass 1 to 6 amino acid residues
VARIANT                 7
                        note = I, Y, F or Sar
DISULFID                8..18
                        note = Intrachain disulfide bond
VARIANT                 10
                        note = W, V, Y, 2-Nal, 1-Nal or 1-Me-Trp
VARIANT                 12
                        note = E or D
VARIANT                 14
                        note = G or Sar
VARIANT                 17
                        note = R, S or K covalently linked to a lipophilic group
                         via its side chain
VARIANT                 19
                        note = T, S, E, I, Sar, K, G or N-Me-Ile
VARIANT                 20..27
                        note = A, E, G, L, K, K covalently linked to a lipophilic
                         group via its side chain, F, P, S, T, W, Y, R, V, Sar,
                         epsilonLys, gammaGlu, betaAsp, betaAla, or a corresponding
                         D form thereof or Peg 3 or Peg4, or 8-aminooctanoyl
                         derivatives thereof or may be absent
VARIANT                 20..27
                        note = This region may encompass 1 to 8 amino acid residues
source                  1..27
                        mol_type = protein
                        organism = synthetic construct
SEQUENCE: 332
XXXXXXXCIX QXWXEHXCXX XXXXXXX                                      27

SEQ ID NO: 333          moltype = AA  length = 27
FEATURE                 Location/Qualifiers
REGION                  1..27
                        note = Description of Artificial Sequence: Synthetic peptide
REGION                  1..27
                        note = compstatin analogue
VARIANT                 1..6
                        note = A, E, G, L, K, K covalently linked to a lipophilic
                         group via its side chain, F, P, S, T, W, Y, R, V or Sar, a
                         corresponding D form thereof or may be absent
```

```
VARIANT               1..6
                      note = This region may encompass 1 to 6 amino acid residues
VARIANT               7
                      note = I, Y, F or Sar
DISULFID              8..18
                      note = Intrachain disulfide bond
VARIANT               10
                      note = W, V, Y, 1-Nal, 2-Nal or 1-Me-Trp
VARIANT               12
                      note = E or D
VARIANT               17
                      note = R, S or K covalently linked to a lipophilic group
                       via its side chain
VARIANT               19
                      note = T, I, S, E, K or Sar
VARIANT               20..27
                      note = A, E, G, L, K, K covalently linked to a lipophilic
                       group via its side chain F, P, S, T, W, Y, R, V, Sar,
                       epsilonLys, gammaGlu, betaAsp, or betaAla, or a
                       corresponding D form thereof or Peg3 or Peg4, or
                       8-aminooctanoyl derivatives thereof or may be absent
VARIANT               20..27
                      note = This region may encompass 1 to 8 amino acid residues
source                1..27
                      mol_type = protein
                      organism = synthetic construct
SEQUENCE: 333
XXXXXXXCIX QXWGEHXCXX XXXXXXX                                      27

SEQ ID NO: 334        moltype = AA  length = 27
FEATURE               Location/Qualifiers
REGION                1..27
                      note = Description of Artificial Sequence: Synthetic peptide
REGION                1..27
                      note = compstatin analogue
VARIANT               1..6
                      note = A, E, G, L, K, K covalently linked to a lipophilic
                       group via its side chain, F, P, S, T, W, Y, R, V or Sar, a
                       corresponding D form thereof or may be absent
VARIANT               1..6
                      note = This region may encompass 1 to 6 amino acid residues
VARIANT               7
                      note = I, Y, F or Sar
DISULFID              8..18
                      note = Intrachain disulfide bond
VARIANT               10
                      note = W, V, 1-Nal, 2-Nal or 1-Me-Trp
VARIANT               12
                      note = E or D
VARIANT               19
                      note = T, S, E or Sar
VARIANT               20..27
                      note = A, E, G, L, K, K covalently linked to a lipophilic
                       group via its side chain, F, P, S, T, W, Y, R, V, Sar,
                       epsilonLys, gammaGlu, betaAsp, or betaAla, or a
                       corresponding D form thereof or Peg3 or Peg4, or
                       8-aminooctanoyl derivatives thereof or may be absent
VARIANT               20..27
                      note = This region may encompass 1 to 8 amino acid residues
source                1..27
                      mol_type = protein
                      organism = synthetic construct
SEQUENCE: 334
XXXXXXXCIX QXWGEHRCXX XXXXXXX                                      27
```